(12) United States Patent
Wissenbach

(10) Patent No.: US 7,205,108 B2
(45) Date of Patent: Apr. 17, 2007

(54) TRP8, TRP9 AND TRP10, NOVEL MARKERS FOR CANCER

(76) Inventor: Ulrich Wissenbach, Institut für Pharmakologie und Toxikologie der Universität des Saarlandes, 66421 Homberg (DE)

( * ) Notice: Subject to any disclaimer, the term of this patent is extended or adjusted under 35 U.S.C. 154(b) by 73 days.

(21) Appl. No.: 10/343,114

(22) PCT Filed: Jul. 18, 2001

(86) PCT No.: PCT/EP01/08309

§ 371 (c)(1),
(2), (4) Date: Jun. 25, 2003

(87) PCT Pub. No.: WO02/10382

PCT Pub. Date: Feb. 7, 2002

(65) Prior Publication Data

US 2004/0072998 A1     Apr. 15, 2004

Related U.S. Application Data

(60) Provisional application No. 60/221,513, filed on Jul. 28, 2000.

(51) Int. Cl.
*C12Q 1/68*     (2006.01)
*G01N 33/53*   (2006.01)

(52) U.S. Cl. .............. 435/6; 435/7.1; 435/7.9; 435/8; 530/387.1; 530/324; 536/23.5

(58) Field of Classification Search ......... 435/7.1, 435/69.1, 7.92, 7.94; 530/350
See application file for complete search history.

(56) References Cited

U.S. PATENT DOCUMENTS 5,885,776 A * 3/1999 Stone et al. .................. 435/6
6,534,642 B1 * 3/2003 Hediger et al. ............ 536/23.5

FOREIGN PATENT DOCUMENTS

| WO | WO 98/15657 | 4/1998 |
|---|---|---|
| WO | WO 98/37093 | 8/1998 |
| WO | WO 99/09166 A | 2/1999 |
| WO | WO 00/40614 A | 7/2000 |
| WO | WO 01/04303 A | 1/2001 |
| WO | WO 01/14423 A | 3/2001 |
| WO | WO 01/42467 A | 6/2001 |
| WO | WO 01/51633 A | 7/2001 |
| WO | WO 01/53348 A | 7/2001 |
| WO | WO 01/62794 E | 8/2001 |
| WO | WO 01/68857 A | 9/2001 |
| WO | WO 02/00722 A | 1/2002 |
| WO | WO 02/14361 A | 2/2002 |
| WO | WO 02/30268 E | 4/2002 |

OTHER PUBLICATIONS

D. Muller et al.: "Molecular cloning, tissue distribution, and chromosomal mapping of the human epithelial Ca2+ channel (ECAC1)," GENOMICS, vol. 67, No. 1, Jul. 1, 2000, pp. 48-53.

Larisa Tsavaler et al.: "TRP-P8, a novel prostate-specific gene, is unregulated in prostate cancer and other malignancies and shares high homology with TRP calcium channel proteins," Proceedings of the American Association for Cancer Research Annual, No. 41, Mar. 2000, p. 694.

C. Harteneck et al.: "From worm to man: three subfamilies of TRP channels," Trends in Neuroscience, Elsevier, Amsterdam, NL, vol. 23, No. 4, Apr. 4, 2000, pp. 159-166.

Ulrich Wissenbach et al.: "Expression of CaT-like, a novel calcium-selective channel, correlates with the malignancy of prostate cancer," Journal of Biological Chemistry, vol. 276, No. 22, Jun. 1, 2001, pp. 19461-19468.

Matthias Boedding et al.: "The recombinant human TRPV6 channel functions as Ca2+ sensor in human embryonic kidney and rat basophilic leukemia cells," Journal of Biological Chemistry, vol. 277, No. 39, Sep. 27, 2002, pp. 36656-36664.

* cited by examiner

*Primary Examiner*—Eileen O'Hara
*Assistant Examiner*—Gyan Chandra
(74) *Attorney, Agent, or Firm*—Buchanan Ingersoll & Rooney PC

(57) ABSTRACT

The present invention relates to gene expression in normal cells and cells of malignant tumors and particularly to novel markers associated with cancer, Trp8, Trp9 and Trp10, and the genes encoding Trp8, Trp9 and Trp10. Also provided are vectors, host cells, antibodies, and recombinant methods for producing these human proteins. The invention further relates to diagnostic and therapeutic methods useful for diagnosing and treating a tumor.

10 Claims, 39 Drawing Sheets

```
htrp8A                                                                MG     2
htrp8B                                                                MG     2
Vr1    MEQRASLDSEESESPPQENSCLDPPDRDPNCKPPPVKPHIFTTRSRTRLFGKGDSEEASP          60
ECaC                                                                  MG     2 htrp8A LSLEKEKG-----LILCLWSKFCRWFQRR---ESWAQSRDEQNLLQQK-RIWESP-LLLR          52
htrp8B LSLEKEKG-----LILCLWSKFCRWFQRR---ESWAQSRDEQNLLQQK-RIWESP-LLLR          52
Vr1    LDCEYEEGGLASCPIITVSSVLTIQRPGDGPASVRPSSQDSVSAGEKPFRLYDRRSIFDA         120
ECaC   ACPEKAKG-----PWAQLQKLLISWPVGE---QDWEQYRVRVNMLQQE-HIRDSP-LLQR          52 htrp8A AKDNDVQAENKLLKYEDCKVH------QRGAMGETADHIRAS-YDR--LEAAMVLMEAR         102
htrp8B AKDNDVQAENKLLKYEDCKVH------QRGAMGETADHIRAS-YDR--LEAAMVLMEAR         102
Vr1    VAQSNCQEEESLLPFLQRSKKRLTDSEFKDPETGKICLLKGMQNLHGQNDTIALLLDVR         180
ECaC   AKENDLRLEKILLLNQSCDFQ------QRGAVGETADHVRAR-YDR--LERATLLMEAR         102 htrp8A ------PELVFEPMTSELYEGQTALHIRVVNQEMNDVRALLARRASVSRRATGTAFRRSP         156
htrp8B ------PELVFEPMTSELYEGQTALHIAVVNQEMNLVRALLARRASVSRRATGTAFRRSP         156
Vr1    RKTDSLKQFVNASYTDSYYKGQTALHIAIERRNMTLAVTLLVENGADVQAAANGDFKKTK         240
ECaC   ------PELAKEPALCEPFVGQTALHIAVMNQHLNLVRALLARGHSVSRRATGAAERRSP         156 htrp8A -HNLIEFGEHPLSFAACVNSEETVRLLIEHG---ADIRRQDSLGNTVLHILILQP-----         207
htrp8B -HNLIEFGEHPLSFAACVNSEETVRLLIEHG---ADIRRQDSLGNTVLHILILQP-----         207
Vr1    GRPGFEFGELELSLAAACTNQLAIVKFLLQNSWQPADISRRDSVGNTVLHALVEVADNTVD        300
ECaC   -HNLIEYGEHPLSFAACVGSEETVRLAIEHG---ADIRRQDSLGNTVLHILILQP-----         207 htrp8A NKTEACQMYNLLESYDRHGDHLQPLDLVPHQGLTFFKLAGVEGNTVMFQHLMQ-----          261
htrp8B NKTEACQMYNLLESYDRHGDHLQPLDLVPHQGLTFFKLAGVEGNTVMFQHLMQ-----          261
Vr1    NTKEVTSMYNEIKILGAKLHPTLKGEEITHRKGLTELALAASSGKIGVLAYILQREIHEP        360
ECaC   NKTEACQMYNLLESYDEHSDHLQSLELVPHQGLTFFKLAGVEGNTVMFQHLMQ-----          261 htrp8A -----KRRHTQWTYGRLTSTLYDLTEIDSSGDEQSLLELIITTK-KREAR-QIEDQTFVK        314
htrp8B -----KRRHTQWTYGRLTSTLYDLTEIDSSGDEQSLLELIITTK-KREAR-QIEDQTFVK        314
Vr1    ECRHLSRKFTEWAYGFVHSSLYDLSCIDTC-EKNSVLEVIAYSSSETPNRHDMLLVEPLN        420
ECaC   -----KRRHVQWTCGFLTSTLIDLTEIDSWGEELSFLELVVSSK-KREAR-QILEQTFVK        314 htrp8A EIVSLRWKRYGRPYECMLGAINLAYISCFIMCCIFRPLKPRTNNRTSFRDNTLLQQRLLQ        374
htrp8B EIVSLKWKRYGRPYECMLGAIHLLYIRCFIMCCIKRELKPRTNNRTSERDNTLLQQKLLQ        374
Vr1    RCLQDKWDREVKRIRYFNFFVNCLYMIFIAAAYNRPVEG-----LPP-----YKLRN--         468
ECaC   EIVSFKWKKYGRPYECVLASLYILQMICFITCCIYRELKLRDDNRTDERDITILQQKLLQ        374
                                       S1 htrp8A EAYETPKDDIRLVGELVTIVIGAIILLVEVPDIFRMGVTRFFGQTILGGPFHVLIITYAF        434
htrp8B EAYETPKDDIRLVGELVTIVIGAIILLVEVPDIFRMGVTRFFGQTILGGPFHVLIITYAF        434
Vr1    ----TVGDYFRVTGEILSVSGGVYFFFRGIQYFLQRRPS--LKSLFVDSYSEILFFVQSL        522
ECaC   EAYVEHQDNIRLVGELVTIVTGAVIILLEIPDIFRVGASRYFGQTILGGPFHVIITYAS        434
                S2                        S3 htrp8A MVLVTMVMRLISASGEVVPMSEADVLGMCNVMQFARGFPQMLGPFTIMIQKMIFGDIMRFC        494
htrp8B MVLVTMVMRLISASGEVVPMSEADVLGMCNVMQFARGFPQMLGPFTIMIQKMIFGDIMRFC        494
Vr1    FMLVSVVLYFSQRKEYVASMVFSLAMGHTNMLYYTRGFQQMGIYAVMIEKMILRDLCREM        582
ECaC   LVFLTMVMRLTNMNGEVVPLSEADVLGNCSVMYFARGFQMLGPFTIMIQKMIFGDIMRFC        494
                                S4 htrp8A WLMAVVILGEASAFYIIFQTED----FEE-----------LG-HFYDYFMALFSTAELV        538
htrp8B WLMAVVILGEASAFYIIFQTED----FEE-----------LG-HFYDYFMALFSTAELV        538
Vr1    FVYLVFLFGFSTAVVTLIEDGKNNSLFMESTPHKCRGSACKFGNSYNSLYSTCLELFKFT        642
ECaC   WLMAVVILGEASAFHITFQTED----FNN-----------LG-EFSDYPTALFSTEELF        538
         S5 htrp8A LTIIDGPANYNVDLPFMYSITYARFAIIATLIMINLLIAMGDTHWRVAHERDELRRAQI        598
htrp8B LTIIDGPANYNVDLPFMYSITYARFAIIATLIMINLLIAMGDTHWRVAHERDELRRAQI        598
Vr1    IGMGDLEFTENYDFKAVFIILLLAYVLTYIILLNMLIFLMGFTVNKIRQESKNIRKLQR        702
ECaC   LTIIDGPANYSVDLPFMYCITYARFAIIATLIMLNLFLAMGDTHWRVAQSRDELRRADV        598
                                          S6 htrp8A VAETVMLERKLPRCLWP--RSG---ICGREYGLGD--RMFLRVEDRQDLNRQRIQRYAQA        671
htrp8B VAETVMLERKLPRCLWP--RSG---IOGREYGLGD--RMFLRVEDRQDLNRQRIQRYAQA        671
Vr1    AIIILDTEKSFLKCMRKAFRSGKLLQVGFTPDGKDDYRNCFRVDEVNWTTWNTNVGIINE        762
ECaC   VAETVMLERKMPRFLWP--RSG---ICGYEYGLGD--RMFLRVENHHDQNPLRVLRYVEA        671 htrp8A FHTR----GSEDLDKDSV-EKLELGCPFSPHLSLPFPSVSRSTSRSSANWERLRQGTLRR        726
htrp8B FHTR----GSEDLDKDSV-EKLELGCPFSPHLSLPFPSVSRSTSRSSANWERLRQGTLRR        726
Vr1    DPGN---CEGVKRTLSFSLRSGRVSGRNWKNFALVPLLRDASTRDRHATQQEEVQLKHYTG        820
ECaC   FKCSDKEDGQEQLSEKRP-STVESGMLSRASVAFQTPSLSRTTSQSSN--SHRGWEILRR        728 htrp8A DLRGIINRGLEDGESWEYQI*                                            746
htrp8B DLRGIINRGLEDGESWEYQI*                                            746
Vr1    SLKPEDAEVFKDSMVPGEK*                                             839
ECaC   NTLGHLNLGLDLGEGDGEEVYHF*                                         751
```

```
                    10                  30                  50
        GCCAAGTGTAACAAACTCACAGCCCTCTCCAAACTGGCTGGGGCTGCTGGGAGACTCCCA
                    70                  90                 110
        AGGAACTCGTCAGGAAGGCAGGAGACAGGAGACGGGACCTCTACAGGGAGACGGTGGGCC
                   130                 150                 170
        GGCCCTTGGGGGGGCTGATGTGGCCCCAAGGCTGAGTCCCGTCAGGGTCTGGCCTCGGCC
                   190                 210                 230
        TCAGGCCCCCAAGGAGCCGGCCCTACACCCCATGGGTTTGTCACTGCCCAAGGAGAAAGG
                                                    M  G  L  S  L  P  K  E  K  G
                   250                 270                 290
        GCTAATTCTCTGCCTATGGAGCAAGTTCTGCAGATGGTTCCAGAGACGGGAGTCCTGGGC
         L  I  L  C  L  W  S  K  F  C  R  W  F  Q  R  R  E  S  W  A
                   310                 330                 350
        CCAGAGCCGAGATGAGCAGAACCTGCTGCAGCAGAAGAGGATCTGGGAGTCTCCTCTCCT
         Q  S  R  D  E  Q  N  L  L  Q  Q  K  R  I  W  E  S  P  L  L
                   370                 390                 410
        TCTAGCTGCCAAAGATAATGATGTCCAGGCCCTGAACAAGTTGCTCAAGTATGAGGATTG
         L  A  A  K  D  N  D  V  Q  A  L  N  K  L  L  K  Y  E  D  C
                   430                 450                 470
        CAAGGTGCACCAGAGAGGAGCCATGGGGGAAACAGCGCTACACATAGCAGCCCTCTATGA
         K  V  H  Q  R  G  A  M  G  E  T  A  L  H  I  A  A  L  Y  D
                   490                 510                 530
        CAACCTGGAGGCCGCCATGGTGCTGATGGAGGCTGCCCCGGAGCTGGTCTTTGAGCCCAT
         N  L  E  A  A  M  V  L  M  E  A  A  P  E  L  V  F  E  P  M
                   550                 570                 590
        GACATCTGAGCTCTATGAGGGTCAGACTGCACTGCACATCGCTGTTGTGAACCAGAACAT
         T  S  E  L  Y  E  G  Q  T  A  L  H  I  A  V  V  N  Q  N  M
                   610                 630                 650
        GAACCTGGTGCGAGCCCTGCTTGCCCGCAGGGCCAGTGTCTCTGCCAGAGCCACAGGCAC
         N  L  V  R  A  L  L  A  R  R  A  S  V  S  A  R  A  T  G  T
                   670                 690                 710
        TGCCTTCCGCCGTAGTCCCCGCAACCTCATCTACTTTGGGGAGCACCCTTTGTCCTTTGC
         A  F  R  R  S  P  R  N  L  I  Y  F  G  E  H  P  L  S  F  A
                   730                 750                 770
        TGCCTGTGTGAACAGTGAGGAGATCGTGCGGCTGCTCATTGAGCATGGAGCTGACATCCG
         A  C  V  N  S  E  E  I  V  R  L  L  I  E  H  G  A  D  I  R
                   790                 810                 830
        GGCCCAGGACTCCCTGGGAAACACAGTGTTACACATCCTCATCCTCCAGCCCAACAAAAC
         A  Q  D  S  L  G  N  T  V  L  H  I  L  I  L  Q  P  N  K  T
                   850                 870                 890
        CTTTGCCTGCCAGATGTACAACCTGTTGCTGTCCTACGACAGACATGGGGACCACCTGCA
         F  A  C  Q  M  Y  N  L  L  L  S  Y  D  R  H  G  D  H  L  Q
                   910                 930                 950
        GCCCCTGGACCTCGTGCCCAATCACCAGGGTCTCACCCCTTTCAAGCTGGCTGGAGTGGA
         P  L  D  L  V  P  N  H  Q  G  L  T  P  F  K  L  A  G  V  E
                   970                 990                1010
        GGGTAACACTGTGATGTTTCAGCACCTGATGCAGAAGCGGAAGCACACCCAGTGGACGTA
         G  N  T  V  M  F  Q  H  L  M  Q  K  R  K  H  T  Q  W  T  Y
                  1030                1050                1070
        TGGACCACTGACCTCGACTCTCTATGACCTCACAGAGATCGACTCCTCAGGGGATGAGCA
         G  P  L  T  S  T  L  Y  D  L  T  E  I  D  S  S  G  D  E  Q
                  1090                1110                1130
        GTCCCTGCTGGAACTTATCATCACCACCAAGAAGCGGGAGGCTCGCCAGATCCTGGACCA
         S  L  L  E  L  I  I  T  T  K  K  R  E  A  R  Q  I  L  D  Q
                  1150                1170                1190
        GACGCCGGTGAAGGAGCTGGTGAGCCTCAAGTGGAAGCGGTACGGGCGGCCCGTACTTCTG
         T  P  V  K  E  L  V  S  L  K  W  K  R  Y  G  R  P  Y  F  C
                  1210                1230                1250
        CATGCTGGGTGCCATATATCTGCTGTACATCATCTGCTTCACCATGTGCTGCATCTACCG
         M  L  G  A  I  Y  L  L  Y  I  I  C  F  T  M  C  C  I  Y  R
                  1270                1290                1310
```

FIGURE 7

```
CCCCCTCAAGCCCAGGACCAATAACCGCACAAGCCCCGGGACAACACCCTCTTACAGCA
  P  L  K  P  R  T  N  N  R  T  S  P  R  D  N  T  L  L  Q  Q
         1330           1350           1370
GAAGCTACTTCAGGAAGCCTACGTGACCCCTAAGGACGATATCCGGCTGGTCGGGGAGCT
  K  L  L  Q  E  A  Y  V  T  P  K  D  D  I  R  L  V  G  E  L
         1390           1410           1430
GGTGACTGTCATTGGGGCTATCATCATCCTGCTGGTAGAGGTTCCAGACATCTTCAGAAT
  V  T  V  I  G  A  I  I  I  L  L  V  E  V  P  D  I  F  R  M
         1450           1470           1490
GGGGGTCACTCGCTTCTTTGGACAGACCATCCTTGGGGGCCCATTCCATGTCCTCATCAT
  G  V  T  R  F  F  G  Q  T  I  L  G  G  P  F  H  V  L  I  I
         1510           1530           1550
CACCTATGCCTTCATGGTGCTGGTGACCATGGTGATGCGGCTCATCAGTGCCAGCGGGGA
  T  Y  A  F  M  V  L  V  T  M  V  N  R  L  I  S  A  S  G  E
         1570           1590           1610
GGTGGTACCCATGTCCTTTGCACTCGTGCTGGGCTGGTGCAACGTCATGTACTTCGCCCG
  V  V  P  M  S  F  A  L  V  L  G  W  C  N  V  M  Y  F  A  R
         1630           1650           1670
AGGATTCCAGATGCTAGGCCCCTTCACCATCATGATTCAGAAGATGATTTTTGGCGACCT
  G  F  Q  M  L  G  P  F  T  I  M  I  Q  K  M  I  F  G  D  L
         1690           1710           1730
GATGCGATTCTGCTGGCTGATGGCTGTGGTCATCCTGGGCTTTGCTTCAGCCTTCTATAT
  M  R  F  C  W  L  M  A  V  V  I  L  G  F  A  S  A  F  Y  I
         1750           1770           1790
CATCTTCCAGACAGAGGACCCCGAGGAGCTAGGCCACTTCTACGACTACCCCATGGCCCT
  I  F  Q  T  E  D  P  E  E  L  G  H  F  Y  D  Y  P  M  A  L
         1810           1830           1850
GTTCAGCACCTTCGAGCTGTTCCTTACCATCATCGATGGCCCAGCCAACTACAACGTGGA
  F  S  T  F  E  L  F  L  T  I  I  D  G  P  A  N  Y  N  V  D
         1870           1890           1910
CCTGCCCTTCATGTACAGCATCACCTATGCTGCCTTTGCCATCATCGCCACACTGCTCAT
  L  P  F  M  Y  S  I  T  Y  A  A  F  A  I  I  A  T  L  L  M
         1930           1950           1970
GCTCAACCTCCTCATTGCCATGATGGGCGACACTCACTGGCGAGTGGCCCATGAGCGGGA
  L  N  L  L  I  A  M  M  G  D  T  H  W  R  V  A  H  E  R  D
         1990           2010           2030
TGAGCTGTGGAGGGCCCAGATTGTGGCCACCACGGTGATGCTGGAGCGGAAGCTGCCTCG
  E  L  W  R  A  Q  I  V  A  T  T  V  M  L  E  R  K  L  P  R
         2050           2070           2090
CTGCCTGTGGCCTCGCTCCGGGATCTGCGGACGGGAGTATGGCCTGGGGGACCGCTGGTT
  C  L  W  P  R  S  G  I  C  G  R  E  Y  G  L  G  D  R  W  F
         2110           2130           2150
CCTGCGGGTGGAAGACAGGCAAGATCTCAACCGGCAGCGGATCCAACGCTACGCACAGGC
  L  R  V  E  D  R  Q  D  L  N  R  Q  R  I  Q  R  Y  A  Q  A
         2170           2190           2210
CTTCCACACCCGGGGCTCTGAGGATTTGGACAAAGACTCAGTGGAAAAACTAGAGCTGGG
  F  H  T  R  G  S  E  D  L  D  K  D  S  V  E  K  L  E  L  G
         2230           2250           2270
CTGTCCCTTCAGCCCCCACCTGTCCCTTCCTACGCCCTCAGTGTCTCGAAGTACCTCCCG
  C  P  F  S  P  H  L  S  L  P  T  P  S  V  S  R  S  T  S  R
         2290           2310           2330
CAGCAGTGCCAATTGGGAAAGGCTTCGGCAAGGGACCCTGAGGAGAGACCTGCGTGGGAT
  S  S  A  N  W  E  R  L  R  Q  G  T  L  R  R  D  L  R  G  I
         2350           2370           2390
AATCAACAGGGGTCTGGAGGACGGGGAGAGCTGGGAATATCAGATCTGACTGCGTGTTCT
  I  N  R  G  L  E  D  G  E  S  W  E  Y  Q  I
         2410           2430           2450
CACTTCGCTTCCTGGAACTTGCTCTCATTTTCCTGGGTGCATCAAACAAAACAAAAACCA
         2470           2490           2510
AACACCCAGAGGTCTCATCTCCCAGGCCCCAGGGAGAAAGAGGAGTAGCATGAACGCCAA
         2530           2550           2570
GGAATGTACGTTGAGAATCACTGCTCCAGGCCTGCATTACTCCTTCAGCTCTGGGGCAGA
```

FIGURE 7

```
          2590                2610                2630
GGAAGCCCAGCCCAAGCACGGGGCTGGCAGGGCGTGAGGAACTCTCCTGTGGCCTGCTCA
          2650                2670                2690
TCACCCTTCCGACAGGAGCACTGCATGTCAGAGCACTTTAAAAACAGGCCAGCCTGCTTG
          2710                2730                2750
GGCCCTCGGTCTCCACCCCAGGGTCATAAGTGGGGAGAGAGCCCTTCCCAGGGCACCCAG
          2770                2790                2810
GCAGGTGCAGGGAAGTGCAGAGCTTGTGGAAAGCGTGTGAGTGAGGGAGACAGGAACGGC
          2830                2850                2870
TCTGGGGGTGGGAAGTGGGGCTAGGTCTTGCCAACTCCATCTTCAATAAAGTCGTTTTCG
          2890                2910
GATCCCTAAAAAAAAAAAAAAAAAAAAAAAAA
```

MGLSLEKEKGLILCLWSKFCRWFQRRESWAQSRDEQNLLQQKRIWESPLLLAAKDNDVQALNKLLKYEDCKVHQRGAMGETALHIA
ALYDNLRAAMVLMEAAPELVFEPMTSELYEGQTALHIAVVNQNMNLVRALLARRASVSARATGTAFRRSPRNLIYFGEHPLSFAAC
VNSEEIVRLLIEHGADIRAQDSLGNTVLHILILQPNKTFACQMYNLLLSYDRHGDHLQPLDLVPNHQGLTPFKLAGVEGNTVMFQH
LMQKRKETQWTYGPLTSTLYDLTEIDSSGDEQSLLELIITTKKREARQILDQTPVKELVSLKWKRYGRPYFCMLGAIYLLYIICFT
MCCIYRPLKPRTNNRTSPRDNTLLQQKLLQEAYVTPKDDIRLVGELVTVIGAIIILLVEVPDIFRMGVTRFFGQTILGGPFHVLII
TYAFMVLVTMVMRLISASGEVVPMSFALVLGWCNVMYFARGFQMLGPFTIMIQKMIFGDLMRFCWLMAVVILGFASAFYIIFQTED
PEELGHFYDYPMALFSTFELFLTIIDGPANYNVDLPFMYSITYAAFAIIATLLMLNLLIAMMGDTHWRVAHERDELWRAQIVATTV
MLERKLPRCLWPRSGICGREYGLGDRWFLRVEDRQDLNRQRIQRYAQAFHTRGSEDLDKDSVEKLELGCPFSPHLSLPTPSVSRST
SRSSANWERLRQGTLRRDLRGIINRGLEDGESWEYQI

FIGURE 8 a)
```
                    ATGGGTTTGTCACTGCCCAAGGAGAAAGGGCTAATTCTCT
                     M  G  L  S  L  P  K  E  K  G  L  I  L  C
          250                 270                 290
GCCTATGGAGCAAGTTCTGCAGATGGTTCCAGAGACGGGAGTCCTGGGCCCAGAGCCGAG
  L  W  S  K  F  C  R  W  F  Q  R  R  E  S  W  A  Q  S  R  D
      310                 330                 350
ATGAGCAGAACCTGCTGCAGCAGAAGAGGATCTGGAGTCTCCTCTCCTTCTAGCTGCCA
    E  Q  N  L  L  Q  Q  K  R  I  W  E  S  P  L  L  L  A  A  K
          370                 390                 410
AAGATAATGATGTCCAGGCCCTGAACAAGTTGCTCAAGTATGAGGATTGCAAGGTGCACC
    D  N  D  V  Q  A  L  N  K  L  L  K  Y  E  D  C  K  V  H  Q
          430                 450                 470
AGAGAGGAGCCATGGGGGAAACAGCGCTACACATAGCAGCCCTCTATGACAACCTGGAGG
      R  G  A  M  G  E  T  A  L  H  I  A  A  L  Y  D  N  L  E  A
          490                 510                 530
CCGCCATGGTGCTGATGGAGGCTGCCCCGGAGCTGGTCTTTGAGCCCATGACATCTGAGC
      A  M  V  L  M  E  A  A  P  E  L  V  F  E  P  M  T  S  E  L
          550                 570                 590
TCTATGAGGGTCAGACTGCACTGCACATCGCTGTTGTGAACCAGAACATGAACCTGGTGC
      Y  E  G  Q  T  A  L  H  I  A  V  V  N  Q  N  M  N  L  V  R
          610                 630                 650
GAGCCCTGCTTGCCCGCAGGGCCAGTGTCTCTGCCAGAGCCACAGGCACTGCCTTCCGCC
      A  L  L  A  R  R  A  S  V  S  A  R  A  T  G  T  A  F  R  R
          670                 690                 710
GTAGTCCCTGCAACCTCATCTACTTTGGGGAGCACCCTTTGTCCTTTGCTGCCTGTGTGA
      S  P  C  N  L  I  Y  F  G  E  H  P  L  S  F  A  A  C  V  N
```

FIGURE 8

```
            730              750              770
ACAGTGAGGAGATCGTGCGGCTGCTCATTGAGCATGGAGCTGACATCCGGGCCCAGGACT
   S  E  E  I  V  R  L  L  I  E  H  G  A  D  I  R  A  Q  D  S
            790              810              830
CCCTGGGAAACACAGTGTTACACATCCTCATCCTCCAGCCCAACAAAACCTTTGCCTGCC
   L  G  N  T  V  L  H  I  L  I  L  Q  P  N  K  T  F  A  C  Q
            850              870              890
AGATGTACAACCTGTTGCTGTCCTACGACAGACATGGGGACCACCTGCAGCCCCTGGACC
   M  Y  N  L  L  L  S  Y  D  R  H  G  D  H  L  Q  P  L  D  L
            910              930              950
TCGTGCCCAATCACCAGGGTCTCACCCCTTTCAAGCTGGCTGGAGTGGAGGGTAACACTG
   V  P  N  H  Q  G  L  T  P  F  K  L  A  G  V  E  G  N  T  V
            970              990             1010
TGATGTTTCAGCACCTGATGCAGAAGCGGAAGCACACCCAGTGGACGTATGGACCACTGA
   M  F  Q  H  L  M  Q  K  R  K  H  T  Q  W  T  Y  G  P  L  T
           1030             1050             1070
CCTCGACTCTCTATGACCTCACAGAGATCGACTCCTCAGGGGATGAGCAGTCCCTGCTGG
   S  T  L  Y  D  L  T  E  I  D  S  S  G  D  E  Q  S  L  L  E
           1090             1110             1130
AACTTATCATCACCACCAAGAAGCGGGAGGCTCGCCAGATCCTGGACCAGACGCCGGTGA
   L  I  I  T  T  K  K  R  E  A  R  Q  I  L  D  Q  T  P  V  K
           1150             1170             1190
AGGAGCTGGTGAGCCTCAAGTGGAAGCGGTACGGGCGGCCGTACTTCTGCATGCTGGGTG
   E  L  V  S  L  K  W  K  R  Y  G  R  P  Y  F  C  M  L  G  A
           1210             1230             1250
CCATATATCTGCTGTACATCATCTGCTTCACCATGTGCTGCATCTACCGCCCCCTCAAGC
   I  Y  L  L  Y  I  I  C  F  T  M  C  C  I  Y  R  P  L  K  P
           1270             1290             1310
CCAGGACCAATAACCGCACGAGCCCCCGGGACAACACCCTCTTACAGCAGAAGCTACTTC
   R  T  N  N  R  T  S  P  R  D  N  T  L  L  Q  Q  K  L  L  Q
           1330             1350             1370
AGGAAGCCTACATGACCCCTAAGGACGATATCCGGCTGGTCGGGGAGCTGGTGACTGTCA
   E  A  Y  M  T  P  K  D  D  I  R  L  V  G  E  L  V  T  V  I
           1390             1410             1430
TTGGGGCTATCATCATCCTGCTGGTAGAGGTTCCAGACATCTTCAGAATGGGGGTCACTC
   G  A  I  I  I  L  L  V  E  V  P  D  I  F  R  M  G  V  T  R
           1450             1470             1490
GCTTCTTTGGACAGACCATCCTTGGGGGCCCATTCCATGTCCTCATCATCACCTATGCCT
   F  F  G  Q  T  I  L  G  G  P  F  H  V  L  I  I  T  Y  A  F
           1510             1530             1550
TCATGGTGCTGGTGACCATGGTGATGCGGCTCATCAGTGCCAGCGGGGAGGTGGTACCCA
   M  V  L  V  T  M  V  M  R  L  I  S  A  S  G  E  V  V  P  M
           1570             1590             1610
TGTCCTTTGCACTCGTGCTGGGCTGGTGCAACGTCATGTACTTCGCCCGAGGATTCCAGA
   S  F  A  L  V  L  G  W  C  N  V  M  Y  F  A  R  G  F  Q  M
           1630             1650             1670
TGCTAGGCCCCTTCACCATCATGATTCAGAAGATGATTTTTGGCGACCTGATGCGATTCT
   L  G  P  F  T  I  M  I  Q  K  M  I  F  G  D  L  M  R  F  C
           1690             1710             1730
GCTGGCTGATGGCTGTGGTCATCCTGGGCTTTGCTTCAGCCTTCTATATCATCTTCCAGA
   W  L  M  A  V  V  I  L  G  F  A  S  A  F  Y  I  I  F  Q  T
           1750             1770             1790
CAGAGGACCCCGAGGAGCTAGGCCACTTCTACGACTACCCCATGGCCCTGTTCAGCACCT
   E  D  P  E  E  L  G  H  F  Y  D  Y  P  M  A  L  F  S  T  F
           1810             1830             1850
TCGAGCTGTTCCTTACCATCATCGATGGCCCAGCCAACTACAACGTGGACCTGCCCTTCA
   E  L  F  L  T  I  I  D  G  P  A  N  Y  N  V  D  L  P  F  M
           1870             1890             1910
TGTACAGCATCACCTATGCTGCCTTTGCCATCATCGCCACACTGCTCATGCTCAACCTCC
   Y  S  I  T  Y  A  A  F  A  I  I  A  T  L  L  M  L  N  L  L
           1930             1950             1970
TCATTGCCATGATGGGCGACACTCACTGGCGAGTGGCCCATGAGCGGGATGAGCTGTGGA
```

FIGURE 8

```
      I  A  M  M  G  D  T  H  W  R  V  A  H  E  R  D  E  L  W  R
          1990              2010              2030
GGGCCCAGATTGTGGCCACCACGGTGATGCTGGAGCGGAAGCTGCCTCGCTGCCTGTGGC
   A  Q  I  V  A  T  T  V  M  L  E  R  K  L  P  R  C  L  W  P
          2050              2070              2090
CTCGCTCCGGGATCTGCGGACGGGAGTATGGCCTGGGAGACCGCTGGTTCCTGCGGGTGG
      R  S  G  I  C  G  R  E  Y  G  L  G  D  R  W  F  L  R  V  E
          2110              2130              2150
AAGACAGGCAAGATCTCAACCGGCAGCGGATCCAACGCTACGCACAGGCCTTCCACACCC
      D  R  Q  D  L  N  R  Q  R  I  Q  R  Y  A  Q  A  F  H  T  R
          2170              2190              2210
GGGGCTCTGAGGATTTGGACAAAGACTCAGTGGAAAAACTAGAGCTGGGCTGTCCCTTCA
      G  S  E  D  L  D  K  D  S  V  E  K  L  E  L  G  C  P  F  S
          2230              2250              2270
GCCCCCACCTGTCCCTTCCTATGCCCTCAGTGTCTCGAAGTACCTCCCGCAGCAGTGCCA
      P  H  L  S  L  P  M  P  S  V  S  R  S  T  S  R  S  S  A  N
          2290              2310              2330
ATTGGGAAAGGCTTCGGCAAGGGACCCTGAGGAGAGACCTGCGTGGGATAATCAACAGGG
      W  E  R  L  R  Q  G  T  L  R  R  D  L  R  G  I  I  N  R  G
          2350              2370              2390
GTCTGGAGGACGGGGAGAGCTGGGAATATCAGATCTGA
      L  E  D  G  E  S  W  E  Y  Q  I  *
```

MGLSLPKERGLILCLWSKFCRWFQRRESWAQSRDEQNLLQQKRIWESPLLLAAKDNDVQALNKLLKYEDCKVHQRGAMGETALHIA
ALYDNLEAAMVLMEAAPELVFEPMTSELYEGQTALHIAVVNQNMNLVRALLARRASVSARATGTAFRRSPCNLIYFGEHPLSFAAC
VNSEEIVRLLIEHGADIRAQDSLGNTVLHILILQPNKTFACQMYNLLLSYDRHGDELQPLDLVPNHQGLTPFKLAGVEGNTVMFQH
LMQKRKHTQWTYGPLTSTLYDLTEIDSSGDEQSLLELIITTKKREARQILDQTPVKELVSLKWKRYGRPYFCMLGAIYLLYIICFT
MCCIYRPLKPRTNNRTSPRDNTLLQQKLLQEAYMTPKDDIRLVGELVTVIGAIIILLVEVPDIFRMGVTRFFGQTILGGPFHVLII
TYAFMVLVTMVMRLISASGEVVPMSFALVLGWCNVMYFARGFQMLGPFTIMIQKMIFGDLMREFCWLMAVVILGFASAFYIIFQTED
PEELGHFYDYPMALFSTFELFLTIIDGPANYNVDLPFMYSITYAAFAIIATLLMLNLLIAMMGDTHWRVAHERDELWRAQIVATTV
MLERKLPRCLWPRSGICGREYGLGDRWFLRVEDRQDLNRQRIQRYAQAFHTRGSEDLDKDSVEKLELGCPFSPHLSLPMPSVSRST
SRSSANWERLRQGTLRRDLRGIINRGLEDGESWEYQI b) 
```
CAAACTCACAGCCCTCTCCAAACTGGCTGGGGCTGCTGGGAGACTCCCAAGGAACTCGTCAGGAAGGCAGGAGACAGGAGACGGGA
CCTCTACAGGGAGACGGTGGGCCGGCCCTTGGGGGGGCTGATGTGGCCCCAAGGCTGAGTCCCGTCAGGGTCTGGCCTCGGCCTCA
GGCCCCCAAGGAGCCGGCCCTACACCCCATGGGTTTGTCACTGCCCAAGGAGAAAGGGCTAATTCTCTGCCTATGGAGCAAGTTCT
GCAGATGGTTCCAGAGACGGGAGTCCTGGGCCCAGAGCCGAGATGAGCAGAACCTGCTGCAGCAGAAGAGGATCTGGGAGTCTCCT
CTCCTTCTAGCTGCCAAAGATAATGATGTCCAGGCCCTGAACAAGTTGCTCAAGTATGAGGATTGCAAGGTGCACCAGAGAGGAGC
CATGGGGGAAACAGCGCTACACATAGCAGCCCTCTATGACAACCTGGAGGCCGCCATGGTGCTGATGGAGGCTGCCCCGGAGCTGG
TCTTTGAGCCCATGACATCTGAGCTCTATGAGGGTCAGACTGCACTGCACATCGCTGTTGTGAACCAGAACATGAACCTGGTGCGA
GCCCTGCTTGCCCGCAGGGCCAGTGTCTCTGCCAGAGCCACAGGCACTGCCTTCCGCCGTAGTCCCCGCAACCTCATCTACTTTGG
GGAGCACCCTTTGTCCTTTGCTGCCTGTGTGAACAGTGAGGAGATCGTCCGGCTGCTCATTGAGCATGGAGCTGACATCCGGGCCC
AGGACTCCCTGGGCCCAACAAAACCTTTGCCTGCCAGATGTACAACCTGTTGCTGTCCTACGACAGACATGGGGACCACCTGCAGCC
CCTGGACCTCGTGCCCAATCACCAGGGTCTCACCCCTTTCAAGCTGGCTGGAGTGGAGGGTAACACTGTGATGTTTCAGCACCTGA
TGCAGAAGCGGAAGCACACCCAGTGGACGTATGGACCACTGACCTCGACTCTCTATGACCTCACAGAGATCGACTCCTCAGGGGAT
GAGCAGTCCCTGCTGGAACTTATCATCACCACCAAGAAGCGGGAGGCTCGCCAGATCCTGGACCAGACGCCGGTGAAGGAGCTGGT
GAGCCTCAAGTGGAAGCGGTACGGCCGGCCGTACTTCTGCATGCTGGGTGCCATATATCTGCTGTACATCATCTGCTTCACCATGT
GCTGCATCTACCGCCCCCTCAAGCCCAGGACCAATAACCGCACAAGCCCCGGGACAACACCCTCTTACAGCAGAAGCTACTTCAG
GAAGCCTACGTGACCCCTAAGGACGATATCCGGCTGGTCGGGGAGCTGGTGACTGTCATTGGGGCTATCATCATCCTGCTGGTAGA
GGTTCCAGACATCTTCAGAATGGGGGTCACTCGCTTCTTTGGACAGACCATCCTTGGGGGCCCATTCCATGTCCTCATCATCACCT
ATGCCTTCATGGTGCTGGTGACCATGGTGATGCGGCTCATATGATTTTTGGCGACCTGATGCGATTCTGCTGGCTGATGGCTGTGG
TCATCCTGGGCTTTGCTTCAGCCTTCTATATCATCTTCCAGACAGAGGACCCCGAGGAGCTAGGCCACTTCTACGACTACCCCATG
GCCCTGTTCAGCACCTTCGAGCTGGTCCTTACCATCATCGATGGCCCAGCCAACTACAACGTGGACCTGCCCTTCATGTACAGCAT
CACCTATGCTGCCTTTGCCATCATCGCCACACTGCTCATGCTCAACCTCCTCATTGCCATGATGGGCGACACTCACTGGCGAGTGG
CCCATGAGCGGGATGAGCTGTGGAGGGCCCAGATTGTGGCCACCACGGTGATGCTGGAGCGGAAGCTGCCTCGCTGCCTGTGGCCT
CGCTCCGGGATCTGCGGACGGGAGTATGGCCTGGGGGACCGCTGGTTCCTGCGGGTGGAAGACAGGCAAGATCTCAACCGGCAGCG
```

FIGURE 8

GATCCAACGCTACGCACAGGCCTTCCACACCCGGGGCTCTGAGGATTTGGACAAAGACTCAGTGGAAAAACTAGAGCTGGGCTGTC
CCTTCAGCCCCCACCTGTCCCTTCCTACGCCCTCAGTGTCTCGAAGTACCTCCCGCAGCAGTGCCAATTGGGAAAGGCTTCGGCAA
GGGACCCTGAGGAGAGACCTGCGTGGGATAATCAACAGGGGTCTGGAGGACGGGGAGAGCTGGGAATATCAGATCTGACTGCGTGT
TCTCACTTCGCTTCCTGGAACTTGCTCTCATTTTCCTGGGTGCATCAAACAAAACAAAAACCAAACACCCAGAGGTCTCATCTCCC
AGGCCCCAGGGAGAAAGAGGAGTAGCATGAACGCCAAGGAATGTACGTTGAGAATCACTGCTCCAGGCCTGCATTACTCCTTCAGC
TCTGGGGCAGAGGAAGCCCAGCCCAAGCACGGGGCTGGCAGGGCGTGAGGAACTCTCCTGTGGCCTGCTCATCACCCTTCCGACAG
GAGCACTGCATGTCAGAGCACTTTAAAAACAGGCCAGCCTGCTTGGGCCCTCGGTCTCCACCCCAGGGTCATAAGTGGGGAGAGAG
CCCTTCCCAGGGCACCCAGGCAGGTGCAGGGAAGTGCAGAGCTTGTGGAAAGCGTGTGAGTGAGGGAGACAGGAACGGCTCTGGGG
GTGGGAAGTGGGGCTAGGTCTTGCCAACTCCATCTTCAATAAAGTCGTTTTCGGATCCCTAAAAAAAAAAAAAAAAAAAAAAAAAA c) CAAACTCACAGCCCTCTCCAAACTGGCTGGGGCTGCTGGGAGACTCCCAAGGAACTCGTCAGGAAGGCAGGAGACAGGAGACGGGA
CCTCTACAGGGAGACGGTGGGCCGGCCCTTGGGGGGGCTGATGTGGCCCCAAGGCTGAGTCCCGTCAGGGTCTGGCCTCGGCCTCA
GGCCCCAAGGAGCCGGCCCTACACCCCATGGGTTTGTCACTGCCCAAGGAGAAAGGGCTAATTCTCTGCCTATGGAGCAAGTTCT
GCAGATGGTTCCAGAGACGGGAGTCCTGGGCCCAGAGCCGAGATGAGCAGAACCTGCTGCAGCAGAAGAGGATCTGGGAGTCTCCT
CTCCTTCTAGCTGCCAAAGATAATGATGTCCAGGCCCTGAACAAGTTGCTCAAGTATGAGGATTGCAAGGTGCACCAGAGAGGAGC
CATGGGGGAAACAGCGCTACACATAGCAGCCCTCTATGACAACCTGGAGGCCGCCATGGTGCTGATGGAGGCTGCCCCGGAGCTGG
TCTTTGAGCCCATGACATCTGAGCTCTATGAGGTCCTGACTGCCCATCACTTGAACGCCTGCCCCCTGAAATGCCAGGGCCTAGAG
AAGAGGAAGAGATGGGCAGCAGCTGGATCCCCTGGGAATCCTGAACACCCGAGAGCTCCCTGTTCTCCATCCCAGGCTACCCCTGA
GGGAAAGAGACTGGGGTGCATATGGGAGGGACCCCCTGCAGGATCCTGGGGACAGACCCGTGACTGACAGCTGTCTCTGGGCCAGG
TCAGACTGCACTGCACATCGCTGTTGTGAACCAGAACATGAACCTGGTGCGAGCCCTGCTTGCCCGCAGGGCCAGTGTCTCTGCCA
GAGCCACAGGCACTGCCTTCCGCCGTAGTCCCTGCAACCTCATCTACTTTGGGGAGCACCCTTTGTCCTTTGCTGCCTGTGTGAAC
AGTGAGGAGATCGTGCGGCTGCTCATTGAGCATGGAGCTGACATCCGGGCCCAGGACTCCCTGGCCCAACAAAACCTTTGCCTGCC
AGATGTACAACCTGTTGCTGTCCTACGACAGACATGGGGACCACCTGCAGCCCCTGGACCTCGTGCCCAATCACCAGGGTCTCACC
CCTTTCAAGCTGGCTGGAGTGGAGGGTAACACTGTGATGTTTCAGCACCTGATGCAGAAGCGGAAGCACACCCAGTGGACGTATGG
ACCACTGACCTCGACTCTCTATGACCTCACAGAGATCGACTCCTCAGGGGATGAGCAGTCCCTGCTGGAACTTATCATCACCACCA
AGAAGCGGGAGGCTCGCCAGATCCTGGACCAGAGCGCCGGTGAAGGAGCTGGTGAGCCTCAAGTGGAAGCGGTACGGGCGGCCGTAC
TTCTGCATGCTGGGTGCCATATATCTGCTGTACATCATCTGCTTCACCATGTGCTGCATCTACCGCCCCCTCAAGCCCAGGACCAA
TAACCGCACGAGCCCCCGGGACAACACCCTCTTACAGCAGAAGCTACTTCAGGAAGCCTACATGACCCCTAAGGACGATATCGGGC
TGGTCGGGGAGCTGGTGACTGTCATTGGGGCTATCATCATCCTGCTGGTAGAGGTTCCAGACATCTTCAGAATGGGGGTCACTCGC
TTCTTTGGACAGACCATCCTTGGGGGCCCATTCCATGTCCTCATCATCACCTATGCCTTCATGGTGCTGGTGACCATGGTGATGCG
GCTCATCAGTGCCGCGGGGAGGTGGTACCCATGTCCTTTGCACTCGTGCTGGGCTGGTGCAACGTCATGTACTTCGCCCGAGGAT
TCCAGATGCTAGGCCCCTTCACCATCATGATTCAGAAGATGATTTTTGGCGACCTGATGCGATTCTGCTGGCTGATGGCTGTGGTC
ATCCTGGGCTTTGCTTAGACAGAGGACCCGAGGGAGCTAGGCCACTTCTACGACTACCCCATGGCCCTGTTCAGCACCTTCCGAGCT
GGTCCTTACCATCATCGATGGCCCAGCCAACTACAACGTGGACCTGCCCCTTCATGTACAGCATCACCTATGCTGCCTTTGCCATCA
TCGCCACACTGCTCATGCTCAACCTCCTCATTGCCATGATGGGCGACACTCACTGGCGAGTGGCCCATGAGCGGGATGAGCTGTGG
AGGGCCCAGATTGTGGCCACCACGGTGATGCTGGAGCGGAAGCTGCCTCGCTGCCTGTGGCCTCGCTCCGGGATCTGCGGACGGGA
GTATGGCCTGGGAGACCGCTGGTTCCTGCGGGTGGAAGACAGGCAAGATCTCAACCGGCAGCGGATCCAACGCTACGCACAGGCCT
TCCACACCCGGGGCTCTGAGGATTTGGACAAAGACTCAGTGGAAAAACTAGAGCTGGGCTGTCTGCCTTCAGCCCCCACCTGTCCCTT
CCTATGCCCTCAGTGTCTCGAAGTACCTCCCGCAGCAGTGCCAATTGGGAAAGGCTTCGCAAGGGACCCTGAGGAGAGACCTGCG
TGGGATAATCAACAGGGGTCTGGAGGACGGGGAGAGCTGGGAATATCAGATCTGACTGCGTGTTCTCACTTCGCTTCCTGGAACTT
GCTCTCATTTTCCTGGGTGCATCAAACAAAACAAAAACCAAACACCCAGAGGTCTCATCTCCCAGGCCCCAGGGAGAAAGAGGAGT
AGCATGAACGCCAAGGAATGTACGTTGAGAATCACTGCTCCAGGCCTGCATTACTCCTTCAGCTCTGGGGCAGAGGAAGCCCAGCC
CAAGCACGGGGCTGGCAGGGCGTGAGGAACTCTCCTGTGGCCTGCTCATCACCCTTCCGACAGGAGCACTGCATGTCAGAGCACTT
TAAAAACAGGCCAGCCTGCTTGGGCCCTCGGTCTCCACCCCAGGGTCATAAGTGGGGAGAGAGCCCTTCCCAGGGCACCCAGGCAG
GTGCAGGGAAGTGCAGAGCTTGTGGAAAGCGTGTGAGTGAGGGAGACAGGAACGGCTCTGGGGGTGGGAAGTGGGGCTAGGTCTTG
CCAACTCCATCTTCAATAAAGTCGTTTTCGGATCCCTAAAAAAAAAAAAAAAAAAAAAAAAAA d) CAAACTCACAGCCCTCTCCAAACTGGCTGGGGCTGCTGGGAGACTCCCAAGGAACTCGTCAGGAAGGCAGGAGACAGGAGACGGGA
CCTCTACAGGGAGACGGTGGGCCGGCCCTTGGGGGGGCTGATGTGGCCCCAAGGCTGAGTCCCGTCAGGGTCTGGCCTCGGCCTCA
GGCCCCAAGGAGCCGGCCCTACACCCCATGGGTTTGTCACTGCCCAAGGAGAAAGGGCTAATTCTCTGCCTATGGAGCAAGTTCT
GCAGATGGTTCCAGAGACGGGAGTCCTGGGCCCAGAGCCGAGATGAGCAGAACCTGCTGCAGCAGAAGAGGATCTGGGAGTCTCCT
CTCCTTCTAGCTGCCAAAGATAATGATGTCCAGGCCCTGAACAAGTTGCTCAAGTATGAGGATTGCAAGGTGCACCAGAGAGGAGC
CATGGGGGAAACAGCGCTACACATAGCAGCCCTCTATGACAACCTGGAGGCCGCCATGGTGCTGATGGAGGCTGCCCCGGAGCTGG
TCTTTGAGCCCATGACATCTGAGCTCTATGAGGGTCAGACTGCACTGCACATCGCTGTTGTGAACCAGAACATGAACCTGGTGCGA
GCCCTGCTTGCCCGCAGGGCCAGTGTCTCTGCCAGAGCCACAGGCACTGCCTTCCGCCGTAGTCCCCGCAACCTCATCTACTTTGG

FIGURE 8

AAACACAGTGTTACACATCCTCATCCTCCAGCCCAACAAAACCTTTGCCTGCCAGATGTACAACCTGTTGCTGTCCTACGACAGAC
ATGGGGACCACCTGCAGCCCCTGGACCTCGTGCCCAATCACCAGGGTCTCACCCCTTTCAAGCTGGCTGGAGTGGAGGGTAACACT
GTGATGTTTCAGCACCTGATGCAGAAGCGGAAGCACACCCAGTGGACGTATGGACCACTGACCTCGACTCTCTATGACCTCACAGA
GATCGACTCCTCAGGGGATGAGCAGTCCCTGCTGGAACTTATCATCACCACCAAGAAGCGGGAGGCTCGCCAGATCCTGGACCAGA
CGCCGGTGAAGGAGCTGGTGAGCCTCAAGTGGAAGCGGTACGGGCGGCCGTACTTCTGCATGCTGGGTGCCATATATCTGCTGTAC
ATCATCTGCTTCACCATGTGCTGCATCTACCGCCCCCTCAAGCCCAGGACCAATAACCGCACAAGCCCCCGGGACAACACCCTCTT
ACAGCAGAAGCTACTTCAGGAAGCCTACGTGACCCCTAAGGACGATATCCGGCTGGTCGGGGAGCTGGTGACTGTCATTGGGGCTA
TCATCATCCTGCTGGTAGAGGTTCCAGACATCTTCAGAATGGGGGTCACTCGCTTCTTTGGACAGACCATCCTTGGGGGCCCATTC
CATGTCCTCATCATCACCTATGCCTTCATGGTGCTGGTGACCATGGTGATGCGGCTCATCAGTGCCAGCGGGGAGGTGGTACCCAT
GTCCTTTGCACTCGTGCTGGGCTGGTGCAACGTCATGTACTTCGCCCGAGGATTCCAGATGCTAGGCCCCTTCACCATCATGATTC
AGAAGATGATTTTTGGCGACCTGATGCGATTCTGCTGGCTGATGGCTGTGGTCATCCTGGGCTTTGCTTCAGCCTTCTATATCATC
TTCCAGACAGAGGACCCCGAGGAGCTAGGCCACTTCTACGACTACCCCATGGCCCTGTTCAGCACCTTCGAGCTGGTCCTTACCAT
CATCGATGGCCCCAGCCAACTACAACGTGGACCTGCCCTTCATGTACAGCATCACCTATGCTGCCTTTGCCATCATCGCCACACTGC
TCATGCTCAACCTCCTCATTGCCATGATGGGCGACACTCACTGGCGAGTGGCCCATGAGCGGGATGAGCTGTGGAGGGCCCAGATT
GTGGCCACCACGGTGATGCTGGAGCGGAAGCTGCCTCGCTGCCTGTGGCCTCGCTCCGGGATCTGCGGACGGGAGTATGGCCTGGG
GGACCGCTGGTTCCTGCGGGTGGAAGACAGGCAAGATCTCAACCGGCAGCGGATCCAACGCTACGCACAGGCCTTCCACACCCGGG
GCTCTGAGGATTTGGACAAAGACTCAGTGGAAAAACTAGAGCTGGGCTGTCCCTTCAGCCCCCACCTGTCCCTTCCTACGCCCTCA
GTGTCTCGAAGTACCTCCCGCAGCAGTGCCAATTGGGAAAGGCTTCGGCAAGGGACCCTGAGGAGAGACCTGCGTGGGATAATCAA
CAGGGGTCTGGAGGACGGGGAGAGCTGGGAATATCAGATCTGACTGCGTGTTCTCACTTCGCTTCCTGGAACTTGCTCTCATTTTC
CTGGGTGCATCAAACAAAACAAAAACCAAACACCCAGAGGTCTCATCTCCCAGGCCCCAGGGAGAAAGAGGAGTAGCATGAACGCC
AAGGAATGTACGTTGAGAATCACTGCTCCAGGCCTGCATTACTCCTTCAGCTCTGGGGCAGAGGAAGCCCAGCCCAAGCACGGGGC
TGGCAGGGCGTGAGGAACTCTCCTGTGGCCTGCTCATCACCCTTCCGACAGGAGCACTGCATGTCAGAGCACTTTAAAAACAGGGC
AGCCTGCTTGGGCCCTCGGTCTCCACCCCAGGGTCATAAGTGGGGAGAGAGCCCTTCCCAGGGCACCCAGGCAGGTGCAGGGAAGT
GCAGAGCTTGTGGAAAGCGTGTGAGTGAGGGAGACAGGAACGGCTCTGGGGGTGGGAAGTGGGGCTAGGTCTTGCCAACTCCATCT
TCAATAAAGTCGTTTTCGGATCCCTAAAAAAAAAAAAAAAAAAAAAAAAAA e) CACACATGGGGCCTCCCAGGAGTGCCCAGGACCCTCGTGCTGTTGGCCTCTGAATCTATCGTCTCCAATCCGCTGTCCCACAGAAGC
CATATAACCCACCTCTCTGTAAATGCCAGGAGCCATGGGGGAAACAGCGCTACACATAGCAGCCCTCTATGACAACCTGGAGGCCG
CCATGGTGCTGATGGAGGCTGCCCCGGAGCTGGTCTTTGAGCCCATGACATCTGAGCTCTATGGAGGGTGAGGGCCCACGGGTCTG
GGGTGAAGAGCAGGAGTGACGTGGTTGGGTATTCAAGTCAGTCTCTGTGATGGATAATTTGGGAAAGACACAGGGGATCTGAGCCT
CCTACTCTTTTTSTCTTCTCTGTCTCCCTTCCGTGTCAGTCCCTGACTGCCCATCACTTGAACGCCTGCCCCCTGAAATGCCAGGG
GCCTAGAGAAGAGGAAGAGATGGGCAGCAGCTGGATCCCCTGGGAATCCTGAACACCCGAGAGCTCCCTGTTCTCCATCCCAGGCT
ACCCCTGAGGGAAAGAGACTAGGGGTGCATATGGGAGGGACCCCCTGCAGGATCCTAGGGGACAGACCCGTGACTGACAGCTGTCT
CTGGGCCAGGTCAGACTGCACTGCACATCGCTGTTGTGAACCAGAACATGAACCTGGTGCTGAGCCCTGCTTGCCCGCAGGGCCAGT
GTCTCTGCCAGAGCCACAGGCACTGCCTTCCGCCGTAGTCCCTGCAACCTCATCTACTTTGGGGAGCACCCTTTGTCCTTTGCTGC
CTGTGTGAACAGTGAGGAGATCGTGCGGCTGCTCATTGAGCATGGAGCTGACATCCGGGCCCAGGACTCCCTGGATGTACAACCTG
TTGCTGTCCTACGACAGACATGGGGACCACCTGCAGCCCCTGGACCTCGTGCCCAATCACCAGGGTCTCACCCCTTTCAAGCTGGC
TGGAGTGGAGGGTAACACTGTGATGTTTCAGCACCTGATGCAGAAGCGGAAGCACACCCAGTGGACGTATGGACCACTGACCTCGA
CTCTCTATGACCTCACAGAGATCGACTCCTCAGGGGATGAGCAGTCCCTGCTGGAACTTATCATCACCACCAAGAAGCGGGAGGCT
CGCCAGATCCTGGACCAGACGCCGGTGAAGGAGCTGGTGAGCCTCAAGTGGAAGCGGTACGGGCGGCCGTACTTCTGCATGCTGGG
TGCCATATATCTGCTGTACATCATCTGCTTCACCATGTGCTGCATCTACCGCCCCCTCAAGCCCAGGACCAATAACCGCACGAGCC
CCCGGGACAACACCCTCTTACAGCAGAAGCTACTTCAGGAAGCCTACATGACCCCTAAGGACGATATCCGGCTGGTCGGGGAGCTG
GTGACTGTCATTGGGGCTATCATCATCCTGCTGGTAGAGGTTCCAGACATCTTCAGAATGGGGGTCACTCGCTTCTTTGGACAGAC
CATCCTTGGGGGCCCATTCCATGTCCTTTGCACTCGTGCTGGGCTGGTGCAACGTCATGTACTTCGCCCGAGGATTCCAGATGCTAGGC
CCCTTCACCATCATGATTCAGAAGATGATTTTTGGCGACCTGATGCGATTCTGCTGGCTGATGGCTGTGGTCATCCTGGGCTTTGC
TTCAGCCTTCTATATCATCTTCCAGACAGAGGACCCCGAGGAGCTAGGCCACTTCTACGACTACCCCATGGCCCTGTTCAGCACCT
TCGAGCTGGTCCTTACCATCATCGATGGCCCAGCCAACTACAACGTGGACCTGCCCTTCATGTACAGCATCACCTATGCTGCCTTT
GCCATCATCGCCACACTGCTCATGCTCAACCTCCTCATTGCCATGATGGGCGACACTCACTGGCGAGTGGCCCATGAGCGGGATGA
GCTGTGGAGGGCCCAGATTGTGGCCACCACGGTGATGCTGGAGCGGAAGCTGCCTCGCTGCCTGTGGCCTCGCTCCGGGATCTGCG
GACGGGAGTATGGCCTGGGAGACCGCTGGTTCCTGCGGGTGGAAGACAGGCAAGATCTCAACCGGCAGCGGATCCAACGCTACGCA
CAGGCCTTCCACACCCGGGGCTCTGAGGATTTGGACAAAGACTCAGTGGAAAAACTAGAGCTGGGCTGTCCCTTCAGCCCCCACCT
GTCCCTTCCTATGCCCTCAGTGTCTCGAAGTACCTCCCGCAGCAGTGCCAATTGGGAAAGGCTTCGGCAAGGGACCCTGAGGAGAG
ACCTGCGTGGGATAATCAACAGGGGTCTGGAGGACGGGGAGAGCTGGGAATATCAGATCTGACTGCGTGTTCTCACTTCGCTTCCT
GGAACTTGCTCTCATTTTCCTGGGTGCATCAAACAAAACAAAAACAAAACACCCAGAGGTCTCATCTCCCAGGCCCCAGGGAGAAA
GAGGAGTAGCATGAACGCCAAGGAATGTACGTTGAGAATCACTGCTCCAGGCCTGCATTACTCCTTCAGCTCTGGGGCAGAGGAAG
CCCAGCCCAAGCACGGGGCTGGCAGGGCGTGAGGAACTCTCCTGTGGCCTGCTCATCACCCTTCCGACAGGAGCACTGCATGTCAG
AGCACTTTAAAAACAGGGCCAGCCTGCTTGGGCCCTCGGTCTCCACCCCAGGGTCATAAGTGGGGAGAGAGCCCTTCCCAGGGCACC

FIGURE 8

CAGGCAGGTGCAGGGAAGTGCAGAGCTTGTGGAAAGCGTGTGAGTGAGGGAGACAGGAACGGCTCTGGGGGTGGGAAGTGGGGCTA
GGTCTTGCCAACTCCATCTTCAATAAAGTCGTTTTCGGATCCCTAAAAAAAAAAAAAAAAAAAAAAAAAAA

FIGURE 9

A.
```
            10                  30                  50
CGGGGCCCTGGGCTGCAGGAGGTTGCGGCGGCCGCGGCAGCATGGTGGTGCCGGAGAAGG
                                         M  V  V  P  E  K  E
            70                  90                 110
AGCAGAGCTGGATCCCCAAGATCTTCAAGAAGAAGACCTGCACGACGTTCATAGTTGACT
 Q  S  W  I  P  K  I  F  K  K  K  T  C  T  T  F  I  V  D  S
           130                 150                 170
CCACAGATCCGGGAGGGACCTTGTGCCAGTGTGGGCGCCCCCGGACCGCCCACCCCGCAG
 T  D  P  G  G  T  L  C  Q  C  G  R  P  R  T  A  H  P  A  V
           190                 210                 230
TGGCCATGGAGGATGCCTTCGGGGCAGCCGTGGTGACCGTGTGGGACAGCGATGCACACA
 A  M  E  D  A  F  G  A  A  V  V  T  V  W  D  S  D  A  H  T
           250                 270                 290
CCACGGAGAAGCCCACCGATGCCTACGGAGAGCTGGACTTCACGGGGGCCGGCCGCAAGC
 T  E  K  P  T  D  A  Y  G  E  L  D  F  T  G  A  G  R  K  B
           310                 330                 350
ACAGCAATTTCCTCCGGCTCTCTGACCGAACGGATCCAGCTGCAGTTTATAGTCTGGTCA
 S  N  F  L  R  L  S  D  R  T  D  P  A  A  V  Y  S  L  V  T
           370                 390                 410
CACGCACATGGGGCTTCCGTGCCCCGAACCTGGTGGTGTCAGTGCTGGGGGGATCGGGGG
 R  T  W  G  F  R  A  P  N  L  V  V  S  V  L  G  G  S  G  G
           430                 450                 470
GCCCCGTCCTCCAGACCTGGCTGCAGGACCTGCTGCGTCGTGGGCTGGTGCGGGCTGCCC
 P  V  L  Q  T  W  L  Q  D  L  L  R  R  G  L  V  R  A  A  Q
           490                 510                 530
AGAGCACAGGAGCCTGGATTGTCACTGGGGGTCTGCACACGGGCATCGGCCGGCATGTTG
 S  T  G  A  W  I  V  T  G  G  L  H  T  G  I  G  R  H  V  G
           550                 570                 590
GTGTGGCTGTACGGGACCATCAGATGGCCAGCACTGGGGGCACCAAGGTGGTGGCCATGG
 V  A  V  R  D  H  Q  M  A  S  T  G  G  T  K  V  V  A  M  G
           610                 630                 650
GTGTGGCCCCCTGGGGTGTGGTCCGGAATAGAGACACCCTCATCAACCCCAAGGGCTCGT
 V  A  P  W  G  V  V  R  N  R  D  T  L  I  N  P  K  G  S  F
           670                 690                 710
TCCCTGCGAGGTACCGGTGGCGCGGTGACCCGGAGGACGGGGTCCAGTTTCCCCTGGACT
 P  A  R  Y  R  W  G  D  P  E  D  G  V  Q  F  P  L  D  Y
           730                 750                 770
ACAACTACTCGGCCTTCTTCCTGGTGGACGACGGCACACACGGCTGCCTGGGGGGCGAGA
 N  Y  S  A  F  F  L  V  D  D  G  T  H  G  C  L  G  G  E  N
           790                 810                 830
ACCGCTTCCGCTTGCGCCTGGAGTCCTACATCTCACAGCAGAAGACGGGCGTGGGAGGGA
 R  F  R  L  R  L  E  S  Y  I  S  Q  Q  K  T  G  V  G  G  T
           850                 870                 890
CTGGAATTGACATCCCTGTCCTGCTCCTCCTGATTGATGGTGATGAGAAGATGTTGACGC
 G  I  D  I  P  V  L  L  L  I  D  G  D  E  K  M  L  T  R
           910                 930                 950
GAATAGAGAACGCCACCCAGGCTCAGCTCCCATGTCTCCTCGTGGCTGGCTCAGGGGGAG
 I  E  N  A  T  Q  A  Q  L  P  C  L  L  V  A  G  S  G  G
           970                 990                1010
CTGCGGACTGCCTGGCGGAGACCCTGGAAGACACTCTGGCCCCAGGGAGTGGGGGAGCCA
 A  D  C  L  A  E  T  L  E  D  T  L  A  P  G  S  G  G  A  R
          1030                1050                1070
GGCAAGGCGAAGCCCGAGATCGAATCAGGCGTTTCTTTCCCAAAGGGGACCTTGAGGTCC
```

FIGURE 9

```
       Q  G  E  A  R  D  R  I  R  R  F  P  K  G  D  L  E  V  L
          1090              1110              1130
TGCAGGCCCAGGTGGAGAGGATTATGACCCGGAAGGAGCTCCTGACAGTCTATTCTTCTG
       Q  A  Q  V  E  R  I  M  T  R  K  E  L  L  T  V  Y  S  S  E
          1150              1170              1190
AGGATGGGTCTGAGGAATTCGAGACCATAGTTTTGAAGGCCCTTGTGAAGGCCTGTGGGA
       D  G  S  E  E  F  E  T  I  V  L  K  A  L  V  K  A  C  G  S
          1210              1230              1250
GCTCGGAGGCCTCAGCCTACCTGGATGAGCTGCGTTTGGCTGTGGCTTGGAACCGCGTGG
       S  E  A  S  A  Y  L  D  E  L  R  L  A  V  A  W  N  R  V  D
          1270              1290              1310
ACATTGCCCAGAGTGAACTCTTTCGGGGGGACATCCAATGGCGGTCCTTCCATCTCGAAG
       I  A  Q  S  E  L  F  R  G  D  I  Q  W  R  S  F  H  L  E  A
          1330              1350              1370
CTTCCCTCATGGACGCCCTGCTGAATGACCGGCCTGAGTTCGTGCGCTTGCTCATTTCCC
       S  L  M  D  A  L  L  N  D  R  P  E  F  V  R  L  L  I  S  H
          1390              1410              1430
ACGGCCTCAGCCTGGGCCACTTCCTGACCCCGATGCGCCTGGCCCAACTCTACAGCGCGG
       G  L  S  L  G  H  F  L  T  P  N  R  L  A  Q  L  Y  S  A  A
          1450              1470              1490
CGCCCTCCAACTCGCTCATCCGCAACCTTTTGGACCAGGCGTCCCACAGCGCAGGCACCA
       P  S  N  S  L  I  R  N  L  L  D  Q  A  S  H  S  A  G  T  K
          1510              1530              1550
AAGCCCCAGCCCTAAAAGGGGGAGCTGCGGAGCTCCGGCCCCCTGACGTGGGGCATGTGC
       A  P  A  L  K  G  G  A  A  E  L  R  P  P  D  V  G  H  V  L
          1570              1590              1610
TGAGGATGCTGCTGGGGAAGATGTGCGCGCCGAGGTACCCCTCCGGGGGCGCCTGGGACC
       R  M  L  L  G  K  M  C  A  P  R  Y  P  S  G  G  A  W  D  P
          1630              1650              1670
CTCACCCAGGCCAGGGCTTCGGGGAGAGCATGTATCTGCTCTCGGACAAGGCCACCTCGC
       H  P  G  Q  G  F  G  E  S  M  Y  L  L  S  D  K  A  T  S  P
          1690              1710              1730
CGCTCTCGCTGGATGCTGGCCTCGGGCAGGCCCCCTGGAGCGACCTGCTTCTTTGGGCAC
       L  S  L  D  A  G  L  G  Q  A  P  W  S  D  L  L  W  A  L
          1750              1770              1790
TGTTGCTGAACAGGGCACAGATGGCCATGTACTTCTGGGAGATGGGTTCCAATGCAGTTT
       L  L  N  R  A  Q  M  A  M  Y  F  W  E  M  G  S  N  A  V  S
          1810              1830              1850
CCTCAGCTCTTGGGGCCTGTTTGCTGCTCCGGGTGATGGCACGCCTGGAGCCTGACGCTG
       S  A  L  G  A  C  L  L  L  R  V  M  A  R  L  P  D  A  E
          1870              1890              1910
AGGAGGCAGCACGGAGGAAAGACCTGGCGTTCAAGTTTGAGGGGATGGGCGTTGACCTCT
       E  A  A  R  R  K  D  L  A  F  K  F  E  G  M  G  V  D  L  F
          1930              1950              1970
TTGGCGAGTGCTATCGCAGCAGTGAGGTGAGGGCTGCCCGCCTCCTCCTCCGTCGCTGCC
       G  E  C  Y  R  S  S  E  V  R  A  A  R  L  L  L  R  R  C  P
          1990              2010              2030
CGCTCTGGGGGGATGCCACTTGCCTCCAGCTGGCCATGCAAGCTGACGCCCGTGCCTTCT
       L  W  G  D  A  T  C  L  Q  L  A  M  Q  A  D  A  R  A  F  F
          2050              2070              2090
TTGCCCAGGATGGGGTACAGTCTCTGCTGACACAGAAGTGGTGGGGAGATATGGCCAGCA
       A  Q  D  G  V  Q  S  L  L  T  Q  K  W  W  G  D  M  A  S  T
          2110              2130              2150
CTACACCCATCTGGGCCCTGGTTCTCGCCTTCTTTTGCCCTCCACTCATCTACACCCGCC
       T  P  I  W  A  L  V  L  A  F  F  C  P  P  L  I  Y  T  R  L
          2170              2190              2210
TCATCACCTTCAGGAAATCAGAAGAGGAGCCCACACGGGAGGAGCTAGAGTTTGACATGG
       I  T  F  R  K  S  E  E  E  P  T  R  E  E  L  E  F  D  M  D
          2230              2250              2270
ATAGTGTCATTAATGGGGAAGGGCCTGTCGGGACGGCGGACCCAGCCGAGAAGACGCCGC
       S  V  I  N  G  E  G  P  V  G  T  A  D  P  A  E  K  T  P  L
          2290              2310              2330
```

FIGURE 9

```
TGGGGGTCCCGCGCCAGTCGGGCCGTCCGGGTTGCTGCGGGGGCCGCTGCGGGGGCGCC
  G  V  P  R  Q  S  G  R  P  G  C  C  G  G  R  C  G  G  R  R
        2350           2370           2390
GGTGCCTACGCCGCTGGTTCCACTTCTGGGGCGTGCCGGTGACCATCTTCATGGGCAACG
  C  L  R  R  W  F  H  F  W  G  V  P  V  T  I  F  M  G  N  V
        2410           2430           2450
TGGTCAGCTACCTGCTGTTCCTGCTGCTTTTCTCGCGGGTGCTGCTCGTGGATTTCCAGC
  V  S  Y  L  L  F  L  L  L  F  S  R  V  L  L  V  D  F  Q  P
        2470           2490           2510
CGGCGCCGCCCGGCTCCCTGGAGCTGCTGCTCTATTTCTGGGCTTTCACGCTGCTGTGCG
  A  P  P  G  S  L  E  L  L  L  Y  F  W  A  F  T  L  L  C  E
        2530           2550           2570
AGGAACTGCGCCAGGGCCTGAGCGGAGGCGGGGGCAGCCTCGCCAGCGGGGGCCCCGGGC
  E  L  R  Q  G  L  S  G  G  G  G  S  L  A  S  G  G  P  G  P
        2590           2610           2630
CTGGCCATGCCTCACTGAGCCAGCGCCTGCGCCTCTACCTCGCCGACAGCTGGAACCAGT
  G  H  A  S  L  S  Q  R  L  R  L  Y  L  A  D  S  W  N  Q  C
        2650           2670           2690
GCGACCTAGTGGCTCTCACCTGCTTCCTCCTGGGCGTGGGCTGCCGGCTGACCCCGGGTT
  D  L  V  A  L  T  C  F  L  L  G  V  G  C  R  L  T  P  G  L
        2710           2730           2750
TGTACCACCTGGGCCGCACTGTCCTCTGCATCGACTTCATGGTTTTCACGGTGCGGCTGC
  Y  H  L  G  R  T  V  L  C  I  D  F  M  V  F  T  V  R  L  L
        2770           2790           2810
TTCACATCTTCACGGTCAACAAACAGCTGGGGCCCAAGATCGTCATCGTGAGCAAGATGA
  H  I  F  T  V  N  K  Q  L  G  P  K  I  V  I  V  S  K  M  M
        2830           2850           2870
TGAAGGACGTGTTCTTCTTCCTCTTCTTCCTCGGCGTGTGGCTGGTAGCCTATGGCGTGG
  K  D  V  F  F  L  F  F  L  G  V  W  L  V  A  Y  G  V  A
        2890           2910           2930
CCACGGAGGGGCTCCTGAGGCCACGGGACAGTGACTTCCCAAGTATCCTGCGCCGCGTCT
  T  E  G  L  L  R  P  R  D  S  D  F  P  S  I  L  R  R  V  F
        2950           2970           2990
TCTACCGTCCCTACCTGCAGATCTTCGGGCAGATTCCCCAGGAGGACATGGACGTGGCCC
  Y  R  P  Y  L  Q  I  F  G  Q  I  P  Q  E  D  M  D  V  A  L
        3010           3030           3050
TCATGGAGCACAGCAACTGCTCGTCGGAGCCCGGCTTCTGGGCACACCCTCCTGGGGCCC
  M  E  H  S  N  C  S  S  E  P  G  F  W  A  H  P  P  G  A  Q
        3070           3090           3110
AGGCGGGCACCTGCGTCTCCCAGTATGCCAACTGCTGGTGGTGCTGCTCCTCCTCATCT
  A  G  T  C  V  S  Q  Y  A  N  W  L  V  V  L  L  L  V  I  F
        3130           3150           3170
TCCTGCTCGTGGCCAACATCCTGCTGGTCAACTTGCTCATTGCCATGTTCAGTTACACAT
  L  L  V  A  N  I  L  L  V  N  L  L  I  A  M  F  S  Y  T  F
        3190           3210           3230
TCGGCAAAGTACAGGGCAACAGCGATCTCTACTGGAAGGCGCAGCGTTACCGCCTCATCC
  G  K  V  Q  G  N  S  D  L  Y  W  K  A  Q  R  Y  R  L  I  R
        3250           3270           3290
GGGAATTCCACTCTCGGCCCGCGCTGGCCCCGCCCTTTATCGTCATCTCCCACTTGCGCC
  E  F  H  S  R  P  A  L  A  P  P  F  I  V  I  S  H  L  R  L
        3310           3330           3350
TCCTGCTCAGGCAATTGTGCAGGCGACCCCGGAGCCCCCAGCCGTCCTCCCCGGCCCTCG
  L  L  R  Q  L  C  R  R  P  R  S  P  Q  P  S  S  P  A  L  E
        3370           3390           3410
AGCATTTCCGGGTTTACCTTTCTAAGGAAGCCGAGCGGAAGCTGCTAACGTGGGAATCGG
  H  F  R  V  Y  L  S  K  E  A  E  R  K  L  L  T  W  E  S  V
        3430           3450           3470
TGCATAAGGAGAACTTTCTGCTGGCACGCGCTAGGGACAAGCGGGAGAGCGACTCCGAGC
  H  K  E  N  F  L  L  A  R  A  R  D  K  R  E  S  D  S  E  R
        3490           3510           3530
GTCTGAAGCGCACGTCCCAGAAGGTGGACTTGGCACTGAAACAGCTGGGACACATCCGCG
  L  K  R  T  S  Q  K  V  D  L  A  L  K  Q  L  G  H  I  R  E
```

FIGURE 9

```
         3550                3570                3590
AGTACGAACAGCGCCTGAAAGTGCTGGAGCGGGAGGTCCAGCAGTGTAGCCGCGTCCTGG
  Y  E  Q  R  L  K  V  L  E  R  E  V  Q  Q  C  S  R  V  L  G
         3610                3630                3650
GGTGGGTGGCCGAGGCCCTGAGCCGCTCTGCCTTGCTGCCCCCAGGTGGGCCGCCACCCC
  W  V  A  E  A  L  S  R  S  A  L  L  P  P  G  G  P  P  P  P
         3670                3690                3710
CTGACCTGCCTGGGTCCAAAGACTGAGCCCTGCTGGCGGACTTCAAGGAGAAGCCCCCAC
  D  L  P  G  S  K  D  *
         3730                3750                3770
AGGGGATTTTGCTCCTAGAGTAAGGCTCATCTGGGCCTCGGCCCCCGCACCTGGTGGCCT
         3790                3810                3830
TGTCCTTGAGGTGAGCCCCATGTCCATCTGGGCCACTGTCAGGACCACCTTTGGGAGTGT
         3850                3870                3890
CATCCTTACAAACCACAGCATGCCCGGCTCCTCCCAGAACCAGTCCCAGCCTGGGAGGAT
         3910                3930                3950
CAAGGCCTGGATCCCGGGCCGTTATCCATCTGGAGGCTGCAGGGTCCTTGGGGTAACAGG
         3970                3990                4010
GACCACAGACCCCTCACCACTCACAGATTCCTCACACTGGGGAAATAAAGCCATTTCAGA
         4030
GGAAAAAAAAAAAAAAAAAAAA
```

```
MVVPEKEQSWIPKIFKKKTCTTFIVDSTDPGGTLCQCGRFRTAHPAVAMEDAFGAAVVTVWDSDAHTTEKPTDAYELDFTGAG
SNFLRLSDRTDPAAVYSLVTRTWGFRAPNLVVSVLGGSGGPVLQTWLQDLLRRGLVRAAQSTGAWIVTGGLHTGIGRHVGVAV
QMASTGGTKVVAMGVAPWGVVRNRDTLINPKGSFPARYRWRGDPEDGVQFPLDYNYSAFELVDDGTHGCLGGENRFRLRLESY
QKTGVGGTGIDIPVLLLLIDGDEKMLTRIENATQAEVPCLLVAGSRGLGMPGGTLEAHLAQDGDHKANQSTNQLLLPKDLSLC
SIDRKTLQSYSERLAVAWNRVDIAQSELFRGDIQWRSFHLEASLMDALLNDRPEFVRLLISHGLSLGHFLTPMRLAQLYSAAE
LIRNLLDQASHSAGTKAPALKGGAAELRPPDVGHVLRMLLGKMCAPRYPSGGAWDPHPGQGFGESMYLLSDKATSPLSLDAGI
PWSDLLLWALLLNRAQMAMYFWEMGSNAVSSALGACLLLRVMARLEPDAEEAARRKDLAFKFEGMGVDLFGECYRSSEVRAAF
RRCPLWGDATCLQLAMQADARAFFAQDGVQSLLTQKWWGDMASTTPIWALVLAFFCPPLIYTRLITFRKSEEEPTREELEFDM
INGEGPVGTADPAEKTPLGVPRQSGRPGCCGRCGGRRCLRRWFHFWGVPVTIFMGNVVSYLLFLLLFSRVLLVDFQPAPPGS
LLYFWAFTLLCEELRQGLSGGGGSLASGGPGPGHASLSQRLRLYLADSWNQCDLVALTCFLLGVGCRLTPGLYHLGRTVLCIC
FTVRLLHIFTVNKQLGPKIVIVSKMMKDVFFFLFFLGVWLVAYGVATEGLLRPRDSDFPSILRRVFYRPYLQIFGQIPQEDMC
MEHSNCSSEPGFWAHPPGAQAGTCVSQYANWLVVLLLVIFLLVANILLVNLLIAMFSYTFGKVQGNSDLYWKAQRYRLIREFF
ALAPPFIVISHLRLLLRQLCRRPRSPQPSSPALEHFRVYLSKEAERKLLTWESVHKENFLLARARDKRESDSERLKRTSQKVE
KQLGHIREYEQRLKVLEREVQQCSRVLGWVAEALSRSALLPPGGPPPPDLPGSKD
```

B.
```
              10                30                50
    ATCCAATGGCGGTCCTTCCATCTCGAAGCTTCCCTCATGGACGCCCTGCTGAATGACCGG
              70                90               110
    CCTGAGTTCGTGCGCTTGCTCATTTCCCACGGCCTCAGCCTGGGCCACTTCCTGACCCCG
             130               150               170
    ATGCGCCTGGCCCAACTCTACAGCGCGGCGCCCTCCAACTCGCTCATCCGCAACCTTTTG
             190               210               230
    GACCAGGCGTCCCACAGCGCAGGCACCAAAGCCCCAGCCCTAAAAGGGGGAGCTGCGGAG
             250               270               290
    CTCCGGCCCCCTGACGTGGGGCATGTGCTGAGGATGCTGCTGGGGAAGATGTGCGCGCCG
             310               330               350
    AGATGTATCTGCTCTCGGACAAGGCCACCTCGCCGCTCTCGCTGGATGCTGGCCTCGGGC
                 M  Y  L  L  S  D  K  A  T  S  P  L  S  L  D  A  G  L  G  Q
             370               390               410
    AGGCCCCCTGGAGCGACCTGCTTCTTTGGGCACTGTTGCTGAACAGGGCACAGATGGCCA
      A  P  W  S  D  L  L  L  W  A  L  L  L  N  R  A  Q  M  A  M
             430               450               470
    TGTACTTCTGGGAGATGGGTTCCAATGCAGTTTCCTCAGCTCTTGGGGCCTGTTTGCTGC
      Y  F  W  E  M  G  S  N  A  V  S  S  A  L  G  A  C  L  L  L
```

FIGURE 9

```
              490               510               530
      TCCGGGTGATGGCACGCCTGGAGCCTGACGCTGAGGAGGCAGCACGGAGGAAAGACCTGG
        R  V  M  A  R  L  E  P  D  A  E  E  A  A  R  R  K  D  L  A
              550               570               590
      CGTTCAAGTTTGAGGGGATGGGCGTTGACCTCTTTGGCGAGTGCTATCGCAGCAGTGAGG
        F  K  F  E  G  M  G  V  D  L  F  G  E  C  Y  R  S  S  E  V
              610               630               650
      TGAGGGCTGCCCGCCTCCTCCTCCGTCGCTGCCCGCTCTGGGGGGATGCCACTTGCCTCC
        R  A  A  R  L  L  L  R  R  C  P  L  W  G  D  A  T  C  L  Q
              670               690               710
      AGCTGGCCATGCAAGCTGACGCCCGTGCCTTCTTTGCCCAGGATGGGGTACAGTCTCTGC
        L  A  M  Q  A  D  A  R  A  F  F  A  Q  D  G  V  Q  S  L  L
              730               750               770
      TGACACAGAAGTGGTGGGGAGATATGGCCAGCACTACACCCATCTGGGCCCTGGTTCTCG
        T  Q  K  W  W  G  D  M  A  S  T  T  P  I  W  A  L  V  L  A
              790               810               830
      CCTTCTTTTGCCCTCCACTCATCTACACCCGCCTCATCACCTTCAGGAAATCAGAAGAGG
        F  F  C  P  P  L  I  Y  T  R  L  I  T  F  R  K  S  E  E  E
              850               870               890
      AGCCCACACGGGAGGAGCTAGAGTTTGACATGGATAGTGTCATTAATGGGGAAGGGCCTG
        P  T  R  E  E  L  E  F  D  M  D  S  V  I  N  G  E  G  P  V
              910               930               950
      TCGGGACGGCGGACCCAGCCGAGAAGACGCCGCTGGGGGTCCCGCGCCAGTCGGGCCGTC
        G  T  A  D  P  A  E  K  T  P  L  G  V  P  R  Q  S  G  R  P
              970               990              1010
      CGGGTTGCTGCGGGGGCCGCTGCGGGGGGCGCCGGTGCCTACGCCGCTGGTTCCACTTCT
        G  C  C  G  G  R  C  G  G  R  R  C  L  R  R  W  F  H  F  W
             1030              1050              1070
      GGGGCGTGCCGGTGACCATCTTCATGGGCAACGTGGTCAGCTACCTGCTGTTCCTGCTGC
        G  V  P  V  T  I  F  M  G  N  V  V  S  Y  L  L  F  L  L  L
             1090              1110              1130
      TTTTCTCGCGGGTGCTGCTCGTGGATTTCCAGCCGGCGCCGCCCGGCTCCCTGGAGCTGC
        F  S  R  V  L  L  V  D  F  Q  P  A  P  P  G  S  L  E  L  L
             1150              1170              1190
      TGCTCTATTTCTGGGCTTTCACGCTGCTGTGCGAGGAACTGCGCCAGGGCCTGAGCGGAG
        L  Y  F  W  A  F  T  L  L  C  E  E  L  R  Q  G  L  S  G  G
             1210              1230              1250
      GCGGGGGCAGCCTCGCCAGCGGGGGCCCCGGGCCTGGCCATGCCTCACTGAGCCAGCGCC
        G  G  S  L  A  S  G  G  P  G  P  G  H  A  S  L  S  Q  R  L
             1270              1290              1310
      TGCGCCTCTACCTCGCCGACAGCTGGAACCAGTGCGACCTAGTGGCTCTCACCTGCTTCC
        R  L  Y  L  A  D  S  W  N  Q  C  D  L  V  A  L  T  C  F  L
             1330              1350              1370
      TCCTGGGCGTGGGCTGCCGGCTGACCCCGGGTTTGTACCACCTGGGCCGCACTGTCCTCT
        L  G  V  G  C  R  L  T  P  G  L  Y  H  L  G  R  T  V  L  C
             1390              1410              1430
      GCATCGACTTCATGGTTTTCACGGTGCGGCTGCTTCACATCTTCACGGTCAACAAACAGC
        I  D  F  M  V  F  T  V  R  L  L  H  I  F  T  V  N  K  Q  L
             1450              1470              1490
      TGGGGCCCAAGATCGTCATCGTGAGCAAGATGATGAAGGACGTGTTCTTCTTCCTCTTCT
        G  P  K  I  V  I  V  S  K  M  M  K  D  V  F  F  L  F  F
             1510              1530              1550
      TCCTCGGCGTGTGGCTGGTAGCCTATGGCGTGGCCACGGAGGGGCTCCTGAGGCCACGGG
        L  G  V  W  L  V  A  Y  G  V  A  T  E  G  L  L  R  P  R  D
             1570              1590              1610
      ACAGTGACTTCCCAAGTATCCTGCGCCGCGTCTTCTACCGTCCCTACCTGCAGATCTTCG
        S  D  F  P  S  I  L  R  R  V  F  Y  R  P  Y  L  Q  I  F  G
             1630              1650              1670
      GGCAGATTCCCCAGGAGGACATGGACGTGGCCCTCATGGAGCACAGCAACTGCTCGTCGG
        Q  I  P  Q  E  D  M  D  V  A  L  M  E  H  S  N  C  S  S  E
             1690              1710              1730
      AGCCCGGCTTCTGGGCACACCCTCCTGGGGCCCAGGCGGGCACCTGCGTCTCCCAGTATG
```

FIGURE 9

```
      P  G  F  W  A  H  P  P  G  A  Q  A  G  T  C  V  S  Q  Y  A
         1750              1770              1790
CCAACTGGCTGGTGGTGCTGCTCCTCGTCATCTTCCTGCTCGTGGCCAACATCCTGCTGG
      N  W  L  V  V  L  L  L  V  I  F  L  L  V  A  N  I  L  L  V
         1810              1830              1850
TCAACTTGCTCATTGCCATGTTCAGTTACACATTCGGCAAAGTACAGGGCAACAGCGATC
      N  L  L  I  A  M  F  S  Y  T  F  G  K  V  Q  G  N  S  D  L
         1870              1890              1910
TCTACTGGAAGGCGCAGCGTTACCGCCTCATCCGGGAATTCCACTCTCGGCCCGCGCTGG
      Y  W  K  A  Q  R  Y  R  L  I  R  E  F  H  S  R  P  A  L  A
         1930              1950              1970
CCCCGCCCTTTATCGTCATCTCCCACTTGCGCCTCCTGCTCAGGCAATTGTGCAGGCGAC
      P  P  F  I  V  I  S  H  L  R  L  L  L  R  Q  L  C  R  R  P
         1990              2010              2030
CCCGGAGCCCCCAGCCGTCCTCCCCGGCCCTCGAGCATTTCCGGGTTTACCTTTCTAAGG
      R  S  P  Q  P  S  S  P  A  L  E  H  F  R  V  Y  L  S  K  E
         2050              2070              2090
AAGCCGAGCGGAAGCTGCTAACGTGGGAATCGGTGCATAAGGAGAACTTTCTGCTGGCAC
      A  E  R  K  L  L  T  W  E  S  V  H  K  E  N  F  L  L  A  R
         2110              2130              2150
GCGCTAGGGACAAGCGGGAGAGCGACTCCGAGCGTCTGAAGCGCACGTCCCAGAAGGTGG
      A  R  D  K  R  E  S  D  S  E  R  L  K  R  T  S  Q  K  V  D
         2170              2190              2210
ACTTGGCACTGAAACAGCTGGGACACATCCGCGAGTACGAACAGCGCCTGAAAGTGCTGG
      L  A  L  K  Q  L  G  H  I  R  E  Y  E  Q  R  L  K  V  L  E
         2230              2250              2270
AGCGGGAGGTCCAGCAGTGTAGCCGCGTCCTGGGGTGGGTGGCCGAGGCCCTGAGCCGCT
      R  E  V  Q  Q  C  S  R  V  L  G  W  V  A  E  A  L  S  R  S
         2290              2310              2330
CTGCCTTGCTGCCCCCAGGTGGGCCGCCACCCCCTGACCTGCCTGGGTCCAAAGACTGAG
      A  L  L  P  P  G  G  P  P  P  P  D  L  P  G  S  K  D  *
         2350              2370              2390
CCCTGCTGGCGGACTTCAAGGAGAAGCCCCCACAGGGGATTTTGCTCCTAGAGTAAGGCT
         2410              2430              2450
CATCTGGGCCTCGGCCCCCGCACCTGGTGGCCTTGTCCTTGAGGTGAGCCCCATGTCCAT
         2470              2490              2510
CTGGGCCACTGTCAGGACCACCTTTGGGAGTGTCATCCTTACAAACCACAGCATGCCCGG
         2530              2550              2570
CTCCTCCCAGAACCAGTCCCAGCCTGGGAGGATCAAGGCCTGGATCCCGGGCCGTTATCC
         2590              2610              2630
ATCTGGAGGCTGCAGGGTCCTTGGGGTAACAGGGACCACAGACCCCTCACCACTCACAGA
         2650              2670              2690
TTCCTCACACTGGGGAAATAAAGCCATTTCAGAGGAAAAAAAAAAAAAAAAAAAA
```

MYLLSDKATSPLSLDAGLGQAPWSDLLLWALLLNRAQMAMYFWEMGSNAVSSALGACLLLRVMARLEPDAEEAARREDLAFKFEGM
GVDLFGECYRSSEVRAARLLLRRCPLWGDATCLQLAMQADARAFFAQDGVQSLLTQKWWGDMASTTPIWALVLAFFCPPLIYTRLI
TFRKSEEEPTREELEFDMDSVINGEGPVGTADPAEKTPLGVPRQSGRPGCCGGRCGGRRCLRRWFHFWGVPVTIFMGNVVSYLLFL
LLFSRVLLVDFQPAPPGSLELLLYFWAFTLLCEELRQGLSGGGGSLASGGPGPGHASLSQRLRLYLADSWNQCDLVALTCFLLGVG
CRLTPGLYHLGRTVLCIDFMVFTVRLLHIFTVNKQLGPKIVIVSKMMKDVFFFLFFLGVWLVAYGVATEGLLRPRDSDFPSILRRV
FYRPYLQIFGQIPQEDMDVALMEHSNCSSEPGFWAHPPGAQAGTCVSQYANWLVVLLLVIFLLVANILLVNLLIAMFSYTFGKVQG
NSDLYWKAQRYRLIREFHSRPALAPPFIVISHLRLLLRQLCRRPRSPQPSSPALEHFRVYLSKEAERKLLTWESVHKENFLLARAR
DKRESDSERLKRTSQKVDLALKQLGHIREYEQRLKVLEREVQQCSRVLGWVAEALSRSALLPPGGPPPPDLPGSKD

FIGURE 10 a)
```
             10                  30                  50
   ATTAAAGTTTATAAACAGTGGCTGGATGGTTGGAGGATGCAGGTGGACAGAAGACGTGG
                                 M  V  G  G  C  R  W  T  E  D  V  E
             70                  90                 110
   AGCCTGCAGAAGTAAAGGAAAAGATGTCCTTTCGGGCAGCCAGGCTCAGCATGAGGAACA
    P  A  E  V  K  E  K  M  S  F  R  A  A  R  L  S  M  R  N  R
            130                 150                 170
   GAAGGAATGACACTCTGGACAGCACCCGGACCCTGTACTCCAGCGCGTCTCGGAGCACAG
    R  N  D  T  L  D  S  T  R  T  L  Y  S  S  A  S  R  S  T  D
            190                 210                 230
   ACTTGTCTTACAGTGAAAGCGCCAGCTTCTACGCTGCCTTCAGGACACAGACGTGCCCAA
    L  S  Y  S  E  S  A  S  F  Y  A  A  F  R  T  Q  T  C  P  I
            250                 270                 290
   TCATGGCTTCTTGGGACTTGGTGAATTTTATTCAAGCAAATTTTAAGAAACGAGAATGTG
    M  A  S  W  D  L  V  N  F  I  Q  A  N  F  K  K  R  E  C  V
            310                 330                 350
   TCTTCTTTACCAAAGATTCCAAGGCCACGGAGAATGTGTGCAAGTGTGGCTATGCCCAGA
    F  F  T  K  D  S  K  A  T  E  N  V  C  K  C  G  Y  A  Q  S
            370                 390                 410
   GCCAGCACATGGAAGGCACCCAGATCAACCAAAGTGAGAAATGGAACTACAAGAAACACA
    Q  H  M  E  G  T  Q  I  N  Q  S  E  K  W  N  Y  K  K  H  T
            430                 450                 470
   CCAAGGAATTTCCTACCGACGCCTTTGGGGATATTCAGTTTGAGACACTGGGGAAGAAAG
    K  E  F  P  T  D  A  F  G  D  I  Q  F  E  T  L  G  K  K  G
            490                 510                 530
   GGAAGTATATACGTCTGTCCTGCGACACGGACGCGGAAATCCTTTACGAGCTGCTGACCC
    K  Y  I  R  L  S  C  D  T  D  A  E  I  L  Y  E  L  L  T  Q
            550                 570                 590
   AGCACTGGCACCTGAAAACACCCAACCTGGTCATTTCTGTGACCGGGGGCGCCAAGAACT
    H  W  H  L  K  T  P  N  L  V  I  S  V  T  G  G  A  K  N  F
            610                 630                 650
   TCGCCCTGAAGCCGCGCATGCGCAAGATCTTCAGCCGGCTCATCTACATCGCGCAGTCCA
    A  L  K  P  R  M  R  K  I  F  S  R  L  I  Y  I  A  Q  S  K
            670                 690                 710
   AAGGTGCTTGGATTCTCACGGGAGGCACCCATTATGGCCTGATGAAGTACATCGGGGAGG
    G  A  W  I  L  T  G  G  T  H  Y  G  L  M  K  Y  I  G  E  V
            730                 750                 770
   TGGTGAGAGATAACACCATCAGCAGGAGTTCAGAGGAGAATATTGTGGCCATTGGCATAG
    V  R  D  N  T  I  S  R  S  S  E  E  N  I  V  A  I  G  I  A
            790                 810                 830
   CAGCTTGGGGCATGGTCTCCAACCGGGACACCCTCATCAGGAATTGCGATGCTGAGGGCT
    A  W  G  M  V  S  N  R  D  T  L  I  R  N  C  D  A  E  G  Y
            850                 870                 890
   ATTTTTTAGCCCAGTACCTTATGGATGACTTCACAAGAGATCCACTGTATATCCTGGACA
    F  L  A  Q  Y  L  M  D  D  F  T  R  D  P  L  Y  I  L  D  N
            910                 930                 950
   ACAACCACACACATTTGCTGCTCGTGGACAATGGCTGTCATGGACATCCCACTGTCGAAG
    N  H  T  H  L  L  L  V  D  N  G  C  H  G  H  P  T  V  E  A
            970                 990                1010
   CAAAGCTCCGGAATCAGCTAGAGAAGTATATCTCTGAGCGCACTATTCAAGATTCCAACT
    K  L  R  N  Q  L  E  K  Y  I  S  E  R  T  I  Q  D  S  N  Y
           1030                1050                1070
   ATGGTGGCAAGATCCCCATTGTGTGTTTTGCCCAAGGAGGTGGAAAAGAGACTTTGAAAG
    G  G  K  I  P  I  V  C  F  A  Q  G  G  G  K  E  T  L  K  A
           1090                1110                1130
   CCATCAATACCTCCATCAAAAATAAAATTCCTTGTGTGGTGGTGGAAGGCTCGGGCCAGA
    I  N  T  S  I  K  N  K  I  P  C  V  V  V  E  G  S  G  Q  I
           1150                1170                1190
   TCGCTGATGTGATCGCTAGCCTGGTGGAGGTGGAGGATGCCCTGACATCTTCTGCCGTCA
    A  D  V  I  A  S  L  V  E  V  E  D  A  L  T  S  S  A  V  K
           1210                1230                1250
```

FIGURE 10

```
AGGAGAAGCTGGTGCGCTTTTTACCCCGCACGGTGTCCCGGCTGCCTGAGGAGGAGACTG
  E  K  L  V  R  F  L  P  R  T  V  S  R  L  P  E  E  E  T  E
           1270              1290              1310
AGAGTTGGATCAAATGGCTCAAAGAAATTCTCGAATGTTCTCACCTATTAACAGTTATTA
  S  W  I  K  W  L  K  E  I  L  E  C  S  H  L  L  T  V  I  K
           1330              1350              1370
AAATGGAAGAAGCTGGGGATGAAATTGTGAGCAATGCCATCTCCTACGCTCTATACAAAG
  M  E  E  A  G  D  E  I  V  S  N  A  I  S  Y  A  L  Y  K  A
           1390              1410              1430
CCTTCAGCACCAGTGAGCAAGACAAGGATAACTGGAATGGGCAGCTGAAGCTTCTGCTGG
  F  S  T  S  E  Q  D  K  D  N  W  N  G  Q  L  K  L  L  L  E
           1450              1470              1490
AGTGGAACCAGCTGGACTTAGCCAATGATGAGATTTTCACCAATGACCGCCGATGGGAGA
  W  N  Q  L  D  L  A  N  D  E  I  F  T  N  D  R  R  W  E  K
           1510              1530              1550
AGAGCAAACCGAGGCTCAGAGACACAATAATCCAGGTCACATGGCTGGAAAATGGTAGAA
  S  K  P  R  L  R  D  T  I  I  Q  V  T  W  L  E  N  G  R  I
           1570              1590              1610
TCAAGGTTGAGAGCAAAGATGTGACTGACGGCAAAGCCTCTTCTCATATGCTGGTGGTTC
  K  V  E  S  K  D  V  T  D  G  K  A  S  S  H  M  L  V  V  L
           1630              1650              1670
TCAAGTCTGCTGACCTTCAAGAAGTCATGTTTACGGCTCTCATAAAGGACAGACCCAAGT
  K  S  A  D  L  Q  E  V  M  F  T  A  L  I  K  D  R  P  K  F
           1690              1710              1730
TTGTCCGCCTCTTTCTGGAGAATGGCTTGAACCTACGGAAGTTTCTCACCCATGATGTCC
  V  R  L  F  L  E  N  G  L  N  L  R  K  F  L  T  H  D  V  L
           1750              1770              1790
TCACTGAACTCTTCTCCAACCACTTCAGCACGCTTGTGTACCGGAATCTGCAGATCGCCA
  T  E  L  F  S  N  H  F  S  T  L  V  Y  R  N  L  Q  I  A  K
           1810              1830              1850
AGAATTCCTATAATGATGCCCTCCTCACGTTTGTCTGGAAACTGGTTGCGAACTTCCGAA
  N  S  Y  N  D  A  L  L  T  F  V  W  K  L  V  A  N  F  R  R
           1870              1890              1910
GAGGCTTCCGGAAGGAAGACAGAAATGGCCGGGACGAGATGGACATAGAACTCCACGACG
  G  F  R  K  E  D  R  N  G  R  D  E  M  D  I  E  L  H  D  V
           1930              1950              1970
TGTCTCCTATTACTCGGCACCCCCTGCAAGCTCTCTTCATCTGGGCCATTCTTCAGAATA
  S  P  I  T  R  H  P  L  Q  A  L  F  I  W  A  I  L  Q  N  K
           1990              2010              2030
AGAAGGAACTCTCCAAAGTCATTTGGGAGCAGACCAGGGGCTGCACTCTGGCAGCCCTGG
  K  E  L  S  K  V  I  W  E  Q  T  R  G  C  T  L  A  A  L  G
           2050              2070              2090
GAGCCAGCAAGCTTCTGAAGACTCTGGCCAAAGTGAAGAACGACATCAATGCTGCTGGGG
  A  S  K  L  L  K  T  L  A  K  V  K  N  D  I  N  A  A  G  E
           2110              2130              2150
AGTCCGAGGAGCTGGCTAATGAGTACGAGACCCGGGCTGTTGGTGAGTCCACAGTGTGGA
  S  E  E  L  A  N  E  Y  E  T  R  A  V  G  E  S  T  V  W  N
           2170              2190              2210
ATGCTGTGGTGGGCGCGGATCTGCCATGTGGCACAGACATTGCCAGCGGCACTCATAGAC
  A  V  V  G  A  D  L  P  C  G  T  D  I  A  S  G  T  H  R  P
           2230              2250              2270
CAGATGGTGGAGAGCTGTTCACTGAGTGTTACAGCAGCGATGAAGACTTGGCAGAACAGC
  D  G  G  E  L  F  T  E  C  Y  S  S  D  E  D  L  A  E  Q  L
           2290              2310              2330
TGCTGGTCTATTCCTGTGAAGCTTGGGGTGGAAGCAACTGTCTGGAGCTGGCGGTGGAGG
  L  V  Y  S  C  E  A  W  G  G  S  N  C  L  E  L  A  V  E  A
           2350              2370              2390
CCACAGACCAGCATTTCATCGCCCAGCCTGGGGTCCAGAATTTTCTTTCTAAGCAATGGT
  T  D  Q  H  F  I  A  Q  P  G  V  Q  N  F  L  S  K  Q  W  Y
           2410              2430              2450
ATGGAGAGATTTCCCGAGACACCAAGAACTGGAAGATTATCCTGTGTCTGTTTATTATAC
  G  E  I  S  R  D  T  K  N  W  K  I  I  L  C  L  F  I  I  P
```

FIGURE 10

```
          2470                2490                2510
CCTTGGTGGGCTGTGGCTTTGTATCATTTAGGAAGAAACCTGTCGACAAGCACAAGAAGC
  L  V  G  C  G  F  V  S  F  R  K  K  P  V  D  K  H  K  K  L
          2530                2550                2570
TGCTTTGGTACTATGTGGCGTTCTTCACCTCCCCCTTCGTGGTCTTCTCCTGGAATGTGG
  L  W  Y  Y  V  A  F  F  T  S  P  F  V  V  F  S  W  N  V  V
          2590                2610                2630
TCTTCTACATCGCCTTCCTCCTGCTGTTTGCCTACGTGCTGCTCATGGATTTCCATTCGG
  F  Y  I  A  F  L  L  L  F  A  Y  V  L  L  M  D  F  H  S  V
          2650                2670                2690
TGCCACACCCCCCCGAGCTGGTCCTGTACTCGCTGGTCTTTGTCCTCTTCTGTGATGAAG
  P  H  P  P  E  L  V  L  Y  S  L  V  F  V  L  F  C  D  E  V
          2710                2730                2750
TGAGACAGGGCCGGCCGGCTGCTCCCAGTGCGGGGCCCGCCAAGCCCACGCCCACCCGGA
  R  Q  G  R  P  A  A  P  S  A  G  P  A  K  P  T  P  T  R  N
          2770                2790                2810
ACTCCATCTGGCCCGCAAGCTCCACACGCAGCCCCGGTTCCCGCTCACGCCACTCCTTCC
  S  I  W  P  A  S  S  T  R  S  P  G  S  R  S  H  S  F  H
          2830                2850                2870
ACACTTCCCTGCAAGCTGAGGGTGCCAGCTCTGGCCTTGGCCAGCCCAGAAAGGGGTGGA
  T  S  L  Q  A  E  G  A  S  S  G  L  G  Q  P  R  K  G  W  T
          2890                2910                2930
CATTTAAAAATCTGGAAATGGTTGATATTTCCAAGCTGCTGATGTCCCTCTCTGTCCCTT
  F  K  N  L  E  M  V  D  I  S  K  L  L  M  S  L  S  V  P  F
          2950                2970                2990
TCTGTACGCAGTGGTACGTAAATGGGGTGAATTATTTTACTGACCTGTGGAATGTGATGG
  C  T  Q  W  Y  V  N  G  V  N  Y  F  T  D  L  W  N  V  M  D
          3010                3030                3050
ACACGCTGGGGCTTTTTTACTTCATAGCAGGAATTGTATTTCGGCAAGGGATCCTTAGGC
  T  L  G  L  F  Y  F  I  A  G  I  V  F  R  Q  G  I  L  R  Q
          3070                3090                3110
AGAATGAGCAGCGCTGGAGGTGGATATTCCGTTCGGTCATCTACGAGCCCTACCTGGCCA
  N  E  Q  R  W  R  W  I  F  R  S  V  I  Y  E  P  Y  L  A  M
          3130                3150                3170
TGTTCGGCCAGGTGCCCAGTGACGTGGATGGTACCACGTATGACTTTGCCCACTGCACCT
  F  G  Q  V  P  S  D  V  D  G  T  T  Y  D  F  A  H  C  T  F
          3190                3210                3230
TCACTGGGAATGAGTCCAAGCCACTGTGTGTGGAGCTGGATGAGCACAACCTGCCCCGGT
  T  G  N  E  S  K  P  L  C  V  E  L  D  E  H  N  L  P  R  F
          3250                3270                3290
TCCCCGAGTGGATCACCATCCCCCTGGTGTGCATCTACATGTTATCCACCAACATCCTGC
  P  E  W  I  T  I  P  L  V  C  I  Y  M  L  S  T  N  I  L  L
          3310                3330                3350
TGGTCAACCTGCTGGTCGCCATGTTTGGCTACACGGTGGGCACCGTCCAGGAGAACAATG
  V  N  L  L  V  A  M  F  G  Y  T  V  G  T  V  Q  E  N  N  D
          3370                3390                3410
ACCAGGTCTGGAAGTTCCAGAGGTACTTCCTGGTGCAGGAGTACTGCAGCCGCCTCAATA
  Q  V  W  K  F  Q  R  Y  F  L  V  Q  E  Y  C  S  R  L  N  I
          3430                3450                3470
TCCCCCTTCCCCTTCATCGTCTTCGCTTACTTCTACATGGTGGTGAAGAAGTGCTTCAAGT
  P  F  P  F  I  V  F  A  Y  F  Y  M  V  V  K  K  C  F  K  C
          3490                3510                3530
GTTGCTGCAAGGAGAAAAACATGGAGTCTTCTGTCTGCTGTGAGTGGTTTATCCATGTGT
  C  C  K  E  K  N  M  E  S  S  V  C  C  E  W  F  I  H  V  Y
          3550                3570                3590
ACTTGGGATCAGAAGCAGCGATTAATTTCAGGGAAGGATGCCTGCATCCAGTGATTGGAA
  L  G  S  E  A  A  I  N  F  R  E  G  C  L  H  P  V  I  G  S
          3610                3630                3650
GCTGGACCCCAGGCTGGCTGGTCTGGACATCCACACGCATTCTCACATGCAGTGCCGGCT
  W  T  P  G  W  L  V  W  T  S  T  R  I  L  T  C  S  A  G  W
          3670                3690                3710
GGCCAGCAGCAGGGAGTCTCAGTGTCACCACACATAGCAGCTGGGTTCCTGCAAAAAGCA
```

FIGURE 10

```
     P  A  A  G  S  L  S  V  T  T  H  S  S  W  V  P  A  K  S  S
        3730              3750              3770
GCAAGTCACAGGCCCACCCAGACAGAACGGGTAGAGAATGTGACTCTGCTTCTGGGTGGG
        K  S  Q  A  H  P  D  R  T  G  R  E  C  D  S  A  S  G  W  E
        3790              3810              3830
AAGGACAGCCTGCCCGGTGGGTGGAAGAATCCGTGGCCCTGTTTGGCCATCGTGGCCCTG
           G  Q  P  A  R  W  V  E  E  S  V  A  L  F  G  H  R  G  P  V
        3850              3870              3890
TTTGGCCACCTACCACTCTAGGCATCACTGAGCTGAATGCGCCGGTCCTCTGA
           W  P  P  T  T  L  G  I  T  E  L  N  A  P  V  L  *
```

MVGGCRWTEDVEPAEVKEKMSFRAARLSMRNRRNDTLDSTRTLYSSASRSTDLSYSESASFYAAFRTQTCPIMASWDLVNFIQANF
KKRECVFFTKDSKATENVCKCGYAQSQHMEGTQINQSEKWNYKKHTKEFPTDAFGDIQEETLGKKGKYIRLSCDTDAEILYELLTQ
HWHLKTPNLVISVTGGAKNFALKPRMRKIFSRLIYIAQSKGAWILTGGTHYGLMKYIGEVVRDNTISRSSEENIVAIGIAAWGMVS
NRDTLIRNCDAEGYFLAQYLMDDFTRDPLYILDNNHTHLLLVDNGCHGHPTVEAKLRNQLEKYISERTIQDSNYGGKIPIVCFAQG
GGKETLKAINTSIKNKIPCVVVEGSGQIADVIASLVEVEDALTSSAVKEKLVRFLPRTVSRLPEEETESWIKWLKEILECSHLLTV
IKMEEAGDEIVSNAISYALYKAFSTSEQDKDNWNGQLKLLLEWNQLDLANDEIFTNDREWBKSKPRLRDTIIQVTWLENGRIKVES
KDVTDGKASSHMLVVLKSADLQEVMFTALIKDRPKFVRLFLENGLNLRKFLTHDVLTELFSNHFSTLVYRNLQIAKNSYNDALLTF
VWKLVANFRRGFRKEDRNGRDEMDIELHDVSPITRHPLQALFIWAILQNKKELSKVIWEQTRGCTLAALGASKLLKTLAKVKNDIN
AAGESEELANEYETRAVGESTVWNAVVGADLPCGTDIASGTHRPDGGELFTECYSSDEDLAEQLLVYSCEAWGGSNCLELAVEATD
QHFIAQPGVQNFLSKQWYGEISRDTKNWKIILCLFIIPLVGCGFVSFRKKFVDKHKKLLWYYVAFFTSPFVVFSWNVVFYIAFLLL
FAYVLLMDFHSVPHPPELVLYSLVFVLFCDEVRQGRPAAPSAGEPAKPTPTRNSIWPASSTRSPGSRSRHSFHTSLQAEGASSGLGQ
PRRGWTEKNLEMVDISKLLMSLSVPFCTQWYVNGVNYFTDLWNVMDTLGLFYFIAGIVFRQGILRQNEQRWRWIFRSVIYEPYLAM
FGQVPSDVDGTTYDFAHCTFTGNESKPLCVELDEHNLPRFPEWITIPLVCIYMLSTNILLVNLLVAMFGYTVGTVQENNDQVWKFQ
RYFLVQEYCSRLNIPFPFIVFAYFYMVVKKCFKCCCKEKNMESSVCCEWFIHVYLGSEAAINFREGCLHPVIGSWTPGWLVWTSTR
ILTCSAGWPAAGSLSVTTHSSWVPAKSSKSQAHPDRTGRECDSASGWEGQPARWVEESVALFGHRGPVWPPTTLGITELNAPVL b)
```
                                                              Q  L
                 2290              2310              2330
TGCTGGTCTATTCCTGTGAAGCTTGGGGTGGAAGCAACTGTCTGGAGCTGGCGGTGGAGG
           L  V  Y  S  C  E  A  W  G  G  S  N  C  L  E  L  A  V  E  A
                 2350              2370              2390
CCACAGACCAGCATTTCATCGCCCAGCCTGGGGTCCAGAATTTTCTTTCTAAGCAATGGT
           T  D  Q  H  F  I  A  Q  P  G  V  Q  N  F  L  S  K  Q  W  Y
                 2410              2430              2450
ATGGAGAGATTTCCCGAGACACCAAGAACTGGAAGATTATCCTGTGTCTGTTTATTATAC
           G  E  I  S  R  D  T  K  N  W  K  I  I  L  C  L  F  I  I  P
                 2470              2490              2510
CCTTGGTGGGCTGTGGCTTTGTATCATTTAGGAAGAAACCTGTCGACAAGCACAAGAAGC
           L  V  G  C  G  F  V  S  F  R  K  K  P  V  D  K
```

FIGURE 11 a) Trp10b cDNA and derived amino acid sequence

```
          10                  30                  50
ATGAAATCCTTCCTTCCTGTCCACACCATCGTGCTTATCAGGGAGAATGTGTGCAAGTGT
 M  K  S  F  L  P  V  H  T  I  V  L  I  R  E  N  V  C  K  C
          70                  90                 110
GGCTATGCCCAGAGCCAGCACATGGAAGGCACCCAGATCAACCAAAGTGAGAAATGGAAC
 G  Y  A  Q  S  Q  H  M  E  G  T  Q  I  N  Q  S  E  K  W  N
         130                 150                 170
TACAAGAAACACACCAAGGAATTTCCTACCGACGCCTTTGGGGATATTCAGTTTGAGACA
 Y  K  K  H  T  K  E  F  P  T  D  A  F  G  D  I  Q  F  E  T
         190                 210                 230
CTGGGGAAGAAAGGGAAGTATATACGTCTGTCCTGCGACACGGACGCGGAAATCCTTTAC
 L  G  K  K  G  K  Y  I  R  L  S  C  D  T  D  A  E  I  L  Y
         250                 270                 290
GAGCTGCTGACCCAGCACTGGCACCTGAAAACACCCAACCTGGTCATTTCTGTGACCGGG
 E  L  L  T  Q  H  W  H  L  K  T  P  N  L  V  I  S  V  T  G
         310                 330                 350
GGCGCCAAGAACTTCGCCCTGAAGCCGCGCATGCGCAAGATCTTCAGCCGGCTCATCTAC
 G  A  K  N  F  A  L  K  P  R  M  R  K  I  F  S  R  L  I  Y
         370                 390                 410
ATCGCGCAGTCCAAAGGTGCTTGGATTCTCACGGGAGGCACCCATTATGGCCTGATGAAG
 I  A  Q  S  K  G  A  W  I  L  T  G  G  T  H  Y  G  L  M  K
         430                 450                 470
TACATCGGGGAGGTGGTGAGAGATAACACCATCAGCAGGAGTTCAGAGGAGAATATTGTG
 Y  I  G  E  V  V  R  D  N  T  I  S  R  S  S  E  E  N  I  V
         490                 510                 530
GCCATTGGCATAGCAGCTTGGGGCATGGTCTCCAACCGGGACACCCTCATCAGGAATTGC
 A  I  G  I  A  A  W  G  M  V  S  N  R  D  T  L  I  R  N  C
         550                 570                 590
GATGCTGAGGGCTATTTTTTAGCCCAGTACCTTATGGATGACTTCACAAGAGATCCACTG
 D  A  E  G  Y  F  L  A  Q  Y  L  M  D  D  F  T  R  D  P  L
         610                 630                 650
TATATCCTGGACAACAACCACACACATTTGCTGCTCGTGGACAATGGCTGTCATGGACAT
 Y  I  L  D  N  N  H  T  H  L  L  L  V  D  N  G  C  H  G  H
         670                 690                 710
CCCACTGTCGAAGCAAAGCTCCGGAATCAGCTAGAGAAGTATATCTCTGAGCGCACTATT
 P  T  V  E  A  K  L  R  N  Q  L  E  K  Y  I  S  E  R  T  I
         730                 750                 770
CAAGATTCCAACTATGGTGGCAAGATCCCCATTGTGTGTTTTGCCCAAGGAGGTGGAAAA
 Q  D  S  N  Y  G  G  K  I  P  I  V  C  F  A  Q  G  G  G  K
         790                 810                 830
GAGACTTTGAAAGCCATCAATACCTCCATCAAAAATAAAATTCCTTGTGTGGTGGTGGAA
 E  T  L  K  A  I  N  T  S  I  K  N  K  I  P  C  V  V  V  E
         850                 870                 890
GGCTCGGGCCAGATCGCTGATGTGATCGCTAGCCTGGTGGAGGTGGAGGATGCCCTGACA
 G  S  G  Q  I  A  D  V  I  A  S  L  V  E  V  E  D  A  L  T
         910                 950
TCTTCTGCCGTCAAGGAGAAGCTGGTGCGCTTTTTACCCCGCACGGTGTCCCGGCTGCCT
 S  S  A  V  K  E  K  L  V  R  F  L  P  R  T  V  S  R  L  P
         970                 990                1010
GAGGAGGAGACTGAGAGTTGGATCAAATGGCTCAAAGAAATTCTCGAATGTTCTCACCTA
 E  E  E  T  E  S  W  I  K  W  L  K  E  I  L  E  C  S  H  L
        1030                1050                1070
TTAACAGTTATTAAAATGGAAGAAGCTGGGGATGAAATTGTGAGCAATGCCATCTCCTAC
 L  T  V  I  K  M  E  E  A  G  D  E  I  V  S  N  A  I  S  Y
        1090                1110                1130
GCTCTATATACAAAGCCTTCAGCACCAGTGAGCAAGACAAGGATAACTGGAATGGGCAGCTG
 A  L  Y  K  A  F  S  T  S  E  Q  D  K  D  N  W  N  G  Q  L
```

FIGURE 11

```
            2410                2430                2450
AGAAACTTAGGACCCAAGATTATAATGCTGCAGAGGATGCTGATCGATGTGTTCTTCTTC
 R  N  L  G  P  K  I  I  M  L  Q  R  M  L  I  D  V  F  F  F
            2470                2490                2510
CTGTTCCTCTTTGCGGTGTGGATGGTGGCCTTTGGCGTGGCCAGGCAAGGGATCCTTAGG
 L  F  L  F  A  V  W  M  V  A  F  G  V  A  R  Q  G  I  L  R
            2530                2550                2570
CAGAATGAGCAGCGCTGGAGGTGGATATTCCGTTCGGTCATCTACGAGCCCTACCTGGCC
 Q  N  E  Q  R  W  R  W  I  F  R  S  V  I  Y  E  P  Y  L  A
            2590                2610                2630
ATGTTCGGCCAGGTGCCCAGTGACGTGGATGGTACCACGTATGACTTTGCCCACTGCACC
 M  F  G  Q  V  P  S  D  V  D  G  T  T  Y  D  F  A  H  C  T
            2650                2670                2690
TTCACTGGGAATGAGTCCAAGCCACTGTGTGTGGAGCTGGATGAGCACAACCTGCCCCGG
 F  T  G  N  E  S  K  P  L  C  V  E  L  D  E  H  N  L  P  R
            2710                2730                2750
TTCCCCGAGTGGATCACCATCCCCCTGGTGTGCATCTACATGTTATCCACCAACATCCTG
 F  P  E  W  I  T  I  P  L  V  C  I  Y  M  L  S  T  N  I  L
            2770                2790                2810
CTGGTCAACCTGCTGGTCGCCATGTTTGGCTACACGGTGGGCACCGTCCAGGAGAACAAT
 L  V  N  L  L  V  A  M  F  G  Y  T  V  G  T  V  Q  E  N  N
            2830                2850                2870
GACCAGGTCTGGAAGTTCCAGAGGTACTTCCTGGTGCAGGAGTACTGCAGCCGCCTCAAT
 D  Q  V  W  K  F  Q  R  Y  F  L  V  Q  E  Y  C  S  R  L  N
            2890                2910                2930
ATCCCCTTCCCCTTCATCGTCTTCGCTTACTTCTACATGGTGGTGAAGAAGTGCTTCAAG
 I  P  F  P  F  I  V  F  A  Y  F  Y  M  V  V  K  K  C  F  K
            2950                2970                2990
TGTTGCTGCAAGGAGAAAAACATGGAGTCTTCTGTCTGCTGTTTCAAAAATGAAGACAAT
 C  C  C  K  E  K  N  M  E  S  S  V  C  C  F  K  N  E  D  N
            3010                3030                3050
GAGACTCTGGCATGGGAGGGTGTCATGAAGGAAAACTACCTTGTCAAGATCAACACAAAA
 E  T  L  A  W  E  G  V  M  K  E  N  Y  L  V  K  I  N  T  K
            3070                3090                3110
GCCAACGACACCTCAGAGGAAATGAGGCATCGATTTAGACAACTGGATACAAAAGCTTAAT
 A  N  D  T  S  E  E  M  R  H  R  F  R  Q  L  D  T  K  L  N
            3130                3150
GATCTCAAGGGTCTACTGAAAGAGATTGCTAATAAAATCAAATAG
 D  L  K  G  L  L  K  E  I  A  N  K  I  K  *
``` b) Trp10 protein:

```
MKSFLPVHTIVLIRENVCKCGYAQSQHMEGTQINQSEKWNYKKHTKFPPTDAFGDIQFETLGKKGKYIRLSCDTDAEILY
ELLTQHWHLKTPNLVISVTGGAKNFALKPRMRKIFSRLIYIAQSKGAWILTGGTHYGLMKYIGEVVRDNTISRSSEENIV
AIGIAAWGMVSNRDTLIRNCDAEGYFLAQYLMDDFTRDPLYILDNNHTHLLLVDNGCHGHPTVEAKLRNQLEKYISERTI
QDSNYGGKIPIVCFAQGGGKETLKAINTSIKNKIPCVVVEGSGQIADVIASLVEVEDALTSSAVKEKLVRFLPRTVSRLP
EEETESWIKWLKEILECSHLLTVIKMEEAGDEIVSNAISYALYKAFSTSEQDKDNWNGQLKLLLEWNQLDLANDEIFTND
RRWESADLQEVMFTALIKDRPKFVRLFLENGLNLRKFLTHDVLTELFSNHFSTLVYRNLQIAKNSYNDALLTFVWKLVAN
FRRGFRKEDRNGRDEMDIELHDVSPITRHPLQALFIWAILQNKKELSKVIWEQTRGCTLAALGASKLLKTLAKVKNDINA
AGESEELANEYETRAVELFTECYSSDEDLAEQLLVYSCEAWGGSNCLELAVEATDQHFIAQPGVQNFLSKQWYGEISRDT
KNWKIILCLFIIPLVGCGFVSFRKKPVDKHKKLLWYYVAFFTSPFVVFSWNVVFYIAFLLLFAYVLLMDFHSVPHPPELV
LYSLVFVLFCDEVRQWYVNGVNYFTDLWNVMDTLGLFYFIAGIVFRLHSSNKSSLYSGRVIFCLDYIIFTLRLIHIFTVS
RNLGPKIIMLQRMLIDVFFFLFLFAVWMVAFGVARQGILRQNEQRWRWIFRSVIYEPYLAMFGQVPSDVDGTTYDFAHCT
FTGNESKPLCVELDEENLPRFPEWITIPLVCIYMLSTNILLVNLLVAMFGYTVGTVQENNDQVWKFQRYFLVQEYCSRLN
IPFPFIVFAYFYMVVKKCFKCCCKEKNMESSVCCFKNEDNETLAWEGVMKENYLVKINTKANDTSEEMRHRFRQLDTKLN
DLKGLLKEIANKIK
```

The Trp8 gene is expressed in endometrial or uterine cancer, but not in normal endometrium Endometrial cancer:

Endometrium:

Expression of human Trp 9 and Trp 10

Expression of Trp10 transcripts and Trp10-antisense transcripts in human prostate cancer and in malignant melanoma Figs. 14C, 14D, 14E, 14H, 14I and 14J
C
H
D
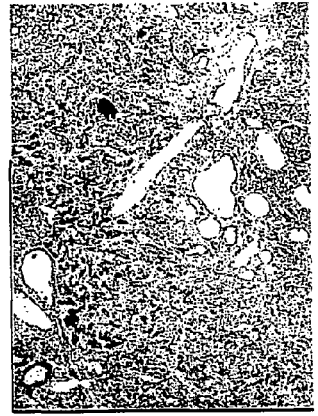
I
J
E

TRP8, TRP9 AND TRP10, NOVEL MARKERS FOR CANCER

The present application claims priority under 35 U.S.C. § 119(e) to U.S. Provisional Application No. 60/221,513 filed on Jul. 28, 2000.

FIELD OF THE INVENTION

The present invention relates to gene expression in normal cells and cells of malignant tumors and particularly to novel markers associated with cancer, Trp8, Trp9 and Trp10, and the genes encoding Trp8, Trp9 and Trp10

BACKGROUND OF THE TECHNOLOGY

Prostate cancer is one of the most common diseases of older men world wide. Diagnosis and monitoring of prostate cancer is difficult because of the heterogeneity of the disease. For diagnosis different grades of malignancy can be distinguished according to the Gleason-Score Diagnosis. For this diagnosis a prostate tissue sample is taken from the patient by biopsy and the morphology of the tissue is investigated. However, this approach only yields subjective results depending on the experience of the pathologist. For confirmation of these results and for obtaining an early diagnosis an additional diagnostic method can be applied which is based on the detection of a prostate specific antigen (PSA). PSA is assayed in serum samples, blood samples etc. using an anti-PSA-antibody. However, since in principle PSA is also expressed in normal prostate tissue there is a requirement for the definition of a threshold value (about 4 ng/ml PSA) in order to be able to distinguish between normal and malign prostate tissue. Unfortunately, this diagnostic method is quite insensitive and often yields false-positive results. Moreover, by using this diagnostic method any conclusions as regards the grade of malignancy, the progression of the tumor and its potential for metastasizing cannot be drawn. Thus, the use of molecular markers would be helpful to distinguish benign from malign tissue and for grading and staging prostate carcinoma, particularly for patients with metastasizing prostate cancer having a very bad prognosis.

The above discussed limitations and failings of the prior art to provide meaningful specific markers which correlate with the presence of prostate tumors, in particular metastasizing tumors, has created a need for markers which can be used diagnostically, prognostically and therapeutically over the course of this disease. The present invention fulfils such a need by the provision of Tpr8, Trp9 and Trp10 and the genes encoding Trp8, Trp9 and Trp10: The genes encoding Trp8 and Trp10 are expressed in prostate carcinoma and prostatic metastasis, but not in normal prostate, benign hyperplasia (BPH) and intraepithelial prostatic neoplasia (PIN). Furthermore, expression of Trp10 transcripts is detectable in carcinoma but not in healthy tissue of the lung, the prostate, the placenta and in melanoma.

SUMMARY OF THE INVENTION

The present invention is based on the isolation of genes encoding novel markers associated witha cancer, Trp8, Trp9 and Trp10. The new calcium channel proteins Trp8, Trp9 and Trp10 are members of the trp (transient receptor potential)—family, isolated from human placenta (Trp8a and Trp8b) and humane prostate (Trp9, Trp10a and Trp10b). Trp proteins belong to a steadily growing family of $Ca^{2+}$ selective and non selective ion channels. In the recent years seven Trp proteins (trp1–trp7) have been identified and suggested to be involved in cation entry, receptor operated calcium entry and pheromone sensory signaling. Structurally related to the trp proteins are the vanilloid receptor (VR1) and the vanilloid like receptor (VRL-1) both involved in nociception triggered by heat. Furthermore, two calcium permeable channels were identified in rat small intestine (CaT1) and rabbit kidney (ECaC). These distantly related channels are suggested to be involved in the uptake of calcium ions from the lumen of the small intestine (CaT1) or in the reuptake of calcium ions in the distal tubule of the kidney (ECaC). Common features or the Trp and related channels are a proposed structure comprising six transmembrane domains including several conserved amino acid motifs. In the present invention the cloning and expression of a CaT1 like calcium channel (Trp8) from human placenta as well as Trp9 and Trp10 (two variants, Trp10a and Trp10b) is described. Two polymorphic variants of the Trp8 cDNA were isolated from placenta (Trp8a and Trp8b). Transient expression of the Trp8b cDNA in HEK (human embryonic kidney) cells results in cytosolic calcium overload implicating that the Trp8 channel is constitutive open in the expression system. Trp8 induces highly calcium selective inward currents in HEK cells. The C-terminus of the Trp8 protein binds calmodulin in a calcium dependent manner. The Trp9 channel is expressed in trophoblasts and syncytiotrophoblasts of placenta and in pancreatic acinar cells. Furthermore, the Trp8 channel is expressed in prostatic carcinoma and prostatic metastases, but not in normal tissue of the prostate. No expression of Trp8 transcripts is detectable in benign prostatic hyperplasia (BPH) or prostatic intraepithelial neoplasia (PIN). Therefore, the Trp8 channel is exclusively expressed in malign prostatic tissues and serves as molecular marker for prostate cancer. From the experimental results it is also apparent that the modulation of Trp8 and/or Trp10, e.g. the inhibition of expression or activity, is of therapeutic interest, e.g. for the prevention of tumor progression.

The present invention, thus, provides a Trp8, Trp9 and Trp10 protein, respectively, as well as nucleic acid molecule encoding the protein and, moreover, an antisense RNA, a ribozyme and an inhibitor, which allow to inhibit the expression or the activity of Trp8, Trp9 and/or Trp10.

In one embodiment, the present invention provides a diagnostic method for detecting a prostate cancer or endometrial cancer (cancer of the uterus) associated with Trp8 or Trp10 in a tissue of a subject, comprising contacting a sample containing Trp8 and/or Trp10 encoding mRNA with a reagent which detects Trp8 and/or Trp10 or the corresponding mRNA.

In a further embodiment, the present invention provides a diagnostic method for detecting a melanoma, chorion carcinoma, cancer of the lung and of the prostate in a tissue of a subject, comprising contacting a sample with a reagent which detects Trp10a and/or Trp10b antisense transcripts or Trp10a and/or Trp10b related antisense transcripts.

In another embodiment, the present invention provides a method of treating a prostate tumor, carcinoma of the lung, carcinoma of the placenta (chorion carcinoma) or melanoma associated with Trp8 and/or Trp10, comprising administering to a subject with such an disorder a therapeutically effect amount of a reagent which modulates, e.g. inhibits, expression of Trp8 and/or Trp10 or the activity of the protein, e.g. the above described compounds.

Finally, the present invention provides a method of gene therapy comprising introducing into cells of a subject an expression vector comprising a nucleotide sequence encoding the above mentioned antisense RNA or ribozyme, in operable linkage with a promoter.

BRIEF DESCRIPTION OF THE DRAWINGS

FIG. 7: Trp8a cDNA sequence (SEQ ID NO:5) and derived amino acid sequence (SEQ ID NO:6)

FIG. 8: A, Trp8b cDNA sequence (SEQ ID NO:45) and derived amino acid sequence (SEQ ID NO:46)

Figure 1A:
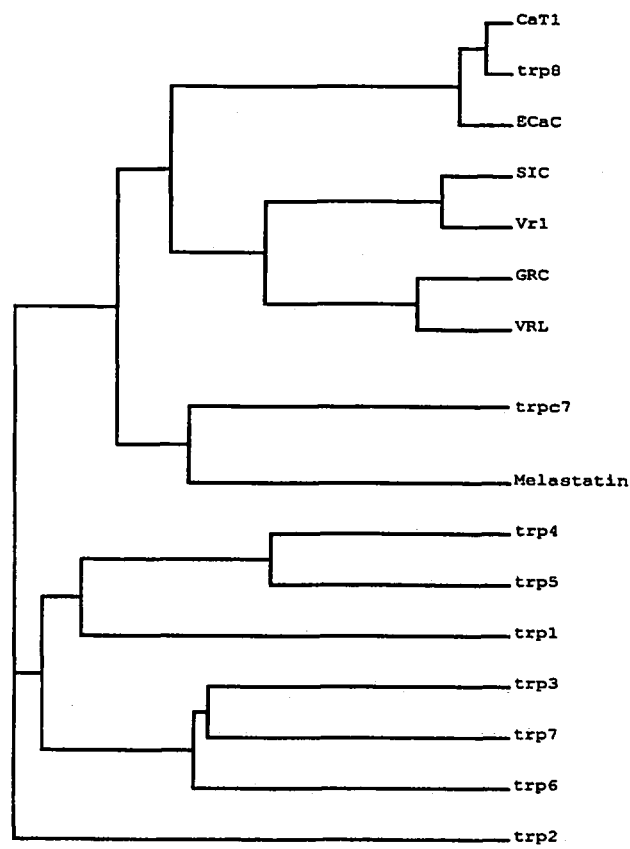
FIG. 1: A, phylogenetic relationship of trp and related proteins. B, hydropathy plot of the Trp8 protein sequence according to Kyte and Doolittle. C, alignment of Trp8a/b to the epithelial calcium channels ECaC (from rabbit) and Vr1 (from rat). Putative transmembrane domains are underlined.

B, cDNA sequence of splice variant 1 (12B1) (SEQ ID NO:13)

C, cDNA sequence of splice variant 2 (17-3) (SEQ ID NO:14)

D, cDNA sequence of splice variant 3 (23A3) (SEQ ID NO:15)

E, cDNA sequence of splice variant 4 (23C3) (SEQ ID NO:16)

FIG. 9: A, Trp9 cDNA sequence (SEQ ID NO:9) and derived amino acid sequence (SEQ ID NO:10) B, cDNA sequence (SEQ ID NO:7) of splice variant 15 and derived amino acid sequence (SEQ ID NO:8)

FIG. 10: A, cDNA sequence (SEQ ID NO:11) of Tip10a and derived amino acid sequence (SEQ ID NO:12) B, cDNA fragment (SEQ ID NO:1) of Trp10a and derived amino acid sequence (SEQ ID NO:2)

FIG. 11: cDNA sequence (SEQ ID NO:3) of Trp10b and derived amino acid sequence (SEQ ID NO:4)

FIG. 12: Expression of Trp8 mRNA in human endometrial cancer or cancer of the uterus. A–D, in situ hybridization with slides of endometrial cancer hybridized with Trp8 antisense (left column) or sense probes as controls (right column). E–F, Trp8 antisense probes hybridized to slides of normal endometrium. It can be clearly seen no hybridization occurs with normal endometrial tissue.

Figure 13:
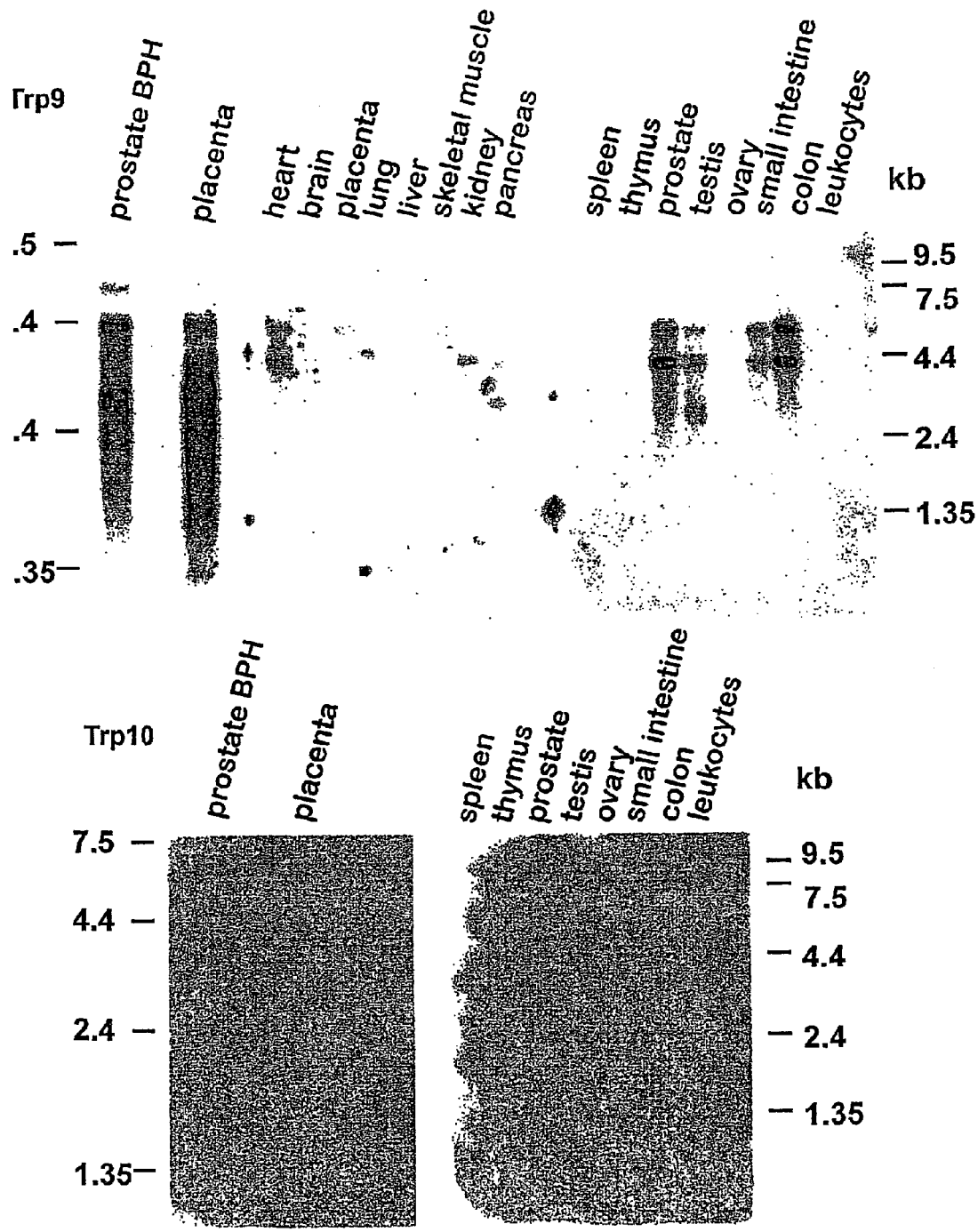
Figures 14A, 14B, 14F, 14G:
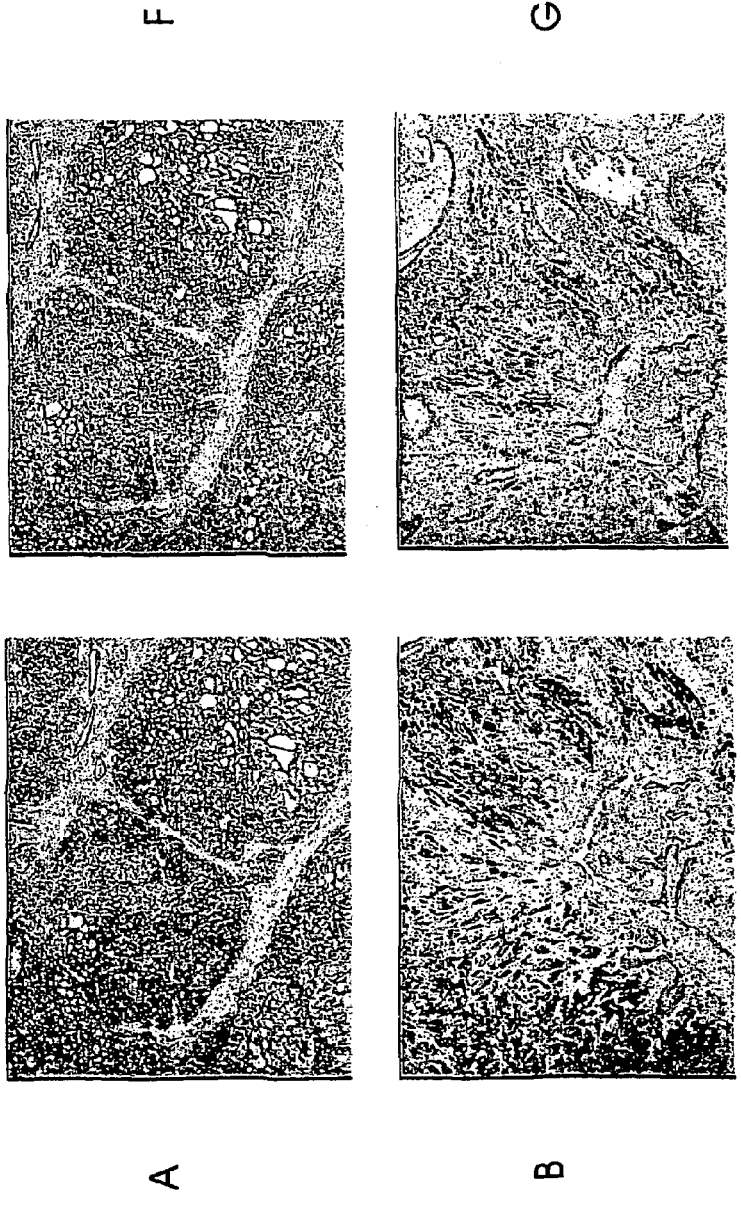
Figure 14K:
Figure 14L:
Figure 14P:
Figure 14Q:
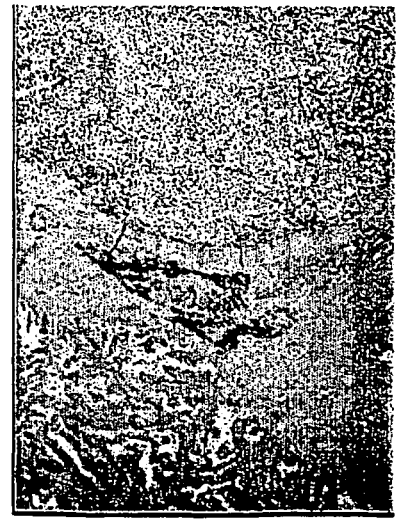
Figure 14M:
Figure 14N:
Figure 14O:
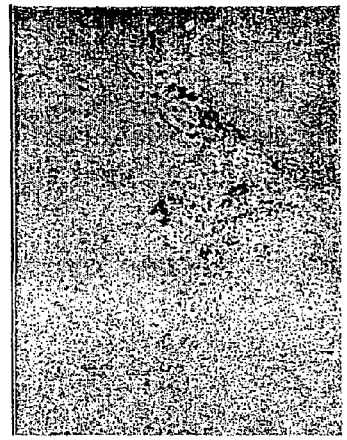
Figure 14R:
Figure 14S:
Figure 14T:
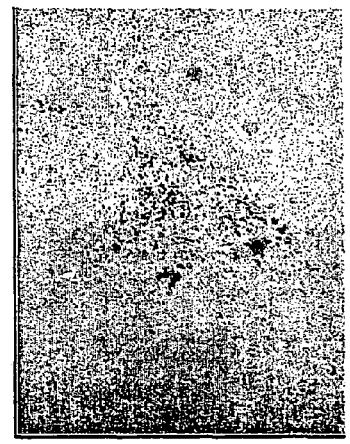

FIG. 13: Expression of human Trp9 and Trp10 genes Northern blots were hybridized using Trp9 (upper panel) or Trp10 (lower panel) specific probes. Expression of the Trp9 cDNA is detectable in many tissues including human prostate and colon as well as in benign prostatic hyperplasia. Expression of Trp10 cDNA is detectable in human prostate of a commercial northern blot (Clontech, right side). This Northern blot contains prostatic tissue collected from 15 human subjects in the range of 14–60 years of age. No expression of Trp10 cDNA was detectable in benign prostatic hyperplasia (left side).

FIG. 14: Expression of Trp10 transcripts and Trp10-antisense transcripts in human prostate cancer and metastasis of a melanoma. In situ hybridizations of slides hybridized with Trp10-antisense (A–E, K–N) and Trp10 related sense probes (F–J, P–R). It can clearly be seen that both probes detect the same cancer cells indicating that these cancer cells express Trp10 transcripts as well as Trp10-antisense transcripts. S, no Trp10 expression is detectable in benign hyperplasia of the prostate (BPH). O and T, show expression of Trp10 transcripts (O) and Trp10-antisense transcripts (T) in a metastasis of a melanoma in human lung. Melanoma cancer cells express both Trp10 transcripts and Trp10-antisense transcripts.

DETAILED DESCRIPTION OF THE INVENTION

The present invention relates to an isolated nucleic acid molecule encoding the human prostate carcinoma associated protein Trp8a, Trp8b, Trp9, Trp10a or Trp10b or a protein exhibiting biological properties of Trp8a, Trp8b, Trp9, Trp10a or Trp10b and being selected from the group consisting of (a) a nucleic acid molecule encoding a protein that comprises the amino acid sequence depicted in FIGS. 7, 8A, 9, 10 or 11;
(b) a nucleic acid molecule comprising the nucleotide sequence depicted in FIGS. 7, 8A, 9, 10, or 11;
(c) a nucleic acid molecule included in DSMZ Deposit no. DSM 13579 (deposit date: 28 Jun. 2000), DSM 13580 (deposit date: 28 Jun. 2000), DSM 13584 (deposit date: 5 Jul. 2000), DSM 13581 (deposit date: 28 Jun. 2000) or DSM . . . (deposit date: . . . );
(d) a nucleic acid molecule with hybridizes to a nucleic acid molecule specified in (a) to (c)
(e) a nucleic acid molecule the nucleic acid sequence of which deviates from the nucleic sequences specified in (a) to (d) due to the degeneration of the genetic code; and
(f) a nucleic acid molecule, which represents a fragment, derivative or allelic variation of a nucleic acid sequence specified in (a) to (e).

As used herein, a protein exhibiting biological properties of Trp8a, Trp8b, Trp9, Trp10a or Trp10b is understood to be a protein having at least one of the activities as illustrated in the Examples, below.

As used herein, the term "isolated nucleic acid molecule" includes nucleic acid molecules substantially free of other nucleic acids, proteins, lipids, carbohydrates or other materials with which it is naturally associated.

In a first embodiment, the invention provides an isolated nucleic acid molecule encoding the human prostate carcinoma associated protein Trp8a, Trp8b, Trp9, Trp10a or Trp10b comprising the amino acid sequence depicted in FIGS. 7, 8A, 9, 10 or 11. The present invention also provides a nucleic acid molecule comprising the nucleotide sequence depicted in FIGS. 7, 8A, 9, 10 or 11.

The present invention provides not only the generated nucleotide sequence identified in FIGS. 7, 8A, 9, 10 or 11, respectively and the predicted translated amino acid sequence, respectively, but also plasmid DNA containing a Trp8a cDNA deposited with the DSMZ, under DSM 13579, a Trp8b cDNA deposited with the DSMZ, under DSM 13580, a Trp9 cDNA deposited with the DSMZ, under DSM 13584, a Trp10a cDNA deposited with the DSMZ, under DSM 13581, and a Trp10b cDNA deposited with the DSMZ, under DSM . . . , respectively. The nucleotide sequence of each deposited Trp-clone can readily be determined by sequencing the deposited clone in accordance with known methods. The predicted amino acid sequence can then be verified from such deposits. Moreover, the amino acid sequence of the protein encoded by each deposited clone can also be directly determined by peptide sequencing or by expressing the protein in a suitable host cell containing the deposited Trp-encoding DNA, collecting the protein, and determining its sequence.

The nucleic acid molecules of the invention can be both DNA and RNA molecules. Suitable DNA molecules are, for example, genomic or cDNA molecules. It is understood that all nucleic acid molecules encoding all or a portion of Trp8a, Trp8b, Trp9, Trp10a or Trp10b are also included, as long as they encode a polypeptide with biological activity. The nucleic acid molecules of the invention an be isolated from natural sources or can be synthesized according to know methods.

The present invention also provides nucleic acid molecules which hybridize to the above nucleic acid molecules.

As used herein, the term "hybridize" has the meaning of hybridization under conventional hybridization conditions, preferably under stringent conditions as described, for example, in Sambrook et al., Molecular Cloning, A Laboratory Manual $2^{nd}$ edition (1989) Cold Spring Harbor Laboratory Press, Cold Spring Harbor, N.Y. Also contemplated are nucleic acid molecules that hybridize to the Trp nucleic acid molecules at lower stringency hybridization conditions. Changes in the stringency of hybridization and signal detection are primarily accomplished through the manipulation of formamide concentration (lower percentages of formamide result in lowered stringency), salt conditions, or temperature. For example, lower stringency conditions include an overnight incubation at 37° C. in a solution comprising 6×SSPE (20×SSPE=3M NaCl; 9.2M $NaH_2PO_4$; 0.02M EDTA, pH7.4), 0.5% SDS, 30% formamide, 100 µg/ml salmon sperm blocking DNA, following by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. The inclusion of specific blocking reagents may require modification of the hybridization conditions described above, due to problems with compatibility.

Nucleic acid molecules that hybridize to the molecules of the invention can be isolated, e.g., from genomic or cDNA libraries that were produced from human cell lines or tissues. In order to identify and isolate such nucleic acid molecules the molecules of the invention or parts of these molecules or the reverse complements of these molecules can be used, for example by means of hybridization according to conventional methods (see, e.g., Sambrook et al., supra). As a hybridization probe nucleic acid molecules can be used, for example, that have exactly or basically the nucleotide sequence depicted in FIGS. 7, 8A, 9, 10 or 11, respectively, or parts of these sequences. The fragments used as hybridization probe can be synthetic fragments that were produced by means of conventional synthetic methods and the sequence of which basically corresponds to the sequence of a nucleic acid molecule of the invention.

The nucleic acid molecules of the present invention also include molecules with sequences that are degenerate as a result of the genetic code.

In a further embodiment, the present invention provides nucleic acid molecules which comprise fragments, derivatives and allelic variants of the nucleic acid molecules described above encoding a protein of the invention. "Fragments" are understood to be parts of the nucleic acid molecules that are long enough to encode one of the described proteins. These fragments comprise nucleic acid molecules specifically hybridizing to transcripts of the nucleic acid molecules of the invention. These nucleic acid molecules can be used, for example, as probes or primers in the diagnostic assay and/or kit described below and, preferably, are oligonucleotides having a length of at least 10, in particular of at least 15 and particularly preferred of at least 50 nucleotides. The nucleic acid molecules and. oligonucleotides of the invention can also be used, for example, as primers for a PCR reaction. Examples of particular useful probes (primers) are shown in Tables 1 and 2.

TABLE 1

Trp8 probes used for in situ hybridization:

Probes (antisense)

1.) 5' TCCGCTGCCGGTTGAGATCTTGCC 3'

2.) 5' CTTGCTCCATAGGCAGAGAATTAG 3'

3.) 5' ATCCTCAGAGCCCCGGGTGTGGAA3'

Controls (sense)

1.) 5' GGCAAGATCTCAACCGGCAGCGGA 3'

2.) 5' CTAATTCTCTGCCTATGGAGCAAG 3'

3.) 5' TTCCACACCCGGGGCTCTGAGGAT 3'

TABELLE 2

Trp 10 probes used for the in situ hybridations shown in FIG. 14:

Probes (antisense)

1.) 5' GCTTCCACCCCAAGCTTCACAGGAATAGA 3'  (FIG. 14A, 14B)

2.) 5' GGCGATGAAATGCTGGTCTGTGGC 3'  (FIG. 14C, 14D, 14N, 14S, 14O)

3.) 5' ATCTTCCAGTTCTTGGTGTCTCGG 3'  (FIG. 14E, 14K)

4.) 5' GCTGCAGTACTCCTGCACCAGGAA 3'  (FIG. 14L, 14M)

Probes (sense)

1.) 5' TCTATTCCTGTGAAGCTTGGGGTGGAAGC 3'  (FIG. 14F, 14G)

2.) 5' GCCACAGACCAGCATTTCATCGCC 3'  (FIG. 14H, 14I, 14T)

3.) 5' CCGAGACACCAAGAACTGGAAGAT 3'  (FIG. 14J, 14P)

4.) 5' TTCCTGGTGCAGGAGTACTGCAGC 3'  (FIG. 14Q, 14R)

The term "derivative" in this context means that the sequences of these molecules differ from the sequences of the nucleic acid molecules described above at one or several positions but have a high level of homology to these sequences. Homology hereby means a sequence identity of at least 40%, in particular an identity of at least 60%, preferably of more than 80% and particularly preferred of more than 90%. These proteins encoded by the nucleic acid molecules have a sequence identity to the amino acid sequence depicted in FIGS. 7, 8A, 9, 10 and 11, respectively, of at least 80%, preferably of 85% and particularly preferred of more than 90%, 97% and 99%. The deviations to the above-described nucleic acid molecules may have been produced by deletion, substitution, insertion or recombination. The definition of the derivatives also includes splice variants, e.g. the splice variants shown in FIGS. 8B to 8E and 9B.

The nucleic acid molecules that are homologous to the above-described molecules and that represent derivatives of these molecules usually are variations of these molecules that represent modifications having the same biological function. They can be naturally occurring variations, for example sequences from other organisms, or mutations that can either occur naturally or that have been introduced by specific mutagenesis. Furthermore the variations can be synthetically produced sequences. The allelic variants can be either naturally occurring variants or synthetically produced variants or variants produced by recombinant DNA processes.

Generally, by means of conventional molecular biological processes it is possible (see, e.g., Sambrook et al., supra) to introduce different mutations into the nucleic acid molecules of the invention. As a result Trp proteins or Trp related proteins with possibly modified biological properties are synthesized. One possibility is the production of deletion mutants in which nucleic acid molecules are produced by continuous deletions from the 5'- or 3'-terminal of the coding DNA sequence and that lead to the synthesis of proteins that are shortened accordingly. Another possibility is the introduction of single-point mutation at positions where a modification of the amino aid sequence influences, e.g., the ion channel properties or the regulations of the trp-ion channel. By this method muteins can be produced, for example, that possess a modified ion conducting pore, a modified $K_m$- value or that are no longer subject to the regulation mechanisms that normally exist in the cell, e.g. with regard to allosteric regulation or covalent modification. Such muteins might also be valuable as therapeutically useful antagonists of Trp8a, Trp8b, Trp9, Trp10a or Trp10b, respectively.

For the manipulation in prokaryotic cells by means of genetic engineering the nucleic acid molecules of the invention or parts of these molecules can be introduced into plasmids allowing a mutagenesis or a modification of a sequence by recombination of DNA sequences. By means of conventional methods (cf Sambrook et al., supra) bases can be exchanged and natural or synthetic sequences can be added. In order to link the DNA fragments with each other adapters or linkers can be added to the fragments. Furthermore, manipulations can be performed that provide suitable cleavage sites or that remove superfluous DNA or cleavage sites. If insertions, deletions or substitutions are possible, in vitro mutagenesis, primer repair, restriction or ligation can be performed. As analysis method usually sequence analysis, restriction analysis and other biochemical or molecular biological methods are used.

The proteins encoded by the various variants of the nucleic acid molecules of the invention show certain common characteristics, such as ion channel activity, molecular weight, immunological reactivity or conformation or physical properties like the electrophoretical mobilty, chromatographic behavior, sedimentation coefficients, solubility, spectroscopic properties, stability; pH optimum, temperature optimum.

The invention furthermore relates to vectors containing the nucleic acid molecules of the invention. Preferably, they are plasmids, cosmids, viruses, bacteriophages and other vectors usually used in the field of genetic engineering. Vectors suitable for use in the present invention include, but are not limited to the T7-based expression vector for expression in mammalian cells and baculovirus-derived vectors for expression in insect cells. Preferably, the nucleic acid molecule of the invention is operatively linked to the regulatory elements in the recombinant vector of the invention that guarantee the transcription and synthesis of an RNA in prokryotic and/or eukaryotic cells that can be translated. The nucleotide sequence to be transcribed can be operably linked to a promoter like a T7, metallothionein I or polyhedrin promoter.

In a further embodiment, the present invention relates to recombinant host cells transiently or stable containing the nucleic acid molecules or vectors or the invention. A host cell is understood to be an organism that is capable to take up in vitro recombinant DNA and, if the case may be, to synthesize the proteins encoded by the nucleic acid molecules of the invention. Preferably, these cells are prokaryotic or eukaryotic cells, for example mammalian cells, bacterial cells, insect cells or yeast cells. The host cells of the invention are preferably characterized by the fact that the introduced nucleic acid molecule of the invention either is heterologous with regard to the transformed cell, i.e. that it does not naturally occur in these cells, or is localized at a place in the genome different from that of the corresponding naturally occurring sequence.

A further embodiment of the invention relates to isolated proteins exhibiting biological properties of the human prostate carcinoma associated protein Trp8a, Trp8b, Trp9, Trp10a or Trp10b and being encoded by the nucleic acid molecules of the invention, as well as to methods for their production, whereby, e.g., a host cell of the invention is cultivated under conditions allowing the synthesis of the protein and the protein is subsequently isolated from the cultivated cells and/or the culture medium. Isolation and purification of the recombinantly produced proteins may be carried out by conventional means including preparative chromatography and affinity and immunological separations involving affinity with an anti-Trp8a-, anti-Trp8b-, anti-Trp9-, anti-Trp10a- or anti-Trp10b-antibody, respectively.

As used herein, the term "isolated protein" includes proteins substantially free of other proteins, nucleic acids, lipids, carbohydrates or other materials with which it is naturally associated. Such proteins however not only comprise recombinantly produced proteins but include isolated naturally occurring proteins, synthetically produced proteins, or proteins produced by a combination of these methods. Means for preparing such proteins are well understood in the art. The Trp proteins are preferably in a substantially purified form. A recombinantly produced version of a human prostate carcinoma associated protein Trp8a, Trp8b, Trp9, Trp10a or Trp10b protein, including the secreted protein, can be substantially purified by the one-step method described in Smith and Johnson, Gene 67; 31–40 (1988).

In a further preferred embodiment, the present invention relates to an antisense RNA sequence characterised that it is complementary to an mRNA transcribed from a nucleic acid molecule of the present invention or a part thereof and can selectively bind to said mRNA, said sequence being capable of inhibiting the synthesis of the protein encoded by said nucleic acid molecules, and a ribozyme characterised in that it is complementary to an mRNA transcribed from a nucleic acid molecule of the present invention or a part thereof and can selectively bind to and cleave said mRNA, thus inhibiting the synthesis of the proteins encoded by said nucleic acid molecules. Riboyzmes which are composed of a single RNA chain are RNA enzymes, i.e. catalytic RNAs, which can intermolecularly cleave a target RNA, for example the mRNA transcribed from one of the Trp genes. It is now possible to construct ribozymes which are able to cleave the target RNA at a specific site by following the strategies described in the literature. (see, e.g., Tanner et al., in: Antisense Research and Applications, CRC Press Inc. (1993), 415–426). The two main requirements for such ribozymes are the catalytic domain and regions which are complementary to the target RNA and which allow them to bind to its substrate, which is a prerequisite for cleavage. Said complementary sequences, i.e., the antisense RNA or ribozyme, are useful for repression of Trp8a-, Trp8b, Trp9-, Trp10a- and Trp10b-expression, respectively, i.e. in the case of the treatment of a prostate cancer or endometrial cancer (carcinoma of the uterus). Preferably, the antisense RNA and ribozyme of the invention are complementary to the coding region. The person skilled in the art provided with the sequences of the nucleic acid molecules of the present invention will be in a position to produce and utilise the above described antisense RNAs or ribozymes. The region of the antisense RNA and ribozyme, respectively, which shows complementarity to the mRNA transcribed from the nucleic acid molecules of the present invention preferably has a length of at least 10, in particular of at least 15 and particularly preferred of at least 50 nucleotides.

In still a further embodiment, the present invention relates to inhibitors of Trp8a, Trp8b, Trp9, Trp10a and Trp10b, respectively, which fulfill a similar purpose as the antisense RNAs or ribozymes mentioned above, i.e. reduction or elimination of biologically active Trp8a, Trp8b, Trp9, Trp10a or Trp10b molecules. Such inhibitors can be, for instance, structural analogues of the corresponding protein that act as antagonists. In addition, such inhibitors comprise molecules identified by the use of the recombinantly produced proteins, e.g. the recombinantly produces protein can be used to screen for and identify inhibitors, for example, by exploiting the capability of potential inhibitors to bind to the protein under appropriate conditions. The inhibitors can, for example, be identified by preparing a test mixture wherein the inhibitor candidate is incubated with Trp8a, Trp8b, Trp9, Trp10a or Trp10b, respectively, under appropriate conditions that allow Trp8a, Trp8b, Trp9, Trp10a or Trp10b to be in a native conformation. Such an in vitro test system can be established according to methods well known in the art. Inhibitors can be identified, for example, by first screening for either synthetic or naturally occurring molecules that bind to the recombinantly produced Trp protein and then, in a second step, by testing those selected molecules in cellular assays for inhibition of the Trp protein, as reflected by inhibition of at least one of the biological activities as described in the examples, below. Such screening for molecules that bind Trp8a, Trp8b, Trp9, Trp10a or Trp10b could easily performed on a large scale, e.g. by screening candidate molecules from libraries of synthetic and/or natural molecules. Such an inhibitor is, e.g., a synthetic organic chemical, a natural fermentation product, a substance extracted from a microorganism, plant or animal, or a peptide. Additional examples of inhibitors are specific antibodies, preferably monoclonal antibodies. Moreover, the nucleic sequences of the invention and the encoded proteins can be used to identify further factors involved in tumor development and progression. In this context it should be emphasized that the modulation of the calcium channel of a member of the trp family can result in the stimulation of the immune response of T lymphocytes leading to proliferation of the T lymphocytes. The proteins of the invention can, e.g., be used to identify further (unrelated) proteins which are associated with the tumor using screening methods based on protein/protein interactions, e.g. the two-hybrid-system Fields, S. and Song, O. (1989) Nature (340): 245–246.

The present invention also provides a method for diagnosing a prostate carcinoma which comprises contacting a target sample suspected to contain the protein Trp8a, Trp8b, Trp10a and/or Trp10b or the Trp8a, Trp8b, Trp10a and/or Trp10b encoding mRNA with a reagent which reacts with Trp8a, Trp8b, Trp10a and/or Trp10b or the Trp8a, Trp8b, Trp10a and/or Trp10b encoding mRNA and detecting Trp8a, Trp8b, Trp10a and/or Trp10b or Trp8a, Trp8b, Trp10a and/or Trp10b encoding mRNA.

It has been found that carcinoma cells of placenta (chorion carcinoma), lung and prostate express Trp10 transcripts as well as Trp10 antisense transcripts and transcripts being in part complementary to Trp10 antisense transcripts. Accordingly, the present invention also provides a method for diagnosing a melanoma, chorion carcinoma, cancer of the lung and of the prostate in a tissue of a subject, comprising contacting a sample with a reagent which detects Trp10a and/or Trp10b antisense RNA.

When the target is mRNA (or antisense RNA), the reagent is typically a nucleic acid probe or a primer for PCR. The person skilled in the art is in a position to design suitable nucleic acids probes based on the information as regards the nucleotide sequence of Trp8a, Trp8b, Trp10a or Trp10b as depicted in FIGS. 7, 8*a*, 10 and 11, respectively, or tables 1 and 2, above. When the target is the protein, the reagent is typically an antibody probe. The term "antibody", preferably, relates to antibodies which consist essentially of pooled monoclonal antibodies with different epitopic specifities, as well as distinct monoclonal antibody preparations. Monoclonal antibodies are made from an antigen containing fragments of the proteins of the invention by methods well known to those skilled in the art (see, e.g., Köhler et al., Nature 256 (1975), 495). As used herein, the term "antibody" (Ab) or "monoclonal antibody" (Mab) is meant to include intact molecules as well as antibody fragments (such as, for example, Fab and F(ab') 2 fragments) which are capable of specifically binding to protein. Fab and f(ab')2 fragments lack the Fc fragment of intact antibody, clear more rapidly from the circulation, and may have less non-specific tissue binding than an intact antibody. (Wahl et al., J. Nucl. Med. 24: 316–325 (1983)). Thus, these fragments are preferred, as well as the products of a FAB or other immunoglobulin expression library. Moreover, antibodies of the present invention include chimerical, single chain, and humanized antibodies. The target cellular component, i.e. Trp8a, Trp8b, Trp10a and/or Trp10b or Trp8a, Trp8b, Trp10a and/or Trp10b encoding mRNA or Trp10a/b antisense transcripts, e.g., in biological fluids or tissues, may be detected directly in situ, e.g. by in situ hybridization (e.g., according to the examples, below) or it may be isolated from other cell components by common methods known to those skilled in the art before contacting with a probe. Detection methods include Northern blot analysis, RNase protection, in situ methods, e.g. in situ hybridization, in vitro amplification methods (PCR, LCR, QRNA replicase or RNA-transcription/amplification (TAS, 3SR), reverse dot blot disclosed in EP-B1 O 237 362)), immunoassays, Western blot and other detection assays that are known to those skilled in the art.

Products obtained by in vitro amplification can be detected according to established methods, e.g. by separating the products on agarose gels and by subsequent staining with ethidium bromide. Alternatively, the amplified products can be detected by using labeled primers for amplification or labeled dNTPs.

The probes can be detectable labeled, for example, with a radioisotope, a bioluminescent, compound, a chemiluminescent compound, a fluorescent compound, a metal chelate, or an enzyme.

Expression of Trp8a, Trp8b, Trp10a and Trp10b, respectively, in tissues can be studied with classical immunohistological methods (Jalkanen et al., J. Cell. Biol. 101 (1985), 976–985; Jalkanen et al., J. Cell. Biol. 105 (1987), 3087–3096; Sobol et al. Clin. Immunpathol. 24 (1982), 139–144; Sobol et al., Cancer 65 (1985), 2005–2010). Other antibody based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^3$H), indium ($^{112}$In), and technetium rhodamine, and biotin. In addition to assaying Trp8a, Trp8b, Trp 10a or Trp10b levels in a biological sample, the protein can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma. A protein-specific antibody or antibody fragment which has been labeled with an appropriate detectable imaging moiety, such as a radioisotope (for example, $^{131}$I, $^{112}$In, $^{99}$mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled antibody or antibody fragment will then preferentially accumulate at he location of cells which contain the specific protein. In vivo tumor imaging is described in S. W. Burchiel et al., "Immunopharmacokinetics of Radiolabeled Antibodies and Their Fragments". (Chapter 13 in Tumor Imaging: The Radiochemical Detection of Cancer, S. W. Burchiel and B. A. Rhodes, eds., Masson Publishing Inc. (1982)).

The marker Trp8a and Trp8b is also useful for prognosis, for monitoring the progression of the tumor and the diagnostic evaluation of the degree of malignancy of a prostate tumor (grading and staging), e.g. by using in situ hybridization: In a primary carcinoma Trp8 is expressed in about 2 to 10% of carcinoma cells, in a rezidive carcinoma in about 10 to 60% of cells and in metastases in about 60 to 90% of cells.

The present invention also relates to a method for diagnosing endometrial cancer (cancer of the uterus) which comprises contacting a target sample suspected to contain the protein Trp8a and/or Trp8b or the Trp8a and/or Trp8b encoding mRNA with a reagent which reacts with Trp8a and/or Trp8b or the encoding mRNA and detecting Trp8a and/or Trp8b encoding mRNA. As regards particular embodiments of this method reference is made to the particular embodiments of the method of diagnosing a prostate cancer outlined above.

For evaluating whether the concentration of Trp8a, Trp8b, Trp10a or Trp10b or the concentration of Trp8a, Trp8b, Trp10a or Trp10b encoding mRNA is normal or increased, thus indicative for the presence of a malignant tumor, the measured concentration is compared with the concentration in a normal tissue, preferably by using the ratio of Trp8a:Trp9, Trp8b:Trp9 or Trp10(a or b)/Trp9 for quantification.

Since the prostate carcinoma forms its own basement membrane when growing invasively, it can be concluded that only cells expressing Trp8 and Trp10 are involved in this phenomenon. Thus, it can be concluded that by inhibiting the expression and/or activity of these proteins an effective therapy of cancers like PCA is provided.

Thus, the present invention also relates to a pharmaceutical composition containing a reagent which decreases or inhibits Trp8a, Trp8b, Trp10a and/or Trp10b expression or the activity of Trp8a, Trp8b, Trp10a and/or Trp10b, and a method for preventing, treating, or ameliorating a prostate tumor, endometrial cancer (uterine carcinoma) tumor, a chorion carcinoma, cancer of the lung or melanoma, which comprises administering to a mammalian subject a therapeutically effective amount of a reagent which decreases or inhibits Trp8a, Trp8b, Trp10a and/or Trp10b expression or the activity of Trp8a, Trp8b, Trp10a and/or Trp10b. Examples of such reagents are the above described antisense RNAs, ribozymes or inhibitors, e.g. specific antibodies. Furthermore, peptides, which inhibit or modulate the biological function of Trp8a, Trp8b, Trp9, Trp10a and/or Trp10b may be useful as therapeutical reagents. For example, these peptides can be obtained by screening combina torial phage display libraries (Cosmix, Braunschweig, Germany) as described by Rottgen, P. and Collins, J. (Gene (1995) 164 (2): 243–250). Furthermore, antigenic epitopes of the Trp8 and Trp10 proteins can be identified by the expression of recombinant Trp8 and Trp10 epitope libraries in *E. coli* (Marquart, A. & Flockerzi, V., FEBS Lett. 407 (1997), 137–140; Trost, C., et al., FEBS Lett. 451 (1999) 257–263 and the consecutive screening of these libraries with serum of patients with cancer of the prostate or of the endometrium. Those Trp8 and Trp10 epitopes which are immunogenic and which lead to the formation of antibodies in the serum of the patients can be then be used as Trp8 or Trp10 derived peptide vaccines for immune inventions against cancer cells which express Trp8 or Trp10. Alternatively to the *E. coli* expression system, Trp8 or Trp10 or epitopes of Trp8 and Trp10 can be expressed in mammalian cell lines such as human embryonic kidney (Hek 293) cells (American Type Culture Collection, ATCC CRL 1573).

Finally, compounds useful for therapy of the above described diseases comprise compounds which act as antagonists or agonists on the ion channels Trp8, Trp9 and Trp10. It could be shown that Trp8 is a highly calcium selective ion channel which in the presence of monovalent (namely sodium) and divalent ions (namely calcium) is only permeable for calcium ions (see Example 4, below, and FIGS. 3A, C, E). Under physiological conditions, Trp8 is a calcium selective channel exhibiting large inward currents. This very large conductance of Trp8 channels (as wells as Trp9 and Trp10a/b channels) is useful to establish systems for screening pharmacological compounds interacting with Trp-channels including high throughput screening systems. Useful high throughput screening systems are well known to the person skilled in the art and include, e.g., the use of cell lines stably or transiently transfected with DNA sequences encoding Trp8, Trp9 and Trp10 channels in assays to detect calcium signaling in biological systems. Such systems include assays based on Ca-sensitive dyes such as aequorin, apoaequorin, Fura-2, Fluo-3 and Indo-1.

Accordingly, the present invention also relates to a method for identifying compounds which act as agonists or antagonists on the ion channels Trp8, Trp9 and/or Trp10, said method comprising contacting a test compound with the ion channel Trp8, Trp9 and/or Trp10, preferably by using a system based on cells stably or transiently transfected with DNA sequences encoding Trp8, Trp9 and/or Trp10, and determining whether said test compound affects the calcium uptake.

For administration the above described reagents are preferably combined with suitable pharmaceutical carriers. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Administration of the suitable compositions may be effected by different ways, e.g. by intravenous, intraperetoneal, subcutaneous, intramuscular, topical or intradermal administration. The route of administration, of course, depends on the nature of the tumor and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind and stage of the tumor, general health and other drugs being administered concurrently.

The delivery of the antisense RNAs or ribozymes of the invention can be achieved by direct application or, preferably, by using a recombinant expression vector such as a chimeric virus containing these compounds or a colloidal dispersion system. By delivering these nucleic acids to the desired target, the intracellular expression of Trp8a, Trp8b, Trp10a and/or Trp10b and, thus, the level of Trp8a, Trp8b, Trp10a and/or Trp10b can be decreased resulting in the inhibition of the negative effects of Trp8a, Trp8b, Trp10a and/or Trp10b, e.g. as regards the metastasis formation of PCA.

Direct application to the target site can be performed, e.g., by ballistic delivery, as a colloidal dispersion system or by catheter to a site in artery. The colloidal dispersion systems which can be used for delivery of the above nucleic, acids include macromolecule complexes, nanocapsules, microspheres, beads and lipid-based systems including oil-in-water emulsions (mixed), micelles, liposomes and lipoplexes, The preferred colloidal system is a liposome. The composition of the liposome is usually a combination of phospholipids and steroids, especially cholesterol. The skilled person is in a position to select such liposomes which are suitable for the delivery of the desired nucleic acid molecule. Organ-specific or cell-specific liposomes can be used in order to achieve delivery only to the desired tumor. The targeting of liposomes can be carried out by the person skilled in the art by applying commonly known methods. This targeting includes passive targeting (utilizing the natural tendency of the liposomes to distribute to cells of the RES in organs which contain sinusoidal capillaries) or active targeting (for example by coupling the liposome to a specific ligand, e.g., an antibody, a receptor, sugar, glycolipid, protein etc., by well known methods). In the present invention monoclonal antibodies are preferably used to target liposomes to specific tumors via specific cell-surface ligands.

Preferred recombinant vectors useful for gene therapy are viral vectors, e.g. adenovirus, herpes virus, vaccinia, or, more preferably, an RNA virus such as a Retrovirus. Even more preferably, the retroviral vector is a derivative of a murine or avian retrovirus. Examples of such retroviral vectors which can be used in the present invention are: Moloney murine leukemia virus (MoMuLV), Harvey murine sarcoma virus (HaMuSV), murine mammary tumor virus (MuMTV) and Rous sarcoma virus (RSV). Most preferably, a non-human primate retroviral vector is employed, such as the gibbon ape leukemia virus (GaLV), providing a broader host range compared to murine vectors. Since recombinant retroviruses are defective, assistance is required in order to produce infectious particles. Such assistance can be provided, e.g., by using helper cell lines that contain plasmids encoding all of the structural genes of the retrovirus under the control of regulatory sequences within the LTR. Suitable helper cell lines are well known to those skilled in the art. Said vectors can additionally contain a gene encoding a selectable marker so that the transduced cells can be identified. Moreover, the retroviral vectors can be modified in such a way that they become target specific. This can be achieved, e.g., by inserting a polynucleotide encoding a sugar, a glycolipid, or a protein, preferably an antibody. Those skilled in the art know additional methods for generating target specific vectors. Further suitable vectors and methods for in vitro- or in vivo-gene therapy are described in the literature and are known to the persons skilled in the art; see, e.g., WO 94/29469 or WO 97/00957.

In order to achieve expression only in the target organ, i.e. tumor to be treated, the nucleic acids encoding, e.g. an antisense RNA or ribozyme can also be operably linked to a tissue specific promoter and used for gene therapy. Such promoters are well known to those skilled in the art (see e.g. Zimmermann et al., (1994) Neuron 12, 11–24; Vidal et al.; (1990) EMBO J. 9, 833–840; Mayford et al., (1995), Cell 81, 891–904; Pinkert et al., (1987) Genes & Dev. 1, 268–76).

For use in the diagnostic research discussed above, kits are also provided by the present invention. Such kits are useful for the detection of a target cellular component, which is Trp8a, Trp8b, Trp10a and/or Trp10b or, alternatively, Trp8a, Trp8b, Trp10a and/or Trp10b encoding mRNA or Trp10a/b antisense transcripts, wherein the presence or an increased concentration of Trp8a, Trp8b, Trp10a and/or Trp10b or, alternatively, Trp8a, Trp8b, Trp10a and/or Trp10b encoding mRNA or Trp10a/b antisense transcripts is indicative for a prostate tumor, endometrial cancer, melanoma, chorion carcinoma or cancer of the lung, said kit comprising a probe for detection of Trp8a, Trp8b, Trp9, Trp10a and/or Trp10b or, alternatively, Trp8a, Trp8b, Trp9, Trp10a and/or Trp10b encoding mRNA or Trp10a/b antisense transcripts. The probe can be detectably labeled. Such probe may be a specific antibody or specific oligonucleotide. In a preferred embodiment, said kit contains an anti-Trp8a-, anti-Trp8b-, anti-Trp9-, anti-Trp10a- and/or anti-Trp10b-antibody and allows said diagnosis, e.g., by ELISA and contains the antibody bound to a solid support, for example, a polystyrene microtiter dish or nitrocellulose paper, using techniques known in the art. Alternatively, said kits are based on a RIA and contain said antibody marked with a radioactive isotope. In a preferred embodiment of the kit of the invention the antibody is labeled with enzymes, fluorescent compounds, luminescent compounds, ferromagnetic probes or radioactive compounds. The kit of the invention may comprise one or more containers filled with, for example, one or more probes of the invention. Associated with container(s) of the kit can be a notice in the form prescribed by a governmental agency regulating the manufacture, use or sale of pharmaceuticals or biological products, which notice reflects approval by the agency of manufacture, us or sale for human administration.

EXAMPLES

The following Examples are intended to illustrate, but not to limit the invention. While such Examples are typical of those that might be used, other methods known to those skilled in the art may alternatively be utilized.

Example 1

Materials and Methods (A) Isolation of cDNA Clones and Northern Blot Analysis

Total RNA was isolated form human placenta and prostate using standard techniques. Isolation of mRNA was performed with poly $(A)^+$RNA—spin columns (New England Biolabs, Beverly, USA) according to the instructions of the manufacturer. Poly (a) $^+$RNA was reverse transcribed using the cDNA choice system (Gibco-BRL, Rockville, USA) and subcloned in λ-Zap phages (Stratagene, La Jolla, USA). An human expressed sequence tag (GenBank accession number 1404042) was used to screen an oligo d(T) primed human placenta cDNA library. Several cDNA clones were identified and isolated. Additional cDNA clones were isolated from two specifically primed cDNA libraries primers (SEQ ID NOS: 31 AND 32) 5'-gca tag gaa ggg aca ggt gg-3' and 5'-gag agt cga ggt cag tgg tcc-3'.

cDNA clones were sequenced using a thermocycler (PE Applied Biosystems, USA) and Thermo Sequenase (Amersham Pharmacia Biotech Europe, Freiburg, Germany). DNA sequences were analyzed with an automated sequencer (Licor, Linccoln, USA).

For Northern blot analysis 5 µg human poly $(A)^+$RNA from human placenta or prostate were separated by electrophoresis on 0.8% agarose gels. Poly $(A)^+$RNA was transferred to Hybond N nylon membranes (Amersham Pharmacia Biotech Europe, Freiburg, Germany). The membranes were hyridized in the presence of 50% formamide at 42° C. over night. DNA probes were labelled using $[\alpha^{32}P]dCTP$ and the "ready prime" labelling kit (Amersham Pharmacia Biotech Europe, Freiburg, Germany). Commercial Northern blots were hybridized according to the distributors instructions (Clontech, Paolo Alto, USA).

(B) Construction of Expression Plasmids and Transfection of HEK 293 Cells

Lipofections were carried out with the recombinant dicistronic eucaryotic expression plasmid pdiTRP8 containing the cDNA of Trp8b under the control of the chicken β-actin promotor followed by an internal ribosome entry side (IRES) and the cDNA of the green fluorescent protein (GFP). To obtain pdiTRP8 carrying the entire protein coding regions of TRP8b and the GFP (Prasher, D. C. et al. (1992), Gene 111, 229–233), the 5' and 3'-untranslated sequences of the TRP8b cDNA were removed, the consensus sequence for initiation of translation in vertebrates (Kozak, M. (1987) Nucleic Acids Research15, 8125–8148) was introduced immediately 5' of the translation initiation codon and the resulting cDNA was subcloned into the pCAGGS vector (Niwa, H., Yamamura, K. and Miyazaki, J (1991), Gene 8, 193–199) downstream of the chicken β-actin promotor. The IRES derived from encephalmyocarditis virus (Kim, D. G., Kang, H. M., Jang, S. K. and Shin H. S. (1992) Mol. Cell. Biol. 12, 3636–3643) followed by the GFP cDNA containing a Ser65Thr mutation (Heim, R., Cubitt, A. B., Tsien, R. Y. (1995) Nature 373, 663–664) was then cloned 3' to the TRP8b cDNA. The IRES sequence allows the simultaneous translation of TRP8b and GFP from one transcript. Thus, transfected cells can be detected unequivocally by the development of green fluorescence.

For monitoring of the intracellular $Ca^{2+}$ concentration human embryonic kidney (HEK 293) cells were cotransfected with the pcDNA3-TRP8b vector and the pcDNA3-GFPvector in a molar ratio of 4:1 in the presence of lipofectamine (Quiagen, Hilden, Germany). To obtain pcDNA3-TRP8b the entire protein coding region of TRP8b including the consensus sequence for initiation of translation in vertebrates (Kozak, M. (1987) Nucleic Acids Research15, 8125–8148) was subcloned into the pcDNA3 vector (Invitrogen, Groningen, Netherlands). Calcium monitoring and patch clamp experiments were carried out two days and one day after transfection, respectively.

(C) Chromosomal Localization of the Trp8 Gene

The chromosomal localization of the human TRP8 gene was performed using NIGMS somatic hybrid mapping panel No. 2 (Coriell Institute, Camden, N.J., USA) previously described (Drwinga, H. L., Toji, L. H., Kim, C. H., Greene, A. E., Mulivor, R. A. (1993) Genomics 16, 311–314; Dubois, B. L. and Naylor, S. L. (1993) Genomics 16, 315–319).

(D) In Vitro Translation, Glutathione—Sepharose and Calmodulin Agarose Binding Assay N- and C-terminal Trp8-fragments were subcloned into the pGEX-4T2 vector (Amersham Pharmacia Europe, Freiburg, Germany) resulting in glutathione-S-transferase (GST)-Trp8 fusion constructs (FIG. 4). The GST-TRP8-fusion proteins were expressed in E. coli BL 21 cells and purified using glutathione—sepharose beads (Amersham Pharmacia Biotech Europe, Freiburg, Germany).

In vitro translation of human Trp8 cDNA and Xenopus laevis calmodulin cDNA (Davis, T. N. and Thorner, J. Proc. Natl. Acad. Sci. USA 86, 7909–7913.) was performed in the presence of $^{35}S$-methionine using the TNT coupled transcription/translation kit (Promega, Madison, USA). Translation products were purified by gel filtration (Sephadex G50, Amersham Pharmacia Biotech Europe, Freiburg, Germany) and equal amounts of $^{35}S$ labeled probes were incubated for 2 h with glutathione beads bound to GST—Trp8 or calmodulin—agarose (Calbiochem) in 50 mM Tris-HCl, pH 7.4, 0.1% Triton X-100, 150 mM NaCl in the presence of 1 mM $Ca^{2+}$ or 2 mM EGTA. After three washes, bound proteins were eluted with SDS sample buffer, fractionated by SDS-PAGE and $^{35}S$ labeled proteins were detected using a Phosphor Imager (Fujifilm, Tokyo, Japan).

(E) Calcium Measurements

The intracellular $Ca^{2+}$ concentration ($[Ca^{2+}]_i$) was determined by dual wavelength fura-2 fluorescence ratio measurements (Tsien, R. Y. (1988) Trends Neurosci. 11, 419–424) using a digital imaging system (T.I.L.L. Photonics, Planegg, Germany). HEK cells were grown in minimal essential medium in the presence of 10% fetal calf serum and cotransfected with the pcDNA3-TRP8b vector and the pCDNA3-GFPvector as described above (B). Transfected cells were detected by development of green fluorescence. The cells were loaded with 4 µM fura-2/AM (Molecular Probes, Oreg., USA) for one hour. After loading the cells were rinsed 3 times with buffer B1 (10 mM Hepes, 115 mM NaCl, 2 mM $MgCl_2$, 5 mM KCl, pH 7.4) and the $[Ca^{2+}]_i$ was calculated from the fluorescence ratios obtained at 340 and 380 nm excitation wavelengths as described (Garcia, D. E., Cavalié, A. and Lux, H. D. (1994) J. Neurosci 14, 545–553).

(F) Electrophysiological Recordings

HEK cells were transfected with the eucaryotic expression plasmid pdiTRP8 described in (B) and electrophysiolocigal recordings were carried out one day after transfection. Single cells were voltage clamped in the whole cell mode of the patch clamp technique as described (Hamill, O. P., Marty, A., Neher, E., Sakmann, B. and Sigworth, F. J. (1981) Pflügers Arch. 391, 85–100; Philipp, S., Cavalié, A., Freichel, M., Wissenbach, U., Zimmer, S., Trost, C., Marquart, A., Murakami, M. and Flockerzi, V. (1996) EMBO J. 6166–6171). The pipette solution contained contained (mM): 140 aspartic acid, 10 EGTA, 10 NaCl, 1 MgCl2, 10 Hepes (pH 7.2 with CsOH) or 125 CsCl, 10 EGTA, 4 $CaCl_2$ 10 Hepes (pH 7, 2 with CsOH). The bath solution contained (mM): 100 NaCl, 10 CsCl, 2 $MgCl_2$, 50 mannitol, 10 glucose, 20 Hepes (pH 7, 4 with CsOH) and 2 $CaCl_2$, or no added $CaCl_2$ (—$Ca^{2+}$ solution). Divalent free bath solution contained (mM): 110 N-methyl-D-glucamine (NMDG). Whole cell currents were recorded during 100 msec voltage ramps from −100 to +100 mV at varying holding potentials.

(G) In Situ Hybridization

In situ hybridizations were carried out using formalin fixed tissue slices of 6–8 µM thickness. The slices were hydrated and incubated in the presence of PBS buffer including 10 µg /ml proteinase K (Roche Diagnostics, Mannheim, Germany) for 0.5 h. The slices were hybridized at 37° C. using biotinylated deoxy-oligonucleotides (0.5 pmol/µl) in the presence of 33% formamide for 12 h. Furthermore the slices were several times rinsed with 2×SSC and incubated at 25° C. for 0.5 h with avidin/biotinylated horse raddish peroxidase complex (ABC, DAKO, Santa Barbara, USA). After several washes with PBS buffer the slices were incubated in the presence of biotinylated tyramid and peroxide (0.15% w/v) for 10 min, rinsed with PBS buffer and additionally incubated with ABC complex for 0.5 h. The slices were washed with PBS buffer and incubated in the presence of DAB solution (diaminobenzidine (50 µg/ml), 50 mM Tris/EDTA buffer pH 8.4, 0.15% $H_2O_2$ in N, N-dimethyl-formamide; Merck, Darmstadt, Germany), The detection was stopped after 4 minutes by incubating the slides in water. Tyramid was biotinylated by incubating NHS-LC Biotin (sulfosuccinimidyl-6-(biotinimid)-hexanoat), 2.5 mg/ml; Pierce, Rockford, USA) and tyramin-HCl (0.75 mg/ml, Sigma) in 25 mM borate buffer pH 8.5 for 12 h. The tyramid solution was diluted 1–5:1000 in PBS buffer.

(H) GenBank Accession Numbers: TRP8a, Aj243500; TRP8b Aj243501

Example 2

Expression of TRP8 Transcripts

Figure 1B:
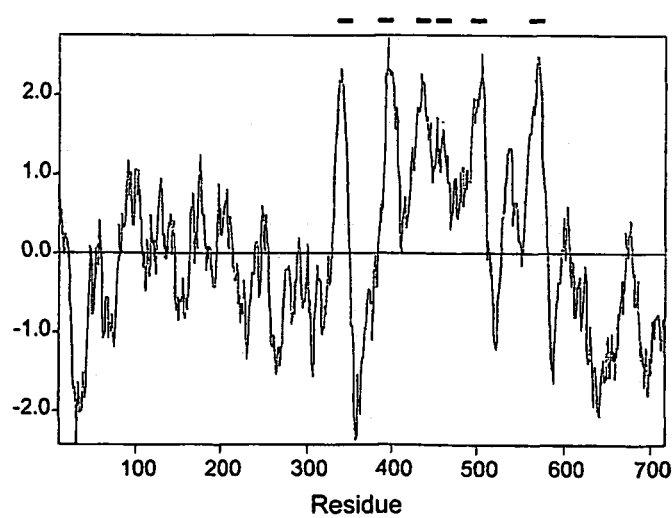

In search of proteins distantly related to the TRP family of ion channels, an human expressed sequence tag (EST, GenBank accession number 1404042) was identified in the GenBank database using BLAST programs (at the National Center for Biotechnology Information (NCBI);

Altschul, S. F., Gish, W., Miller, W., Myers, E. W. and Lipman, D. J. J. (1990) Mol. Biol. 5, 403–410) being slightly homologous to the VR1 gene. Several human placenta cDNA libraries were constructed and screeened with this EST DNA as probe. Several full length cDNA clones were identified and isolated. The full length cDNA clones encoded two putative proteins differing in three amino acids and were termed Trp8a and Trp8b (FIGS. 1c, 2a, 7 and 8A). This finding was reproduced by isolating cDNA clones from two cDNA libraries constructed from two individual placentas. The derived protein sequence(s) comprises six transmembrane domains, a characteristic overall feature of trp channels and related proteins (FIG. 1b). The sequence is closely related to the meanwhile published calcium uptake transport protein 1 (CaT1), isolated from rat intestine (Peng, J. B., Chen, X. Z., Berger, U. V., Vassilev, P. M., Tsukaguchi, H., Brown, E. M. and Hediger M. A. (1999) J Biol Chem. 6; 274, 22739–22746) and to the epithelial calcium uptake channel (ECaC) isolated from rabbit kidney (Hoenderop, J. G., van der Kemp, A. W., Hartog, A., van de Graaf, S. F., van Os, C. H., Willems, P. H. and Bindels, R. J. (1999) J Biol Chem. 26; 274, 8375–8378). Expression of Trp8a/b transcripts are detectable in human placenta, pancreas and prostate (FIG. 5) and the size of the Northern signal (3.0 kb) corresponds with the size of the isolated full length cDNAs. In addition, a shorter transcript of 1.8 kb, probably a splice variant, is detectable in human testis. The Trp8 mRNA is not expressed in small intestine or colon (FIG. 5) implicating that Trp8 is not the human ortholog of the rat CaT1 or rabbit ECaC proteins. To investigate whether there are other related sequences Trp8a/b derived primers (SEQ ID NOS: 33 AND 34) (UW241, 5'-TAT GAG GGT TCA GAC TGC-3' and UW242, 5'-CAA AGT AGA TGA GGT TGC-3') were used to amplify a 105 bp fragment from human genomic DNA being 95% identical on the nucleotide level to the Trp8 sequence (data not shown). This indicates the existence of several similar sequences in humans at least at the genomic level.

Example 3

Two Variants of the Trp8 Protein (Trp8a and Trp8b) Arise by Polymorphism

Figures 2A, 2B:
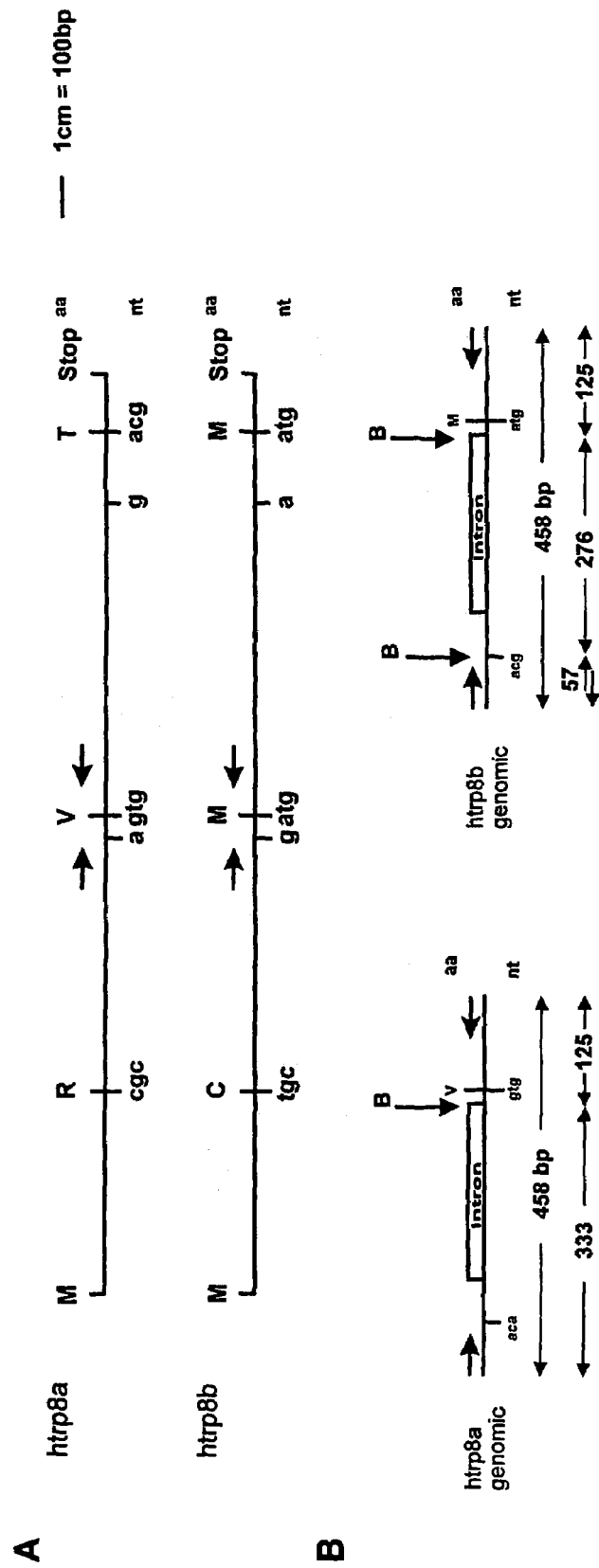
FIG. 2: A, polymorphism of the Trp8 gene. The polymorphic variants Trp8a and Trp8b differ in five base pairs resulting in three amino acid exchanges in the derived protein sequences. Specific primers were derived from the Trp8 gene as indicated by arrows. B, the Trp8a and Trp8b genes are distinguishable by a single restriction site. Genomic fragments of the Trp8 gene can be amplified using specific primers (shown in A). The genomic fragment of the Trp8b gene contains an additional site of the restriction enzyme BSP1286I (B). C, the Trp8 gene is located on chromosome 7. D, genotyping of eleven human subjects. A 458 bp genomic fragment of the Trp8 gene was amplified using specific primers (shown in A) and restricted with BSP1286I. The resulting fragments were analyzed by PAGE electrophoresis.
Figure 2C:
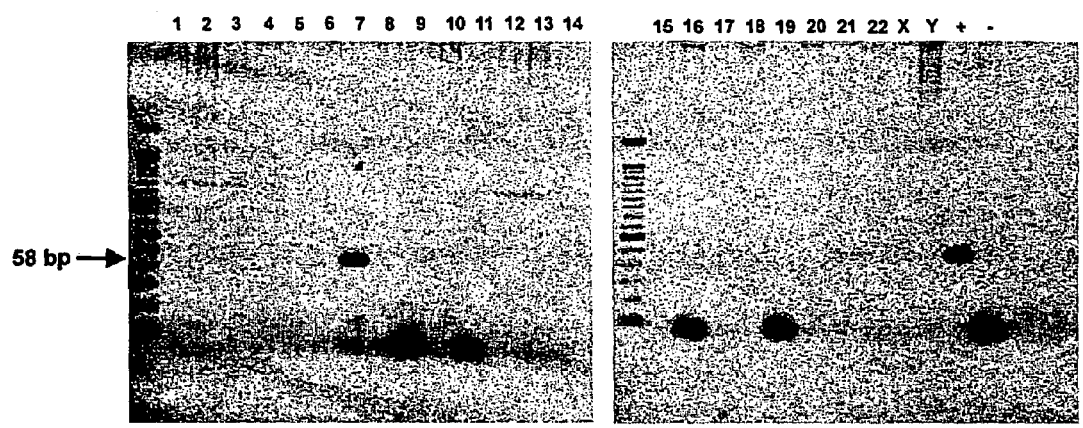
Figure 2D:
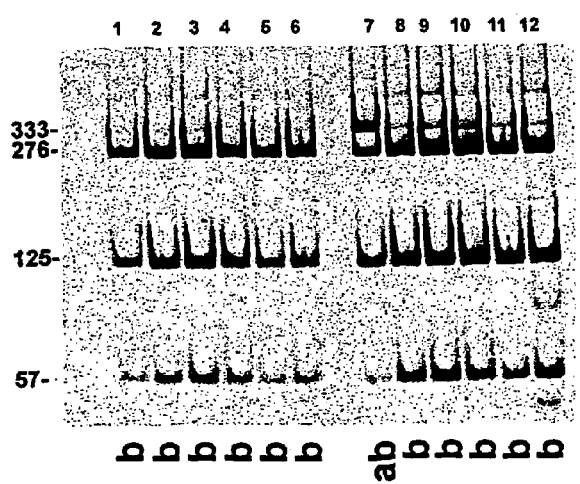

Two variants of the Trp8 cDNA were isolated from human placenta (FIGS. 2A, 7 and 8A) which encoded two proteins which differ in three amino acids and were termed Trp8a and Trp8b. Trp8a/b specific primers were designed to amplify a DNA fragment of 458 bp of the Trp8 gene from genomic DNA isolated from human T-lymphocytes (primer pair (SEQ ID NOS: 35 AND 36): UW243, 5'-CAC CAT GTG CTG CAT CTA CC-3' and UW244, 5'-CAA TGA CAG TCA CCA GCTCC-3'). The amplification product contains a part of the sequence where the derived protein sequence of Trp8a comprises the amino acid valine and the Trp8b sequence methionine as well as a silent base pair exchange (g versus a) and an intron of 303 bp (FIGS. 2A, B). Both variants of the Trp8 genes (a, b) were amplified from genomic DNA in equal amounts indicating the existence of both variants in the human genome and therefore being not the result of RNA editing (FIG. 2B). The Trp8a gene can be distinguished from the Trp8b gene by cutting the genomic fragment of 458 bp with the restriction enzyme Bsp1286I (FIG. 2B). Using human genomic DNA isolated from blood of twelve human subjects as template, the 458 bp fragment was amplified and restricted with BSP1286I. In eleven of the tested subjects only the Trp8b gene is detectable, while one subject (7) contains Trp8a and Trp8b genes (FIG. 2D). These implicates that the two Trp8 variants arise by polymorphism and do not represent individual genes. Using Trp8 specific primers and chromosomal DNA as template, the Trp8 locus is detectable on chromosome 7 (FIG. 2C).

Example 4

Trp8b is a Calcium Permeable Channel

The protein coding sequence of the Trp8b cDNA was subcloned into pcDNA3 vector (Invitrogen, Groningen, Netherlands) under the control of the cytomegalovirus promotor (CMV). Human embryonic kidney (HEK 293) cells were cotransfected with the Trp8b pcDNA3 construct (pcDNA3-Trp8b vector) and the pcDNA3-GFPvector encoding the green fluorescent protein (GFP) in 4:1 ratio. The Trp8b cDNA and the cDNA of the reporter, GFP, was transiently expressed in human embryonic kidney (HEK 293) cells. The intracellular $Ca^{2+}$ concentration ($[Ca^{2+}]_i$) and changes of $[Ca^{2+}]_i$ were determined by dual wavelength fura-2 fluorescence ratio measurements (FIG. 3F) in cotransfected cells which were identified by the green fluorescence of the reporter gene GFP.

Dual wavelength fura-2 fluorescence ratio measurement is a standard procedure (e.g. in: An introduction of Molecular Neurobiology (ed. Hall, Z. W.) Sinauer Associates, Sunderland, USA (1992)) using fura-2, which is a fluorescent $Ca_{2+}$ sensitive dye and which was designed by R. Y. Tsien (e.g. Trends Neurosci. 11, 419–424 (1988) based upon the structure of EGTA. Its fluorescence emission spectrum is altered by binding to $Ca^{2+}$ in the physiological concentration range. In the absence of $Ca^{2+}$, fura-2 fluoresces most strongly at an excitation wavelength of 385 nm; when it binds $Ca^{2+}$, the most effective excitation wavelength shifts to 345 nm. This property is used to measure local $Ca^{2+}$ concentrations within cells. Cells can be loaded with fura-2 esters (e.g. fura-2AM) that diffuse across cell membranes and are hydrolyzed to active fura-2 by cytosolic esterases.

Figures 3A, 3B, 3C, 3D, 3E, 3F:
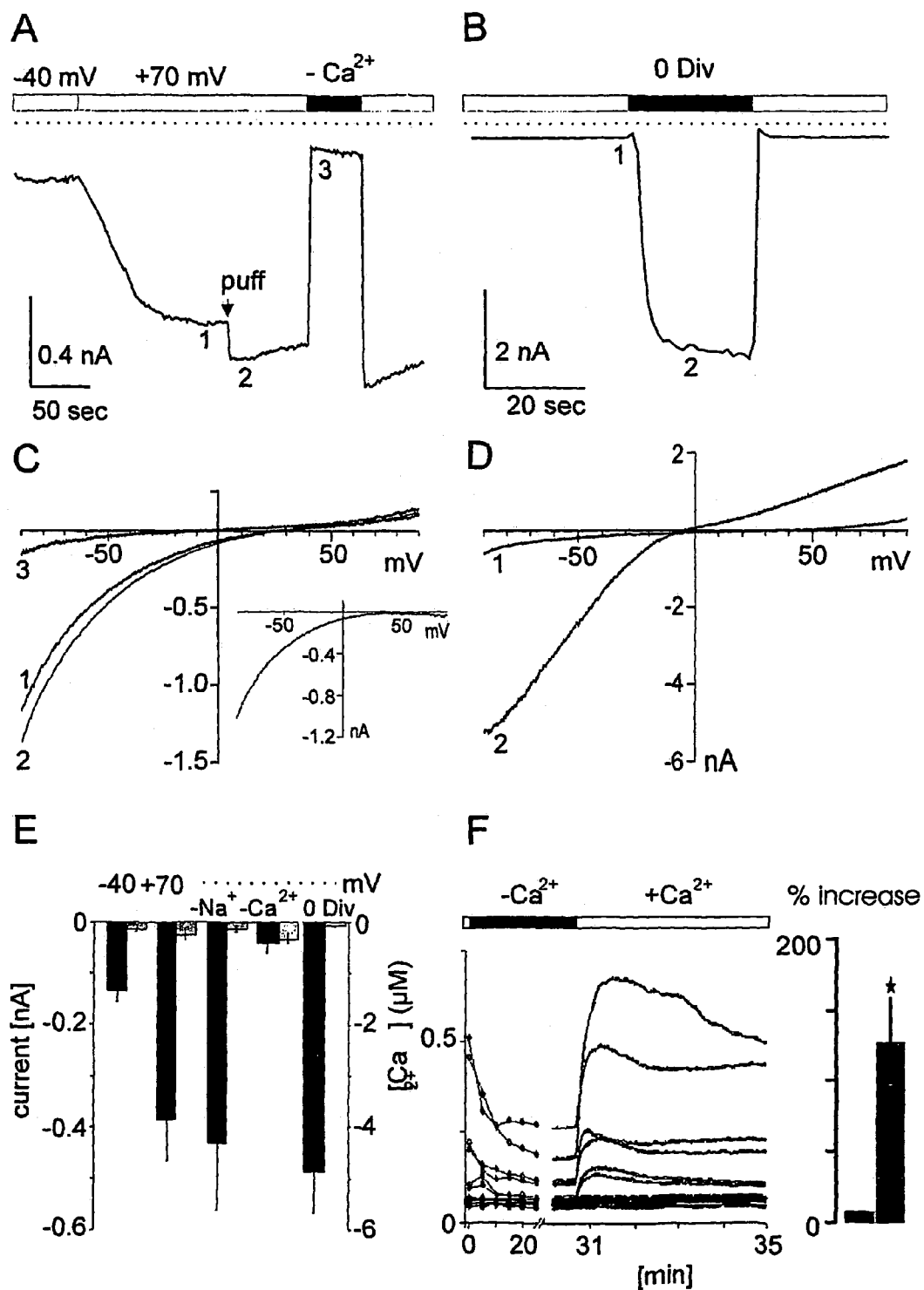
FIG. 3: The Trp8b protein is a calcium selective ion channel. A, representative trace of a pdiTrp8b transfected HEK 293 cell. Trp8b mediated currents are activated by voltage ramps (−100 mV−+100 mV) of 100 msec at −40 mV or +70 mV holding potential. 1, Trp8b currents in the presence at 2 mm $[Ca^{2+}]_o$; 2, effect of solution switch alone 3, switch to nominal zero calcium solution. B, Trp8b currents in the presence of zero divalent cations. C, current voltage relationship of the currents shown in A. Inset, leak subtracted current. D, current voltage relationship of the current shown in B. E, statistics of representative experiments. Black: Trp8 transfected cells, gray: control cells. Columns from left to right: Trp8 currents at −40 mV (n=12) and +70 mV holding potential (n=12). Trp8 currents in standard bath solution including 120 mM NMDG without sodium (n=7) and with nominal zero calcium ions (n=8) or in the presence of 1 mM EGTA with zero divalent cations (n=6). F, representative changes in $[Ca^{2+}]_i$ in Trp8b transfected HEK cells (gray) and controls (black) in the presence or absence of 1 mM $[Ca^{2+}]_o$. Inset, relative increase of cytosolic calcium concentration of Trp8b transfected HEK cells, before and after readdition of 1 mM $[Ca^{2+}]_o$ in comparison to control cells.

In the presence of 1 mM $Ca^{2+}$, Trp8 expressing cells typically contained more than 300 nM cytosolic $Ca^{2+}$, while non transfected controls contained less than 100 nM $Ca^{2+}$ ions (FIG. 3F).

When Trp8b transfected cells were incubated without extracellular $Ca^{2+}$, the intracellular $Ca^{2+}$ concentration ($[Ca^{2+}]_i$) decreased to levels comparable to non transfected cells. Readdition of 1 mM $Ca^{2+}$ to the bath resulted in significant increase of the cytosolic $[Ca^{2+}]$ in Trp8b transfected cells, but not in controls (FIG. 3F). After readdition of $Ca^{2+}$ ions to the bath solution, the cytosolic $Ca^{2+}$ concentration remains on a high steady state level in the Trp8b transfected cells.

Example 5

Trp8 Expressing Cells Show Calcium Selective Inward Currents

To characterize in detail the electrophysiological properties of TRP8, TRP8 and GFP were coexpressed in HEK293 cells using the dicistronic expression vector pdiTRP8 and measured currents using the patch clamp technique in the whole cell mode (Hamill, O. P., Marty, A., Neher, E., Sakmann, B. and Sigworth, F. J. (1981) Pflugers Arch., 391, 85–100).

The eucaryotic expression plasmid pdiTRP8 contains the cDNA of Trp8b under the control of the chicken β-actin promotor followed by an internal ribosome entry side (IRES) and the cDNA of the green fluorescent protein (GFP). To obtain pdiTRP8 carrying the entire protein coding regions of TRP8b and the GFP (Prasher, D. C. et al. (1992), Gene 111, 229–233), the 5' and 3'-untranslated sequences of the TRP8b cDNA were removed, the consensus sequence for initiation of translation in vertebrates (Kozak, M. (1987) Nucleic Acids Research15, 8125–8148) was introduced immediately 5' of the translation initiation codon and the resulting cDNA was subcloned into the pCAGGS vector (Niwa, H., Yamamura, K. and Miyazaki, J (1991), Gene 8, 193–199) downstream of the chicken β-actin promotor. The IRES derived from encephalmyocarditis virus (Kim, D. G., Kang, H. M., Jang, S. K. and Shin H. S. (1992) Mol. Cell. Biol. 12, 3636–3643) followed by the GFP cDNA containing a Ser65Thr mutation (Heim, R., Cubitt, A. B., Tsien, R. Y. (1995) Nature 373, 663–664) was then cloned 3' to the TRP8b cDNA. The IRES sequence allows the simultaneous translation of TRP8b and GFP from one transcript. Thus, transfected cells can be detected unequivocally by the development of green fluorescence.

In the presence of 2 mM external calcium, Trp8b transfected HEK cells show inwardly rectifying currents, the size of which depends on the level of intracellular calcium and the electrochemical driving force. The resting membrane potential was held either at −40 mV, or, to lower the driving force for calcium influx in between pulses, at +70 mV. Current traces were recorded in response to voltage ramps from −100 to +100 mV, that were applied every second. To monitor inward and outward currents over time, we analyzed the current size at −80 and +80 mV of the ramps. FIG. 3A shows a representative trace of the current at −80 mV over time. Both at a holding potential of −40 mV or at +70 mV, the currents are significantly larger than in cells transfected with only the GFP containing vector (FIG. 3E). Interestingly, after changing to a positive holding potential, current size in Trp8 transfected cells slowly increases and reaches steady state after approximately 70 seconds (FIG. 3A). To determine the selectivity of the induced currents, we then perfused the cells with solutions that either contain no sodium, no added $Ca^{2+}$ (FIGS. 3A, C) or a sodium containing, but divalent ion free bath solution. To control for the effect of the solution change alone, we also perfused with normal bath (see puff in FIG. 3A). While removal of external $Ca^{2+}$ completely abolishes the trp 8 induced currents—the remaining current being identical in size and shape to the control (FIGS. 3A, C, E), removal of external sodium has no effect (FIG. 3E). An important hallmark of calcium selective channels (e.g. Vennekens, R., Hoenderop, G. J., Prenen, J., Stuiover, M., Willems, PHGM, Droogmans, G., Nilius, B. and Bindels, R. J. M (1999) J. Biol. Chem. 275, 3963–3969), is their ability to conduct sodium only if all external divalent ions, namely $Ca^{2+}$ and magnesium are removed. To test whether the trp 8 channel conforms with this phenomenon normal bath solution was switched to a solution containing only sodium and 1 mM EGTA. As can be seen in FIGS. 3B and D, Trp8 transfected cells can now conduct very large sodium currents. Interestingly, immediately after the solution change, the currents first become smaller before increasing rapidly, indicating that the pore may initially still be blocked by calcium a phenomenon usually called anomalous mole fraction behaviour (Warnat, J., Philipp, S., Zimmer, S., .Flockerzi, V., and Cavalié A.(1999) J. Physiol. (Lond) 518, 631–638). The measured outward currents of Trp8 transfected cells in normal bath solution are not significantly different from non-transfected control cells or cells which only express the reporter gene GFP. As the removal of external $Ca^{2+}$ abolishes the Trp8 specific current, the remaining current was subtracted from the current before the solution change to obtain the uncontaminated Trp8 conductance (see inset in FIG. 3C). As expected from the given ionic conditions (high EGTA inside, 2 mM $Ca^{2+}$ outside), the current-voltage relationship now shows prominent inward rectification with little to no outward current.

Both the time course of the development of Trp8 currents and the size of the currents depend on the frequency of stimulation (data not shown), the internal and external $Ca^{2+}$ concentration and the resting membrane potential, suggesting that Trp8 calcium conductance is intrically regulated by a $Ca^{2+}$ mediated feedback mechanisms.

Example 6

$Ca^{2+}$/Calmodulin Binds to the C-terminus of the Trp8 Protein

Figures 4A, 4B, 4C:
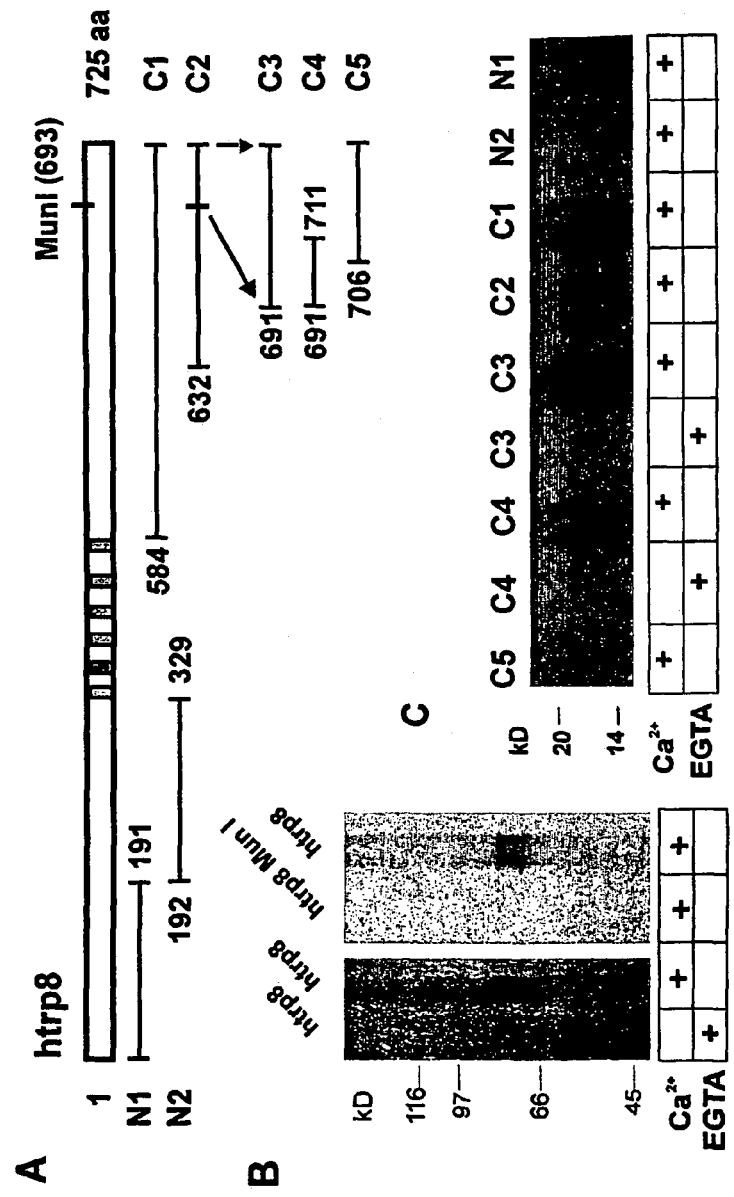
FIG. 4: The C-terminal region of the Trp8 protein binds calmodulin. A, N- and C-terminal fragments of the Trp8 protein used for calmodulin binding studies. B, the Trp8 protein and a truncated Trp8 protein which was in vitro translated after MunI cut of the cDNA, which lacks the C-terminal 32 amino acid residues, were in vitro translated in the presence of $^{35}$S-methionine and incubated with calmodulin coupled agarose beads in the presence of 1 mM $Ca^{2+}$ or 2 mM EGTA. C, calmodulin binding to N- and C-terminal fragments of the Trp8 protein in the presence of $Ca^{2+}$ (1 mM) or EGTA (2 mM)

To test whether calmodulin, a prime mediator of calcium regulated feedback, is involved, first it was investigated biochemically whether Trp8 protein can bind calmodulin. Trp8 cDNA was in vitro translated in the presence of $^{35}S$-methionine and the product incubated with calmodulin-agarose beads. After several washes either in the presence or abscence of $Ca^{2+}$, the beads were incubated in Laemmli buffer and subjected to SDS-polyacrylamide gel electrophoresis. In the presence of $Ca^{2+}$ (1 mM), but not in the absence of $Ca^{2+}$, Trp8 protein binds to calmodulin (FIG. 4B).

To narrow down the binding site, two approaches were undertaken: Firstly, GST-TRP8 fusion proteins of various intracellular domains of Trp8 were constructed, expressed in E. coli and bound to gluthathione sepharose beads. These beads were then incubated with in vitro translated $^{35}S$-labeled calmodulin, washed and subjected to gel electrophoresis. Secondly, truncated versions of in vitro translated Trp8 protein were used in the above described binding to calmodulin-agarose. As shown in FIGS. 4A, and C, fusion proteins of the N-terminal region (N1, N2) of Trp8 did not bind calmodulin, while C-terminal fragments (C1, C2, C3, C4) showed calmodulin binding in the presence of calcium (for localization of fragments within the entire Trp8 protein see FIG. 4C). Accordingly, a truncated version of in vitro translated Trp8, which lacks the C-terminal 32 amino acid residues did not bind to calmodulin-agarose (4B). We have restricted the calmodulin binding site to amino acid residues 691 to 711 of the Trp8 protein. This calmodulin binding site does not resemble the typical conserved IQ—motif of conventional myosins, but has limited sequence homology to the calcium dependent calmodulin binding site 1 of the transient receptor potential like (trp1) protein of Drosophila melanogaster (Warr and Kelly, 1996) with several charged amino acid residues conserved. The sequence of the calmodulin binding site of the Trp8 protein resembles a putative amphipathic α-helical wheel structure with a charged and a hydrophobic site according to a model proposed by Erickson-Vitanen and De Grado (1987, Methods Enzymol. 139, 455–478.).

Example 7

Expression of Trp8 Transcripts in Human Placenta and Pancreas

Several slides from a human placenta of a ten week old abort were used for in situ hybridization experiments. The in situ hybridization experiments revealed expression of Trp8 transcripts in human placenta (FIG. 5B). Expression was detectable in trophoblasts and syncytiotrophoblasts of the placenta, but not in Langhans cells.

Figure 5A:
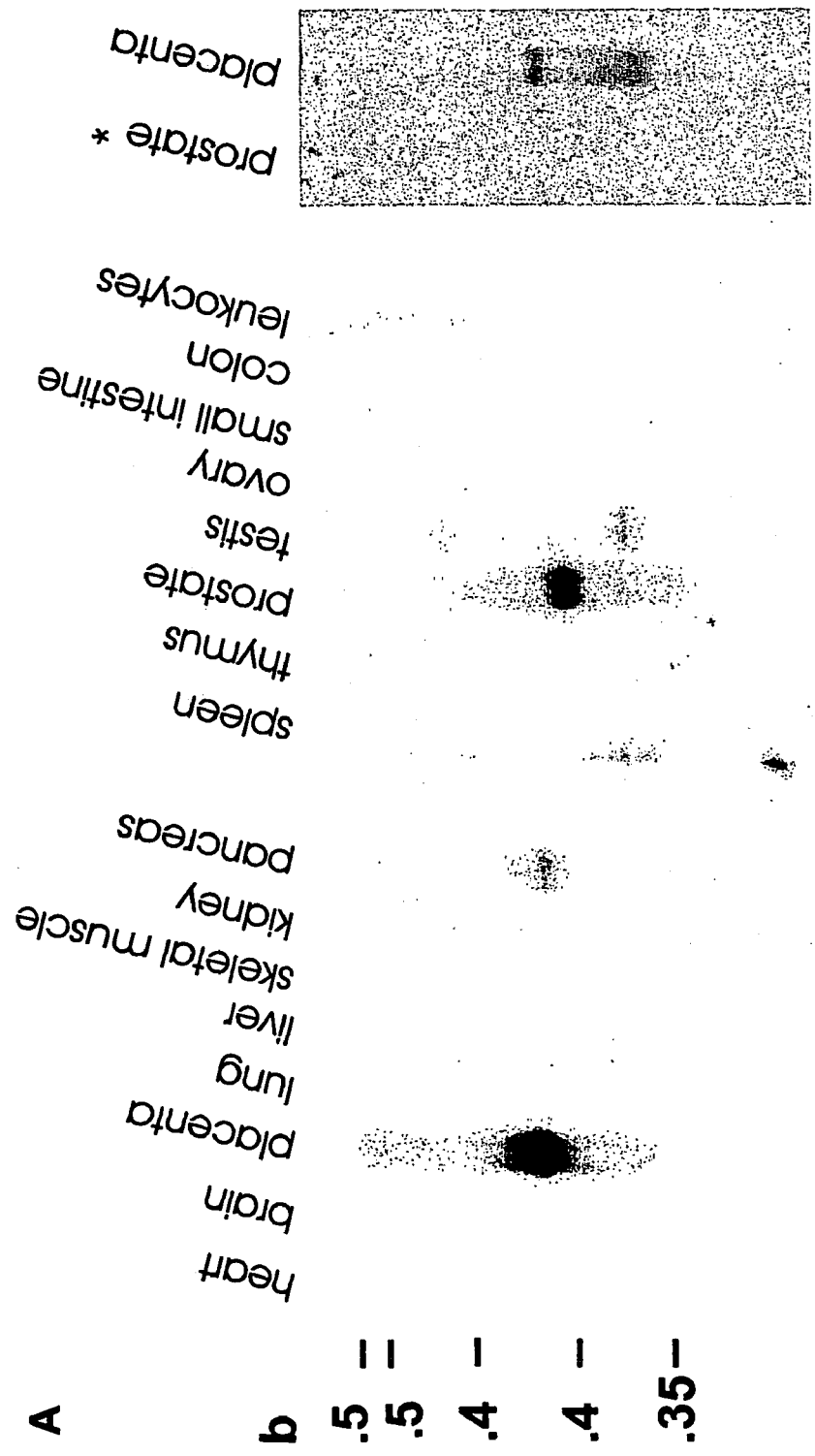
FIG. 5: Expression pattern of the Trp8 cDNA. A, Northern blots (left panels, Clontech, Palo Alto) were hybridized using a 348 bp NcoI/BamHI fragment of the Trp9 cDNA. The probe hybridizes to mRNA species isolated from the commercial blot, but not to mRNA species isolated from benign prostate hyperplasia (right panel, mRNA isolated from 20 human subjects with benign prostate hyperplasia). B,C, in situ hybridization with biotinylated Trp8 specific oligonucleotides on slides of human tissues. Left column antisense probes, right column sense probes. D, antisense probes.
Figure 5B:
Figure 5C:
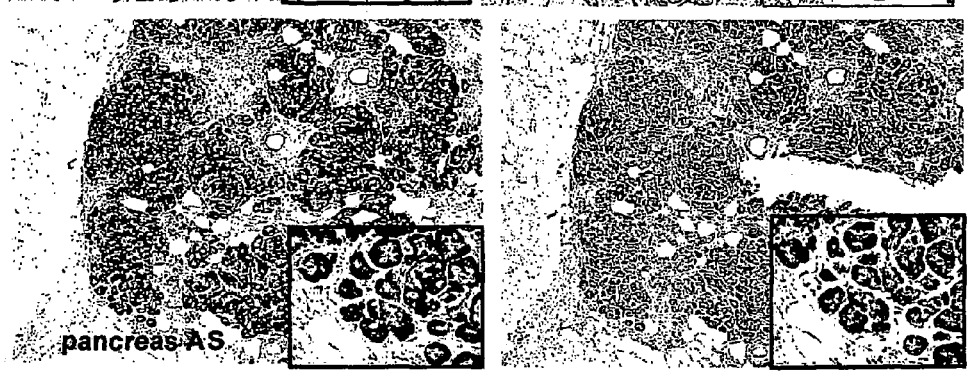
Figure 5D:
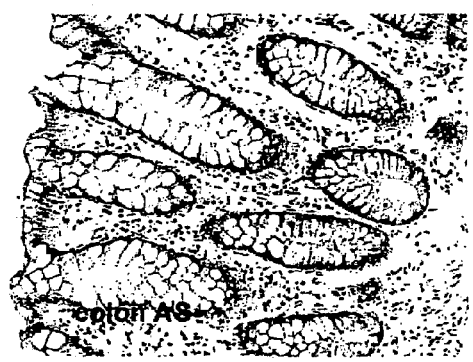

Trp8 transcripts are detectable in human pancreas (FIG. 5A). Therefore Trp8 probes were hybridized to tissue sections of human pancreas. The pancreatic tissues were removed from patients with pancreas cancer. Trp8 expression is detectable in pancreatic acinar cells, but not in Langerhans islets (FIG. 5C). No Trp8 expression was found in regions of pancreatic carcinomas (data not shown).

Furthermore, the Trp8 cDNA is not detectable in human colon nor in human kidney by in situ hybridization as well as by Northern analysis (FIGS. 5A, D). The Northern results taken together with the in situ expression data indicate that the Trp8 protein is not the human ortholog of the CaT1 and ECaC channels cloned from rat intestine (Peng, J. B., Chen, X. Z., Berger, U. V., Vassilev, P. M., Tsukaguchi, H., Brown, E. M. and Hediger M. A. (1999) J Biol Chem. 6; 274, 22739–22746) and from rabbit kidney (Hoenderop, J. G., van der Kemp, A. W., Hartog, A., van de Graaf, S. F., van Os, C. H., Willems, P. H. and Bindels, R. J. (1999) J Biol Chem. 26; 274, 8375–8378), respectively. Trp8 is unlikely to represent the human version of CaT1 as its expression is undetectable in the small intestine and colon tissues where CaT1 is abundantly expressed. If, however, Trp8 is the human version of rat CaT1, a second gene product appears to be required for $Ca^{2+}$ uptake in human small intestine and colon attributed to CaT1 in rat small intestine and colon.

Example 8

Figures 6A, 6B:
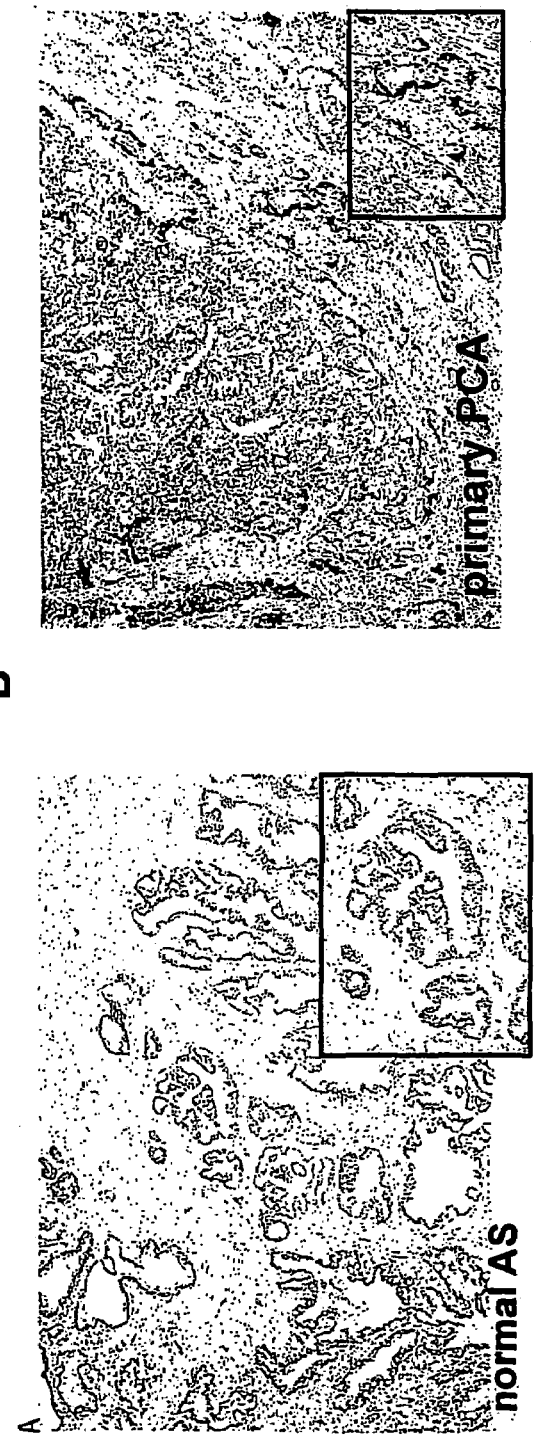
FIG. 6: Differential expression of Trp8 cDNA in human prostate. A–F, in situ hybridization with prostatic tissues. A, normal prostate, B, primary carcinoma, C, benign hyperplasia, D, rezidive carcinoma, E, prostatic intraepithelial neoplasia, F, lymphnode metastasis of the prostata.
Figure 6C:
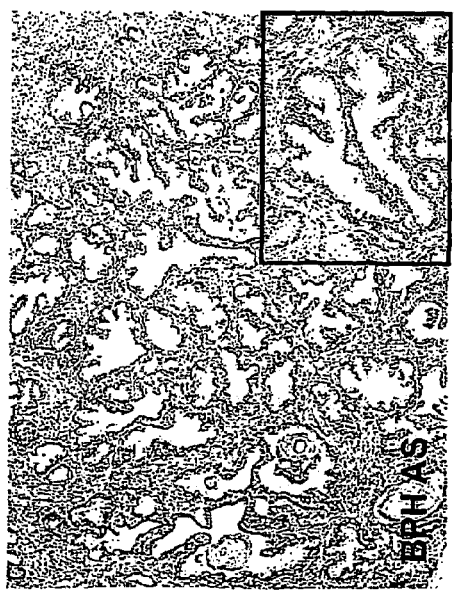
Figure 6D:
Figure 6E:
Figure 6F:
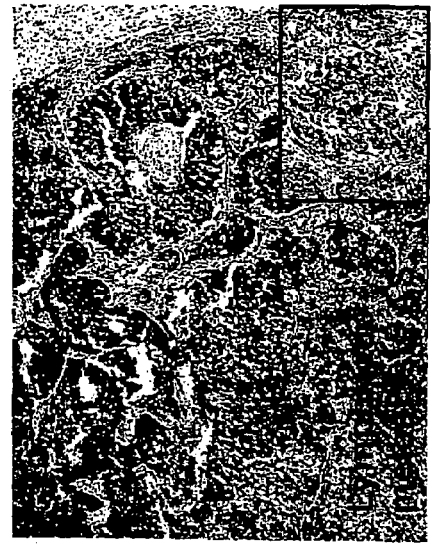
Figure 12A:
Figure 12B:
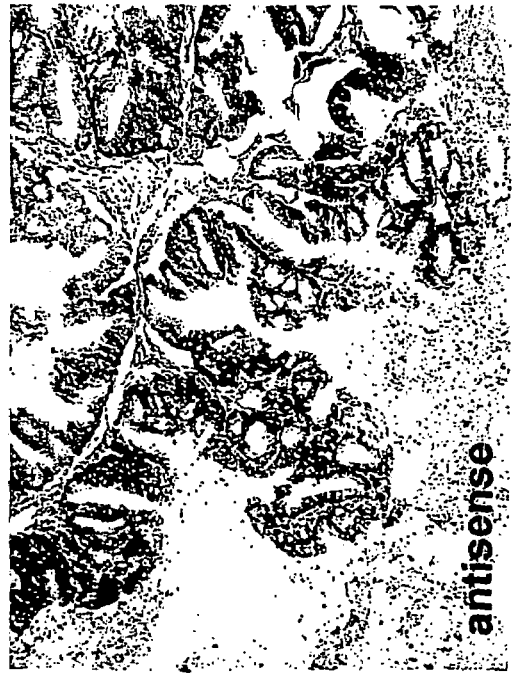
Figures 12C, 12D:
Figure 12E:
Figure 12F:
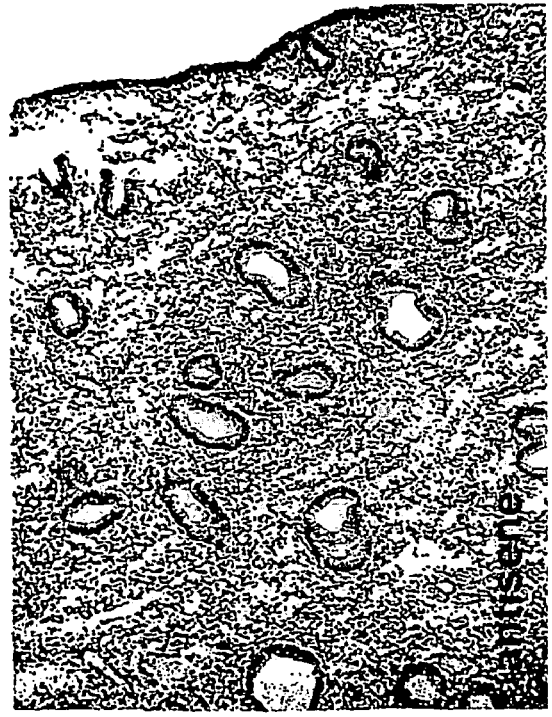

Differential Expression of Trp8 Transcripts in Benign and Malign Tissue of the Prostate The Trp8 transcripts are expressed in human prostate as shown by hybridization of a Trp8 probe to a commercial Northern blot (Clontech, Palo Alto, USA) (FIG. 5A). Trp8 transcripts were not detectable by Northern blot analysis using pooled mRNA of patients with benign prostatic hyperplasia (BPH) (FIG. 5A, prostate*). To examine Trp8 expression on the cellular level, sections of prostate tissues were hybridized using Trp8 specific cDNA probes (Table 3). Expression of Trp8 transcripts is not detectable in normal prostate (n=3), benign hyperplasia (BPH, n=15) or prostatic intraepithelial neoplasia (PIN, n=9) (FIGS. 6A, C, E). Trp8 transcripts were only detectable in prostate carcinoma (PCA), although with different expression levels. Low expression levels were found in primary carcinomas (2–10% of the carcinoma cells, n=8) (FIG. 7B). Much stronger expression was detectable in rezidive carcinoma (10–60%) (FIG. 7D, n=6) and metastases of the prostate (60–90%, n=4) (FIG. 7F). Thus it has to be concluded that the commercial Northern blot used in FIG. 5A contains not only normal prostate mRNA as indicated by the distributor. According to the distributors instructions the prostate mRNA used for this Northern blot was collected from 15 human subjects in the range of 14 to 60 years of age. This prostate tissue was not examined by pathologic means. Since Trp8 expression is not detectable in normal or benign prostate, this finding implicates that the mRNA used for this Northern blot was extracted in part from prostatic carcinoma tissue. To summarize, Trp8 expression is only detectable in malign prostate and, thus, the Trp8 cDNA is a marker for prostate carcinoma. The results are summarized in Table 4.

TABLE 3

Trp8 probes used for in situ hybridization:

Probes (antisense)

1.) 5' TCCGCTGCCGGTTGAGATCTTGCC 3'

2.) 5' CTTGCTCCATAGGCAGAGAATTAG 3'

3.) 5' ATCCTCAGAGCCCCGGGTGTGGAA 3'

Controls (sense)

1.) 5' GGCAAGATCTCAACCGGCAGCGGA 3'

2.) 5' CTAATTCTCTGCCTATGGAGCAAG 3'

3.) 5' TTCCACACCCGGGGCTCTGAGGAT 3'

TABLE 4

| Prostate | total | negative | positive |
|---|---|---|---|
| normal | 3 | 3 | 0 |
| BPH | 15 | 15 | 0 |
| PIN | 9 | 9 | 0 |
| carcinoma | 18 | 1 | 17 |

(B) Differential Expression of Trp8 Transcripts in Benign and Malign Tissue of the Uterus Moreover it could be shown that Trp8 is expresed in endometrial cancer (also called cancer of the uterus, to be distinguished from uterine sarcoma or cancer of the cervix) whereas no expression was observed in normal uterus tissue. Thus, Trp8 also is a specific marker for the diagnosis of the above cancer (FIG. 12).

Example 9

Characterization of Trp9

The complete protein coding sequence of Trp9 was determined (FIG. 9). Trp 9 transcripts are predominantly expressed in the human prostate and in human colon. As it could be shown by Northern blot analysis, there is no difference of the expression of TRP9 in benigne prostata hyperplasia (BPH, FIG. 13, upper panel left) or prostate carcinoma (FIG. 13, upper panel right). However, Trp9 is useful as a reference marker for prostata carcinoma, i.e. can be used for quantifying the expression level of Trp8. The ratio of the expression of Trp8:Trp9 in patients and healthy individuals is useful for the development of a quantitative assay.

Example 10

Characterization of Trp10

The complete protein coding sequence of TRP10 (a and b) was determined by biocomputing (FIGS. 10 and 11). Using a 235 bp fragment of the Trp10 cDNA as probe in Northern blot analysis TRP10 transcripts could only be detected in mRNA isolated from individuals with prostate cancer (FIG. 13, bottom panel) but not in mRNA isolated from benign tissue of the prostate (prostate BPH) nor in mRNA isolated from heart, brain, placenta, lung, liver, skeletal muscle, kidney and pancreas. The 235 bp cDNA fragment of the Trp10 cDNA was amplified using the primer pair (SEQ ID NOS: 43 AND 44) UW248 5'-ACA GCT GCT GGT CTA TTC C-3' and UW249 5'-TAT GTG CCT TGG TTT GTA CC-3' and prostate cDNA as template. In summary, Trp10a and Trp10b, like TRP8 are also expressed in malignant prostate tissue. So far, its expression could not be observed in any other tissue examined (see above). Thus, Trp 10a and Trp10b are also useful markers which are specific for malignant prostate tissue.

Furthermore, database searches in public databases of the national center for biological information (NCBI) revealed the existence of several expressed sequence tags (EST clones) being in part identical to the Trp10 sequence. These EST clones were originally isolated from cancer tissues of lung, placenta, prostate and from melanoma. These clones include the clones with the following accession numbers: BE274448, BE408880, BE207083, BE791173, AI671853, BE390627. The results demonstrate that cancer cells of these tissues express Trp10 related transcripts whereas no expression of Trp10 transcripts in the corresponding healthy tissues are detectable (FIG. 13). Furthermore, it could be shown that in cancer cells of melanoma and prostate cancer Trp10 transcripts are expressed as shown by in situ hybridizations using 4 antisense probes (FIGS. 14A–E and 13K–O and Table 2, above). Furthermore, it could clearly be shown that cancer cells of these tissues expressing Trp10 transcripts also express Trp10-antisense transcripts as shown in FIGS. 14F–J, FIGS. 14P–R and FIG. 14T by in situ hybridizations using 4 sense probes (Table 2, above). The in situ hybridization experiments demonstrate that detection of a subset of cancer cells derived from carcinoma of lung, placenta, prostate and melanoma is feasible using antisense as well as sense probes complementary to Ttp10 transcripts or complementary to Trp10-antisense transcripts, respectively.

The foregoing is meant to illustrate but not to limit the scope of the invention. The person skilled in the art can readily envision and produce further embodiment, based on the above teachings, without undue experimentation.

What is claimed is:

1. A method for diagnosing a prostate carcinoma which comprises:
   (i) contacting a target sample with a reagent which reacts with Trp8a and/or Trp8b;
   and detecting Trp8a and/or Trp8b, wherein an increased concentration of Trp8a and/or Trp8b relative to a normal tissue control is indicative of prostate carcinoma.

2. The method of claim 1, wherein the reagent is a nucleic acid.

3. The method of claim 1, wherein the reagent is an antibody.

4. The method of claim 1, wherein the reagent is detectably labeled.

5. The method of claim 4, wherein the label is selected from the group consisting of a radioisotope, a bioluminescent compound, a chemiluminescent compound, a fluorescent compound, a metal chelate, or an enzyme.

6. A method for diagnosing an endometrial cancer (carcinoma of the uterus) which comprises (i) contacting a target sample with a reagent which reacts with Trp8a and/or Trp8b;
   and detecting Trp8a and/or Trp8b, wherein an increased concentration of Trp8a and/or Trp8b relative to a normal tissue control is indicative of endometrial cancer.

7. The method of claim 6, wherein the reagent is a nucleic acid.

8. The method of claim 6, wherein the reagent is an antibody.

9. The method of claim 6, wherein the reagent is detectably labeled.

10. The method of claim 9, wherein the label is selected from the group consisting of a radioisotope, a bioluminescent compound, a chemiluminescent compound, a fluorescent compound, a metal chelate, and an enzyme.

* * * * *

SEQUENCE LISTING

<160> NUMBER OF SEQ ID NOS: 46

<210> SEQ ID NO 1
<211> LENGTH: 240
<212> TYPE: DNA
<213> ORGANISM: Homo sapiens
<220> FEATURE:
<221> NAME/KEY: CDS
<222> LOCATION: (3)...(230)

<400> SEQUENCE: 1

```
tg ctg gtc tat tcc tgt gaa gct tgg ggt gga agc aac tgt ctg gag        47
   Leu Val Tyr Ser Cys Glu Ala Trp Gly Gly Ser Asn Cys Leu Glu
    1               5                  10                  15 ctg gcg gtg gag gcc aca gac cag cat ttc atc gcc cag cct ggg gtc        95
Leu Ala Val Glu Ala Thr Asp Gln His Phe Ile Ala Gln Pro Gly Val
                20                  25                  30 cag aat ttt ctt tct aag caa tgg tat gga gag att tcc cga gac acc       143
Gln Asn Phe Leu Ser Lys Gln Trp Tyr Gly Glu Ile Ser Arg Asp Thr
            35                  40                  45 aag aac tgg aag att atc ctg tgt ctg ttt att ata ccc ttg gtg ggc       191
Lys Asn Trp Lys Ile Ile Leu Cys Leu Phe Ile Ile Pro Leu Val Gly
        50                  55                  60 tgt ggc ttt gta tca ttt agg aag aaa cct gtc gac aag cacaagaagc        240
Cys Gly Phe Val Ser Phe Arg Lys Lys Pro Val Asp Lys
    65                  70                  75
```

<210> SEQ ID NO 2
<211> LENGTH: 76
<212> TYPE: PRT
<213> ORGANISM: Homo sapiens

<400> SEQUENCE: 2

```
Leu Val Tyr Ser Cys Glu Ala Trp Gly Gly Ser Asn Cys Leu Glu Leu
1               5                  10                  15

Ala Val Glu Ala Thr Asp Gln His Phe Ile Ala Gln Pro Gly Val Gln
            20                  25                  30

Asn Phe Leu Ser Lys Gln Trp Tyr Gly Glu Ile Ser Arg Asp Thr Lys
        35                  40                  45

Asn Trp Lys Ile Ile Leu Cys Leu Phe Ile Ile Pro Leu Val Gly Cys
    50                  55                  60
```

```
Gly Phe Val Ser Phe Arg Lys Lys Pro Val Asp Lys
65              70              75

<210> SEQ ID NO 3
<211> LENGTH: 3165
<212> TYPE: DNA
<213> ORGANISM: Homo sapien
<220> FEATURE:
<221> NAME/KEY: CDS
<222> LOCATION: (1)...(3162)

<400> SEQUENCE: 3 atg aaa tcc ttc ctt cct gtc cac acc atc gtg ctt atc agg gag aat        48
Met Lys Ser Phe Leu Pro Val His Thr Ile Val Leu Ile Arg Glu Asn
1               5                   10                  15 gtg tgc aag tgt ggc tat gcc cag agc cag cac atg gaa ggc acc cag        96
Val Cys Lys Cys Gly Tyr Ala Gln Ser Gln His Met Glu Gly Thr Gln
                20                  25                  30 atc aac caa agt gag aaa tgg aac tac aag aaa cac acc aag gaa ttt       144
Ile Asn Gln Ser Glu Lys Trp Asn Tyr Lys Lys His Thr Lys Glu Phe
            35                  40                  45 cct acc gac gcc ttt ggg gat att cag ttt gag aca ctg ggg aag aaa       192
Pro Thr Asp Ala Phe Gly Asp Ile Gln Phe Glu Thr Leu Gly Lys Lys
        50                  55                  60 ggg aag tat ata cgt ctg tcc tgc gac acg gac gcg gaa atc ctt tac       240
Gly Lys Tyr Ile Arg Leu Ser Cys Asp Thr Asp Ala Glu Ile Leu Tyr
65              70                  75                  80 gag ctg ctg acc cag cac tgg cac ctg aaa aca ccc aac ctg gtc att       288
Glu Leu Leu Thr Gln His Trp His Leu Lys Thr Pro Asn Leu Val Ile
                85                  90                  95 tct gtg acc ggg ggc gcc aag aac ttc gcc ctg aag ccg cgc atg cgc       336
Ser Val Thr Gly Gly Ala Lys Asn Phe Ala Leu Lys Pro Arg Met Arg
                100                 105                 110 aag atc ttc agc cgg ctc atc tac atc gcg cag tcc aaa ggt gct tgg       384
Lys Ile Phe Ser Arg Leu Ile Tyr Ile Ala Gln Ser Lys Gly Ala Trp
            115                 120                 125 att ctc acg gga ggc acc cat tat ggc ctg atg aag tac atc ggg gag       432
Ile Leu Thr Gly Gly Thr His Tyr Gly Leu Met Lys Tyr Ile Gly Glu
        130                 135                 140 gtg gta aga gat aac acc atc agc agg agt tca gag gag aat att gtg       480
Val Val Arg Asp Asn Thr Ile Ser Arg Ser Ser Glu Glu Asn Ile Val
145             150                 155                 160 gcc att ggc ata gca gct tgg ggc atg gtc tcc aac cgg gac acc ctc       528
Ala Ile Gly Ile Ala Ala Trp Gly Met Val Ser Asn Arg Asp Thr Leu
                165                 170                 175 atc agg aat tgc gat gct gag ggc tat ttt tta gcc cag tac ctt atg       576
Ile Arg Asn Cys Asp Ala Glu Gly Tyr Phe Leu Ala Gln Tyr Leu Met
            180                 185                 190 gat gac ttc aca aga gat cca ctg tat atc ctg gac aac aac cac aca       624
Asp Asp Phe Thr Arg Asp Pro Leu Tyr Ile Leu Asp Asn Asn His Thr
        195                 200                 205 cat ttg ctg ctc gtg gac aat ggc tgt cat gga cat ccc act gtc gaa       672
His Leu Leu Leu Val Asp Asn Gly Cys His Gly His Pro Thr Val Glu
    210                 215                 220 gca aag ctc cgg aat cag cta gag aag tat atc tct gag cgc act att       720
Ala Lys Leu Arg Asn Gln Leu Glu Lys Tyr Ile Ser Glu Arg Thr Ile
225                 230                 235                 240 caa gat tcc aac tat ggt ggc aag atc ccc att gtg tgt ttt gcc caa       768
Gln Asp Ser Asn Tyr Gly Gly Lys Ile Pro Ile Val Cys Phe Ala Gln
                245                 250                 255
```

```
                                              -continued gga ggt gga aaa gag act ttg aaa gcc atc aat acc tcc atc aaa aat    816
Gly Gly Gly Lys Glu Thr Leu Lys Ala Ile Asn Thr Ser Ile Lys Asn
            260                 265                 270 aaa att cct tgt gtg gtg gtg gaa ggc tcg ggc cag atc gct gat gtg    864
Lys Ile Pro Cys Val Val Val Glu Gly Ser Gly Gln Ile Ala Asp Val
        275                 280                 285 atc gct agc ctg gtg gag gtg gag gat gcc ctg aca tct tct gcc gtc    912
Ile Ala Ser Leu Val Glu Val Glu Asp Ala Leu Thr Ser Ser Ala Val
    290                 295                 300 aag gag aag ctg gtg cgc ttt tta ccc cgc acg gtg tcc cgg ctg cct    960
Lys Glu Lys Leu Val Arg Phe Leu Pro Arg Thr Val Ser Arg Leu Pro
305                 310                 315                 320 gag gag gag act gag agt tgg atc aaa tgg ctc aaa gaa att ctc gaa   1008
Glu Glu Glu Thr Glu Ser Trp Ile Lys Trp Leu Lys Glu Ile Leu Glu
                325                 330                 335 tgt tct cac cta tta aca gtt att aaa atg gaa gaa gct ggg gat gaa   1056
Cys Ser His Leu Leu Thr Val Ile Lys Met Glu Glu Ala Gly Asp Glu
            340                 345                 350 att gtg agc aat gcc atc tcc tac gct cta tac aaa gcc ttc agc acc   1104
Ile Val Ser Asn Ala Ile Ser Tyr Ala Leu Tyr Lys Ala Phe Ser Thr
        355                 360                 365 agt gag caa gac aag gat aac tgg aat ggg cag ctg aag ctt ctg ctg   1152
Ser Glu Gln Asp Lys Asp Asn Trp Asn Gly Gln Leu Lys Leu Leu Leu
    370                 375                 380 gag tgg aac cag ctg gac tta gcc aat gat gag att ttc acc aat gac   1200
Glu Trp Asn Gln Leu Asp Leu Ala Asn Asp Glu Ile Phe Thr Asn Asp
385                 390                 395                 400 cgc cga tgg gag tct gct gac ctt caa gaa gtc atg ttt acg gct ctc   1248
Arg Arg Trp Glu Ser Ala Asp Leu Gln Glu Val Met Phe Thr Ala Leu
                405                 410                 415 ata aag gac aga ccc aag ttt gtc cgc ctc ttt ctg gag aat ggc ttg   1296
Ile Lys Asp Arg Pro Lys Phe Val Arg Leu Phe Leu Glu Asn Gly Leu
            420                 425                 430 aac cta cgg aag ttt ctc acc cat gat gtc ctc act gaa ctc ttc tcc   1344
Asn Leu Arg Lys Phe Leu Thr His Asp Val Leu Thr Glu Leu Phe Ser
        435                 440                 445 aac cac ttc agc acg ctt gtg tac cgg aat ctg cag atc gcc aag aat   1392
Asn His Phe Ser Thr Leu Val Tyr Arg Asn Leu Gln Ile Ala Lys Asn
    450                 455                 460 tcc tat aat gat gcc ctc ctc acg ttt gtc tgg aaa ctg gtt gcg aac   1440
Ser Tyr Asn Asp Ala Leu Leu Thr Phe Val Trp Lys Leu Val Ala Asn
465                 470                 475                 480 ttc cga aga ggc ttc cgg aag gaa gac aga aat ggc cgg gac gag atg   1488
Phe Arg Arg Gly Phe Arg Lys Glu Asp Arg Asn Gly Arg Asp Glu Met
                485                 490                 495 gac ata gaa ctc cac gac gtg tct cct att act cgg cac ccc ctg caa   1536
Asp Ile Glu Leu His Asp Val Ser Pro Ile Thr Arg His Pro Leu Gln
            500                 505                 510 gct ctc ttc atc tgg gcc att ctt cag aat aag aag gaa ctc tcc aaa   1584
Ala Leu Phe Ile Trp Ala Ile Leu Gln Asn Lys Lys Glu Leu Ser Lys
        515                 520                 525 gtc att tgg gag cag acc agg ggc tgc act ctg gca gcc ctg gga gcc   1632
Val Ile Trp Glu Gln Thr Arg Gly Cys Thr Leu Ala Ala Leu Gly Ala
    530                 535                 540 agc aag ctt ctg aag act ctg gcc aaa gtg aag aac gac atc aat gct   1680
Ser Lys Leu Leu Lys Thr Leu Ala Lys Val Lys Asn Asp Ile Asn Ala
545                 550                 555                 560 gct ggg gag tcc gag gag ctg gct aat gag tac gag acc cgg gct gtt   1728
Ala Gly Glu Ser Glu Glu Leu Ala Asn Glu Tyr Glu Thr Arg Ala Val
                565                 570                 575
```

-continued

| | | |
|---|---|---|
| gag ctg ttc act gag tgt tac agc agc gat gaa gac ttg gca gaa cag<br>Glu Leu Phe Thr Glu Cys Tyr Ser Ser Asp Glu Asp Leu Ala Glu Gln<br>580                          585                    590 | 1776 |

```
gag ctg ttc act gag tgt tac agc agc gat gaa gac ttg gca gaa cag    1776
Glu Leu Phe Thr Glu Cys Tyr Ser Ser Asp Glu Asp Leu Ala Glu Gln
        580                 585                 590 ctg ctg gtc tat tcc tgt gaa gct tgg ggt gga agc aac tgt ctg gag    1824
Leu Leu Val Tyr Ser Cys Glu Ala Trp Gly Gly Ser Asn Cys Leu Glu
            595                 600                 605 ctg gcg gtg gag gcc aca gac cag cat ttc atc gcc cag cct ggg gtc    1872
Leu Ala Val Glu Ala Thr Asp Gln His Phe Ile Ala Gln Pro Gly Val
610                 615                 620 cag aat ttt ctt tct aag caa tgg tat gga gag att tcc cga gac acc    1920
Gln Asn Phe Leu Ser Lys Gln Trp Tyr Gly Glu Ile Ser Arg Asp Thr
625                 630                 635                 640 aag aac tgg aag att atc ctg tgt ctg ttt att ata ccc ttg gtg ggc    1968
Lys Asn Trp Lys Ile Ile Leu Cys Leu Phe Ile Ile Pro Leu Val Gly
                645                 650                 655 tgt ggc ttt gta tca ttt agg aag aaa cct gtc gac aag cac aag aag    2016
Cys Gly Phe Val Ser Phe Arg Lys Lys Pro Val Asp Lys His Lys Lys
            660                 665                 670 ctg ctt tgg tac tat gtg gcg ttc ttc acc tcc ccc ttc gtg gtc ttc    2064
Leu Leu Trp Tyr Tyr Val Ala Phe Phe Thr Ser Pro Phe Val Val Phe
        675                 680                 685 tcc tgg aat gtg gtc ttc tac atc gcc ttc ctc ctg ttt gcc tac        2112
Ser Trp Asn Val Val Phe Tyr Ile Ala Phe Leu Leu Phe Ala Tyr
    690                 695                 700 gtg ctg ctc atg gat ttc cat tcg gtg cca cac ccc ccc gag ctg gtc    2160
Val Leu Leu Met Asp Phe His Ser Val Pro His Pro Pro Glu Leu Val
705                 710                 715                 720 ctg tac tcg ctg gtc ttt gtc ctc ttc tgt gat gaa gtg aga cag tgg    2208
Leu Tyr Ser Leu Val Phe Val Leu Phe Cys Asp Glu Val Arg Gln Trp
                725                 730                 735 tac gta aat ggg gtg aat tat ttt act gac ctg gtg aat gtg atg gac    2256
Tyr Val Asn Gly Val Asn Tyr Phe Thr Asp Leu Val Asn Val Met Asp
            740                 745                 750 acg ctg ggg ctt ttt tac ttc ata gca gga att gta ttt cgg ctc cac    2304
Thr Leu Gly Leu Phe Tyr Phe Ile Ala Gly Ile Val Phe Arg Leu His
        755                 760                 765 tct tct aat aaa agc tct ttg tat tct gga cga gtc att ttc tgt ctg    2352
Ser Ser Asn Lys Ser Ser Leu Tyr Ser Gly Arg Val Ile Phe Cys Leu
    770                 775                 780 gac tac att att ttc act cta aga ttg atc cac att ttt act gta agc    2400
Asp Tyr Ile Ile Phe Thr Leu Arg Leu Ile His Ile Phe Thr Val Ser
785                 790                 795                 800 aga aac tta gga ccc aag att ata atg ctg cag agg atg ctg atc gat    2448
Arg Asn Leu Gly Pro Lys Ile Ile Met Leu Gln Arg Met Leu Ile Asp
                805                 810                 815 gtg ttc ttc ttc ctg ttc ctc ttt gcg gtg tgg atg gtg gcc ttt ggc    2496
Val Phe Phe Phe Leu Phe Leu Phe Ala Val Trp Met Val Ala Phe Gly
            820                 825                 830 gtg gcc agg caa ggg atc ctt agg cag aat gag cag cgc tgg agg tgg    2544
Val Ala Arg Gln Gly Ile Leu Arg Gln Asn Glu Gln Arg Trp Arg Trp
        835                 840                 845 ata ttc cgt tcg gtc atc tac gag ccc tac ctg gcc atg ttc ggc cag    2592
Ile Phe Arg Ser Val Ile Tyr Glu Pro Tyr Leu Ala Met Phe Gly Gln
    850                 855                 860 gtg ccc agt gac gtg gat ggt acc acg tat gac ttt gcc cac tgc acc    2640
Val Pro Ser Asp Val Asp Gly Thr Thr Tyr Asp Phe Ala His Cys Thr
865                 870                 875                 880 ttc act ggg aat gag tcc aag cca ctg tgt gtg gag ctg gat gag cac    2688
Phe Thr Gly Asn Glu Ser Lys Pro Leu Cys Val Glu Leu Asp Glu His
```

```
                      885                 890                 895
aac ctg ccc cgg ttc ccc gag tgg atc acc atc ccc ctg gtg tgc atc          2736
Asn Leu Pro Arg Phe Pro Glu Trp Ile Thr Ile Pro Leu Val Cys Ile
            900                 905                 910 tac atg tta tcc acc aac atc ctg ctg gtc aac ctg ctg gtc gcc atg          2784
Tyr Met Leu Ser Thr Asn Ile Leu Leu Val Asn Leu Leu Val Ala Met
        915                 920                 925 ttt ggc tac acg gtg ggc acc gtc cag gag aac aat gac cag gtc tgg          2832
Phe Gly Tyr Thr Val Gly Thr Val Gln Glu Asn Asn Asp Gln Val Trp
    930                 935                 940 aag ttc cag agg tac ttc ctg gtg cag gag tac tgc agc cgc ctc aat          2880
Lys Phe Gln Arg Tyr Phe Leu Val Gln Glu Tyr Cys Ser Arg Leu Asn
945                 950                 955                 960 atc ccc ttc ccc ttc atc gtc ttc gct tac ttc tac atg gtg gtg aag          2928
Ile Pro Phe Pro Phe Ile Val Phe Ala Tyr Phe Tyr Met Val Val Lys
                965                 970                 975 aag tgc ttc aag tgt tgc tgc aag gag aaa aac atg gag tct tct gtc          2976
Lys Cys Phe Lys Cys Cys Cys Lys Glu Lys Asn Met Glu Ser Ser Val
            980                 985                 990 tgc tgt ttc aaa aat gaa gac aat gag act ctg gca tgg gag ggt gtc          3024
Cys Cys Phe Lys Asn Glu Asp Asn Glu Thr Leu Ala Trp Glu Gly Val
        995                 1000                1005 atg aag gaa aac tac ctt gtc aag atc aac aca aaa gcc aac gac acc          3072
Met Lys Glu Asn Tyr Leu Val Lys Ile Asn Thr Lys Ala Asn Asp Thr
    1010                1015                1020 tca gag gaa atg agg cat cga ttt aga caa ctg gat aca aag ctt aat          3120
Ser Glu Glu Met Arg His Arg Phe Arg Gln Leu Asp Thr Lys Leu Asn
1025                1030                1035                1040 gat ctc aag ggt cta ctg aaa gag att gct aat aaa atc aaa              3162
Asp Leu Lys Gly Leu Leu Lys Glu Ile Ala Asn Lys Ile Lys
                1045                1050 tag                                                                  3165

<210> SEQ ID NO 4
<211> LENGTH: 1054
<212> TYPE: PRT
<213> ORGANISM: Homo sapien

<400> SEQUENCE: 4

Met Lys Ser Phe Leu Pro Val His Thr Ile Val Leu Ile Arg Glu Asn
1               5                   10                  15

Val Cys Lys Cys Gly Tyr Ala Gln Ser Gln His Met Glu Gly Thr Gln
            20                  25                  30

Ile Asn Gln Ser Glu Lys Trp Asn Tyr Lys Lys His Thr Lys Glu Phe
        35                  40                  45

Pro Thr Asp Ala Phe Gly Asp Ile Gln Phe Glu Thr Leu Gly Lys Lys
    50                  55                  60

Gly Lys Tyr Ile Arg Leu Ser Cys Asp Thr Asp Ala Glu Ile Leu Tyr
65                  70                  75                  80

Glu Leu Leu Thr Gln His Trp His Leu Lys Thr Pro Asn Leu Val Ile
                85                  90                  95

Ser Val Thr Gly Gly Ala Lys Asn Phe Ala Leu Lys Pro Arg Met Arg
            100                 105                 110

Lys Ile Phe Ser Arg Leu Ile Tyr Ile Ala Gln Ser Lys Gly Ala Trp
        115                 120                 125

Ile Leu Thr Gly Gly Thr His Tyr Gly Leu Met Lys Tyr Ile Gly Glu
    130                 135                 140
```

```
Val Val Arg Asp Asn Thr Ile Ser Arg Ser Ser Glu Glu Asn Ile Val
145                 150                 155                 160

Ala Ile Gly Ile Ala Ala Trp Gly Met Val Ser Asn Arg Asp Thr Leu
                165                 170                 175

Ile Arg Asn Cys Asp Ala Glu Gly Tyr Phe Leu Ala Gln Tyr Leu Met
            180                 185                 190

Asp Asp Phe Thr Arg Asp Pro Leu Tyr Ile Leu Asp Asn Asn His Thr
        195                 200                 205

His Leu Leu Leu Val Asp Asn Gly Cys His Gly His Pro Thr Val Glu
    210                 215                 220

Ala Lys Leu Arg Asn Gln Leu Glu Lys Tyr Ile Ser Glu Arg Thr Ile
225                 230                 235                 240

Gln Asp Ser Asn Tyr Gly Gly Lys Ile Pro Ile Val Cys Phe Ala Gln
                245                 250                 255

Gly Gly Gly Lys Glu Thr Leu Lys Ala Ile Asn Thr Ser Ile Lys Asn
                260                 265                 270

Lys Ile Pro Cys Val Val Glu Gly Ser Gly Gln Ile Ala Asp Val
            275                 280                 285

Ile Ala Ser Leu Val Glu Val Glu Asp Ala Leu Thr Ser Ser Ala Val
        290                 295                 300

Lys Glu Lys Leu Val Arg Phe Leu Pro Arg Thr Val Ser Arg Leu Pro
305                 310                 315                 320

Glu Glu Glu Thr Glu Ser Trp Ile Lys Trp Leu Lys Glu Ile Leu Glu
                325                 330                 335

Cys Ser His Leu Leu Thr Val Ile Lys Met Glu Glu Ala Gly Asp Glu
            340                 345                 350

Ile Val Ser Asn Ala Ile Ser Tyr Ala Leu Tyr Lys Ala Phe Ser Thr
        355                 360                 365

Ser Glu Gln Asp Lys Asp Asn Trp Asn Gly Gln Leu Lys Leu Leu Leu
    370                 375                 380

Glu Trp Asn Gln Leu Asp Leu Ala Asn Asp Glu Ile Phe Thr Asn Asp
385                 390                 395                 400

Arg Arg Trp Glu Ser Ala Asp Leu Gln Glu Val Met Phe Thr Ala Leu
                405                 410                 415

Ile Lys Asp Arg Pro Lys Phe Val Arg Leu Phe Leu Glu Asn Gly Leu
            420                 425                 430

Asn Leu Arg Lys Phe Leu Thr His Asp Val Leu Thr Glu Leu Phe Ser
        435                 440                 445

Asn His Phe Ser Thr Leu Val Tyr Arg Asn Leu Gln Ile Ala Lys Asn
    450                 455                 460

Ser Tyr Asn Asp Ala Leu Leu Thr Phe Val Trp Lys Leu Val Ala Asn
465                 470                 475                 480

Phe Arg Arg Gly Phe Arg Lys Glu Asp Arg Asn Gly Arg Asp Glu Met
                485                 490                 495

Asp Ile Glu Leu His Asp Val Ser Pro Ile Thr Arg His Pro Leu Gln
            500                 505                 510

Ala Leu Phe Ile Trp Ala Ile Leu Gln Asn Lys Lys Glu Leu Ser Lys
        515                 520                 525

Val Ile Trp Glu Gln Thr Arg Gly Cys Thr Leu Ala Ala Leu Gly Ala
    530                 535                 540

Ser Lys Leu Leu Lys Thr Leu Ala Lys Val Lys Asn Asp Ile Asn Ala
545                 550                 555                 560

Ala Gly Glu Ser Glu Glu Leu Ala Asn Glu Tyr Glu Thr Arg Ala Val
```

```
                  565                 570                 575
Glu Leu Phe Thr Glu Cys Tyr Ser Ser Asp Glu Asp Leu Ala Glu Gln
            580                 585                 590
Leu Leu Val Tyr Ser Cys Glu Ala Trp Gly Ser Asn Cys Leu Glu
        595                 600                 605
Leu Ala Val Glu Ala Thr Asp Gln His Phe Ile Ala Gln Pro Gly Val
610                 615                 620
Gln Asn Phe Leu Ser Lys Gln Trp Tyr Gly Glu Ile Ser Arg Asp Thr
625                 630                 635                 640
Lys Asn Trp Lys Ile Ile Leu Cys Leu Phe Ile Pro Leu Val Gly
                645                 650                 655
Cys Gly Phe Val Ser Phe Arg Lys Lys Pro Val Asp Lys His Lys Lys
            660                 665                 670
Leu Leu Trp Tyr Tyr Val Ala Phe Phe Thr Ser Pro Phe Val Val Phe
        675                 680                 685
Ser Trp Asn Val Val Phe Tyr Ile Ala Phe Leu Leu Phe Ala Tyr
        690                 695                 700
Val Leu Leu Met Asp Phe His Ser Val Pro His Pro Glu Leu Val
705                 710                 715                 720
Leu Tyr Ser Leu Val Phe Val Leu Phe Cys Asp Glu Val Arg Gln Trp
                725                 730                 735
Tyr Val Asn Gly Val Asn Tyr Phe Thr Asp Leu Val Asn Val Met Asp
            740                 745                 750
Thr Leu Gly Leu Phe Tyr Phe Ile Ala Gly Ile Val Phe Arg Leu His
        755                 760                 765
Ser Ser Asn Lys Ser Ser Leu Tyr Ser Gly Arg Val Ile Phe Cys Leu
770                 775                 780
Asp Tyr Ile Ile Phe Thr Leu Arg Leu Ile His Ile Phe Thr Val Ser
785                 790                 795                 800
Arg Asn Leu Gly Pro Lys Ile Ile Met Leu Gln Arg Met Leu Ile Asp
                805                 810                 815
Val Phe Phe Phe Leu Phe Leu Phe Ala Val Trp Met Val Ala Phe Gly
            820                 825                 830
Val Ala Arg Gln Gly Ile Leu Arg Gln Asn Glu Gln Arg Trp Arg Trp
        835                 840                 845
Ile Phe Arg Ser Val Ile Tyr Glu Pro Tyr Leu Ala Met Phe Gly Gln
        850                 855                 860
Val Pro Ser Asp Val Asp Gly Thr Thr Tyr Asp Phe Ala His Cys Thr
865                 870                 875                 880
Phe Thr Gly Asn Glu Ser Lys Pro Leu Cys Val Glu Leu Asp Glu His
                885                 890                 895
Asn Leu Pro Arg Phe Pro Glu Trp Ile Thr Ile Pro Leu Val Cys Ile
            900                 905                 910
Tyr Met Leu Ser Thr Asn Ile Leu Leu Val Asn Leu Leu Val Ala Met
        915                 920                 925
Phe Gly Tyr Thr Val Gly Thr Val Gln Glu Asn Asn Asp Gln Val Trp
    930                 935                 940
Lys Phe Gln Arg Tyr Phe Leu Val Gln Glu Tyr Cys Ser Arg Leu Asn
945                 950                 955                 960
Ile Pro Phe Pro Phe Ile Val Phe Ala Tyr Phe Tyr Met Val Val Lys
                965                 970                 975
Lys Cys Phe Lys Cys Cys Cys Lys Glu Lys Asn Met Glu Ser Ser Val
            980                 985                 990
```

```
Cys Cys Phe Lys Asn Glu Asp Asn Glu Thr Leu Ala Trp Glu Gly Val
        995                 1000                1005

Met Lys Glu Asn Tyr Leu Val Lys Ile Asn Thr Lys Ala Asn Asp Thr
    1010                1015                1020

Ser Glu Glu Met Arg His Arg Phe Arg Gln Leu Asp Thr Lys Leu Asn
1025                1030                1035                1040

Asp Leu Lys Gly Leu Leu Lys Glu Ile Ala Asn Lys Ile Lys
                1045                1050

<210> SEQ ID NO 5
<211> LENGTH: 2913
<212> TYPE: DNA
<213> ORGANISM: Homo sapiens
<220> FEATURE:
<221> NAME/KEY: CDS
<222> LOCATION: (212)...(2386)

<400> SEQUENCE: 5
gccaagtgta acaaactcac agccctctcc aaactggctg gggctgctgg gagactccca      60
aggaactcgt caggaaggca ggagacagga gacgggacct ctacaggag acggtgggcc     120 ggcccttggg ggggctgatg tggccccaag gctgagtccc gtcagggtct ggcctcggcc     180
tcaggccccc aaggagccgg ccctacaccc c atg ggt ttg tca ctg ccc aag        232
                                  Met Gly Leu Ser Leu Pro Lys
                                   1               5 gag aaa ggg cta att ctc tgc cta tgg agc aag ttc tgc aga tgg ttc       280
Glu Lys Gly Leu Ile Leu Cys Leu Trp Ser Lys Phe Cys Arg Trp Phe
        10                  15                  20 cag aga cgg gag tcc tgg gcc cag agc cga gat gag cag aac ctg ctg       328
Gln Arg Arg Glu Ser Trp Ala Gln Ser Arg Asp Glu Gln Asn Leu Leu
25                  30                  35 cag cag aag agg atc tgg gag tct cct ctc ctt cta gct gcc aaa gat       376
Gln Gln Lys Arg Ile Trp Glu Ser Pro Leu Leu Leu Ala Ala Lys Asp
40                  45                  50                  55 aat gat gtc cag gcc ctg aac aag ttg ctc aag tat gag gat tgc aag       424
Asn Asp Val Gln Ala Leu Asn Lys Leu Leu Lys Tyr Glu Asp Cys Lys
                60                  65                  70 gtg cac cag aga gga gcc atg ggg gaa aca gcg cta cac ata gca gcc       472
Val His Gln Arg Gly Ala Met Gly Glu Thr Ala Leu His Ile Ala Ala
            75                  80                  85 ctc tat gac aac ctg gag gcc gcc atg gtg ctg atg gag gct gcc ccg       520
Leu Tyr Asp Asn Leu Glu Ala Ala Met Val Leu Met Glu Ala Ala Pro
        90                  95                  100 gag ctg gtc ttt gag ccc atg aca tct gag ctc tat gag ggt cag act       568
Glu Leu Val Phe Glu Pro Met Thr Ser Glu Leu Tyr Glu Gly Gln Thr
    105                 110                 115 gca ctg cac atc gct gtt gtg aac cag aac atg aac ctg gtg cga gcc       616
Ala Leu His Ile Ala Val Val Asn Gln Asn Met Asn Leu Val Arg Ala
120                 125                 130                 135 ctg ctt gcc cgc agg gcc agt gtc tct gcc aga gcc aca ggc act gcc       664
Leu Leu Ala Arg Arg Ala Ser Val Ser Ala Arg Ala Thr Gly Thr Ala
                140                 145                 150 ttc cgc cgt agt ccc cgc aac ctc atc tac ttt ggg gag cac cct ttg       712
Phe Arg Arg Ser Pro Arg Asn Leu Ile Tyr Phe Gly Glu His Pro Leu
            155                 160                 165 tcc ttt gct gcc tgt gtg aac agt gag gag atc gtg cgg ctg ctc att       760
Ser Phe Ala Ala Cys Val Asn Ser Glu Glu Ile Val Arg Leu Leu Ile
        170                 175                 180 gag cat gga gct gac atc cgg gcc cag gac tcc ctg gga aac aca gtg       808
```

```

Glu His Gly Ala Asp Ile Arg Ala Gln Asp Ser Leu Gly Asn Thr Val
    185                 190                 195 tta cac atc ctc atc ctc cag ccc aac aaa acc ttt gcc tgc cag atg       856
Leu His Ile Leu Ile Leu Gln Pro Asn Lys Thr Phe Ala Cys Gln Met
200                 205                 210                 215 tac aac ctg ttg ctg tcc tac gac aga cat ggg gac cac ctg cag ccc       904
Tyr Asn Leu Leu Leu Ser Tyr Asp Arg His Gly Asp His Leu Gln Pro
                220                 225                 230 ctg gac ctc gtg ccc aat cac cag ggt ctc acc cct ttc aag ctg gct       952
Leu Asp Leu Val Pro Asn His Gln Gly Leu Thr Pro Phe Lys Leu Ala
            235                 240                 245 gga gtg gag ggt aac act gtg atg ttt cag cac ctg atg cac aag cgg      1000
Gly Val Glu Gly Asn Thr Val Met Phe Gln His Leu Met His Lys Arg
        250                 255                 260 aag cac acc cag tgg acg tat gga cca ctg acc tcg act ctc tat gac      1048
Lys His Thr Gln Trp Thr Tyr Gly Pro Leu Thr Ser Thr Leu Tyr Asp
    265                 270                 275 ctc aca gag atc gac tcc tca ggg gat gag cag tcc ctg ctg gaa ctt      1096
Leu Thr Glu Ile Asp Ser Ser Gly Asp Glu Gln Ser Leu Leu Glu Leu
280                 285                 290                 295 atc atc acc acc aag aag cgg gag gct cgc cag atc ctg gac cag acg      1144
Ile Ile Thr Thr Lys Lys Arg Glu Ala Arg Gln Ile Leu Asp Gln Thr
                300                 305                 310 ccg gtg aag gag ctg gtg agc ctc aag tgg aag cgg tac ggg cgg ccg      1192
Pro Val Lys Glu Leu Val Ser Leu Lys Trp Lys Arg Tyr Gly Arg Pro
            315                 320                 325 tac ttc tgc atg ctg ggt gcc ata tat ctg ctg tac atc atc tgc ttc      1240
Tyr Phe Cys Met Leu Gly Ala Ile Tyr Leu Leu Tyr Ile Ile Cys Phe
        330                 335                 340 acc atg tgc tgc atc tac cgc ccc ctc aag ccc agg acc aat aac cgc      1288
Thr Met Cys Cys Ile Tyr Arg Pro Leu Lys Pro Arg Thr Asn Asn Arg
    345                 350                 355 aca agc ccc cgg gac aac acc ctc tta cag cag aag cta ctt cag gaa      1336
Thr Ser Pro Arg Asp Asn Thr Leu Leu Gln Gln Lys Leu Leu Gln Glu
360                 365                 370                 375 gcc tac gtg acc cct aag gac gat atc cgg ctg gtc ggg gag ctg gtg      1384
Ala Tyr Val Thr Pro Lys Asp Asp Ile Arg Leu Val Gly Glu Leu Val
                380                 385                 390 act gtc att ggg gct atc atc atc ctg ctg gta gag gtt cca gac atc      1432
Thr Val Ile Gly Ala Ile Ile Ile Leu Leu Val Glu Val Pro Asp Ile
            395                 400                 405 ttc aga atg ggg gtc act cgc ttc ttt gga cag acc atc ctt ggg ggc      1480
Phe Arg Met Gly Val Thr Arg Phe Phe Gly Gln Thr Ile Leu Gly Gly
        410                 415                 420 cca ttc cat gtc ctc atc atc acc tat gcc ttc atg gtg ctg gtg acc      1528
Pro Phe His Val Leu Ile Ile Thr Tyr Ala Phe Met Val Leu Val Thr
    425                 430                 435 atg gtg atg cgg ctc atc agt gcc agc ggg gag gtg gta ccc atg tcc      1576
Met Val Met Arg Leu Ile Ser Ala Ser Gly Glu Val Val Pro Met Ser
440                 445                 450                 455 ttt gca ctc gtg ctg ggc tgg tgc aac gtc atg tac ttc gcc cga gga      1624
Phe Ala Leu Val Leu Gly Trp Cys Asn Val Met Tyr Phe Ala Arg Gly
                460                 465                 470 ttc cag atg cta ggc ccc ttc acc atc atg att cag aag atg att ttt      1672
Phe Gln Met Leu Gly Pro Phe Thr Ile Met Ile Gln Lys Met Ile Phe
            475                 480                 485 ggc gac ctg atg cga ttc tgc tgg ctg atg gct gtg gtc atc ctg ggc      1720
Gly Asp Leu Met Arg Phe Cys Trp Leu Met Ala Val Val Ile Leu Gly
        490                 495                 500
```

```
ttt gct tca gcc ttc tat atc atc ttc cag aca gag gac ccc gag gag      1768
Phe Ala Ser Ala Phe Tyr Ile Ile Phe Gln Thr Glu Asp Pro Glu Glu
    505                 510                 515 cta ggc cac ttc tac gac tac ccc atg gcc ctg ttc agc acc ttc gag      1816
Leu Gly His Phe Tyr Asp Tyr Pro Met Ala Leu Phe Ser Thr Phe Glu
520                 525                 530                 535 ctg ttc ctt acc atc atc gat ggc cca gcc aac tac aac gtg gac ctg      1864
Leu Phe Leu Thr Ile Ile Asp Gly Pro Ala Asn Tyr Asn Val Asp Leu
                540                 545                 550 ccc ttc atg tac agc atc acc tat gct gcc ttt gcc atc atc gcc aca      1912
Pro Phe Met Tyr Ser Ile Thr Tyr Ala Ala Phe Ala Ile Ile Ala Thr
            555                 560                 565 ctg ctc atg ctc aac ctc ctc att gcc atg atg ggc gac act cac tgg      1960
Leu Leu Met Leu Asn Leu Leu Ile Ala Met Met Gly Asp Thr His Trp
        570                 575                 580 cga gtg gcc cat gag cgg gat gag ctg tgg agg gcc cag att gtg gcc      2008
Arg Val Ala His Glu Arg Asp Glu Leu Trp Arg Ala Gln Ile Val Ala
    585                 590                 595 acc acg gtg atg ctg gag cgg aag ctg cct cgc tgc ctg tgg cct cgc      2056
Thr Thr Val Met Leu Glu Arg Lys Leu Pro Arg Cys Leu Trp Pro Arg
600                 605                 610                 615 tcc ggg atc tgc gga cgg gag tat ggc ctg ggg gac cgc tgg ttc ctg      2104
Ser Gly Ile Cys Gly Arg Glu Tyr Gly Leu Gly Asp Arg Trp Phe Leu
                620                 625                 630 cgg gtg gaa gac agg caa gat ctc aac cgg cag cgg atc caa cgc tac      2152
Arg Val Glu Asp Arg Gln Asp Leu Asn Arg Gln Arg Ile Gln Arg Tyr
            635                 640                 645 gca cag gcc ttc cac acc cgg ggc tct gag gat ttg gac aaa gac tca      2200
Ala Gln Ala Phe His Thr Arg Gly Ser Glu Asp Leu Asp Lys Asp Ser
        650                 655                 660 gtg gaa aaa cta gag ctg ggc tgt ccc ttc agc ccc cac ctg tcc ctt      2248
Val Glu Lys Leu Glu Leu Gly Cys Pro Phe Ser Pro His Leu Ser Leu
    665                 670                 675 cct acg ccc tca gtg tct cga agt acc tcc cgc agc agt gcc aat tgg      2296
Pro Thr Pro Ser Val Ser Arg Ser Thr Ser Arg Ser Ser Ala Asn Trp
680                 685                 690                 695 gaa agg ctt cgg caa ggg acc ctg agg aga gac ctg cgt ggg ata atc      2344
Glu Arg Leu Arg Gln Gly Thr Leu Arg Arg Asp Leu Arg Gly Ile Ile
                700                 705                 710 aac agg ggt ctg gag gac ggg gag agc tgg gaa tat cag atc                2386
Asn Arg Gly Leu Glu Asp Gly Glu Ser Trp Glu Tyr Gln Ile
            715                 720                 725 tgactgcgtg ttctcacttc gcttcctgga acttgctctc attttcctgg gtgcatcaaa    2446
caaaacaaaa accaaacacc cagaggtctc atctcccagg ccccagggag aaagaggagt    2506
agcatgaacg ccaaggaatg tacgttgaga atcactgctc caggcctgca ttactccttc    2566
agctctgggg cagaggaagc ccagcccaag cacgggctg gcagggcgtg aggaactctc     2626
ctgtggcctc ctcatcaccc ttccgacagg agcactgcat gtcagagcac tttaaaaaca    2686
ggccagcctg cttgggccct cggtctccac cccagggtca taagtgggga gagagcccttt  2746 cccagggcac ccaggcaggt gcagggaagt gcagagcttg tggaaagcgt gtgagtgagg    2806
gagacaggaa cggctctggg ggtgggaagt ggggctaggt cttgccaact ccatcttcaa    2866
taaagtcgtt ttcggatccc taaaaaaaaa aaaaaaaaa aaaaaaa                   2913
```

<210> SEQ ID NO 6
<211> LENGTH: 725
<212> TYPE: PRT
<213> ORGANISM: Homo sapiens

<400> SEQUENCE: 6

```
Met Gly Leu Ser Leu Pro Lys Glu Lys Gly Leu Ile Leu Cys Leu Trp
1               5                   10                  15

Ser Lys Phe Cys Arg Trp Phe Gln Arg Arg Glu Ser Trp Ala Gln Ser
            20                  25                  30

Arg Asp Glu Gln Asn Leu Leu Gln Gln Lys Arg Ile Trp Glu Ser Pro
        35                  40                  45

Leu Leu Leu Ala Ala Lys Asp Asn Asp Val Gln Ala Leu Asn Lys Leu
    50                  55                  60

Leu Lys Tyr Glu Asp Cys Lys Val His Gln Arg Gly Ala Met Gly Glu
65                  70                  75                  80

Thr Ala Leu His Ile Ala Ala Leu Tyr Asp Asn Leu Glu Ala Ala Met
                85                  90                  95

Val Leu Met Glu Ala Ala Pro Glu Leu Val Phe Glu Pro Met Thr Ser
            100                 105                 110

Glu Leu Tyr Glu Gly Gln Thr Ala Leu His Ile Ala Val Val Asn Gln
        115                 120                 125

Asn Met Asn Leu Val Arg Ala Leu Leu Ala Arg Arg Ala Ser Val Ser
    130                 135                 140

Ala Arg Ala Thr Gly Thr Ala Phe Arg Arg Ser Pro Arg Asn Leu Ile
145                 150                 155                 160

Tyr Phe Gly Glu His Pro Leu Ser Phe Ala Ala Cys Val Asn Ser Glu
                165                 170                 175

Glu Ile Val Arg Leu Leu Ile Glu His Gly Ala Asp Ile Arg Ala Gln
            180                 185                 190

Asp Ser Leu Gly Asn Thr Val Leu His Ile Leu Ile Leu Gln Pro Asn
        195                 200                 205

Lys Thr Phe Ala Cys Gln Met Tyr Asn Leu Leu Leu Ser Tyr Asp Arg
    210                 215                 220

His Gly Asp His Leu Gln Pro Leu Asp Leu Val Pro Asn His Gln Gly
225                 230                 235                 240

Leu Thr Pro Phe Lys Leu Ala Gly Val Glu Gly Asn Thr Val Met Phe
                245                 250                 255

Gln His Leu Met His Lys Arg Lys His Thr Gln Trp Thr Tyr Gly Pro
            260                 265                 270

Leu Thr Ser Thr Leu Tyr Asp Leu Thr Glu Ile Asp Ser Ser Gly Asp
        275                 280                 285

Glu Gln Ser Leu Leu Glu Leu Ile Ile Thr Thr Lys Lys Arg Glu Ala
    290                 295                 300

Arg Gln Ile Leu Asp Gln Thr Pro Val Lys Glu Leu Val Ser Leu Lys
305                 310                 315                 320

Trp Lys Arg Tyr Gly Arg Pro Tyr Phe Cys Met Leu Gly Ala Ile Tyr
                325                 330                 335

Leu Leu Tyr Ile Ile Cys Phe Thr Met Cys Cys Ile Tyr Arg Pro Leu
            340                 345                 350

Lys Pro Arg Thr Asn Asn Arg Thr Ser Pro Arg Asp Asn Thr Leu Leu
        355                 360                 365

Gln Gln Lys Leu Leu Gln Glu Ala Tyr Val Thr Pro Lys Asp Asp Ile
    370                 375                 380

Arg Leu Val Gly Glu Leu Val Thr Val Ile Gly Ala Ile Ile Ile Leu
385                 390                 395                 400

Leu Val Glu Val Pro Asp Ile Phe Arg Met Gly Val Thr Arg Phe Phe
```

```
                    405                 410                 415
Gly Gln Thr Ile Leu Gly Gly Pro Phe His Val Leu Ile Ile Thr Tyr
            420                 425                 430
Ala Phe Met Val Leu Val Thr Met Val Met Arg Leu Ile Ser Ala Ser
            435                 440                 445
Gly Glu Val Val Pro Met Ser Phe Ala Leu Val Leu Gly Trp Cys Asn
            450                 455                 460
Val Met Tyr Phe Ala Arg Gly Phe Gln Met Leu Gly Pro Phe Thr Ile
465                 470                 475                 480
Met Ile Gln Lys Met Ile Phe Gly Asp Leu Met Arg Phe Cys Trp Leu
                485                 490                 495
Met Ala Val Val Ile Leu Gly Phe Ala Ser Ala Phe Tyr Ile Ile Phe
                500                 505                 510
Gln Thr Glu Asp Pro Glu Glu Leu Gly His Phe Tyr Asp Tyr Pro Met
            515                 520                 525
Ala Leu Phe Ser Thr Phe Glu Leu Phe Leu Thr Ile Ile Asp Gly Pro
    530                 535                 540
Ala Asn Tyr Asn Val Asp Leu Pro Phe Met Tyr Ser Ile Thr Tyr Ala
545                 550                 555                 560
Ala Phe Ala Ile Ile Ala Thr Leu Leu Met Leu Asn Leu Leu Ile Ala
                565                 570                 575
Met Met Gly Asp Thr His Trp Arg Val Ala His Glu Arg Asp Glu Leu
            580                 585                 590
Trp Arg Ala Gln Ile Val Ala Thr Thr Val Met Leu Glu Arg Lys Leu
            595                 600                 605
Pro Arg Cys Leu Trp Pro Arg Ser Gly Ile Cys Gly Arg Glu Tyr Gly
    610                 615                 620
Leu Gly Asp Arg Trp Phe Leu Arg Val Glu Asp Arg Gln Asp Leu Asn
625                 630                 635                 640
Arg Gln Arg Ile Gln Arg Tyr Ala Gln Ala Phe His Thr Arg Gly Ser
                645                 650                 655
Glu Asp Leu Asp Lys Asp Ser Val Glu Lys Leu Glu Leu Gly Cys Pro
            660                 665                 670
Phe Ser Pro His Leu Ser Leu Pro Thr Pro Ser Val Ser Arg Ser Thr
            675                 680                 685
Ser Arg Ser Ser Ala Asn Trp Glu Arg Leu Arg Gln Gly Thr Leu Arg
        690                 695                 700
Arg Asp Leu Arg Gly Ile Ile Asn Arg Gly Leu Glu Asp Gly Glu Ser
705                 710                 715                 720
Trp Glu Tyr Gln Ile
                725
```

<210> SEQ ID NO 7
<211> LENGTH: 2695
<212> TYPE: DNA
<213> ORGANISM: Homo sapien
<220> FEATURE:
<221> NAME/KEY: CDS
<222> LOCATION: (303)...(2336)

<400> SEQUENCE: 7

```
atccaatggc ggtccttcca tctcgaagct tccctcatgg acgccctgct gaatgaccgg      60
cctgagttcg tgcgcttgct catttcccac ggcctcagcc tgggccactt cctgaccccg     120
atgcgcctgg cccaactcta cagcgcggcg ccctccaact cgctcatccg caaccttttg     180
```

-continued

```
gaccaggcgt cccacagcgc aggcaccaaa gccccagccc taaaaggggg agctgcggag      240
ctccggcccc ctgacgtggg gcatgtgctg aggatgctgc tggggaagat gtgcgcgccg      300 ag atg tat ctg ctc tcg gac aag gcc acc tcg ccg ctc tcg ctg gat        347
   Met Tyr Leu Leu Ser Asp Lys Ala Thr Ser Pro Leu Ser Leu Asp
   1               5                  10                  15 gct ggc ctc ggg cag gcc ccc tgg agc gac ctg ctt ctt tgg gca ctg        395
Ala Gly Leu Gly Gln Ala Pro Trp Ser Asp Leu Leu Leu Trp Ala Leu
                20                  25                  30 ttg ctg aac agg gca cag atg gcc atg tac ttc tgg gag atg ggt tcc        443
Leu Leu Asn Arg Ala Gln Met Ala Met Tyr Phe Trp Glu Met Gly Ser
            35                  40                  45 aat gca gtt tcc tca gct ctt ggg gcc tgt ttg ctc cgg gtg atg            491
Asn Ala Val Ser Ser Ala Leu Gly Ala Cys Leu Leu Arg Val Met
        50                  55                  60 gca cgc ctg gag cct gac gct gag gag gca gca cgg agg aaa gac ctg        539
Ala Arg Leu Glu Pro Asp Ala Glu Glu Ala Ala Arg Arg Lys Asp Leu
65                  70                  75 gcg ttc aag ttt gag ggg atg ggc gtt gac ctc ttt ggc gag tgc tat        587
Ala Phe Lys Phe Glu Gly Met Gly Val Asp Leu Phe Gly Glu Cys Tyr
80                  85                  90                  95 cgc agc agt gag gtg agg gct gcc cgc ctc ctc ctc cgt cgc tgc ccg        635
Arg Ser Ser Glu Val Arg Ala Ala Arg Leu Leu Leu Arg Arg Cys Pro
                100                 105                 110 ctc tgg ggg gat gcc act tgc ctc cag ctg gcc atg caa gct gac gcc        683
Leu Trp Gly Asp Ala Thr Cys Leu Gln Leu Ala Met Gln Ala Asp Ala
            115                 120                 125 cgt gcc ttc ttt gcc cag gat ggg gta cag tct ctg ctg aca cag aag        731
Arg Ala Phe Phe Ala Gln Asp Gly Val Gln Ser Leu Leu Thr Gln Lys
        130                 135                 140 tgg tgg gga gat atg gcc agc act aca ccc atc tgg gcc ctg gtt ctc        779
Trp Trp Gly Asp Met Ala Ser Thr Thr Pro Ile Trp Ala Leu Val Leu
    145                 150                 155 gcc ttc ttt tgc cct cca ctc atc tac acc cgc ctc atc acc ttc agg        827
Ala Phe Phe Cys Pro Pro Leu Ile Tyr Thr Arg Leu Ile Thr Phe Arg
160                 165                 170                 175 aaa tca gaa gag gag ccc aca cgg gag gag cta gag ttt gac atg gat        875
Lys Ser Glu Glu Glu Pro Thr Arg Glu Glu Leu Glu Phe Asp Met Asp
                180                 185                 190 agt gtc att aat ggg gaa ggg cct gtc ggg acg gcg gac cca gcc gag        923
Ser Val Ile Asn Gly Glu Gly Pro Val Gly Thr Ala Asp Pro Ala Glu
            195                 200                 205 aag acg ccg ctg ggg gtc ccg cgc cag tcg ggc cgt ccg ggt tgc tgc        971
Lys Thr Pro Leu Gly Val Pro Arg Gln Ser Gly Arg Pro Gly Cys Cys
        210                 215                 220 ggg ggc cgc tgc ggg ggc cgc cgg tgc cta cgc cgc tgg ttc cac ttc       1019
Gly Gly Arg Cys Gly Gly Arg Arg Cys Leu Arg Arg Trp Phe His Phe
    225                 230                 235 tgg ggc gtg ccg gtg acc atc ttc atg ggc aac gtg gtc agc tac ctg       1067
Trp Gly Val Pro Val Thr Ile Phe Met Gly Asn Val Val Ser Tyr Leu
240                 245                 250                 255 ctg ttc ctg ctg ctt ttc tcg cgg gtg ctg ctc gtg gat ttc cag ccg       1115
Leu Phe Leu Leu Leu Phe Ser Arg Val Leu Leu Val Asp Phe Gln Pro
                260                 265                 270 gcg ccg ccc ggc tcc ctg gag ctg ctc tat ttc tgg gct ttc acg           1163
Ala Pro Pro Gly Ser Leu Glu Leu Leu Leu Tyr Phe Trp Ala Phe Thr
            275                 280                 285 ctg ctg tgc gag gaa ctg cgc cag ggc ctg agc gga ggc ggg ggc agc       1211
Leu Leu Cys Glu Glu Leu Arg Gln Gly Leu Ser Gly Gly Gly Gly Ser
        290                 295                 300
```

```
ctc gcc agc ggg ggc ccc ggg cct ggc cat gcc tca ctg agc cag cgc     1259
Leu Ala Ser Gly Gly Pro Gly Pro Gly His Ala Ser Leu Ser Gln Arg
        305                 310                 315 ctg cgc ctc tac ctc gcc gac agc tgg aac cag tgc gac cta gtg gct     1307
Leu Arg Leu Tyr Leu Ala Asp Ser Trp Asn Gln Cys Asp Leu Val Ala
320                 325                 330                 335 ctc acc tgc ttc ctc ctg ggc gtg ggc tgc cgg ctg acc ccg ggt ttg     1355
Leu Thr Cys Phe Leu Leu Gly Val Gly Cys Arg Leu Thr Pro Gly Leu
                340                 345                 350 tac cac ctg ggc cgc act gtc ctc tgc atc gac ttc atg gtt ttc acg     1403
Tyr His Leu Gly Arg Thr Val Leu Cys Ile Asp Phe Met Val Phe Thr
            355                 360                 365 gtg cgg ctg ctt cac atc ttc acg gtc aac aaa cag ctg ggg ccc aag     1451
Val Arg Leu Leu His Ile Phe Thr Val Asn Lys Gln Leu Gly Pro Lys
        370                 375                 380 atc gtc atc gtg agc aag atg atg aag gac gtg ttc ttc ctc ttc         1499
Ile Val Ile Val Ser Lys Met Met Lys Asp Val Phe Phe Leu Phe
    385                 390                 395 ttc ctc ggc gtg tgg ctg gta gcc tat ggc gtg gcc acg gag ggg ctc     1547
Phe Leu Gly Val Trp Leu Val Ala Tyr Gly Val Ala Thr Glu Gly Leu
400                 405                 410                 415 ctg agg cca cgg gac agt gac ttc cca agt atc ctg cgc cgc gtc ttc     1595
Leu Arg Pro Arg Asp Ser Asp Phe Pro Ser Ile Leu Arg Arg Val Phe
                420                 425                 430 tac cgt ccc tac ctg cag atc ttc ggg cag att ccc cag gag gac atg     1643
Tyr Arg Pro Tyr Leu Gln Ile Phe Gly Gln Ile Pro Gln Glu Asp Met
            435                 440                 445 gac gtg gcc ctc atg gag cac agc aac tgc tcg tcg gag ccc ggc ttc     1691
Asp Val Ala Leu Met Glu His Ser Asn Cys Ser Ser Glu Pro Gly Phe
        450                 455                 460 tgg gca cac cct cct ggg gcc cag gcg ggc acc tgc gtc tcc cag tat     1739
Trp Ala His Pro Pro Gly Ala Gln Ala Gly Thr Cys Val Ser Gln Tyr
    465                 470                 475 gcc aac tgg ctg gtg gtg ctc ctc gtc atc ttc ctg ctc gtg gcc         1787
Ala Asn Trp Leu Val Val Leu Leu Val Ile Phe Leu Leu Val Ala
480                 485                 490                 495 aac atc ctg ctg gtc aac ttg ctc att gcc atg ttc agt tac aca ttc     1835
Asn Ile Leu Leu Val Asn Leu Leu Ile Ala Met Phe Ser Tyr Thr Phe
                500                 505                 510 ggc aaa gta cag ggc aac agc gat ctc tac tgg aag gcg cag cgt tac     1883
Gly Lys Val Gln Gly Asn Ser Asp Leu Tyr Trp Lys Ala Gln Arg Tyr
            515                 520                 525 cgc ctc atc cgg gaa ttc cac tct cgg ccc gcg ctg gcc ccg ccc ttt     1931
Arg Leu Ile Arg Glu Phe His Ser Arg Pro Ala Leu Ala Pro Pro Phe
        530                 535                 540 atc gtc atc tcc cac ttg cgc ctc ctc agg caa ttg tgc agg cga         1979
Ile Val Ile Ser His Leu Arg Leu Leu Arg Gln Leu Cys Arg Arg
    545                 550                 555 ccc cgg agc ccc cag ccg tcc tcc ccg gcc ctc gag cat ttc cgg gtt     2027
Pro Arg Ser Pro Gln Pro Ser Ser Pro Ala Leu Glu His Phe Arg Val
560                 565                 570                 575 tac ctt tct aag gaa gcc gag cgg aag ctg cta acg tgg gaa tcg gtg     2075
Tyr Leu Ser Lys Glu Ala Glu Arg Lys Leu Leu Thr Trp Glu Ser Val
                580                 585                 590 cat aag gag aac ttt ctg ctg gca cgc gct agg gac aag cgg gag agc     2123
His Lys Glu Asn Phe Leu Leu Ala Arg Ala Arg Asp Lys Arg Glu Ser
            595                 600                 605 gac tcc gag cgt ctg aag cgc acg tcc cag aag gtg gac ttg gca ctg     2171
Asp Ser Glu Arg Leu Lys Arg Thr Ser Gln Lys Val Asp Leu Ala Leu
```

```
                    610                 615                 620
aaa cag ctg gga cac atc cgc gag tac gaa cag cgc ctg aaa gtg ctg         2219
Lys Gln Leu Gly His Ile Arg Glu Tyr Glu Gln Arg Leu Lys Val Leu
        625                 630                 635 gag cgg gag gtc cag cag tgt agc cgc gtc ctg ggg tgg gtg gcc gag         2267
Glu Arg Glu Val Gln Gln Cys Ser Arg Val Leu Gly Trp Val Ala Glu
640                 645                 650                 655 gcc ctg agc cgc tct gcc ttg ctg ccc cca ggt ggg ccg cca ccc cct         2315
Ala Leu Ser Arg Ser Ala Leu Leu Pro Pro Gly Gly Pro Pro Pro Pro
                    660                 665                 670 gac ctg cct ggg tcc aaa gac tgagccctgc tggcggactt caaggagaag           2366
Asp Leu Pro Gly Ser Lys Asp
                675 cccccacagg ggattttgct cctagagtaa ggctcatctg ggcctcggcc cccgcacctg        2426 gtggccttgt ccttgaggtg agccccatgt ccatctgggc cactgtcagg accacctttg       2486 ggagtgtcaa ccttacaaac cacagcatgc ccggctcctc ccagaaccag tcccagcctg       2546 ggaggatcaa ggcctggatc ccgggccgtt atccatctgg aggctgcagg gtccttgggg      2606 taacagggac cacagacccc tcaccactca cagattcctc cactgggga aataaagcca       2666 tttcagagga aaaaaaaaaa aaaaaaaa                                         2695

<210> SEQ ID NO 8
<211> LENGTH: 678
<212> TYPE: PRT
<213> ORGANISM: Homo sapien

<400> SEQUENCE: 8

Met Tyr Leu Leu Ser Asp Lys Ala Thr Ser Pro Leu Ser Leu Asp Ala
1               5                   10                  15

Gly Leu Gly Gln Ala Pro Trp Ser Asp Leu Leu Trp Ala Leu Leu
            20                  25                  30

Leu Asn Arg Ala Gln Met Ala Met Tyr Phe Trp Glu Met Gly Ser Asn
            35                  40                  45

Ala Val Ser Ser Ala Leu Gly Ala Cys Leu Leu Arg Val Met Ala
        50                  55                  60

Arg Leu Glu Pro Asp Ala Glu Ala Ala Arg Arg Lys Asp Leu Ala
65                  70                  75                  80

Phe Lys Phe Glu Gly Met Gly Val Asp Leu Phe Gly Glu Cys Tyr Arg
                85                  90                  95

Ser Ser Glu Val Arg Ala Ala Arg Leu Leu Leu Arg Arg Cys Pro Leu
            100                 105                 110

Trp Gly Asp Ala Thr Cys Leu Gln Leu Ala Met Gln Ala Asp Ala Arg
        115                 120                 125

Ala Phe Phe Ala Gln Asp Gly Val Gln Ser Leu Leu Thr Gln Lys Trp
    130                 135                 140

Trp Gly Asp Met Ala Ser Thr Thr Pro Ile Trp Ala Leu Val Leu Ala
145                 150                 155                 160

Phe Phe Cys Pro Pro Leu Ile Tyr Thr Arg Leu Ile Thr Phe Arg Lys
                165                 170                 175

Ser Glu Glu Glu Pro Thr Arg Glu Glu Leu Glu Phe Asp Met Asp Ser
            180                 185                 190

Val Ile Asn Gly Glu Gly Pro Val Gly Thr Ala Asp Pro Ala Glu Lys
        195                 200                 205

Thr Pro Leu Gly Val Pro Arg Gln Ser Gly Arg Pro Gly Cys Cys Gly
    210                 215                 220
```

-continued

```
Gly Arg Cys Gly Gly Arg Arg Cys Leu Arg Arg Trp Phe His Phe Trp
225                 230                 235                 240

Gly Val Pro Val Thr Ile Phe Met Gly Asn Val Val Ser Tyr Leu Leu
            245                 250                 255

Phe Leu Leu Leu Phe Ser Arg Val Leu Leu Val Asp Phe Gln Pro Ala
            260                 265                 270

Pro Pro Gly Ser Leu Glu Leu Leu Tyr Phe Trp Ala Phe Thr Leu
        275                 280                 285

Leu Cys Glu Glu Leu Arg Gln Gly Leu Ser Gly Gly Gly Ser Leu
290                 295                 300

Ala Ser Gly Gly Pro Gly Pro Gly His Ala Ser Leu Ser Gln Arg Leu
305                 310                 315                 320

Arg Leu Tyr Leu Ala Asp Ser Trp Asn Gln Cys Asp Leu Val Ala Leu
                325                 330                 335

Thr Cys Phe Leu Leu Gly Val Gly Cys Arg Leu Thr Pro Gly Leu Tyr
                340                 345                 350

His Leu Gly Arg Thr Val Leu Cys Ile Asp Phe Met Val Phe Thr Val
                355                 360                 365

Arg Leu Leu His Ile Phe Thr Val Asn Lys Gln Leu Gly Pro Lys Ile
370                 375                 380

Val Ile Val Ser Lys Met Met Lys Asp Val Phe Phe Leu Phe Phe
385                 390                 395                 400

Leu Gly Val Trp Leu Val Ala Tyr Gly Val Ala Thr Glu Gly Leu Leu
                405                 410                 415

Arg Pro Arg Asp Ser Asp Phe Pro Ser Ile Leu Arg Arg Val Phe Tyr
                420                 425                 430

Arg Pro Tyr Leu Gln Ile Phe Gly Gln Ile Pro Gln Glu Asp Met Asp
                435                 440                 445

Val Ala Leu Met Glu His Ser Asn Cys Ser Ser Glu Pro Gly Phe Trp
450                 455                 460

Ala His Pro Pro Gly Ala Gln Ala Gly Thr Cys Val Ser Gln Tyr Ala
465                 470                 475                 480

Asn Trp Leu Val Val Leu Leu Val Ile Phe Leu Leu Val Ala Asn
                485                 490                 495

Ile Leu Leu Val Asn Leu Leu Ile Ala Met Phe Ser Tyr Thr Phe Gly
                500                 505                 510

Lys Val Gln Gly Asn Ser Asp Leu Tyr Trp Lys Ala Gln Arg Tyr Arg
            515                 520                 525

Leu Ile Arg Glu Phe His Ser Arg Pro Ala Leu Ala Pro Pro Phe Ile
530                 535                 540

Val Ile Ser His Leu Arg Leu Leu Leu Arg Gln Leu Cys Arg Arg Pro
545                 550                 555                 560

Arg Ser Pro Gln Pro Ser Ser Pro Ala Leu Glu His Phe Arg Val Tyr
                565                 570                 575

Leu Ser Lys Glu Ala Glu Arg Lys Leu Leu Thr Trp Glu Ser Val His
            580                 585                 590

Lys Glu Asn Phe Leu Leu Ala Arg Ala Arg Asp Lys Arg Glu Ser Asp
            595                 600                 605

Ser Glu Arg Leu Lys Arg Thr Ser Gln Lys Val Asp Leu Ala Leu Lys
610                 615                 620

Gln Leu Gly His Ile Arg Glu Tyr Glu Gln Arg Leu Lys Val Leu Glu
625                 630                 635                 640
```

-continued

```
Arg Glu Val Gln Gln Cys Ser Arg Val Leu Gly Trp Val Ala Glu Ala
              645                 650                 655

Leu Ser Arg Ser Ala Leu Leu Pro Pro Gly Gly Pro Pro Pro Asp
        660                 665                 670

Leu Pro Gly Ser Lys Asp
        675

<210> SEQ ID NO 9
<211> LENGTH: 4042
<212> TYPE: DNA
<213> ORGANISM: Homo sapiens
<220> FEATURE:
<221> NAME/KEY: CDS
<222> LOCATION: (42)...(3683)

<400> SEQUENCE: 9
cggggccctg ggctgcagga ggttgcggcg ccgcggcag c atg gtg gtg ccg gag      56
                                            Met Val Val Pro Glu
                                            1               5 aag gag cag agc tgg atc ccc aag atc ttc aag aag aag acc tgc acg     104
Lys Glu Gln Ser Trp Ile Pro Lys Ile Phe Lys Lys Lys Thr Cys Thr
            10                  15                  20 acg ttc ata gtt gac tcc aca gat ccg gga ggg acc ttg tgc cag tgt    152
Thr Phe Ile Val Asp Ser Thr Asp Pro Gly Gly Thr Leu Cys Gln Cys
        25                  30                  35 ggg cgc ccc cgg acc gcc cac ccc gca gtg gcc atg gag gat gcc ttc    200
Gly Arg Pro Arg Thr Ala His Pro Ala Val Ala Met Glu Asp Ala Phe
    40                  45                  50 ggg gca gcc gtg gtg acc gtg tgg gac agc gat gca cac acg acg gag    248
Gly Ala Ala Val Val Thr Val Trp Asp Ser Asp Ala His Thr Thr Glu
55                  60                  65 aag ccc acc gat gcc tac gga gag ctg gac ttc acg ggg gcc ggc cgc    296
Lys Pro Thr Asp Ala Tyr Gly Glu Leu Asp Phe Thr Gly Ala Gly Arg
70                  75                  80                  85 aag cac agc aat ttc ctc cgg ctc tct gac cga acg gat cca gct gca    344
Lys His Ser Asn Phe Leu Arg Leu Ser Asp Arg Thr Asp Pro Ala Ala
            90                  95                  100 gtt tat agt ctg gtc aca cgc aca tgg ggc ttc cgt gcc ccg aac ctg    392
Val Tyr Ser Leu Val Thr Arg Thr Trp Gly Phe Arg Ala Pro Asn Leu
        105                 110                 115 gtg gtg tca gtg ctg ggg gga tcg ggg ggc ccc gtc ctc cag acc tgg    440
Val Val Ser Val Leu Gly Gly Ser Gly Gly Pro Val Leu Gln Thr Trp
    120                 125                 130 ctg cag gac ctg ctg cgt cgt ggg ctg gtg cgg gct gcc cag agc aca    488
Leu Gln Asp Leu Leu Arg Arg Gly Leu Val Arg Ala Ala Gln Ser Thr
135                 140                 145 gga gcc tgg att gtc act ggg ggt ctg cac acg ggc atc ggc cgg cat    536
Gly Ala Trp Ile Val Thr Gly Gly Leu His Thr Gly Ile Gly Arg His
150                 155                 160                 165 gtt ggt gtg gct gta cgg gac cat cag atg gcc agc act ggg ggc acc    584
Val Gly Val Ala Val Arg Asp His Gln Met Ala Ser Thr Gly Gly Thr
            170                 175                 180 aag gtg gtg gcc atg ggt gtg gcc ccc tgg ggt gtg gtc cgg aat aga    632
Lys Val Val Ala Met Gly Val Ala Pro Trp Gly Val Val Arg Asn Arg
        185                 190                 195 gac acc ctc atc aac ccc aag ggc tcg ttc cct gcg agg tac cgg tgg    680
Asp Thr Leu Ile Asn Pro Lys Gly Ser Phe Pro Ala Arg Tyr Arg Trp
    200                 205                 210 cgc ggt gac ccg gag gac ggg gtc cag ttt ccc ctg gac tac aac tac    728
Arg Gly Asp Pro Glu Asp Gly Val Gln Phe Pro Leu Asp Tyr Asn Tyr
215                 220                 225
```

-continued

```
tcg gcc ttc ttc ctg gtg gac gac ggc aca cac ggc tgc ctg ggg ggc    776
Ser Ala Phe Phe Leu Val Asp Asp Gly Thr His Gly Cys Leu Gly Gly
230                 235                 240                 245 gag aac cgc ttc cgc ttg cgc ctg gag tcc tac atc tca cag cag aag    824
Glu Asn Arg Phe Arg Leu Arg Leu Glu Ser Tyr Ile Ser Gln Gln Lys
            250                 255                 260 acg ggc gtg gga ggg act gga att gac atc cct gtc ctg ctc ctc ctg    872
Thr Gly Val Gly Gly Thr Gly Ile Asp Ile Pro Val Leu Leu Leu Leu
265                 270                 275 att gat ggt gat gag aag atg ttg acg cga ata gag aac gcc acc cag    920
Ile Asp Gly Asp Glu Lys Met Leu Thr Arg Ile Glu Asn Ala Thr Gln
        280                 285                 290 gct cag ctc cca tgt ctc ctc gtg gct ggc tca ggg gga gct gcg gac    968
Ala Gln Leu Pro Cys Leu Leu Val Ala Gly Ser Gly Gly Ala Ala Asp
    295                 300                 305 tgc ctg gcg gag acc ctg gaa gac act ctg gcc cca ggg agt ggg gga   1016
Cys Leu Ala Glu Thr Leu Glu Asp Thr Leu Ala Pro Gly Ser Gly Gly
310                 315                 320                 325 gcc agg caa ggc gaa gcc cga gat cga atc agg cgt ttc ttt ccc aaa   1064
Ala Arg Gln Gly Glu Ala Arg Asp Arg Ile Arg Arg Phe Phe Pro Lys
            330                 335                 340 ggg gac ctt gag gtc ctg cag gcc cag gtg gag agg att atg acc cgg   1112
Gly Asp Leu Glu Val Leu Gln Ala Gln Val Glu Arg Ile Met Thr Arg
345                 350                 355 aag gag ctc ctg aca gtc tat tct tct gag gat ggg tct gag gaa ttc   1160
Lys Glu Leu Leu Thr Val Tyr Ser Ser Glu Asp Gly Ser Glu Glu Phe
        360                 365                 370 gag acc ata gtt ttg aag gcc ctt gtg aag gcc tgt ggg agc tcg gag   1208
Glu Thr Ile Val Leu Lys Ala Leu Val Lys Ala Cys Gly Ser Ser Glu
    375                 380                 385 gcc tca gcc tac ctg gat gag ctg cgt ttg gct gtg gct tgg aac cgc   1256
Ala Ser Ala Tyr Leu Asp Glu Leu Arg Leu Ala Val Ala Trp Asn Arg
390                 395                 400                 405 gtg gac att gcc cag agt gaa ctc ttt cgg ggg gac atc caa tgg cgg   1304
Val Asp Ile Ala Gln Ser Glu Leu Phe Arg Gly Asp Ile Gln Trp Arg
            410                 415                 420 tcc ttc cat ctc gaa gct tcc ctc atg gac gcc ctg ctg aat gac cgg   1352
Ser Phe His Leu Glu Ala Ser Leu Met Asp Ala Leu Leu Asn Asp Arg
                425                 430                 435 cct gag ttc gtg cgc ttg ctc att tcc cac ggc ctc agc ctg ggc cac   1400
Pro Glu Phe Val Arg Leu Leu Ile Ser His Gly Leu Ser Leu Gly His
    440                 445                 450 ttc ctg acc ccg atg cgc ctg gcc caa ctc tac agc gcg gcg ccc tcc   1448
Phe Leu Thr Pro Met Arg Leu Ala Gln Leu Tyr Ser Ala Ala Pro Ser
455                 460                 465 aac tcg ctc atc cgc aac ctt ttg gac cag gcg tcc cac agc gca ggc   1496
Asn Ser Leu Ile Arg Asn Leu Leu Asp Gln Ala Ser His Ser Ala Gly
470                 475                 480                 485 acc aaa gcc cca gcc cta aaa ggg gga gct gcg gag ctc cgg ccc cct   1544
Thr Lys Ala Pro Ala Leu Lys Gly Gly Ala Ala Glu Leu Arg Pro Pro
            490                 495                 500 gac gtg ggg cat gtg ctg agg atg ctg ctg ggg aag atg tgc gcg ccg   1592
Asp Val Gly His Val Leu Arg Met Leu Leu Gly Lys Met Cys Ala Pro
                505                 510                 515 agg tac ccc tcc ggg ggc gcc tgg gac cct cac cca ggc cag ggc ttc   1640
Arg Tyr Pro Ser Gly Gly Ala Trp Asp Pro His Pro Gly Gln Gly Phe
            520                 525                 530 ggg gag agc atg tat ctg ctc tcg gac aag gcc acc tcg ccg ctc tcg   1688
Gly Glu Ser Met Tyr Leu Leu Ser Asp Lys Ala Thr Ser Pro Leu Ser
```

-continued

| | | | | | | | | | | | | |
|---|---|---|---|---|---|---|---|---|---|---|---|---|
| | 535 | | | 540 | | | 545 | | | | | |
| ctg | gat | gct | ggc | ctc | ggg | cag | gcc | ccc | tgg | agc | gac | ctg ctt ctt tgg | 1736 |
| Leu | Asp | Ala | Gly | Leu | Gly | Gln | Ala | Pro | Trp | Ser | Asp | Leu Leu Leu Trp |
| 550 | | | | 555 | | | | 560 | | | | 565 | gca ctg ttg ctg aac agg gca cag atg gcc atg tac ttc tgg gag atg  1784
Ala Leu Leu Leu Asn Arg Ala Gln Met Ala Met Tyr Phe Trp Glu Met
        570                     575                 580 ggt tcc aat gca gtt tcc tca gct ctt ggg gcc tgt ttg ctg ctc cgg  1832
Gly Ser Asn Ala Val Ser Ser Ala Leu Gly Ala Cys Leu Leu Leu Arg
            585                     590                 595 gtg atg gca cgc ctg gag cct gac gct gag gag gca gca cgg agg aaa  1880
Val Met Ala Arg Leu Glu Pro Asp Ala Glu Glu Ala Ala Arg Arg Lys
        600                     605                 610 gac ctg gcg ttc aag ttt gag ggg atg ggc gtt gac ctc ttt ggc gag  1928
Asp Leu Ala Phe Lys Phe Glu Gly Met Gly Val Asp Leu Phe Gly Glu
        615                     620                 625 tgc tat cgc agc agt gag gtg agg gct gcc cgc ctc ctc ctc cgt cgc  1976
Cys Tyr Arg Ser Ser Glu Val Arg Ala Ala Arg Leu Leu Leu Arg Arg
630                     635                     640             645 tgc ccg ctc tgg ggg gat gcc act tgc ctc cag ctg gcc atg caa gct  2024
Cys Pro Leu Trp Gly Asp Ala Thr Cys Leu Gln Leu Ala Met Gln Ala
                650                     655                 660 gac gcc cgt gcc ttc ttt gcc cag gat ggg gta cag tct ctg ctg aca  2072
Asp Ala Arg Ala Phe Phe Ala Gln Asp Gly Val Gln Ser Leu Leu Thr
        665                     670                 675 cag aag tgg tgg gga gat atg gcc agc act aca ccc atc tgg gcc ctg  2120
Gln Lys Trp Trp Gly Asp Met Ala Ser Thr Thr Pro Ile Trp Ala Leu
        680                     685                 690 gtt ctc gcc ttc ttt tgc cct cca ctc atc tac acc cgc ctc atc acc  2168
Val Leu Ala Phe Phe Cys Pro Pro Leu Ile Tyr Thr Arg Leu Ile Thr
695                     700                     705 ttc agg aaa tca gaa gag gag ccc aca cgg gag gag cta gag ttt gac  2216
Phe Arg Lys Ser Glu Glu Glu Pro Thr Arg Glu Glu Leu Glu Phe Asp
710                     715                     720             725 atg gat agt gtc att aat ggg gaa ggg cct gtc ggg acg gcg gac cca  2264
Met Asp Ser Val Ile Asn Gly Glu Gly Pro Val Gly Thr Ala Asp Pro
                730                     735                 740 gcc gag aag acg ccg ctg ggg gtc ccg cgc cag tcg ggc cgt ccg ggt  2312
Ala Glu Lys Thr Pro Leu Gly Val Pro Arg Gln Ser Gly Arg Pro Gly
        745                     750                 755 tgc tgc ggg ggc cgc tgc ggg ggg cgc cgg tgc cta cgc cgc tgg ttc  2360
Cys Cys Gly Gly Arg Cys Gly Gly Arg Arg Cys Leu Arg Arg Trp Phe
            760                     765                 770 cac ttc tgg ggc gtg ccg gtg acc atc ttc atg ggc aac gtg gtc agc  2408
His Phe Trp Gly Val Pro Val Thr Ile Phe Met Gly Asn Val Val Ser
775                     780                     785 tac ctg ctg ttc ctg ctg ctt ttc tcg cgg gtg ctg ctc gtg gat ttc  2456
Tyr Leu Leu Phe Leu Leu Leu Phe Ser Arg Val Leu Leu Val Asp Phe
790                     795                     800             805 cag ccg gcg ccg ccc ggc tcc ctg gag ctg ctg ctc tat ttc tgg gct  2504
Gln Pro Ala Pro Pro Gly Ser Leu Glu Leu Leu Leu Tyr Phe Trp Ala
                810                     815                 820 ttc acg ctg ctg tgc gag gaa ctg cgc cag ggc ctg agc gga ggc ggg  2552
Phe Thr Leu Leu Cys Glu Glu Leu Arg Gln Gly Leu Ser Gly Gly Gly
        825                     830                 835 ggc agc ctc gcc agc ggg ggc ccc ggg cct ggc cat gcc tca ctg agc  2600
Gly Ser Leu Ala Ser Gly Gly Pro Gly Pro Gly His Ala Ser Leu Ser
        840                     845                 850 cag cgc ctg cgc ctc tac ctc gcc gac agc tgg aac cag tgc gac cta  2648

```
                                                                              -continued
Gln Arg Leu Arg Leu Tyr Leu Ala Asp Ser Trp Asn Gln Cys Asp Leu
    855                 860                 865 gtg gct ctc acc tgc ttc ctc ctg ggc gtg ggc tgc cgg ctg acc ccg        2696
Val Ala Leu Thr Cys Phe Leu Leu Gly Val Gly Cys Arg Leu Thr Pro
870                 875                 880                 885 ggt ttg tac cac ctg ggc cgc act gtc ctc tgc atc gac ttc atg gtt        2744
Gly Leu Tyr His Leu Gly Arg Thr Val Leu Cys Ile Asp Phe Met Val
                    890                 895                 900 ttc acg gtg cgg ctg ctt cac atc ttc acg gtc aac aaa cag ctg ggg        2792
Phe Thr Val Arg Leu Leu His Ile Phe Thr Val Asn Lys Gln Leu Gly
                905                 910                 915 ccc aag atc gtc atc gtg agc aag atg atg aag gac gtg ttc ttc ttc        2840
Pro Lys Ile Val Ile Val Ser Lys Met Met Lys Asp Val Phe Phe Phe
            920                 925                 930 ctc ttc ttc ctc ggc gtg tgg ctg gta gcc tat ggc gtg gcc acg gag        2888
Leu Phe Phe Leu Gly Val Trp Leu Val Ala Tyr Gly Val Ala Thr Glu
        935                 940                 945 ggg ctc ctg agg cca cgg gac agt gac ttc cca agt atc ctg cgc cgc        2936
Gly Leu Leu Arg Pro Arg Asp Ser Asp Phe Pro Ser Ile Leu Arg Arg
950                 955                 960                 965 gtc ttc tac cgt ccc tac ctg cag atc ttc ggg cag att ccc cag gag        2984
Val Phe Tyr Arg Pro Tyr Leu Gln Ile Phe Gly Gln Ile Pro Gln Glu
                970                 975                 980 gac atg gac gtg gcc ctc atg gag cac agc aac tgc tcg tcg gag ccc        3032
Asp Met Asp Val Ala Leu Met Glu His Ser Asn Cys Ser Ser Glu Pro
                985                 990                 995 ggc ttc tgg gca cac cct cct ggg gcc cag gcg ggc acc tgc gtc tcc        3080
Gly Phe Trp Ala His Pro Pro Gly Ala Gln Ala Gly Thr Cys Val Ser
            1000                1005                1010 cag tat gcc aac tgg ctg gtg gtg ctc ctc gtc atc ttc ctg ctc            3128
Gln Tyr Ala Asn Trp Leu Val Val Leu Leu Val Ile Phe Leu Leu
        1015                1020                1025 gtg gcc aac atc ctg ctg gtc aac ttg ctc att gcc atg ttc agt tac        3176
Val Ala Asn Ile Leu Leu Val Asn Leu Leu Ile Ala Met Phe Ser Tyr
1030                1035                1040                1045 aca ttc ggc aaa gta cag ggc aac agc gat ctc tac tgg aag gcg cag        3224
Thr Phe Gly Lys Val Gln Gly Asn Ser Asp Leu Tyr Trp Lys Ala Gln
                1050                1055                1060 cgt tac cgc ctc atc cgg gaa ttc cac tct cgg ccc gcg ctg gcc ccg        3272
Arg Tyr Arg Leu Ile Arg Glu Phe His Ser Arg Pro Ala Leu Ala Pro
                1065                1070                1075 ccc ttt atc gtc atc tcc cac ttg cgc ctc ctc agg caa ttg tgc            3320
Pro Phe Ile Val Ile Ser His Leu Arg Leu Leu Arg Gln Leu Cys
        1080                1085                1090 agg cga ccc cgg agc ccc cag ccg tcc tcc ccg gcc ctc gag cat ttc        3368
Arg Arg Pro Arg Ser Pro Gln Pro Ser Ser Pro Ala Leu Glu His Phe
        1095                1100                1105 cgg gtt tac ctt tct aag gaa gcc gag cgg aag ctg cta acg tgg gaa        3416
Arg Val Tyr Leu Ser Lys Glu Ala Glu Arg Lys Leu Leu Thr Trp Glu
1110                1115                1120                1125 tcg gtg cat aag gag aac ttt ctg ctg gca cgc gct agg gac aag cgg        3464
Ser Val His Lys Glu Asn Phe Leu Leu Ala Arg Ala Arg Asp Lys Arg
                1130                1135                1140 gag agc gac tcc gag cgt ctg aag cgc acg tcc cag aag gtg gac ttg        3512
Glu Ser Asp Ser Glu Arg Leu Lys Arg Thr Ser Gln Lys Val Asp Leu
                1145                1150                1155 gca ctg aaa cag ctg gga cac atc cgc gag tac gaa cag cgc ctg aaa        3560
Ala Leu Lys Gln Leu Gly His Ile Arg Glu Tyr Glu Gln Arg Leu Lys
                1160                1165                1170
```

```
gtg ctg gag cgg gag gtc cag cag tgt agc cgc gtc ctg ggg tgg gtg      3608
Val Leu Glu Arg Glu Val Gln Gln Cys Ser Arg Val Leu Gly Trp Val
         1175                1180                1185 gcc gag gcc ctg agc cgc tct gcc ttg ctg ccc cca ggt ggg ccg cca      3656
Ala Glu Ala Leu Ser Arg Ser Ala Leu Leu Pro Pro Gly Gly Pro Pro
1190            1195                1200                1205 ccc cct gac ctg cct ggg tcc aaa gac tgagccctgc tgcggactt             3703
Pro Pro Asp Leu Pro Gly Ser Lys Asp
                1210 caaggagaag cccccacagg ggattttgct cctagagtaa ggctcatctg ggcctcggcc    3763 cccgcacctg gtggccttgt ccttgaggtg agccccatgt ccatctgggc cactgtcagg    3823 accacctttg ggagtgtcat ccttacaaac cacagcatgc ccggctcctc ccagaaccag    3883 tcccagcctg ggaggatcaa ggcctggatc ccgggccgtt atccatctgg aggctgcagg    3943 gtccttgggg taacagggac cacagacccc tcaccactca cagattcctc acactgggga   4003 aataaagcca tttcagagga aaaaaaaaaa aaaaaaaa                            4042
```

<210> SEQ ID NO 10
<211> LENGTH: 1214
<212> TYPE: PRT
<213> ORGANISM: Homo sapiens

<400> SEQUENCE: 10

```
Met Val Val Pro Glu Lys Glu Gln Ser Trp Ile Pro Lys Ile Phe Lys
1               5                   10                  15

Lys Lys Thr Cys Thr Thr Phe Ile Val Asp Ser Thr Asp Pro Gly Gly
            20                  25                  30

Thr Leu Cys Gln Cys Gly Arg Pro Arg Thr Ala His Pro Ala Val Ala
        35                  40                  45

Met Glu Asp Ala Phe Gly Ala Ala Val Thr Val Trp Asp Ser Asp
    50                  55                  60

Ala His Thr Thr Glu Lys Pro Thr Asp Ala Tyr Gly Glu Leu Asp Phe
65                  70                  75                  80

Thr Gly Ala Gly Arg Lys His Ser Asn Phe Leu Arg Leu Ser Asp Arg
                85                  90                  95

Thr Asp Pro Ala Ala Val Tyr Ser Leu Val Thr Arg Thr Trp Gly Phe
            100                 105                 110

Arg Ala Pro Asn Leu Val Val Ser Val Leu Gly Gly Ser Gly Gly Pro
        115                 120                 125

Val Leu Gln Thr Trp Leu Gln Asp Leu Leu Arg Arg Gly Leu Val Arg
    130                 135                 140

Ala Ala Gln Ser Thr Gly Ala Trp Ile Val Thr Gly Gly Leu His Thr
145                 150                 155                 160

Gly Ile Gly Arg His Val Gly Val Ala Val Arg Asp His Gln Met Ala
                165                 170                 175

Ser Thr Gly Gly Thr Lys Val Val Ala Met Gly Val Ala Pro Trp Gly
            180                 185                 190

Val Val Arg Asn Arg Asp Thr Leu Ile Asn Pro Lys Gly Ser Phe Pro
        195                 200                 205

Ala Arg Tyr Arg Trp Arg Gly Asp Pro Glu Asp Gly Val Gln Phe Pro
    210                 215                 220

Leu Asp Tyr Asn Tyr Ser Ala Phe Phe Leu Val Asp Asp Gly Thr His
225                 230                 235                 240

Gly Cys Leu Gly Gly Glu Asn Arg Phe Arg Leu Arg Leu Glu Ser Tyr
                245                 250                 255
```

-continued

```
Ile Ser Gln Gln Lys Thr Gly Val Gly Thr Gly Ile Asp Ile Pro
        260                 265                 270

Val Leu Leu Leu Ile Asp Gly Asp Glu Lys Met Leu Thr Arg Ile
        275                 280                 285

Glu Asn Ala Thr Gln Ala Gln Leu Pro Cys Leu Leu Val Ala Gly Ser
        290                 295                 300

Gly Gly Ala Ala Asp Cys Leu Ala Glu Thr Leu Glu Asp Thr Leu Ala
305                 310                 315                 320

Pro Gly Ser Gly Gly Ala Arg Gln Gly Glu Ala Arg Asp Arg Ile Arg
                    325                 330                 335

Arg Phe Phe Pro Lys Gly Asp Leu Glu Val Leu Gln Ala Gln Val Glu
                340                 345                 350

Arg Ile Met Thr Arg Lys Glu Leu Leu Thr Val Tyr Ser Ser Glu Asp
                355                 360                 365

Gly Ser Glu Glu Phe Glu Thr Ile Val Leu Lys Ala Leu Val Lys Ala
            370                 375                 380

Cys Gly Ser Ser Glu Ala Ser Ala Tyr Leu Asp Glu Leu Arg Leu Ala
385                 390                 395                 400

Val Ala Trp Asn Arg Val Asp Ile Ala Gln Ser Glu Leu Phe Arg Gly
                    405                 410                 415

Asp Ile Gln Trp Arg Ser Phe His Leu Glu Ala Ser Leu Met Asp Ala
                420                 425                 430

Leu Leu Asn Asp Arg Pro Glu Phe Val Arg Leu Leu Ile Ser His Gly
            435                 440                 445

Leu Ser Leu Gly His Phe Leu Thr Pro Met Arg Leu Ala Gln Leu Tyr
450                 455                 460

Ser Ala Ala Pro Ser Asn Ser Leu Ile Arg Asn Leu Leu Asp Gln Ala
465                 470                 475                 480

Ser His Ser Ala Gly Thr Lys Ala Pro Ala Leu Lys Gly Gly Ala Ala
                    485                 490                 495

Glu Leu Arg Pro Pro Asp Val Gly His Val Leu Arg Met Leu Leu Gly
                500                 505                 510

Lys Met Cys Ala Pro Arg Tyr Pro Ser Gly Gly Ala Trp Asp Pro His
                515                 520                 525

Pro Gly Gln Gly Phe Gly Glu Ser Met Tyr Leu Leu Ser Asp Lys Ala
            530                 535                 540

Thr Ser Pro Leu Ser Leu Asp Ala Gly Leu Gly Gln Ala Pro Trp Ser
545                 550                 555                 560

Asp Leu Leu Leu Trp Ala Leu Leu Asn Arg Ala Gln Met Ala Met
                    565                 570                 575

Tyr Phe Trp Glu Met Gly Ser Asn Ala Val Ser Ser Ala Leu Gly Ala
                580                 585                 590

Cys Leu Leu Leu Arg Val Met Ala Arg Leu Glu Pro Asp Ala Glu Glu
                595                 600                 605

Ala Ala Arg Arg Lys Asp Leu Ala Phe Lys Phe Glu Gly Met Gly Val
        610                 615                 620

Asp Leu Phe Gly Glu Cys Tyr Arg Ser Ser Glu Val Arg Ala Ala Arg
625                 630                 635                 640

Leu Leu Leu Arg Arg Cys Pro Leu Trp Gly Asp Ala Thr Cys Leu Gln
                    645                 650                 655

Leu Ala Met Gln Ala Asp Ala Arg Ala Phe Phe Ala Gln Asp Gly Val
                660                 665                 670
```

```
                        -continued

Gln Ser Leu Leu Thr Gln Lys Trp Trp Gly Asp Met Ala Ser Thr Thr
        675                 680                 685

Pro Ile Trp Ala Leu Val Leu Ala Phe Phe Cys Pro Pro Leu Ile Tyr
690                 695                 700

Thr Arg Leu Ile Thr Phe Arg Lys Ser Glu Glu Pro Thr Arg Glu
705                 710                 715                 720

Glu Leu Glu Phe Asp Met Asp Ser Val Ile Asn Gly Glu Gly Pro Val
                725                 730                 735

Gly Thr Ala Asp Pro Ala Glu Lys Thr Pro Leu Gly Val Pro Arg Gln
                740                 745                 750

Ser Gly Arg Pro Gly Cys Cys Gly Arg Cys Gly Arg Arg Cys
        755                 760                 765

Leu Arg Arg Trp Phe His Phe Trp Gly Val Pro Val Thr Ile Phe Met
770                 775                 780

Gly Asn Val Val Ser Tyr Leu Leu Phe Leu Leu Phe Ser Arg Val
785                 790                 795                 800

Leu Leu Val Asp Phe Gln Pro Ala Pro Pro Gly Ser Leu Glu Leu Leu
                805                 810                 815

Leu Tyr Phe Trp Ala Phe Thr Leu Leu Cys Glu Glu Leu Arg Gln Gly
                820                 825                 830

Leu Ser Gly Gly Gly Gly Ser Leu Ala Ser Gly Gly Pro Gly Pro Gly
        835                 840                 845

His Ala Ser Leu Ser Gln Arg Leu Arg Leu Tyr Leu Ala Asp Ser Trp
850                 855                 860

Asn Gln Cys Asp Leu Val Ala Leu Thr Cys Phe Leu Leu Gly Val Gly
865                 870                 875                 880

Cys Arg Leu Thr Pro Gly Leu Tyr His Leu Gly Arg Thr Val Leu Cys
                885                 890                 895

Ile Asp Phe Met Val Phe Thr Val Arg Leu Leu His Ile Phe Thr Val
                900                 905                 910

Asn Lys Gln Leu Gly Pro Lys Ile Val Ile Ser Lys Met Met Lys
        915                 920                 925

Asp Val Phe Phe Phe Leu Phe Phe Leu Gly Val Trp Leu Val Ala Tyr
930                 935                 940

Gly Val Ala Thr Glu Gly Leu Leu Arg Pro Arg Asp Ser Asp Phe Pro
945                 950                 955                 960

Ser Ile Leu Arg Arg Val Phe Tyr Arg Pro Tyr Leu Gln Ile Phe Gly
                965                 970                 975

Gln Ile Pro Gln Glu Asp Met Asp Val Ala Leu Met Glu His Ser Asn
                980                 985                 990

Cys Ser Ser Glu Pro Gly Phe Trp Ala His Pro Pro Gly Ala Gln Ala
        995                 1000                1005

Gly Thr Cys Val Ser Gln Tyr Ala Asn Trp Leu Val Val Leu Leu Leu
        1010                1015                1020

Val Ile Phe Leu Leu Val Ala Asn Ile Leu Leu Val Asn Leu Leu Ile
1025                1030                1035                1040

Ala Met Phe Ser Tyr Thr Phe Gly Lys Val Gln Gly Asn Ser Asp Leu
                1045                1050                1055

Tyr Trp Lys Ala Gln Arg Tyr Arg Leu Ile Arg Glu Phe His Ser Arg
                1060                1065                1070

Pro Ala Leu Ala Pro Pro Phe Ile Val Ile Ser His Leu Arg Leu Leu
        1075                1080                1085

Leu Arg Gln Leu Cys Arg Arg Pro Arg Ser Pro Gln Pro Ser Ser Pro
```

```
                1090               1095               1100
Ala Leu Glu His Phe Arg Val Tyr Leu Ser Lys Glu Ala Glu Arg Lys
1105                1110                1115                1120

Leu Leu Thr Trp Glu Ser Val His Lys Glu Asn Phe Leu Leu Ala Arg
                1125                1130                1135

Ala Arg Asp Lys Arg Glu Ser Asp Ser Glu Arg Leu Lys Arg Thr Ser
            1140                1145                1150

Gln Lys Val Asp Leu Ala Leu Lys Gln Leu Gly His Ile Arg Glu Tyr
        1155                1160                1165

Glu Gln Arg Leu Lys Val Leu Glu Arg Glu Val Gln Gln Cys Ser Arg
    1170                1175                1180

Val Leu Gly Trp Val Ala Glu Ala Leu Ser Arg Ser Ala Leu Leu Pro
1185                1190                1195                1200

Pro Gly Gly Pro Pro Pro Asp Leu Pro Gly Ser Lys Asp
                1205                1210

<210> SEQ ID NO 11
<211> LENGTH: 3893
<212> TYPE: DNA
<213> ORGANISM: Homo sapiens
<220> FEATURE:
<221> NAME/KEY: CDS
<222> LOCATION: (27)...(3890)

<400> SEQUENCE: 11
attaaagttt ataaaacagt ggctgg atg gtt gga gga tgc agg tgg aca gaa     53
                             Met Val Gly Gly Cys Arg Trp Thr Glu
                             1               5 gac gtg gag cct gca gaa gta aag gaa aag atg tcc ttt cgg gca gcc    101
Asp Val Glu Pro Ala Glu Val Lys Glu Lys Met Ser Phe Arg Ala Ala
10              15                  20                  25 agg ctc agc atg agg aac aga agg aat gac act ctg gac agc acc cgg    149
Arg Leu Ser Met Arg Asn Arg Arg Asn Asp Thr Leu Asp Ser Thr Arg
                30                  35                  40 acc ctg tac tcc agc gcg tct cgg agc aca gac ttg tct tac agt gaa    197
Thr Leu Tyr Ser Ser Ala Ser Arg Ser Thr Asp Leu Ser Tyr Ser Glu
            45                  50                  55 agc gcc agc ttc tac gct gcc ttc agg aca cag acg tgc cca atc atg    245
Ser Ala Ser Phe Tyr Ala Ala Phe Arg Thr Gln Thr Cys Pro Ile Met
        60                  65                  70 gct tct tgg gac ttg gtg aat ttt att caa gca aat ttt aag aaa cga    293
Ala Ser Trp Asp Leu Val Asn Phe Ile Gln Ala Asn Phe Lys Lys Arg
    75                  80                  85 gaa tgt gtc ttc ttt acc aaa gat tcc aag gcc acg gag aat gtg tgc    341
Glu Cys Val Phe Phe Thr Lys Asp Ser Lys Ala Thr Glu Asn Val Cys
90                  95                 100                 105 aag tgt ggc tat gcc cag agc cag cac atg gaa ggc acc cag atc aac    389
Lys Cys Gly Tyr Ala Gln Ser Gln His Met Glu Gly Thr Gln Ile Asn
                110                 115                 120 caa agt gag aaa tgg aac tac aag aaa cac acc aag gaa ttt cct acc    437
Gln Ser Glu Lys Trp Asn Tyr Lys Lys His Thr Lys Glu Phe Pro Thr
            125                 130                 135 gac gcc ttt ggg gat att cag ttt gag aca ctg ggg aag aaa ggg aag    485
Asp Ala Phe Gly Asp Ile Gln Phe Glu Thr Leu Gly Lys Lys Gly Lys
        140                 145                 150 tat ata cgt ctg tcc tgc gac acg gac gcg gaa atc ctt tac gag ctg    533
Tyr Ile Arg Leu Ser Cys Asp Thr Asp Ala Glu Ile Leu Tyr Glu Leu
    155                 160                 165 ctg acc cag cac tgg cac ctg aaa aca ccc aac ctg gtc att tct gtg    581
```

```
                Leu Thr Gln His Trp His Leu Lys Thr Pro Asn Leu Val Ile Ser Val
                170                 175                 180                 185 acc ggg ggc gcc aag aac ttc gcc ctg aag ccg cgc atg cgc aag atc            629
Thr Gly Gly Ala Lys Asn Phe Ala Leu Lys Pro Arg Met Arg Lys Ile
                    190                 195                 200 ttc agc cgg ctc atc tac atc gcg cag tcc aaa ggt gct tgg att ctc            677
Phe Ser Arg Leu Ile Tyr Ile Ala Gln Ser Lys Gly Ala Trp Ile Leu
            205                 210                 215 acg gga ggc acc cat tat ggc ctg atg aag tac atc ggg gag gtg gtg            725
Thr Gly Gly Thr His Tyr Gly Leu Met Lys Tyr Ile Gly Glu Val Val
        220                 225                 230 aga gat aac acc atc agc agg agt tca gag gag aat att gtg gcc att            773
Arg Asp Asn Thr Ile Ser Arg Ser Ser Glu Glu Asn Ile Val Ala Ile
    235                 240                 245 ggc ata gca gct tgg ggc atg gtc tcc aac cgg gac acc ctc atc agg            821
Gly Ile Ala Ala Trp Gly Met Val Ser Asn Arg Asp Thr Leu Ile Arg
250                 255                 260                 265 aat tgc gat gct gag ggc tat ttt tta gcc cag tac ctt atg gat gac            869
Asn Cys Asp Ala Glu Gly Tyr Phe Leu Ala Gln Tyr Leu Met Asp Asp
                270                 275                 280 ttc aca aga gat cca ctg tat atc ctg gac aac aac cac aca cat ttg            917
Phe Thr Arg Asp Pro Leu Tyr Ile Leu Asp Asn Asn His Thr His Leu
            285                 290                 295 ctg ctc gtg gac aat ggc tgt cat gga cat ccc act gtc gaa gca aag            965
Leu Leu Val Asp Asn Gly Cys His Gly His Pro Thr Val Glu Ala Lys
        300                 305                 310 ctc cgg aat cag cta gag aag tat atc tct gag cgc act att caa gat           1013
Leu Arg Asn Gln Leu Glu Lys Tyr Ile Ser Glu Arg Thr Ile Gln Asp
    315                 320                 325 tcc aac tat ggt ggc aag atc ccc att gtg tgt ttt gcc caa gga ggt           1061
Ser Asn Tyr Gly Gly Lys Ile Pro Ile Val Cys Phe Ala Gln Gly Gly
330                 335                 340                 345 gga aaa gag act ttg aaa gcc atc aat acc tcc atc aaa aat aaa att           1109
Gly Lys Glu Thr Leu Lys Ala Ile Asn Thr Ser Ile Lys Asn Lys Ile
                350                 355                 360 cct tgt gtg gtg gtg gaa ggc tcg ggc cag atc gct gat gtg atc gct           1157
Pro Cys Val Val Val Glu Gly Ser Gly Gln Ile Ala Asp Val Ile Ala
            365                 370                 375 agc ctg gtg gag gtg gag gat gcc ctg aca tct tct gcc gtc aag gag           1205
Ser Leu Val Glu Val Glu Asp Ala Leu Thr Ser Ser Ala Val Lys Glu
        380                 385                 390 aag ctg gtg cgc ttt tta ccc cgc acg gtg tcc cgg ctg cct gag gag           1253
Lys Leu Val Arg Phe Leu Pro Arg Thr Val Ser Arg Leu Pro Glu Glu
    395                 400                 405 gag act gag agt tgg atc aaa tgg ctc aaa gaa att ctc gaa tgt tct           1301
Glu Thr Glu Ser Trp Ile Lys Trp Leu Lys Glu Ile Leu Glu Cys Ser
410                 415                 420                 425 cac cta tta aca gtt att aaa atg gaa gaa gct ggg gat gaa att gtg           1349
His Leu Leu Thr Val Ile Lys Met Glu Glu Ala Gly Asp Glu Ile Val
                430                 435                 440 agc aat gcc atc tcc tac gct cta tac aaa gcc ttc agc acc agt gag           1397
Ser Asn Ala Ile Ser Tyr Ala Leu Tyr Lys Ala Phe Ser Thr Ser Glu
            445                 450                 455 caa gac aag gat aac tgg aat ggg cag ctg aag ctt ctg ctg gag tgg           1445
Gln Asp Lys Asp Asn Trp Asn Gly Gln Leu Lys Leu Leu Leu Glu Trp
        460                 465                 470 aac cag ctg gac tta gcc aat gat gag att ttc acc aat gac cgc cga           1493
Asn Gln Leu Asp Leu Ala Asn Asp Glu Ile Phe Thr Asn Asp Arg Arg
    475                 480                 485
```

```
tgg gag aag agc aaa ccg agg ctc aga gac aca ata atc cag gtc aca    1541
Trp Glu Lys Ser Lys Pro Arg Leu Arg Asp Thr Ile Ile Gln Val Thr
490             495                 500                 505 tgg ctg gaa aat ggt aga atc aag gtt gag agc aaa gat gtg act gac    1589
Trp Leu Glu Asn Gly Arg Ile Lys Val Glu Ser Lys Asp Val Thr Asp
        510                 515                 520 ggc aaa gcc tct tct cat atg ctg gtg gtt ctc aag tct gct gac ctt    1637
Gly Lys Ala Ser Ser His Met Leu Val Val Leu Lys Ser Ala Asp Leu
            525                 530                 535 caa gaa gtc atg ttt acg gct ctc ata aag gac aga ccc aag ttt gtc    1685
Gln Glu Val Met Phe Thr Ala Leu Ile Lys Asp Arg Pro Lys Phe Val
        540                 545                 550 cgc ctc ttt ctg gag aat ggc ttg aac cta cgg aag ttt ctc acc cat    1733
Arg Leu Phe Leu Glu Asn Gly Leu Asn Leu Arg Lys Phe Leu Thr His
555             560                 565 gat gtc ctc act gaa ctc ttc tcc aac cac ttc agc acg ctt gtg tac    1781
Asp Val Leu Thr Glu Leu Phe Ser Asn His Phe Ser Thr Leu Val Tyr
570             575                 580                 585 cgg aat ctg cag atc gcc aag aat tcc tat aat gat gcc ctc ctc acg    1829
Arg Asn Leu Gln Ile Ala Lys Asn Ser Tyr Asn Asp Ala Leu Leu Thr
                590                 595                 600 ttt gtc tgg aaa ctg gtt gcg aac ttc cga aga ggc ttc cgg aag gaa    1877
Phe Val Trp Lys Leu Val Ala Asn Phe Arg Arg Gly Phe Arg Lys Glu
            605                 610                 615 gac aga aat ggc cgg gac gag atg gac ata gaa ctc cac gac gtg tct    1925
Asp Arg Asn Gly Arg Asp Glu Met Asp Ile Glu Leu His Asp Val Ser
        620                 625                 630 cct att act cgg cac ccc ctg caa gct ctc ttc atc tgg gcc att ctt    1973
Pro Ile Thr Arg His Pro Leu Gln Ala Leu Phe Ile Trp Ala Ile Leu
635             640                 645 cag aat aag aag gaa ctc tcc aaa gtc att tgg gag cag acc agg ggc    2021
Gln Asn Lys Lys Glu Leu Ser Lys Val Ile Trp Glu Gln Thr Arg Gly
650             655                 660                 665 tgc act ctg gca gcc ctg gga gcc agc aag ctt ctg aag act ctg gcc    2069
Cys Thr Leu Ala Ala Leu Gly Ala Ser Lys Leu Leu Lys Thr Leu Ala
            670                 675                 680 aaa gtg aag aac gac atc aat gct gct ggg gag tcc gag gag ctg gct    2117
Lys Val Lys Asn Asp Ile Asn Ala Ala Gly Glu Ser Glu Glu Leu Ala
        685                 690                 695 aat gag tac gag acc cgg gct gtt ggt gag tcc aca gtg tgg aat gct    2165
Asn Glu Tyr Glu Thr Arg Ala Val Gly Glu Ser Thr Val Trp Asn Ala
            700                 705                 710 gtg gtg ggc gcg gat ctg cca tgt ggc aca gac att gcc agc ggc act    2213
Val Val Gly Ala Asp Leu Pro Cys Gly Thr Asp Ile Ala Ser Gly Thr
715             720                 725 cat aga cca gat ggt gga gag ctg ttc act gag tgt tac agc agc gat    2261
His Arg Pro Asp Gly Gly Glu Leu Phe Thr Glu Cys Tyr Ser Ser Asp
730                 735                 740                 745 gaa gac ttg gca gaa cag ctg ctg gtc tat tcc tgt gaa gct tgg ggt    2309
Glu Asp Leu Ala Glu Gln Leu Leu Val Tyr Ser Cys Glu Ala Trp Gly
            750                 755                 760 gga agc aac tgt ctg gag ctg gcg gtg gag gcc aca gac cag cat ttc    2357
Gly Ser Asn Cys Leu Glu Leu Ala Val Glu Ala Thr Asp Gln His Phe
        765                 770                 775 atc gcc cag cct ggg gtc cag aat ttt ctt tct aag caa tgg tat gga    2405
Ile Ala Gln Pro Gly Val Gln Asn Phe Leu Ser Lys Gln Trp Tyr Gly
            780                 785                 790 gag att tcc cga gac acc aag aac tgg aag att atc ctg tgt ctg ttt    2453
Glu Ile Ser Arg Asp Thr Lys Asn Trp Lys Ile Ile Leu Cys Leu Phe
795                 800                 805
```

```
att ata ccc ttg gtg ggc tgt ggc ttt gta tca ttt agg aag aaa cct      2501
Ile Ile Pro Leu Val Gly Cys Gly Phe Val Ser Phe Arg Lys Lys Pro
810             815                 820                 825 gtc gac aag cac aag aag ctg ctt tgg tac tat gtg gcg ttc ttc acc      2549
Val Asp Lys His Lys Lys Leu Leu Trp Tyr Tyr Val Ala Phe Phe Thr
                830                 835                 840 tcc ccc ttc gtg gtc ttc tcc tgg aat gtg gtc ttc tac atc gcc ttc      2597
Ser Pro Phe Val Val Phe Ser Trp Asn Val Val Phe Tyr Ile Ala Phe
            845                 850                 855 ctc ctg ctg ttt gcc tac gtg ctg ctc atg gat ttc cat tcg gtg cca      2645
Leu Leu Leu Phe Ala Tyr Val Leu Leu Met Asp Phe His Ser Val Pro
        860                 865                 870 cac ccc ccc gag ctg gtc ctg tac tcg ctg gtc ttt gtc ctc ttc tgt      2693
His Pro Pro Glu Leu Val Leu Tyr Ser Leu Val Phe Val Leu Phe Cys
    875                 880                 885 gat gaa gtg aga cag ggc cgg ccg gct gct ccc agt gcg ggg ccc gcc      2741
Asp Glu Val Arg Gln Gly Arg Pro Ala Ala Pro Ser Ala Gly Pro Ala
890                 895                 900                 905 aag ccc acg ccc acc cgg aac tcc atc tgg ccc gca agc tcc aca cgc      2789
Lys Pro Thr Pro Thr Arg Asn Ser Ile Trp Pro Ala Ser Ser Thr Arg
                910                 915                 920 agc ccc ggt tcc cgc tca cgc cac tcc ttc cac act tcc ctg caa gct      2837
Ser Pro Gly Ser Arg Ser Arg His Ser Phe His Thr Ser Leu Gln Ala
            925                 930                 935 gag ggt gcc agc tct ggc ctt ggc cag ccc aga aag ggg tgg aca ttt      2885
Glu Gly Ala Ser Ser Gly Leu Gly Gln Pro Arg Lys Gly Trp Thr Phe
        940                 945                 950 aaa aat ctg gaa atg gtt gat att tcc aag ctg ctg atg tcc ctc tct      2933
Lys Asn Leu Glu Met Val Asp Ile Ser Lys Leu Leu Met Ser Leu Ser
    955                 960                 965 gtc cct ttc tgt acg cag tgg tac gta aat ggg gtg aat tat ttt act      2981
Val Pro Phe Cys Thr Gln Trp Tyr Val Asn Gly Val Asn Tyr Phe Thr
970                 975                 980                 985 gac ctg tgg aat gtg atg gac acg ctg ggg ctt ttt tac ttc ata gca      3029
Asp Leu Trp Asn Val Met Asp Thr Leu Gly Leu Phe Tyr Phe Ile Ala
                990                 995                 1000 gga att gta ttt cgg caa ggg atc ctt agg cag aat gag cag cgc tgg      3077
Gly Ile Val Phe Arg Gln Gly Ile Leu Arg Gln Asn Glu Gln Arg Trp
            1005                1010                1015 agg tgg ata ttc cgt tcg gtc atc tac gag ccc tac ctg gcc atg ttc      3125
Arg Trp Ile Phe Arg Ser Val Ile Tyr Glu Pro Tyr Leu Ala Met Phe
        1020                1025                1030 ggc cag gtg ccc agt gac gtg gat ggt acc acg tat gac ttt gcc cac      3173
Gly Gln Val Pro Ser Asp Val Asp Gly Thr Thr Tyr Asp Phe Ala His
    1035                1040                1045 tgc acc ttc act ggg aat gag tcc aag cca ctg tgt gtg gag ctg gat      3221
Cys Thr Phe Thr Gly Asn Glu Ser Lys Pro Leu Cys Val Glu Leu Asp
1050                1055                1060                1065 gag cac aac ctg ccc cgg ttc ccc gag tgg atc acc atc ccc ctg gtg      3269
Glu His Asn Leu Pro Arg Phe Pro Glu Trp Ile Thr Ile Pro Leu Val
                1070                1075                1080 tgc atc tac atg tta tcc acc aac atc ctg ctg gtc aac ctg ctg gtc      3317
Cys Ile Tyr Met Leu Ser Thr Asn Ile Leu Leu Val Asn Leu Leu Val
            1085                1090                1095 gcc atg ttt ggc tac acg gtg ggc acc gtc cag gag aac aat gac cag      3365
Ala Met Phe Gly Tyr Thr Val Gly Thr Val Gln Glu Asn Asn Asp Gln
        1100                1105                1110 gtc tgg aag ttc cag agg tac ttc ctg gtg cag gag tac tgc agc cgc      3413
Val Trp Lys Phe Gln Arg Tyr Phe Leu Val Gln Glu Tyr Cys Ser Arg
```

```
                                                              -continued 1115               1120                1125
ctc aat atc ccc ttc ccc ttc atc gtc ttc gct tac ttc tac atg gtg        3461
Leu Asn Ile Pro Phe Pro Phe Ile Val Phe Ala Tyr Phe Tyr Met Val
1130                1135                 1140               1145 gtg aag aag tgc ttc aag tgt tgc tgc aag gag aaa aac atg gag tct        3509
Val Lys Lys Cys Phe Lys Cys Cys Cys Lys Glu Lys Asn Met Glu Ser
                1150                 1155                1160 tct gtc tgc tgt gag tgg ttt atc cat gtg tac ttg gga tca gaa gca        3557
Ser Val Cys Cys Glu Trp Phe Ile His Val Tyr Leu Gly Ser Glu Ala
            1165                 1170                 1175 gcg att aat ttc agg gaa gga tgc ctg cat cca gtg att gga agc tgg        3605
Ala Ile Asn Phe Arg Glu Gly Cys Leu His Pro Val Ile Gly Ser Trp
        1180                1185                1190 acc cca ggc tgg ctg gtc tgg aca tcc aca cgc att ctc aca tgc agt        3653
Thr Pro Gly Trp Leu Val Trp Thr Ser Thr Arg Ile Leu Thr Cys Ser
    1195                1200                1205 gcc ggc tgg cca gca gca ggg agt ctc agt gtc acc aca cat agc agc        3701
Ala Gly Trp Pro Ala Ala Gly Ser Leu Ser Val Thr Thr His Ser Ser
1210                1215                1220                1225 tgg gtt cct gca aaa agc agc aag tca cag gcc cac cca gac aga acg        3749
Trp Val Pro Ala Lys Ser Ser Lys Ser Gln Ala His Pro Asp Arg Thr
                1230                1235                1240 ggt aga gaa tgt gac tct gct tct ggg tgg gaa gga cag cct gcc cgg        3797
Gly Arg Glu Cys Asp Ser Ala Ser Gly Trp Glu Gly Gln Pro Ala Arg
            1245                1250                1255 tgg gtg gaa gaa tcc gtg gcc ctg ttt ggc cat cgt ggc cct gtt tgg        3845
Trp Val Glu Glu Ser Val Ala Leu Phe Gly His Arg Gly Pro Val Trp
        1260                1265                1270 cca cct acc act cta ggc atc act gag cta aat gcg ccg gtc ctc            3890
Pro Pro Thr Thr Leu Gly Ile Thr Glu Leu Asn Ala Pro Val Leu
    1275                1280                1285 tga                                                                    3893

<210> SEQ ID NO 12
<211> LENGTH: 1288
<212> TYPE: PRT
<213> ORGANISM: Homo sapiens

<400> SEQUENCE: 12

Met Val Gly Gly Cys Arg Trp Thr Glu Asp Val Glu Pro Ala Glu Val
1               5                   10                  15

Lys Glu Lys Met Ser Phe Arg Ala Ala Arg Leu Ser Met Arg Asn Arg
                20                  25                  30

Arg Asn Asp Thr Leu Asp Ser Thr Arg Thr Leu Tyr Ser Ser Ala Ser
            35                  40                  45

Arg Ser Thr Asp Leu Ser Tyr Ser Glu Ser Ala Ser Phe Tyr Ala Ala
        50                  55                  60

Phe Arg Thr Gln Thr Cys Pro Ile Met Ala Ser Trp Asp Leu Val Asn
65                  70                  75                  80

Phe Ile Gln Ala Asn Phe Lys Lys Arg Glu Cys Val Phe Phe Thr Lys
                85                  90                  95

Asp Ser Lys Ala Thr Glu Asn Val Cys Lys Cys Gly Tyr Ala Gln Ser
            100                 105                 110

Gln His Met Glu Gly Thr Gln Ile Asn Gln Ser Glu Lys Trp Asn Tyr
        115                 120                 125

Lys Lys His Thr Lys Glu Phe Pro Thr Asp Ala Phe Gly Asp Ile Gln
    130                 135                 140
```

```
Phe Glu Thr Leu Gly Lys Lys Gly Lys Tyr Ile Arg Leu Ser Cys Asp
145                 150                 155                 160

Thr Asp Ala Glu Ile Leu Tyr Glu Leu Leu Thr Gln His Trp His Leu
            165                 170                 175

Lys Thr Pro Asn Leu Val Ile Ser Val Thr Gly Gly Ala Lys Asn Phe
        180                 185                 190

Ala Leu Lys Pro Arg Met Arg Lys Ile Phe Ser Arg Leu Ile Tyr Ile
    195                 200                 205

Ala Gln Ser Lys Gly Ala Trp Ile Leu Thr Gly Gly Thr His Tyr Gly
210                 215                 220

Leu Met Lys Tyr Ile Gly Glu Val Val Arg Asp Asn Thr Ile Ser Arg
225                 230                 235                 240

Ser Ser Glu Glu Asn Ile Val Ala Ile Gly Ile Ala Ala Trp Gly Met
                245                 250                 255

Val Ser Asn Arg Asp Thr Leu Ile Arg Asn Cys Asp Ala Glu Gly Tyr
            260                 265                 270

Phe Leu Ala Gln Tyr Leu Met Asp Asp Phe Thr Arg Asp Pro Leu Tyr
        275                 280                 285

Ile Leu Asp Asn Asn His Thr His Leu Leu Val Asp Asn Gly Cys
    290                 295                 300

His Gly His Pro Thr Val Glu Ala Lys Leu Arg Asn Gln Leu Glu Lys
305                 310                 315                 320

Tyr Ile Ser Glu Arg Thr Ile Gln Asp Ser Asn Tyr Gly Gly Lys Ile
                325                 330                 335

Pro Ile Val Cys Phe Ala Gln Gly Gly Gly Lys Glu Thr Leu Lys Ala
            340                 345                 350

Ile Asn Thr Ser Ile Lys Asn Lys Ile Pro Cys Val Val Val Glu Gly
        355                 360                 365

Ser Gly Gln Ile Ala Asp Val Ile Ala Ser Leu Val Glu Val Glu Asp
    370                 375                 380

Ala Leu Thr Ser Ser Ala Val Lys Glu Lys Leu Val Arg Phe Leu Pro
385                 390                 395                 400

Arg Thr Val Ser Arg Leu Pro Glu Glu Thr Glu Ser Trp Ile Lys
                405                 410                 415

Trp Leu Lys Glu Ile Leu Glu Cys Ser His Leu Leu Thr Val Ile Lys
            420                 425                 430

Met Glu Glu Ala Gly Asp Glu Ile Val Ser Asn Ala Ile Ser Tyr Ala
        435                 440                 445

Leu Tyr Lys Ala Phe Ser Thr Ser Glu Gln Asp Lys Asp Asn Trp Asn
    450                 455                 460

Gly Gln Leu Lys Leu Leu Leu Glu Trp Asn Gln Leu Asp Leu Ala Asn
465                 470                 475                 480

Asp Glu Ile Phe Thr Asn Asp Arg Arg Trp Glu Lys Ser Lys Pro Arg
                485                 490                 495

Leu Arg Asp Thr Ile Ile Gln Val Thr Trp Leu Glu Asn Gly Arg Ile
            500                 505                 510

Lys Val Glu Ser Lys Asp Val Thr Asp Gly Lys Ala Ser Ser His Met
        515                 520                 525

Leu Val Val Leu Lys Ser Ala Asp Leu Gln Glu Val Met Phe Thr Ala
    530                 535                 540

Leu Ile Lys Asp Arg Pro Lys Phe Val Arg Leu Phe Leu Glu Asn Gly
545                 550                 555                 560

Leu Asn Leu Arg Lys Phe Leu Thr His Asp Val Leu Thr Glu Leu Phe
```

-continued

```
                565                 570                 575
Ser Asn His Phe Ser Thr Leu Val Tyr Arg Asn Leu Gln Ile Ala Lys
            580                 585                 590
Asn Ser Tyr Asn Asp Ala Leu Leu Thr Phe Val Trp Lys Leu Val Ala
        595                 600                 605
Asn Phe Arg Arg Gly Phe Arg Lys Glu Asp Arg Asn Gly Arg Asp Glu
    610                 615                 620
Met Asp Ile Glu Leu His Asp Val Ser Pro Ile Thr Arg His Pro Leu
625                 630                 635                 640
Gln Ala Leu Phe Ile Trp Ala Ile Leu Gln Asn Lys Lys Glu Leu Ser
            645                 650                 655
Lys Val Ile Trp Glu Gln Thr Arg Gly Cys Thr Leu Ala Ala Leu Gly
            660                 665                 670
Ala Ser Lys Leu Leu Lys Thr Leu Ala Lys Val Lys Asn Asp Ile Asn
        675                 680                 685
Ala Ala Gly Glu Ser Glu Leu Ala Asn Glu Tyr Glu Thr Arg Ala
    690                 695                 700
Val Gly Glu Ser Thr Val Trp Asn Ala Val Gly Ala Asp Leu Pro
705                 710                 715                 720
Cys Gly Thr Asp Ile Ala Ser Gly Thr His Arg Pro Asp Gly Gly Glu
            725                 730                 735
Leu Phe Thr Glu Cys Tyr Ser Ser Asp Glu Asp Leu Ala Glu Gln Leu
            740                 745                 750
Leu Val Tyr Ser Cys Glu Ala Trp Gly Gly Ser Asn Cys Leu Glu Leu
        755                 760                 765
Ala Val Glu Ala Thr Asp Gln His Phe Ile Ala Gln Pro Gly Val Gln
    770                 775                 780
Asn Phe Leu Ser Lys Gln Trp Tyr Gly Glu Ile Ser Arg Asp Thr Lys
785                 790                 795                 800
Asn Trp Lys Ile Ile Leu Cys Leu Phe Ile Ile Pro Leu Val Gly Cys
            805                 810                 815
Gly Phe Val Ser Phe Arg Lys Lys Pro Val Asp Lys His Lys Lys Leu
        820                 825                 830
Leu Trp Tyr Tyr Val Ala Phe Phe Thr Ser Pro Phe Val Val Phe Ser
    835                 840                 845
Trp Asn Val Val Phe Tyr Ile Ala Phe Leu Leu Phe Ala Tyr Val
850                 855                 860
Leu Leu Met Asp Phe His Ser Val Pro His Pro Glu Leu Val Leu
865                 870                 875                 880
Tyr Ser Leu Val Phe Val Leu Phe Cys Asp Glu Val Arg Gln Gly Arg
            885                 890                 895
Pro Ala Ala Pro Ser Ala Gly Pro Ala Lys Pro Thr Pro Thr Arg Asn
            900                 905                 910
Ser Ile Trp Pro Ala Ser Ser Thr Arg Ser Pro Gly Ser Arg Ser Arg
        915                 920                 925
His Ser Phe His Thr Ser Leu Gln Ala Glu Gly Ala Ser Ser Gly Leu
    930                 935                 940
Gly Gln Pro Arg Lys Gly Trp Thr Phe Lys Asn Leu Glu Met Val Asp
945                 950                 955                 960
Ile Ser Lys Leu Leu Met Ser Leu Ser Val Pro Phe Cys Thr Gln Trp
            965                 970                 975
Tyr Val Asn Gly Val Asn Tyr Phe Thr Asp Leu Trp Asn Val Met Asp
            980                 985                 990
```

```
Thr Leu Gly Leu Phe Tyr Phe Ile Ala Gly Ile Val Phe Arg Gln Gly
        995                 1000                1005

Ile Leu Arg Gln Asn Glu Gln Arg Trp Arg Trp Ile Phe Arg Ser Val
    1010                1015                1020

Ile Tyr Glu Pro Tyr Leu Ala Met Phe Gly Gln Val Pro Ser Asp Val
1025                1030                1035                1040

Asp Gly Thr Thr Tyr Asp Phe Ala His Cys Thr Phe Thr Gly Asn Glu
            1045                1050                1055

Ser Lys Pro Leu Cys Val Glu Leu Asp Glu His Asn Leu Pro Arg Phe
        1060                1065                1070

Pro Glu Trp Ile Thr Ile Pro Leu Val Cys Ile Tyr Met Leu Ser Thr
    1075                1080                1085

Asn Ile Leu Leu Val Asn Leu Leu Val Ala Met Phe Gly Tyr Thr Val
    1090                1095                1100

Gly Thr Val Gln Glu Asn Asn Asp Gln Val Trp Lys Phe Gln Arg Tyr
1105                1110                1115                1120

Phe Leu Val Gln Glu Tyr Cys Ser Arg Leu Asn Ile Pro Phe Pro Phe
            1125                1130                1135

Ile Val Phe Ala Tyr Phe Tyr Met Val Val Lys Lys Cys Phe Lys Cys
        1140                1145                1150

Cys Cys Lys Glu Lys Asn Met Glu Ser Ser Val Cys Cys Glu Trp Phe
    1155                1160                1165

Ile His Val Tyr Leu Gly Ser Glu Ala Ala Ile Asn Phe Arg Glu Gly
    1170                1175                1180

Cys Leu His Pro Val Ile Gly Ser Trp Thr Pro Gly Trp Leu Val Trp
1185                1190                1195                1200

Thr Ser Thr Arg Ile Leu Thr Cys Ser Ala Gly Trp Pro Ala Ala Gly
            1205                1210                1215

Ser Leu Ser Val Thr Thr His Ser Ser Trp Val Pro Ala Lys Ser Ser
        1220                1225                1230

Lys Ser Gln Ala His Pro Asp Arg Thr Gly Arg Glu Cys Asp Ser Ala
    1235                1240                1245

Ser Gly Trp Glu Gly Gln Pro Ala Arg Trp Val Glu Glu Ser Val Ala
    1250                1255                1260

Leu Phe Gly His Arg Gly Pro Val Trp Pro Thr Thr Leu Gly Ile
1265                1270                1275                1280

Thr Glu Leu Asn Ala Pro Val Leu
            1285

<210> SEQ ID NO 13
<211> LENGTH: 2752
<212> TYPE: DNA
<213> ORGANISM: Homo sapiens

<400> SEQUENCE: 13
caaactcaca gccctctcca aactggctgg ggctgctggg agactcccaa ggaactcgtc      60
aggaaggcag agacaggag  acgggacctc tacaggagag cggtgggccg gcccttgggg     120
gggctgatgt ggccccaagg ctgagtcccg tcagggtctg gcctcggcct caggccccca    180
aggagccggc cctacacccc atgggtttgt cactgcccaa ggagaaaggg ctaattctct    240
gcctatggag caagttctgc agatggttcc agagacggga gtcctgggcc cagagccgag    300
atgagcagaa cctgctgcag cagaagagga tctgggagtc tcctctcctt ctagctgcca    360
aagataatga tgtccaggcc ctgaacaagt tgctcaagta tgaggattgc aaggtgcacc    420
```

-continued

```
agagaggagc catgggggaa acagcgctac acatagcagc cctctatgac aacctggagg    480
ccgccatggt gctgatggag gctgccccgg agctggtctt tgagcccatg acatctgagc    540
tctatgaggg tcagactgca ctgcacatcg ctgttgtgaa ccagaacatg aacctggtgc    600
gagccctgct tgcccgcagg gccagtgtct ctgccagagc cacaggcact gccttccgcc    660
gtagtccccg caacctcatc tactttgggg agcacccttt gtcctttgct gcctgtgtga    720
acagtgagga gatcgtgcgg ctgctcattg agcatggagc tgacatccgg gcccaggact    780
ccctggccca acaaaacctt tgcctgccag atgtacaacc tgttgctgtc ctacgacaga    840
catggggacc acctgcagcc cctggacctc gtgcccaatc accagggtct cacccctttc    900
aagctggctg gagtggaggg taacactgtg atgtttcagc acctgatgca gaagcggaag    960
cacacccagt ggacgtatgg accactgacc tcgactctct atgacctcac agagatcgac   1020
tcctcagggg atgagcagtc cctgctggaa cttatcatca ccaccaagaa gcgggaggct   1080
cgccagatcc tggaccagac gccggtgaag gagctggtga gcctcaagtg gaagcggtac   1140
gggcggccgt acttctgcat gctgggtgcc atatatctgc tgtacatcat ctgcttcacc   1200
atgtgctgca tctaccgccc cctcaagccc aggaccaata accgcacaag ccccgggac   1260
aacaccctct tacagcagaa gctacttcag gaagcctacg tgaccccta  ggacgatatc   1320
cggctggtcg gggagctggt gactgtcatt ggggctatca tcatcctgct ggtagaggtt   1380
ccagacatct tcagaatggg ggtcactcgc ttctttggac agaccatcct ggggggccca   1440
ttccatgtcc tcatcatcac ctatgccttc atggtgctgg tgaccatggt gatgcggctc   1500
atatgatttt tggcgacctg atgcgattct gctggctgat ggctgtggtc atcctgggct   1560
ttgcttcagc cttctatatc atcttccaga cagaggaccc cgaggagcta ggccacttct   1620
acgactaccc catggccctg ttcagcacct tcgagctggt ccttaccatc atcgatggcc   1680
cagccaacta caacgtggac ctgcccttca tgtacagcat cacctatgct gccttttgcca   1740
tcatcgccac actgctcatg ctcaacctcc tcattgccat gatgggcgac actcactggc   1800
gagtggccca tgagcgggat gagctgtgga gggcccagat tgtggccacc acggtgatgc   1860
tggagcggaa gctgcctcgc tgcctgtggc ctcgctccgg gatctgcgga cgggagtatg   1920
gcctggggga ccgctggttc ctgcgggtgg aagacaggca agatctcaac ggcagcggga   1980
tccaacgcta cgcacaggcc ttccacaccc ggggctctga ggatttggac aaagactcag   2040
tggaaaaact agagctgggc tgtcccttca gccccccacct gtcccttcct acgccctcag   2100
tgtctcgaag tacctcccgc agcagtgcca attgggaaag gcttcggcaa gggaccctga   2160
ggagagacct gcgtgggata atcaacaggg gtctggagga cggggagagc tgggaatatc   2220
agatctgact gcgtgttctc acttcgcttc ctggaacttg ctctcatttt cctgggtgca   2280
tcaaacaaaa caaaaaccaa acacccagag gtctcatctc ccaggcccca gggagaaaga   2340
ggagtagcat gaacgccaag gaatgtacgt tgagaatcac tgctccaggc ctgcattact   2400
ccttcagctc tggggcagag gaagcccagc ccaagcacgg ggctggcagg gcgtgaggaa   2460
ctctcctgtg gcctgctcat caccccttccg acaggagcac tgcatgtcag agcactttaa   2520
aaacaggcca gcctgcttgg gccctcggtc tccaccccag ggtcataagt ggggagagag   2580
cccttcccag ggcacccagg caggtgcagg gaagtgcaga gcttgtggaa agcgtgtgag   2640
tgagggagac aggaacggct ctgggggtgg gaagtgggc taggtcttgc caactccatc   2700
ttcaataaag tcgttttcgg atccctaaaa aaaaaaaaaa aaaaaaaaaa aa           2752
```

<210> SEQ ID NO 14
<211> LENGTH: 3073
<212> TYPE: DNA
<213> ORGANISM: Homo sapiens

<400> SEQUENCE: 14

```
caaactcaca gccctctcca aactggctgg ggctgctggg agactcccaa ggaactcgtc        60
aggaaggcag agacaggag  acgggacctc tacagggaga cggtgggccg gcccttgggg       120
gggctgatgt ggccccaagg ctgagtcccg tcagggtctg gcctcggcct caggcccca        180
aggagccggc cctacacccc atgggtttgt cactgcccaa ggagaaaggg ctaattctct       240
gcctatggag caagttctgc agatggttcc agagacggga gtcctgggcc cagagccgag       300
atgagcagaa cctgctgcag cagaagagga tctgggagtc tcctctcctt ctagctgcca       360
aagataatga tgtccaggcc ctgaacaagt tgctcaagta tgaggattgc aaggtgcacc       420
agagaggagc catgggggaa acagcgctac acatagcagc cctctatgac aacctggagg       480
ccgccatggt gctgatggag gctgccccgg agctggtctt tgagcccatg acatctgagc       540
tctatgaggt cctgactgcc catcacttga acgcctgccc cctgaaatgc cagggcctag       600
agaagaggaa gagatgggca gcagctggat cccctgggaa tcctgaacac ccgagagctc       660
cctgttctcc atcccaggct accctgagg  gaaagagact ggggtgcata tgggagggac       720
cccctgcagg atcctgggga cagacccgtg actgacagct gtctctgggc caggtcagac       780
tgcactgcac atcgctgttg tgaaccagaa catgaacctg gtgcgagccc tgcttgcccg       840
cagggccagt gtctctgcca gagccacagg cactgccttc cgccgtagtc cctgcaacct       900
catctacttt ggggagcacc ctttgtcctt tgctgcctgt gtgaacagtg aggagatcgt       960
gcggctgctc attgagcatg gagctgacat ccgggcccag gactccctgg cccaacaaaa      1020
cctttgcctg ccagatgtac aacctgttgc tgtcctacga cagacatggg gaccacctgc      1080
agcccctgga cctcgtgccc aatcaccagg gtctcacccc tttcaagctg ctggagtgg       1140
agggtaacac tgtgatgttt cagcacctga tgcagaagcg gaagcacacc cagtggacgt      1200
atggaccact gacctcgact ctctatgacc tcacagagat cgactcctca ggggatgagc      1260
agtccctgct ggaacttatc atcaccacca agaagcggga ggctcgccag atcctggacc      1320
agacgccggt gaaggagctg gtgagcctca gtggaagcg  gtacgggcgg ccgtacttct      1380
gcatgctggg tgccatatat ctgctgtaca tcatctgctt caccatgtgc tgcatctacc      1440
gcccctcaa  gcccaggacc aataaccgca cgagcccccg ggacaacacc ctcttacagc      1500
agaagctact tcaggaagcc tacatgaccc taaggacga  tatccggctg gtcgggagc       1560
tggtgactgt cattgggct  atcatcatcc tgctggtaga ggttccagac atcttcagaa      1620
tgggggtcac tcgcttcttt ggacagacca tccttggggg cccattccat gtcctcatca      1680
tcacctatgc cttcatggtg ctggtgacca tggtgatgcg gctcatcagt gccagcgggg      1740
aggtggtacc catgtccttt gcactcgtgc tgggctggtg caacgtcatg tacttcgccc      1800
gaggattcca gatgctaggc ccttccacca tcatgattca aagatgatt  tttggcgacc      1860
tgatgcgatt ctgctggctg atggctgtgg tcatcctggg ctttgcttag acagaggacc      1920
ccgaggagct aggccacttc tacgactacc ccatggccct gttcagcacc ttcgagctgg      1980
tccttaccat catcgatggc ccagccaact acaacgtgga cctgcccttc atgtacagca      2040
tcacctatgc tgcctttgcc atcatcgcca cactgctcat gctcaacctc ctcattgcca      2100
tgatgggcga cactcactgg cgagtggccc atgagcggga tgagctgtgg agggcccaga      2160
```

-continued

| | |
|---|---|
| ttgtggccac cacggtgatg ctggagcgga agctgcctcg ctgcctgtgg cctcgctccg | 2220 |
| ggatctgcgg acgggagtat ggcctgggag accgctggtt cctgcgggtg aagacaggc | 2280 |
| aagatctcaa ccggcagcgg atccaacgct acgcacaggc cttccacacc cggggctctg | 2340 |
| aggatttgga caaagactca gtggaaaaac tagagctggg ctgtcccttc agccccacc | 2400 |
| tgtcccttcc tatgccctca gtgtctcgaa gtacctcccg cagcagtgcc aattgggaaa | 2460 |
| ggcttcggca agggaccctg aggagagacc tgcgtggat aatcaacagg gtctggagg | 2520 |
| acggggagag ctgggaatat cagatctgac tgcgtgttct cacttcgctt cctggaactt | 2580 |
| gctctcattt tcctgggtgc atcaaacaaa acaaaaacca acacccaga ggtctcatct | 2640 |
| cccaggcccc agggagaaag aggagtagca tgaacgccaa ggaatgtacg ttgagaatca | 2700 |
| ctgctccagg cctgcattac tccttcagct ctggggcaga ggaagcccag cccaagcacg | 2760 |
| gggctggcag ggcgtgagga actctcctgt ggcctgctca tcacccttcc gacaggagca | 2820 |
| ctgcatgtca gagcacttta aaaacaggcc agcctgcttg ggcctcggt ctccacccca | 2880 |
| gggtcataag tggggagaga gcccttccca gggcacccag gcaggtgcag ggaagtgcag | 2940 |
| agcttgtgga aagcgtgtga gtgagggaga caggaacggc tctgggggtg ggaagtgggg | 3000 |
| ctaggtcttg ccaactccat cttcaataaa gtcgttttcg gatccctaaa aaaaaaaaa | 3060 |
| aaaaaaaaaa aaa | 3073 |

<210> SEQ ID NO 15
<211> LENGTH: 2803
<212> TYPE: DNA
<213> ORGANISM: Homo sapiens

<400> SEQUENCE: 15

| | |
|---|---|
| caaactcaca gccctctcca aactggctgg ggctgctggg agactcccaa ggaactcgtc | 60 |
| aggaaggcag gagacaggag acgggacctc tacagggaga cggtgggccg gcccttgggg | 120 |
| gggctgatgt ggccccaagg ctgagtcccg tcagggtctg gcctcggcct caggccccca | 180 |
| aggagccggc cctacacccc atgggtttgt cactgcccaa ggagaaaggg ctaattctct | 240 |
| gcctatggag caagttctgc agatggttcc agagacggga gtcctgggcc cagagccgag | 300 |
| atgagcagaa cctgctgcag cagaagagga tctgggagtc tcctctcctt ctagctgcca | 360 |
| aagataatga tgtccaggcc ctgaacaagt tgctcaagta tgaggattgc aaggtgcacc | 420 |
| agagaggagc catgggggaa acagcgctac acatagcagc cctctatgac aacctggagg | 480 |
| ccgccatggt gctgatggag gctgccccgg agctggtctt tgagcccatg acatctgagc | 540 |
| tctatgaggg tcagactgca ctgcacatcg ctgttgtgaa ccagaacatg aacctggtgc | 600 |
| gagccctgct tgcccgcagg gccagtgtct ctgccagagc cacaggcact gccttccgcc | 660 |
| gtagtccccg caacctcatc tactttggaa acacagtgtt acacatcctc atcctccagc | 720 |
| ccaacaaaac ctttgcctgc cagatgtaca acctgttgct gtcctacgac agacatgggg | 780 |
| accacctgca gccctggac ctcgtgccca atcaccaggg tctcacccct ttcaagctgg | 840 |
| ctggagtgga gggtaacact gtgatgtttc agcacctgat gcagaagcgg aagcacaccc | 900 |
| agtggacgta tggaccactg acctcgactc tctatgacct cacagagatc gactcctcag | 960 |
| gggatgagca gtccctgctg gaacttatca tcaccaccaa gaagcgggag gctcgccaga | 1020 |
| tcctggacca gacgccggtg aaggagctgg tgagcctcaa gtggaagcgg tacggcggc | 1080 |
| cgtacttctg catgctgggt gccatatatc tgctgtacat catctgcttc accatgtgct | 1140 |

```
gcatctaccg cccctcaag cccaggacca ataaccgcac aagccccgg gacaacaccc      1200 tcttacagca gaagctactt caggaagcct acgtgacccc taaggacgat atccggctgg      1260
tcggggagct ggtgactgtc attggggcta tcatcatcct gctggtagag gttccagaca      1320
tcttcagaat gggggtcact cgcttctttg gacagaccat ccttgggggc ccattccatg      1380
tcctcatcat cacctatgcc ttcatggtgc tggtgaccat ggtgatgcgg ctcatcagtg      1440
ccagcgggga ggtggtaccc atgtcctttg cactcgtgct gggctggtgc aacgtcatgt      1500
acttcgcccg aggattccag atgctaggcc ccttcaccat catgattcag aagatgattt      1560
ttggcgacct gatgcgattc tgctggctga tggctgtggt catcctgggc tttgcttcag      1620
ccttctatat catcttccag acagaggacc ccgaggagct aggccacttc tacgactacc      1680
ccatggccct gttcagcacc ttcgagctgg tccttaccat catcgatggc ccagccaact      1740
acaacgtgga cctgcccttc atgtacagca tcacctatgc tgcctttgcc atcatcgcca      1800
cactgctcat gctcaacctc ctcattgcca tgatgggcga cactcactgg cgagtggccc      1860
atgagcggga tgagctgtgg agggcccaga ttgtggccac cacggtgatg ctggagcgga      1920
agctgcctcg ctgcctgtgg cctcgctccg ggatctgcgg acgggagtat ggcctggggg      1980
accgctggtt cctgcgggtg gaagacaggc aagatctcaa ccggcagcgg atccaacgct      2040
acgcacaggc cttccacacc cggggctctg aggatttgga caaagactca gtggaaaaac      2100
tagagctggg ctgtcccttc agcccccacc tgtcccttcc tacgccctca gtgtctcgaa      2160
gtacctcccg cagcagtgcc aattgggaaa ggcttcggca agggaccctg aggagagacc      2220
tgcgtgggat aatcaacagg ggtctggagg acggggagag ctgggaatat cagatctgac      2280
tgcgtgttct cacttcgctt cctgaacttg ctctcatttt cctgggtgc atcaaacaaa      2340 acaaaaacca acacccaga ggtctcatct cccaggcccc agggagaaag aggagtagca      2400
tgaacgccaa ggaatgtacg ttgagaatca ctgctccagg cctgcattac tccttcagct      2460
ctggggcaga ggaagcccag cccaagcacg gggctggcag ggcgtgagga actctcctgt      2520
ggcctgctca tcacccttcc gacaggagca ctgcatgtca gagcacttta aaaacaggcc      2580
agcctgcttg ggccctcggt ctccaccca gggtcataag tggggagaga gcccttccca      2640
gggcacccag gcaggtgcag ggaagtgcag agcttgtgga aagcgtgtga gtgagggaga      2700
caggaacggc tctgggggtg ggaagtgggg ctaggtcttg ccaactccat cttcaataaa      2760
gtcgttttcg gatccctaaa aaaaaaaaa aaaaaaaaa aaa      2803
```

<210> SEQ ID NO 16
<211> LENGTH: 2908
<212> TYPE: DNA
<213> ORGANISM: Homo sapiens

<400> SEQUENCE: 16

```
cacacatggg gcctcccagg agtgcccagg acctcgtgct gttggcctct gaatctatcg       60
tctccaatcc gctgtcccac agaagccata taacccacct ctctgtaaat gccaggagcc      120 atggggaaa cagcgctaca catagcagcc ctctatgaca acctggaggc cgccatggtg      180
ctgatggagg ctgccccgga gctggtcttt gagcccatga catctgagct ctatggaggg      240
tgagggccca cgggtctggg gtgaagcagc ggagtgacgt ggttgggtat tcaagtcagt      300
ctctgtgatg gataatttgg gaaagacaca ggggatctga gcctcctact cttttttstct      360 tctctgtctc ccttccgtgt cagtcccctga ctgcccatca cttgaacgcc tgccccctga      420
aatgccaggg gcctagagaa gaggaagaga tgggcagcag ctggatcccc tgggaatcct      480
```

```
gaacacccga gagctccctg ttctccatcc caggctaccc ctgagggaaa gagactaggg      540
gtgcatatgg gagggacccc ctgcaggatc ctaggggaca gacccgtgac tgacagctgt      600
ctctgggcca ggtcagactg cactgcacat cgctgttgtg aaccagaaca tgaacctggt      660
gcgagccctg cttgcccgca gggccagtgt ctctgccaga gccacaggca ctgccttccg      720
ccgtagtccc tgcaacctca tctactttgg ggagcaccct tgtcctttg ctgcctgtgt       780 gaacagtgag gagatcgtgc ggctgctcat tgagcatgga gctgacatcc gggcccagga      840
ctccctggat gtacaacctg ttgctgtcct acgacagaca tggggaccac ctgcagcccc      900
tggacctcgt gcccaatcac cagggtctca cccctttcaa gctggctgga gtggagggta      960
acactgtgat gtttcagcac ctgatgcaga agcggaagca cacccagtgg acgtatggac     1020
cactgacctc gactctctat gacctcacag agatcgactc ctcagggat gagcagtccc      1080 tgctggaact tatcatcacc accaagaagc gggaggctcg ccagatcctg gaccagacgc     1140
cggtgaagga gctggtgagc ctcaagtgga agcggtacgg gcggccgtac ttctgcatgc     1200
tgggtgccat atatctgctg tacatcatct gcttcaccat gtgctgcatc taccgccccc     1260
tcaagcccag gaccaataac cgcacgagcc cccgggacaa caccctctta cagcagaagc     1320
tacttcagga agcctacatg acccctaagg acgatatccg gctggtcggg gagctggtga     1380
ctgtcattgg ggctatcatc atcctgctgg tagaggttcc agacatcttc agaatggggg     1440
tcactcgctt ctttggacag accatccttg ggggcccatt ccatgtcctc atcatcacct     1500
atgccttcat ggtgctggtg accatggtga tgcggctcat cagtgccagc ggggaggtgg     1560
tacccatgtc ctttgcactc gtgctgggct ggtgcaacgt catgtacttc gcccgaggat     1620
tccagatgct aggccccttc accatcatga ttcagaagat gatttttggc gacctgatgc     1680
gattctgctg gctgatggct gtggtcatcc tgggcttgc ttcagccttc tatatcatct      1740
tccagacaga ggaccccgag gagctaggcc acttctacga ctaccccatg gccctgttca     1800
gcaccttcga gctggtcctt accatcatcg atggcccagc caactacaac gtggacctgc     1860
ccttcatgta cagcatcacc tatgctgcct ttgccatcat cgccacactg ctcatgctca     1920
acctcctcat tgccatgatg ggcgacactc actggcgagt ggcccatgag cgggatgagc     1980
tgtggagggc ccagattgtg gccaccacgt tgatgctgga gcggaagctg cctcgctgcc     2040
tgtggcctcg ctccgggatc tgcggacggg agtatggcct gggagaccgc tggttcctgc     2100
gggtggaaga caggcaagat ctcaaccggc agcggatcca acgctacgca caggccttcc     2160
acacccgggg ctctgaggat ttggacaaag actcagtgga aaaactagag ctgggctgtc     2220
ccttcagccc ccacctgtcc cttcctatgc cctcagtgtc tcgaagtacc tcccgcagca     2280
gtgccaattg ggaaaggctt cggcaaggga ccctgaggag agacctgcgt gggataatca     2340 acagggtct ggaggacggg gagagctggg aatatcagat ctgactgcgt gttctcactt      2400
cgcttcctgg aacttgctct cattttcctg ggtgcatcaa acaaaacaaa aaccaaacac     2460
ccagaggtct catctcccag gccccaggga gaaagaggag tagcatgaac gccaaggaat     2520
gtacgttgag aatcactgct ccaggcctgc attactcctt cagctctggg gcagaggaag     2580
cccagcccaa gcacgggct ggcagggcgt gaggaactct cctgtggcct gctcatcacc      2640
cttccgacag gagcactgca tgtcagagca ctttaaaaac aggccagcct gcttgggccc     2700
tcggtctcca ccccagggtc ataagtgggg agagagccct tcccagggca ccaggcagg     2760 tgcagggaag tgcagagctt gtggaaagcg tgtgagtgag ggagacagga acggctctgg     2820
```

```
gggtgggaag tggggctagg tcttgccaac tccatcttca ataaagtcgt tttcggatcc    2880
ctaaaaaaaa aaaaaaaaaa aaaaaaaa                                      2908

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
tccgctgccg gttgagatct tgcc                                            24

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
cttgctccat aggcagagaa ttag                                            24

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
atcctcagag ccccgggtgt ggaa                                            24

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
ggcaagatct caaccggcag cgga                                            24

<210> SEQ ID NO 21
<211> LENGTH: 24
<212> TYPE: DNA
<213> ORGANISM: Artificial Sequence
<220> FEATURE:
<223> OTHER INFORMATION: primer

<400> SEQUENCE: 21
ctaattctct gcctatggag caag                                            24

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
ttccacaccc ggggctctga ggat                                            24

<210> SEQ ID NO 23
<211> LENGTH: 29
```

```
<212> TYPE: DNA
<213> ORGANISM: Artificial Sequence
<220> FEATURE:
<223> OTHER INFORMATION: primer

<400> SEQUENCE: 23
gcttccaccc caagcttcac aggaataga                                29

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
ggcgatgaaa tgctggtctg tggc                                     24

<210> SEQ ID NO 25
<211> LENGTH: 24
<212> TYPE: DNA
<213> ORGANISM: Artificial Sequence
<220> FEATURE:
<223> OTHER INFORMATION: primer

<400> SEQUENCE: 25
atcttccagt tcttggtgtc tcgg                                     24

<210> SEQ ID NO 26
<211> LENGTH: 24
<212> TYPE: DNA
<213> ORGANISM: Artificial Sequence
<220> FEATURE:
<223> OTHER INFORMATION: primer

<400> SEQUENCE: 26
gctgcagtac tcctgcacca ggaa                                     24

<210> SEQ ID NO 27
<211> LENGTH: 29
<212> TYPE: DNA
<213> ORGANISM: Artificial Sequence
<220> FEATURE:
<223> OTHER INFORMATION: primer

<400> SEQUENCE: 27
tctattcctg tgaagcttgg ggtggaagc                                29

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
gccacagacc agcatttcat cgcc                                     24

<210> SEQ ID NO 29
<211> LENGTH: 24
<212> TYPE: DNA
<213> ORGANISM: Artificial Sequence
<220> FEATURE:
<223> OTHER INFORMATION: primer

<400> SEQUENCE: 29
```

-continued

```
ccgagacacc aagaactgga agat                                    24

<210> SEQ ID NO 30
<211> LENGTH: 24
<212> TYPE: DNA
<213> ORGANISM: Artificial Sequence
<220> FEATURE:
<223> OTHER INFORMATION: primer

<400> SEQUENCE: 30
ttcctggtgc aggagtactg cagc                                    24

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
gcataggaag ggacaggtgg                                         20

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
gagagtcgag gtcagtggtc c                                       21

<210> SEQ ID NO 33
<211> LENGTH: 18
<212> TYPE: DNA
<213> ORGANISM: Artificial Sequence
<220> FEATURE:
<223> OTHER INFORMATION: primer

<400> SEQUENCE: 33
tatgagggtt cagactgc                                           18

<210> SEQ ID NO 34
<211> LENGTH: 18
<212> TYPE: DNA
<213> ORGANISM: Artificial Sequence
<220> FEATURE:
<223> OTHER INFORMATION: primer

<400> SEQUENCE: 34
caaagtagat gaggttgc                                           18

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
caccatgtgc tgcatctacc                                         20

<210> SEQ ID NO 36
<211> LENGTH: 20
<212> TYPE: DNA
<213> ORGANISM: Artificial Sequence
```

<220> FEATURE:
<223> OTHER INFORMATION: primer

<400> SEQUENCE: 36
caatgacagt caccagctcc 20

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
tccgctgccg gttgagatct tgcc 24

<210> SEQ ID NO 38
<211> LENGTH: 24
<212> TYPE: DNA
<213> ORGANISM: Artificial Sequence
<220> FEATURE:
<223> OTHER INFORMATION: primer

<400> SEQUENCE: 38
cttgctccat aggcagagaa ttag 24

<210> SEQ ID NO 39
<211> LENGTH: 24
<212> TYPE: DNA
<213> ORGANISM: Artificial Sequence
<220> FEATURE:
<223> OTHER INFORMATION: primer

<400> SEQUENCE: 39
atcctcagag ccccgggtgt ggaa 24

<210> SEQ ID NO 40
<211> LENGTH: 24
<212> TYPE: DNA
<213> ORGANISM: Artificial Sequence
<220> FEATURE:
<223> OTHER INFORMATION: primer

<400> SEQUENCE: 40
ggcaagatct caaccggcag cgga 24

<210> SEQ ID NO 41
<211> LENGTH: 24
<212> TYPE: DNA
<213> ORGANISM: Artificial Sequence
<220> FEATURE:
<223> OTHER INFORMATION: primer

<400> SEQUENCE: 41
ctaattctct gcctatggag caag 24

<210> SEQ ID NO 42
<211> LENGTH: 24
<212> TYPE: DNA
<213> ORGANISM: Artificial Sequence
<220> FEATURE:
<223> OTHER INFORMATION: primer

<400> SEQUENCE: 42
ttccacaccc ggggctctga ggat 24

```
<210> SEQ ID NO 43
<211> LENGTH: 19
<212> TYPE: DNA
<213> ORGANISM: Artificial Sequence
<220> FEATURE:
<223> OTHER INFORMATION: primer

<400> SEQUENCE: 43
acagctgctg gtctattcc                                                   19

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
tatgtgcctt ggtttgtacc                                                  20

<210> SEQ ID NO 45
<211> LENGTH: 2178
<212> TYPE: DNA
<213> ORGANISM: Homo sapiens
<220> FEATURE:
<221> NAME/KEY: CDS
<222> LOCATION: (1)...(2175)

<400> SEQUENCE: 45 atg ggt ttg tca ctg ccc aag gag aaa ggg cta att ctc tgc cta tgg        48
Met Gly Leu Ser Leu Pro Lys Glu Lys Gly Leu Ile Leu Cys Leu Trp
1               5                  10                  15 agc aag ttc tgc aga tgg ttc cag aga cgg gag tcc tgg gcc cag agc        96
Ser Lys Phe Cys Arg Trp Phe Gln Arg Arg Glu Ser Trp Ala Gln Ser
            20                  25                  30 cga gat gag cag aac ctg ctg cag cag aag agg atc tgg gag tct cct       144
Arg Asp Glu Gln Asn Leu Leu Gln Gln Lys Arg Ile Trp Glu Ser Pro
        35                  40                  45 ctc ctt cta gct gcc aaa gat aat gat gtc cag gcc ctg aac aag ttg       192
Leu Leu Leu Ala Ala Lys Asp Asn Asp Val Gln Ala Leu Asn Lys Leu
    50                  55                  60 ctc aag tat gag gat tgc aag gtg cac cag aga gga gcc atg ggg gaa       240
Leu Lys Tyr Glu Asp Cys Lys Val His Gln Arg Gly Ala Met Gly Glu
65                  70                  75                  80 aca gcg cta cac ata gca gcc ctc tat gac aac ctg gag gcc gcc atg       288
Thr Ala Leu His Ile Ala Ala Leu Tyr Asp Asn Leu Glu Ala Ala Met
                85                  90                  95 gtg ctg atg gag gct gcc ccg gag ctg gtc ttt gag ccc atg aca tct       336
Val Leu Met Glu Ala Ala Pro Glu Leu Val Phe Glu Pro Met Thr Ser
            100                 105                 110 gag ctc tat gag ggt cag act gca ctg cac atc gct gtt gtg aac cag       384
Glu Leu Tyr Glu Gly Gln Thr Ala Leu His Ile Ala Val Val Asn Gln
        115                 120                 125 aac atg aac ctg gtg cga gcc ctg ctt gcc cgc agg gcc agt gtc tct       432
Asn Met Asn Leu Val Arg Ala Leu Leu Ala Arg Arg Ala Ser Val Ser
    130                 135                 140 gcc aga gcc aca ggc act gcc ttc cgc cgt agt ccc tgc aac ctc atc       480
Ala Arg Ala Thr Gly Thr Ala Phe Arg Arg Ser Pro Cys Asn Leu Ile
145                 150                 155                 160 tac ttt ggg gag cac cct ttg tcc ttt gct gcc tgt gtg aac agt gag       528
Tyr Phe Gly Glu His Pro Leu Ser Phe Ala Ala Cys Val Asn Ser Glu
                165                 170                 175
```

-continued

```
gag atc gtg cgg ctg ctc att gag cat gga gct gac atc cgg gcc cag         576
Glu Ile Val Arg Leu Leu Ile Glu His Gly Ala Asp Ile Arg Ala Gln
        180                 185                 190 gac tcc ctg gga aac aca gtg tta cac atc ctc atc ctc cag ccc aac         624
Asp Ser Leu Gly Asn Thr Val Leu His Ile Leu Ile Leu Gln Pro Asn
            195                 200                 205 aaa acc ttt gcc tgc cag atg tac aac ctg ttg ctg tcc tac gac aga         672
Lys Thr Phe Ala Cys Gln Met Tyr Asn Leu Leu Leu Ser Tyr Asp Arg
210                 215                 220 cat ggg gac cac ctg cag ccc ctg gac ctc gtg ccc aat cac cag ggt         720
His Gly Asp His Leu Gln Pro Leu Asp Leu Val Pro Asn His Gln Gly
225                 230                 235                 240 ctc acc cct ttc aag ctg gct gga gtg gag ggt aac act gtg atg ttt         768
Leu Thr Pro Phe Lys Leu Ala Gly Val Glu Gly Asn Thr Val Met Phe
                245                 250                 255 cag cac ctg atg cag aag cgg aag cac acc cag tgg acg tat gga cca         816
Gln His Leu Met Gln Lys Arg Lys His Thr Gln Trp Thr Tyr Gly Pro
            260                 265                 270 ctg acc tcg act ctc tat gac ctc aca gag atc gac tcc tca ggg gat         864
Leu Thr Ser Thr Leu Tyr Asp Leu Thr Glu Ile Asp Ser Ser Gly Asp
        275                 280                 285 gag cag tcc ctg ctg gaa ctt atc atc acc acc aag aag cgg gag gct         912
Glu Gln Ser Leu Leu Glu Leu Ile Ile Thr Thr Lys Lys Arg Glu Ala
290                 295                 300 cgc cag atc ctg gac cag acg ccg gtg aag gag ctg gtg agc ctc aag         960
Arg Gln Ile Leu Asp Gln Thr Pro Val Lys Glu Leu Val Ser Leu Lys
305                 310                 315                 320 tgg aag cgg tac ggg cgg ccg tac ttc tgc atg ctg ggt gcc ata tat        1008
Trp Lys Arg Tyr Gly Arg Pro Tyr Phe Cys Met Leu Gly Ala Ile Tyr
                325                 330                 335 ctg ctg tac atc atc tgc ttc acc atg tgc tgc atc tac cgc ccc ctc        1056
Leu Leu Tyr Ile Ile Cys Phe Thr Met Cys Cys Ile Tyr Arg Pro Leu
            340                 345                 350 aag ccc agg acc aat aac cgc acg agc ccc cgg gac aac acc ctc tta        1104
Lys Pro Arg Thr Asn Asn Arg Thr Ser Pro Arg Asp Asn Thr Leu Leu
        355                 360                 365 cag cag aag cta ctt cag gaa gcc tac atg acc cct aag gac gat atc        1152
Gln Gln Lys Leu Leu Gln Glu Ala Tyr Met Thr Pro Lys Asp Asp Ile
370                 375                 380 cgg ctg gtc ggg gag ctg gtg act gtc att ggg gct atc atc atc ctg        1200
Arg Leu Val Gly Glu Leu Val Thr Val Ile Gly Ala Ile Ile Ile Leu
385                 390                 395                 400 ctg gta gag gtt cca gac atc ttc aga atg ggg gtc act cgc ttc ttt        1248
Leu Val Glu Val Pro Asp Ile Phe Arg Met Gly Val Thr Arg Phe Phe
                405                 410                 415 gga cag acc atc ctt ggg ggc cca ttc cat gtc ctc atc atc acc tat        1296
Gly Gln Thr Ile Leu Gly Gly Pro Phe His Val Leu Ile Ile Thr Tyr
            420                 425                 430 gcc ttc atg gtg ctg gtg acc atg gtg atg cgg ctc atc agt gcc agc        1344
Ala Phe Met Val Leu Val Thr Met Val Met Arg Leu Ile Ser Ala Ser
        435                 440                 445 ggg gag gtg gta ccc atg tcc ttt gca ctc gtg ctg ggc tgg tgc aac        1392
Gly Glu Val Val Pro Met Ser Phe Ala Leu Val Leu Gly Trp Cys Asn
450                 455                 460 gtc atg tac ttc gcc cga gga ttc cag atg cta ggc ccc ttc acc atc        1440
Val Met Tyr Phe Ala Arg Gly Phe Gln Met Leu Gly Pro Phe Thr Ile
465                 470                 475                 480 atg att cag aag atg att ttt ggc gac ctg atg cga ttc tgc tgg ctg        1488
Met Ile Gln Lys Met Ile Phe Gly Asp Leu Met Arg Phe Cys Trp Leu
                485                 490                 495
```

```
atg gct gtg gtc atc ctg ggc ttt gct tca gcc ttc tat atc atc ttc      1536
Met Ala Val Val Ile Leu Gly Phe Ala Ser Ala Phe Tyr Ile Ile Phe
            500                 505                 510 cag aca gag gac ccc gag gag cta ggc cac ttc tac gac tac ccc atg      1584
Gln Thr Glu Asp Pro Glu Glu Leu Gly His Phe Tyr Asp Tyr Pro Met
        515                 520                 525 gcc ctg ttc agc acc ttc gag ctg ttc ctt acc atc atc gat ggc cca      1632
Ala Leu Phe Ser Thr Phe Glu Leu Phe Leu Thr Ile Ile Asp Gly Pro
    530                 535                 540 gcc aac tac aac gtg gac ctg ccc ttc atg tac agc atc acc tat gct      1680
Ala Asn Tyr Asn Val Asp Leu Pro Phe Met Tyr Ser Ile Thr Tyr Ala
545                 550                 555                 560 gcc ttt gcc atc atc gcc aca ctg ctc atg ctc aac ctc ctc att gcc      1728
Ala Phe Ala Ile Ile Ala Thr Leu Leu Met Leu Asn Leu Leu Ile Ala
                565                 570                 575 atg atg ggc gac act cac tgg cga gtg gcc cat gag cgg gat gag ctg      1776
Met Met Gly Asp Thr His Trp Arg Val Ala His Glu Arg Asp Glu Leu
            580                 585                 590 tgg agg gcc cag att gtg gcc acc acg gtg atg ctg gag cgg aag ctg      1824
Trp Arg Ala Gln Ile Val Ala Thr Thr Val Met Leu Glu Arg Lys Leu
        595                 600                 605 cct cgc tgc ctg tgg cct cgc tcc ggg atc tgc gga cgg gag tat ggc      1872
Pro Arg Cys Leu Trp Pro Arg Ser Gly Ile Cys Gly Arg Glu Tyr Gly
    610                 615                 620 ctg gga gac cgc tgg ttc ctg cgg gtg gaa gac agg caa gat ctc aac      1920
Leu Gly Asp Arg Trp Phe Leu Arg Val Glu Asp Arg Gln Asp Leu Asn
625                 630                 635                 640 cgg cag cgg atc caa cgc tac gca cag gcc ttc cac acc agg ggc tct      1968
Arg Gln Arg Ile Gln Arg Tyr Ala Gln Ala Phe His Thr Arg Gly Ser
                645                 650                 655 gag gat ttg gac aaa gac tca gtg gaa aaa cta gag ctg ggc tgt ccc      2016
Glu Asp Leu Asp Lys Asp Ser Val Glu Lys Leu Glu Leu Gly Cys Pro
            660                 665                 670 ttc agc ccc cac ctg tcc ctt cct atg ccc tca gtg tct cga agt acc      2064
Phe Ser Pro His Leu Ser Leu Pro Met Pro Ser Val Ser Arg Ser Thr
        675                 680                 685 tcc cgc agc agt gcc aat tgg gaa agg ctt cgg caa ggg acc ctg agg      2112
Ser Arg Ser Ser Ala Asn Trp Glu Arg Leu Arg Gln Gly Thr Leu Arg
    690                 695                 700 aga gac ctg cgt ggg ata atc aac agg ggt ctg gag gac ggg gag agc      2160
Arg Asp Leu Arg Gly Ile Ile Asn Arg Gly Leu Glu Asp Gly Glu Ser
705                 710                 715                 720 tgg gaa tat cag atc tga                                              2178
Trp Glu Tyr Gln Ile
                725

<210> SEQ ID NO 46
<211> LENGTH: 725
<212> TYPE: PRT
<213> ORGANISM: Homo sapiens

<400> SEQUENCE: 46

Met Gly Leu Ser Leu Pro Lys Glu Lys Gly Leu Ile Leu Cys Leu Trp
1               5                   10                  15

Ser Lys Phe Cys Arg Trp Phe Gln Arg Arg Glu Ser Trp Ala Gln Ser
            20                  25                  30

Arg Asp Glu Gln Asn Leu Leu Gln Gln Lys Arg Ile Trp Glu Ser Pro
        35                  40                  45

Leu Leu Leu Ala Ala Lys Asp Asn Asp Val Gln Ala Leu Asn Lys Leu
```

```
                  50                  55                  60
Leu Lys Tyr Glu Asp Cys Lys Val His Gln Arg Gly Ala Met Gly Glu
 65                  70                  75                  80

Thr Ala Leu His Ile Ala Ala Leu Tyr Asp Asn Leu Glu Ala Ala Met
                 85                  90                  95

Val Leu Met Glu Ala Ala Pro Glu Leu Val Phe Glu Pro Met Thr Ser
                100                 105                 110

Glu Leu Tyr Glu Gly Gln Thr Ala Leu His Ile Ala Val Val Asn Gln
                115                 120                 125

Asn Met Asn Leu Val Arg Ala Leu Leu Ala Arg Arg Ala Ser Val Ser
130                 135                 140

Ala Arg Ala Thr Gly Thr Ala Phe Arg Arg Ser Pro Cys Asn Leu Ile
145                 150                 155                 160

Tyr Phe Gly Glu His Pro Leu Ser Phe Ala Ala Cys Val Asn Ser Glu
                165                 170                 175

Glu Ile Val Arg Leu Leu Ile Glu His Gly Ala Asp Ile Arg Ala Gln
                180                 185                 190

Asp Ser Leu Gly Asn Thr Val Leu His Ile Leu Ile Leu Gln Pro Asn
                195                 200                 205

Lys Thr Phe Ala Cys Gln Met Tyr Asn Leu Leu Leu Ser Tyr Asp Arg
210                 215                 220

His Gly Asp His Leu Gln Pro Leu Asp Leu Val Pro Asn His Gln Gly
225                 230                 235                 240

Leu Thr Pro Phe Lys Leu Ala Gly Val Glu Gly Asn Thr Val Met Phe
                245                 250                 255

Gln His Leu Met Gln Lys Arg Lys His Thr Gln Trp Thr Tyr Gly Pro
                260                 265                 270

Leu Thr Ser Thr Leu Tyr Asp Leu Thr Glu Ile Asp Ser Ser Gly Asp
                275                 280                 285

Glu Gln Ser Leu Leu Glu Leu Ile Ile Thr Thr Lys Lys Arg Glu Ala
                290                 295                 300

Arg Gln Ile Leu Asp Gln Thr Pro Val Lys Glu Leu Val Ser Leu Lys
305                 310                 315                 320

Trp Lys Arg Tyr Gly Arg Pro Tyr Phe Cys Met Leu Gly Ala Ile Tyr
                325                 330                 335

Leu Leu Tyr Ile Ile Cys Phe Thr Met Cys Cys Ile Tyr Arg Pro Leu
                340                 345                 350

Lys Pro Arg Thr Asn Asn Arg Thr Ser Pro Arg Asp Asn Thr Leu Leu
                355                 360                 365

Gln Gln Lys Leu Leu Gln Glu Ala Tyr Met Thr Pro Lys Asp Asp Ile
                370                 375                 380

Arg Leu Val Gly Glu Leu Val Thr Val Ile Gly Ala Ile Ile Ile Leu
385                 390                 395                 400

Leu Val Glu Val Pro Asp Ile Phe Arg Met Gly Val Thr Arg Phe Phe
                405                 410                 415

Gly Gln Thr Ile Leu Gly Gly Pro Phe His Val Leu Ile Ile Thr Tyr
                420                 425                 430

Ala Phe Met Val Leu Val Thr Met Val Met Arg Leu Ile Ser Ala Ser
                435                 440                 445

Gly Glu Val Val Pro Met Ser Phe Ala Leu Val Leu Gly Trp Cys Asn
                450                 455                 460

Val Met Tyr Phe Ala Arg Gly Phe Gln Met Leu Gly Pro Phe Thr Ile
465                 470                 475                 480
```

```
                                            -continued

Met Ile Gln Lys Met Ile Phe Gly Asp Leu Met Arg Phe Cys Trp Leu
            485                 490                 495

Met Ala Val Val Ile Leu Gly Phe Ala Ser Ala Phe Tyr Ile Ile Phe
            500                 505                 510

Gln Thr Glu Asp Pro Glu Glu Leu Gly His Phe Tyr Asp Tyr Pro Met
            515                 520                 525

Ala Leu Phe Ser Thr Phe Glu Leu Phe Leu Thr Ile Ile Asp Gly Pro
            530                 535                 540

Ala Asn Tyr Asn Val Asp Leu Pro Phe Met Tyr Ser Ile Thr Tyr Ala
545                 550                 555                 560

Ala Phe Ala Ile Ile Ala Thr Leu Leu Met Leu Asn Leu Leu Ile Ala
            565                 570                 575

Met Met Gly Asp Thr His Trp Arg Val Ala His Glu Arg Asp Glu Leu
            580                 585                 590

Trp Arg Ala Gln Ile Val Ala Thr Thr Val Met Leu Glu Arg Lys Leu
            595                 600                 605

Pro Arg Cys Leu Trp Pro Arg Ser Gly Ile Cys Gly Arg Glu Tyr Gly
            610                 615                 620

Leu Gly Asp Arg Trp Phe Leu Arg Val Glu Asp Arg Gln Asp Leu Asn
625                 630                 635                 640

Arg Gln Arg Ile Gln Arg Tyr Ala Gln Ala Phe His Thr Arg Gly Ser
            645                 650                 655

Glu Asp Leu Asp Lys Asp Ser Val Glu Lys Leu Glu Leu Gly Cys Pro
            660                 665                 670

Phe Ser Pro His Leu Ser Leu Pro Met Pro Ser Val Ser Arg Ser Thr
            675                 680                 685

Ser Arg Ser Ser Ala Asn Trp Glu Arg Leu Arg Gln Gly Thr Leu Arg
            690                 695                 700

Arg Asp Leu Arg Gly Ile Ile Asn Arg Gly Leu Glu Asp Gly Glu Ser
705                 710                 715                 720

Trp Glu Tyr Gln Ile
            725
```